(12) United States Patent
Putnam et al.

(10) Patent No.: US 11,497,980 B2
(45) Date of Patent: Nov. 15, 2022

(54) REFLECTIVE VIDEO DISPLAY APPARATUS FOR INTERACTIVE TRAINING AND DEMONSTRATION AND METHODS OF USING SAME

(71) Applicant: Curiouser Products Inc., New York, NY (US)

(72) Inventors: Brynn Putnam, New York, NY (US); Kristie D'Ambrosio-Correll, Sands Point, NY (US)

(73) Assignee: Curiouser Products Inc., New York, NY (US)

( * ) Notice: Subject to any disclaimer, the term of this patent is extended or adjusted under 35 U.S.C. 154(b) by 0 days.

(21) Appl. No.: 17/243,705

(22) Filed: Apr. 29, 2021

(65) Prior Publication Data

US 2021/0342952 A1 Nov. 4, 2021

Related U.S. Application Data

(60) Provisional application No. 63/173,587, filed on Apr. 12, 2021, provisional application No. 63/017,781, filed on Apr. 30, 2020.

(51) Int. Cl.
*G06Q 50/00* (2012.01)
*A63B 71/06* (2006.01)
(Continued)

(52) U.S. Cl.
CPC ...... *A63B 71/0622* (2013.01); *A63B 24/0006* (2013.01); *G06Q 50/01* (2013.01);
(Continued)

(58) Field of Classification Search
CPC ............... G06Q 50/01; H04N 21/2187; H04N 21/47202; G16H 20/30; A63B 24/0075
(Continued)

(56) References Cited

U.S. PATENT DOCUMENTS 5,681,223 A 10/1997 Weinreich
6,059,692 A 5/2000 Hickman
(Continued)

FOREIGN PATENT DOCUMENTS

CN 102413886 A 4/2012
CN 203311128 U 11/2013
(Continued)

OTHER PUBLICATIONS

Extended European Search Report dated May 25, 2021 for European Application No. 19810957.1, 7 pages.
(Continued)

*Primary Examiner* — Thai Q Tran
*Assistant Examiner* — Stephen R Smith
(74) *Attorney, Agent, or Firm* — Cooley LLP

(57) ABSTRACT

An interactive exercise method includes streaming exercise content to an interactive video system for display via a mirror, the exercise content including a depiction of an instructor performing a repetitive movement. A video stream of a user performing the repetitive movement is received, via a camera of the interactive video system, and the user is detected in the video stream. The user or a body portion thereof is tracked in the video stream as the user performs the repetitive movement. The method also includes generating a measure of a difference between a form of the user performing the repetitive movement and a predetermined form for the repetitive movement. A corrective movement is displayed to the user, via the display and during the display of the instructor performing the repetitive movement, based on the measure, to conform the form of the user to the predetermined form for the repetitive movement.

20 Claims, 94 Drawing Sheets

(51) Int. Cl.
  *A63B 24/00*      (2006.01)
  *G16H 20/30*      (2018.01)
  *H04N 21/2187*    (2011.01)
  *H04N 21/472*     (2011.01)

(52) U.S. Cl.
  CPC .......... *G16H 20/30* (2018.01); *H04N 21/2187* (2013.01); *H04N 21/47202* (2013.01); *A63B 24/0075* (2013.01); *A63B 2024/0015* (2013.01); *A63B 2071/065* (2013.01); *A63B 2071/0658* (2013.01); *A63B 2071/0683* (2013.01); *A63B 2071/0694* (2013.01); *A63B 2225/12* (2013.01)

(58) Field of Classification Search
  USPC .................. 434/247; 345/643, 633; 482/9, 8
  See application file for complete search history.

(56) References Cited

U.S. PATENT DOCUMENTS

| | | |
|---|---|---|
| 6,921,351 B1 | 7/2005 | Hickman et al. |
| 7,010,508 B1 | 3/2006 | Lockwood |
| 7,020,888 B2 | 3/2006 | Reynolds et al. |
| 7,055,169 B2 | 5/2006 | Delpuch et al. |
| 7,152,470 B2 | 12/2006 | Impioe et al. |
| 7,206,250 B2 | 4/2007 | Groux |
| 7,455,412 B2 | 11/2008 | Rottcher |
| 7,589,893 B2 | 9/2009 | Rottcher |
| 7,631,338 B2 | 12/2009 | Del Sesto et al. |
| 7,699,753 B2 | 4/2010 | Daikeler et al. |
| 7,725,740 B2 | 5/2010 | Kudelski et al. |
| 7,931,604 B2 | 4/2011 | Even et al. |
| 7,946,961 B2 | 5/2011 | Blum et al. |
| 8,081,158 B2 | 12/2011 | Harris |
| 8,311,474 B2 | 11/2012 | McAvoy et al. |
| 8,496,563 B2 | 7/2013 | Komatsu et al. |
| 8,519,938 B2 | 8/2013 | Hernandez et al. |
| 8,620,413 B2 | 12/2013 | Prstojevich et al. |
| 8,821,350 B2 | 9/2014 | Maertz |
| 8,882,641 B2 | 11/2014 | Cutler et al. |
| 8,912,909 B2 | 12/2014 | Al-Ali et al. |
| 8,951,168 B2 | 2/2015 | Baudhuin |
| 9,011,293 B2 | 4/2015 | Shavit et al. |
| D728,710 S | 5/2015 | Koduri et al. |
| 9,037,530 B2 | 5/2015 | Tan et al. |
| 9,122,320 B1 | 9/2015 | Rowles et al. |
| 9,174,085 B2 | 11/2015 | Foley et al. |
| 9,233,276 B1 | 1/2016 | Foley et al. |
| 9,259,615 B2 | 2/2016 | Weast et al. |
| 9,278,256 B2 | 3/2016 | Tchao et al. |
| 9,292,935 B2 | 3/2016 | Koduri et al. |
| 9,330,239 B2 | 5/2016 | Koduri et al. |
| 9,364,714 B2 | 6/2016 | Koduri et al. |
| 9,406,336 B2 | 8/2016 | Bose et al. |
| 9,712,581 B2 | 7/2017 | Tinsman |
| 9,842,508 B2 | 12/2017 | Crabtree |
| 9,861,855 B2 | 1/2018 | Foley et al. |
| 10,143,405 B2 | 4/2018 | Jayalath et al. |
| 9,975,002 B2 | 5/2018 | Pinkerton |
| 10,021,188 B2 | 7/2018 | Oleson et al. |
| 10,022,590 B2 | 7/2018 | Foley et al. |
| 10,068,257 B1 | 9/2018 | Mosthaf |
| 10,109,216 B2 | 10/2018 | Lagree et al. |
| 10,188,930 B2 | 1/2019 | Winsper et al. |
| 10,232,220 B2 | 1/2019 | Winsper et al. |
| 10,467,926 B2 | 5/2019 | Ghaffari et al. |
| 10,322,315 B2 | 6/2019 | Foley et al. |
| 10,375,429 B1 | 8/2019 | Greenfield |
| 10,413,250 B2 | 9/2019 | Leboeuf et al. |
| 10,486,026 B2 | 11/2019 | Foley et al. |
| 10,575,759 B2 | 3/2020 | Salamatian et al. |
| 10,639,521 B2 | 5/2020 | Foley et al. |
| 10,692,407 B2 | 6/2020 | Dunn et al. |
| 10,702,760 B2 | 7/2020 | Lagree et al. |
| 10,716,969 B2 | 7/2020 | Hoang |
| 10,744,371 B2 | 8/2020 | Mohrman et al. |
| 10,758,780 B2 | 9/2020 | Putnam |
| 10,828,551 B2 | 11/2020 | Putnam |
| 10,898,760 B2 | 1/2021 | Packles et al. |
| 10,923,225 B2 | 2/2021 | Riley et al. |
| 10,960,266 B2 | 3/2021 | Messinger |
| 10,981,047 B2 | 4/2021 | Putnam |
| 11,045,709 B2 | 6/2021 | Putnam |
| 11,065,527 B2 | 7/2021 | Putnam |
| 11,081,224 B2 | 8/2021 | Foley et al. |
| 11,090,547 B2 | 8/2021 | Putnam |
| 11,110,336 B2 | 9/2021 | Putnam |
| 11,117,038 B2 | 9/2021 | Putnam |
| 11,117,039 B2 | 9/2021 | Putnam |
| 11,123,626 B1 | 9/2021 | Putnam |
| 11,135,503 B2 | 10/2021 | Putnam |
| 11,135,504 B1 | 10/2021 | Putnam |
| 11,135,505 B2 | 10/2021 | Putnam |
| 11,167,172 B1 | 11/2021 | Putnam |
| 11,173,377 B1 | 11/2021 | Putnam |
| 11,173,378 B2 | 11/2021 | Putnam |
| 11,179,620 B2 | 11/2021 | Putnam |
| 11,219,816 B2 | 1/2022 | Putnam |
| 11,253,770 B2 | 2/2022 | Putnam |
| 2002/0080494 A1 | 6/2002 | Meine |
| 2005/0063566 A1 | 3/2005 | van Beek et al. |
| 2005/0192156 A1 | 9/2005 | Daikeler et al. |
| 2006/0184427 A1 | 8/2006 | Singh |
| 2007/0069977 A1 | 3/2007 | Adderton |
| 2007/0219057 A1 | 9/2007 | Fleishman |
| 2007/0219059 A1 | 9/2007 | Schwartz et al. |
| 2008/0146887 A1 | 6/2008 | Rao et al. |
| 2008/0204327 A1 | 8/2008 | Lee et al. |
| 2008/0207401 A1 | 8/2008 | Harding |
| 2008/0303949 A1 | 12/2008 | Ciudad et al. |
| 2009/0291726 A1 | 11/2009 | Svensson |
| 2009/0291805 A1 | 11/2009 | Blum et al. |
| 2009/0298650 A1 | 12/2009 | Kutliroff |
| 2010/0022351 A1 | 1/2010 | Lanfermann et al. |
| 2010/0214662 A1 | 8/2010 | Takayanagi et al. |
| 2010/0281432 A1 | 11/2010 | Geisner et al. |
| 2011/0056102 A1 | 3/2011 | Reid et al. |
| 2011/0154258 A1 | 6/2011 | Hope et al. |
| 2011/0172064 A1 | 7/2011 | Cutler et al. |
| 2011/0224999 A1 | 9/2011 | Baccarella-Garcia et al. |
| 2011/0267488 A1 | 11/2011 | Matsuura et al. |
| 2011/0275940 A1 | 11/2011 | Nims et al. |
| 2012/0069131 A1 | 3/2012 | Abelow |
| 2012/0206577 A1 | 8/2012 | Guckenberger et al. |
| 2012/0212484 A1 | 8/2012 | Haddick et al. |
| 2012/0289850 A1 | 11/2012 | Xu et al. |
| 2013/0141607 A1 | 6/2013 | Anabuki |
| 2013/0171601 A1 | 7/2013 | Yuasa et al. |
| 2013/0286047 A1 | 10/2013 | Katano et al. |
| 2014/0038781 A1 | 2/2014 | Foley et al. |
| 2014/0135173 A1 | 5/2014 | Watterson |
| 2014/0209400 A1 | 7/2014 | Yao et al. |
| 2014/0228985 A1 | 8/2014 | Elliott et al. |
| 2015/0003621 A1 | 1/2015 | Trammell |
| 2015/0038806 A1 | 2/2015 | Kaleal et al. |
| 2015/0061891 A1 | 3/2015 | Oleson et al. |
| 2015/0082408 A1 | 3/2015 | Yeh et al. |
| 2015/0134773 A1 | 5/2015 | Salem |
| 2015/0146778 A1 | 5/2015 | de Cicco et al. |
| 2015/0157938 A1 | 6/2015 | Domansky et al. |
| 2015/0182798 A1 | 7/2015 | Carriveau et al. |
| 2015/0339854 A1 | 11/2015 | Adler et al. |
| 2015/0348429 A1 | 12/2015 | Dalal et al. |
| 2016/0089574 A1 | 3/2016 | Henning et al. |
| 2016/0121165 A1 | 5/2016 | Foley et al. |
| 2016/0193502 A1 | 7/2016 | Kim et al. |
| 2016/0220808 A1 | 8/2016 | Hyde et al. |
| 2016/0240100 A1 | 8/2016 | Rauhala et al. |
| 2016/0321932 A1 | 11/2016 | Mitchell et al. |
| 2017/0189752 A1 | 7/2017 | Mohrman et al. |
| 2017/0199576 A1 | 7/2017 | Schmitz-Le Hanne |
| 2017/0296874 A1 | 10/2017 | Zamir et al. |
| 2017/0319906 A1 | 11/2017 | Chang et al. |

(56) References Cited

U.S. PATENT DOCUMENTS

| | | | |
|---|---|---|---|
| 2018/0028896 A1 | 2/2018 | Ray | |
| 2018/0056132 A1* | 3/2018 | Foley | A63B 23/0405 |
| 2018/0126223 A1 | 5/2018 | Foley et al. | |
| 2018/0126248 A1 | 5/2018 | Dion et al. | |
| 2018/0126249 A1 | 5/2018 | Consiglio et al. | |
| 2018/0140903 A1 | 5/2018 | Re et al. | |
| 2018/0268747 A1 | 9/2018 | Braun | |
| 2018/0271409 A1 | 9/2018 | Gong et al. | |
| 2018/0304118 A1 | 10/2018 | French | |
| 2018/0318647 A1 | 11/2018 | Foley et al. | |
| 2018/0339195 A1 | 11/2018 | Bernotas | |
| 2018/0369642 A1 | 12/2018 | Chang et al. | |
| 2019/0021616 A1 | 1/2019 | Day et al. | |
| 2019/0022388 A1 | 1/2019 | Stucke | |
| 2019/0111318 A1 | 4/2019 | Evancha et al. | |
| 2019/0126099 A1 | 5/2019 | Hoang | |
| 2019/0163431 A1 | 5/2019 | Rodriguez et al. | |
| 2019/0184234 A1 | 6/2019 | Packles et al. | |
| 2019/0209777 A1 | 7/2019 | O'Connell et al. | |
| 2019/0290965 A1 | 9/2019 | Oren | |
| 2019/0320140 A1 | 10/2019 | Lyu | |
| 2019/0336827 A1* | 11/2019 | Intonato | A63B 71/0622 |
| 2020/0009444 A1 | 1/2020 | Putnam | |
| 2020/0014967 A1 | 1/2020 | Putnam | |
| 2020/0016457 A1 | 1/2020 | Ben-Chanoch et al. | |
| 2020/0047030 A1 | 2/2020 | Ward et al. | |
| 2020/0054931 A1 | 2/2020 | Martin et al. | |
| 2020/0114203 A1 | 4/2020 | DeLuca | |
| 2020/0261770 A1 | 8/2020 | Foley et al. | |
| 2020/0359147 A1 | 11/2020 | Reilly et al. | |
| 2021/0008413 A1* | 1/2021 | Asikainen | G06F 3/011 |
| 2021/0046374 A1 | 2/2021 | Putnam | |
| 2021/0138332 A1 | 5/2021 | Dalebout et al. | |
| 2021/0146197 A1 | 5/2021 | Packles et al. | |
| 2021/0146222 A1 | 5/2021 | Putnam | |
| 2021/0150773 A1 | 5/2021 | Muendel et al. | |
| 2021/0154559 A1 | 5/2021 | Putnam | |
| 2021/0178246 A1 | 6/2021 | Putnam | |
| 2021/0205689 A1 | 7/2021 | Putnam | |
| 2021/0228968 A1 | 7/2021 | Putnam | |
| 2021/0228969 A1 | 7/2021 | Putnam | |
| 2021/0236874 A1 | 8/2021 | Ward et al. | |
| 2021/0252369 A1 | 8/2021 | Devine et al. | |
| 2021/0268361 A1 | 9/2021 | Putnam | |
| 2021/0283488 A1 | 9/2021 | Putnam | |
| 2021/0291033 A1 | 9/2021 | Putnam | |
| 2021/0322854 A1 | 10/2021 | Putnam | |
| 2021/0322855 A1 | 10/2021 | Putnam | |
| 2021/0339110 A1 | 11/2021 | Putnam | |
| 2021/0346781 A1 | 11/2021 | Putnam | |
| 2021/0354022 A1 | 11/2021 | Putnam | |
| 2021/0362030 A1 | 11/2021 | Putnam | |
| 2021/0362031 A1 | 11/2021 | Putnam | |
| 2021/0370153 A1 | 12/2021 | Putnam | |
| 2021/0370154 A1 | 12/2021 | Putnam | |
| 2021/0379471 A1 | 12/2021 | Putnam | |
| 2021/0379472 A1 | 12/2021 | Putnam | |
| 2021/0379473 A1 | 12/2021 | Putnam | |
| 2022/0023738 A1 | 1/2022 | Putnam | |
| 2022/0032162 A1 | 2/2022 | Putnam | |
| 2022/0032163 A1 | 2/2022 | Putnam | |
| 2022/0071415 A1 | 3/2022 | Putnam et al. | |
| 2022/0072375 A1 | 3/2022 | Putnam et al. | |
| 2022/0072376 A1 | 3/2022 | Putnam et al. | |
| 2022/0072379 A1 | 3/2022 | Putnam et al. | |
| 2022/0078503 A1 | 3/2022 | Putnam et al. | |

FOREIGN PATENT DOCUMENTS

| | | |
|---|---|---|
| CN | 104144201 A | 11/2014 |
| CN | 106055082 A | 10/2016 |
| CN | 107613867 A | 1/2018 |
| CN | 108525261 A | 9/2018 |
| JP | 2009-226131 A | 10/2009 |
| JP | 2009-277195 A | 11/2009 |
| JP | 2018-020010 A | 2/2018 |
| KR | 10-1998-0082935 A | 12/1998 |
| KR | 10-2010-0007116 A | 1/2010 |
| KR | 10-2012-0098854 A | 9/2012 |
| KR | 10-2016-0016263 A | 2/2016 |
| KR | 20-0431902 Y1 | 11/2016 |
| KR | 2016-0130085 A | 11/2016 |
| WO | WO 2005/087323 A2 | 9/2005 |
| WO | WO 2011/072111 A1 | 6/2011 |
| WO | WO 2013/035125 A1 | 3/2013 |
| WO | WO 2018/075523 A1 | 4/2018 |
| WO | WO 2019/016406 A1 | 1/2019 |
| WO | WO 2019/231982 A1 | 12/2019 |
| WO | WO 2021/138620 A1 | 7/2021 |

OTHER PUBLICATIONS

First Examination Report dated May 24, 2021 for Indian Application No. 202017056758, 5 pages.
Notice of Preliminary Rejection dated Apr. 29, 2021 for Korean Application No. 10-2020-7037528, with English translation, 11 pages.
U.S. Appl. No. 17/315,790, filed May 10, 2021.
U.S. Appl. No. 17/315,986, filed May 10, 2021.
U.S. Appl. No. 17/188,725, filed Mar. 1, 2021.
U.S. Appl. No. 17/315,558, filed May 10, 2021.
U.S. Appl. No. 17/339,337, filed Jun. 4, 2021.
U.S. Appl. No. 17/339,365, filed Jun. 4, 2021.
International Search Report and Written Opinion dated Oct. 9, 2019 for International Application No. PCT/US2019/034292, 18 pages.
Examination Report No. 1 dated Jan. 13, 2021 for Australian Application No. 2019277220, 7 pages.
Examination Report No. 2 dated Mar. 18, 2021 for Australian Application No. 2019277220, 4 pages.
Andreu, Y. et al., "Wize Mirror—a smart, multisensory cardio-metabolic risk monitoring system," Computer Vision and Image Understanding, 148:3-22 (2016).
Capritto, A., "Smart fitness device Mirror launches one-on-one personal training," CNET, Oct. 8, 2019, 5 pages; https://www.cnet.com/health/smart-fitness-device-mirror-launches-one-on-one-personal-training/.
Chaudhry, A., "How to watch videos with friends online," The Verge, Jul. 1, 2020, 13 pages; https://www.theverge.com/21307583/watch-videos-movies-online-friends-streaming-netflix-hulu-amazon-scener-extensions.
Choi, W. et al., "SwimTrain: Exploring Exergame Design for Group Fitness Swimming," Proceedings of the 2016 CHI Conference on Human Factors in Computing Systems, pp. 1692-1704 (May 7, 2016); retrieved at https://www.microsoft.com/en-us/research/wp-content/uploads/2016/07/p1692-choi.pdf.
"Everything You Need to Know About Throwing an obe Workout Party," Obé News, retrieved on Apr. 29, 2021 at http://obefitness.com/blog/workout-parties-faq, 8 pages.
Gartenberg, C., "Bulding your own smart mirror is surprisingly easy," Circuit Breaker, Aug. 17, 2017; Accessed at https://www.theverge.com/circuitbreaker/2017/8/17/16158104/smart-mirror-diy-raspberry-pi-commute-weather-time-gadget, 6 pages.
Magic Mirror[2], "The open source modular smart mirror platform," Accessed at https://magicmirror.builders, Mar. 18, 2019, 4 pages.
"Mirror, mirror on the wall, is the device that livestreams exercise classes in the home any good?" Business Insider, Accessed at https:www.scmp.com/magazines/style/tech-design/article/2176110/mirror-mirror-wall-device-livestreams-exercise-classes, 17 pages.
Muoio, D., "Mirror launches its in-home fitness platform, raises another $25M from lead investor," MobiHealth News, Sep. 6, 2018,1 page; https://www.mobihealthnews.com/content/mirror-launches-its-home-fitness-platform-raises-another-25m-lead-investor.
U.S. Appl. No. 29/704,708, filed Sep. 6, 2019.
U.S. Appl. No. 29/704,709, filed Sep. 6, 2019.
U.S. Appl. No. 17/165,307, filed Feb. 2, 2021.
U.S. Appl. No. 17/187,234, filed Feb. 26, 2021.
U.S. Appl. No. 17/189,464, filed Mar. 2, 2021.
U.S. Appl. No. 17/163,775, filed Feb. 1, 2021.

(56) References Cited

OTHER PUBLICATIONS

U.S. Appl. No. 17/229,573, filed Apr. 13, 2021.
U.S. Appl. No. 17/163,876, filed Feb. 1, 2021.
U.S. Appl. No. 17/222,854, filed Apr. 5, 2021.
U.S. Appl. No. 17/188,862, filed Mar. 1, 2021.
U.S. Appl. No. 17/230,909, filed Apr. 14, 2021.
U.S. Appl. No. 17/205,927, filed Mar. 18, 2021.
U.S. Appl. No. 17/243,710, filed Apr. 30, 2021.
U.S. Appl. No. 17/151,987, filed Jan. 19, 2021.
First Office Action and Search Report dated May 28, 2021 for Chinese Application No. CN201910975221.3, with English translation, 41 pages.
Office Action dated Jun. 14, 2021 for Japanese Application No. 2020-573560, with English translation, 6 pages.
International Search Report and Written Opinion dated Jul. 16, 2021 for International Application No. PCT/US2021/029786, 12 pages.
U.S. Appl. No. 17/322,177, filed May 17, 2021.
U.S. Appl. No. 17/398,492, filed Aug. 10, 2021.
U.S. Appl. No. 17/406,516, filed Aug. 19, 2021.
U.S. Appl. No. 17/398,836, filed Aug. 10, 2021.
U.S. Appl. No. 17/398,635, filed Aug. 10, 2021.
U.S. Appl. No. 17/398,669, filed Aug. 10, 2021.
U.S. Appl. No. 17/409,015, filed Aug. 23, 2021.
U.S. Appl. No. 17/409,046, filed Aug. 23, 2021.
Evaluation Report dated Aug. 30, 2021 for Chinese Application No. 201921724053.2, with English translation, 20 pages.
Search Report and Written Opinion dated Oct. 25, 2021 for Singapore Application No. 11202011803X, 12 pages.
Perez, Sarah, "Scener now lets you co-watch HBO or Netflix in a 'virtual theater' with up to 20 people," May 2020; https://techcrunch.com/2020/05/14/scener-now-lets-youwatch-hbo-or-netflix-in-a-virtual-theater-with-up-to-20-people; 2020, 2 pages.
Scene, Inc., "Scener—Watch party tips: Getting started with watch parties," Jan. 2021; https://web.archive.org/web/202101232132220; https://scener.com/watch-party-tips, 2021, 40 pages.
U.S. Appl. No. 17/464,960, filed Sep. 2, 2021.
U.S. Appl. No. 17/504,233, filed Oct. 18, 2021.
U.S. Appl. No. 17/493,513, filed Oct. 4, 2021.
U.S. Appl. No. 17/505,269, filed Oct. 19, 2021.
U.S. Appl. No. 17/504,066, filed Oct. 18, 2021.
Second Office Action and Search Report dated Dec. 28, 2021 for Chinese Application No. 201910975221.3, with English translation, 33 pages.
U.S. Appl. No. 17/562,489, filed Dec. 27, 2021.
U.S. Appl. No. 17/562,498, filed Dec. 27, 2021.
U.S. Appl. No. 17/562,506, filed Dec. 27, 2021.
U.S. Appl. No. 17/562,534, filed Dec. 27, 2021.
U.S. Appl. No. 17/574,156, filed Jan. 12, 2022.
First Office Action dated Jan. 5, 2022 for Chinese Application No. 202121225607.1, with English translation, 4 pages.
Notice of Final Rejection dated Feb. 9, 2022 for Korean Application No. 10-2020-7037528, with English translation, 7 pages.
International Search Report and Written Opinion dated Feb. 24, 2022 for International Application No. PCT/US2021/048837, 32 pages.
U.S. Appl. No. 17/689,366, filed Mar. 8, 2022.
Notice of Preliminary Rejection dated Apr. 14, 2022 for Korean Application No. 10-2020-7037528, with English translation, 14 pages.
Excerpts from "Training Mirror" video posted on YouTube, dated May 24, 2016 and accessed on May 16, 2022 at https://www.youtube.com/watch?app=desktop&v=xbgTJI7pgrg, with machine translation into English of description, 7 pages.
First Office Action and Search Report dated Jun. 20, 2022 for Chinese Application No. 202110946212.9, with English translation, 58 pages.
Extended European Search Report dated Jul. 4, 2022 for European Application No. 21216666.4, 8 pages.
Examination Report No. 1 dated Aug. 1, 2022 for Australian Application No. 2021212007, 4 pages.
Third Office Action and Search Report dated Jun. 6, 2022 for Chinese Application No. 201910975221.3, with English translation, 38 pages.

\* cited by examiner

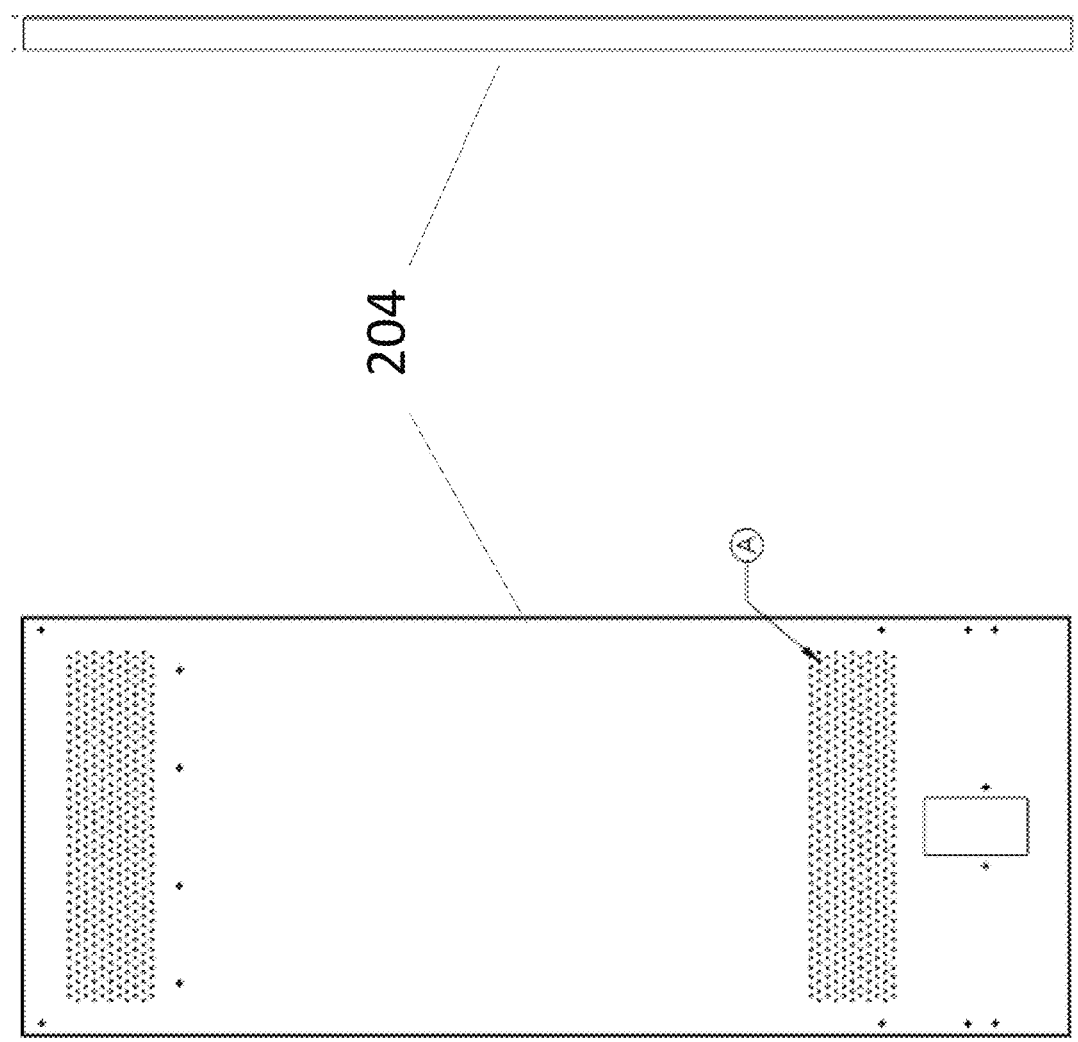

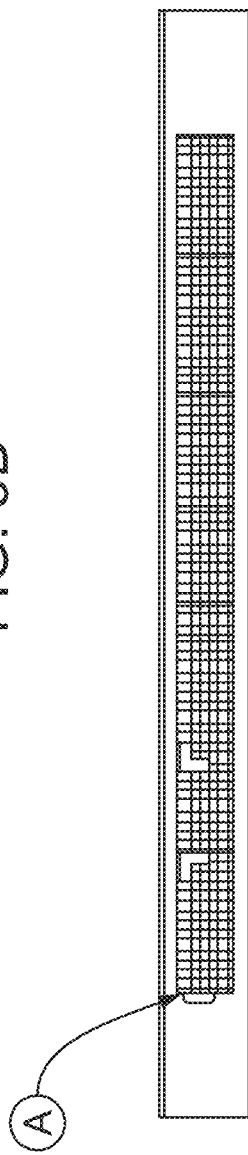
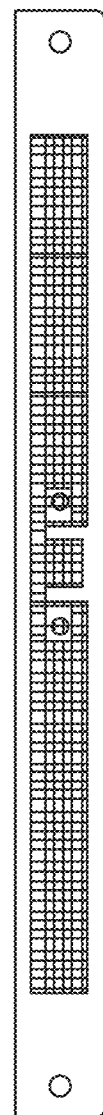

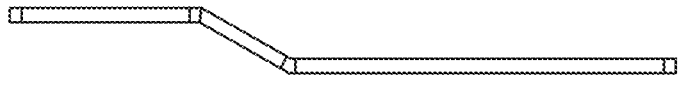
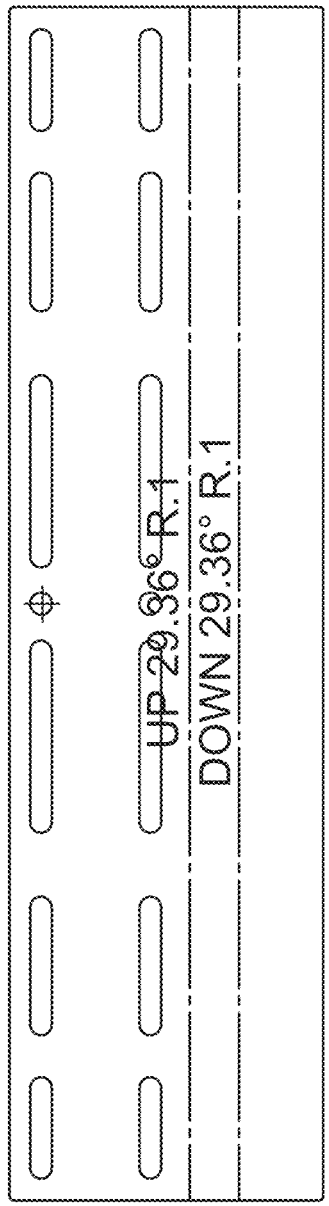
FLAT PATTERN
FIG. 7B
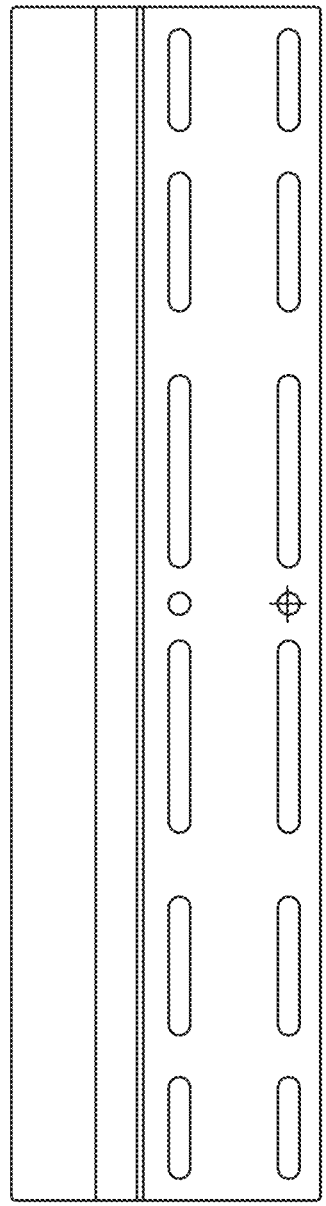
FIG. 7C
FIG. 7D

FLAT PATTERN

FLAT PATTERN

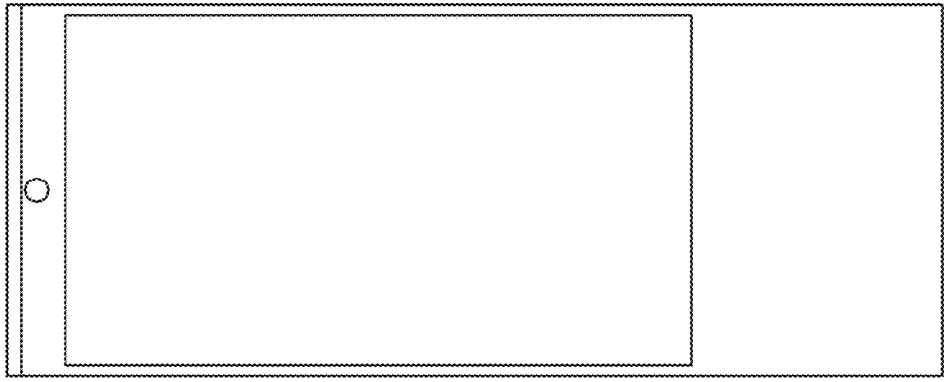
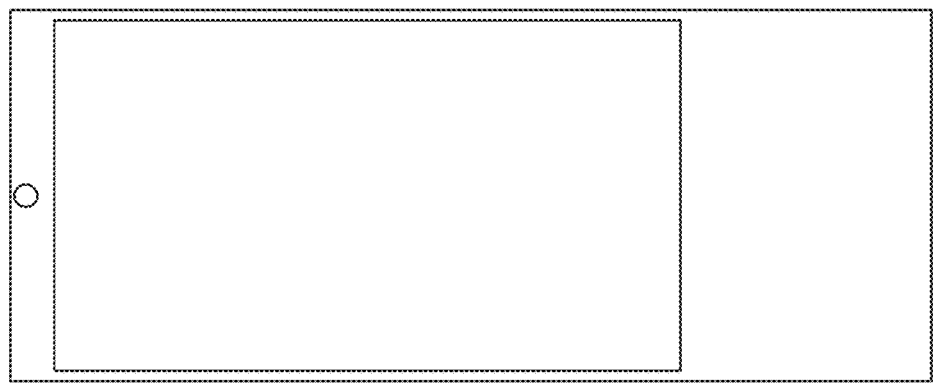
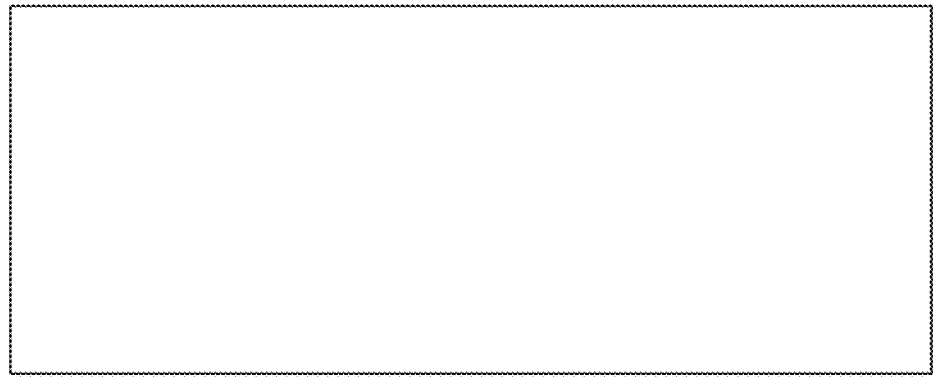

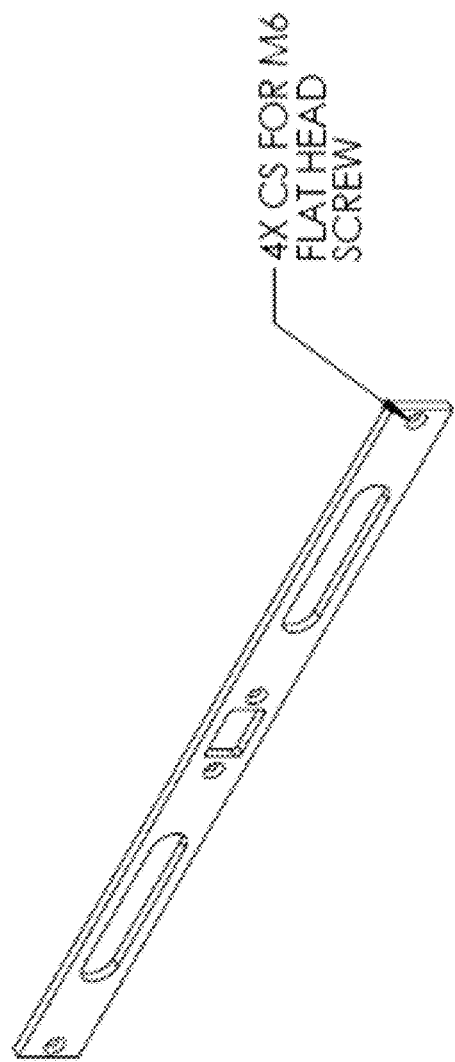
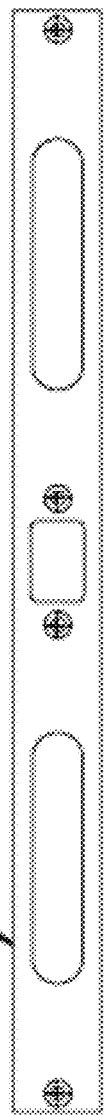
FIG. 11E
FIG. 11F

1300

FLAT PATTERN

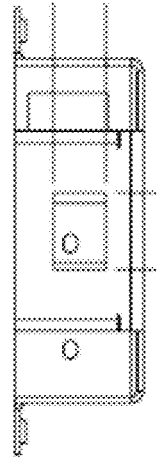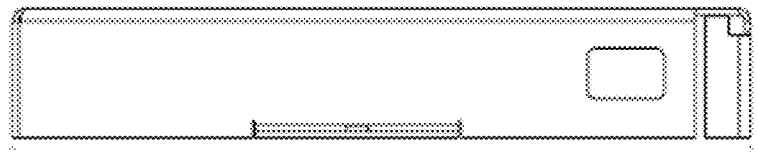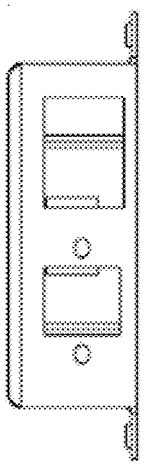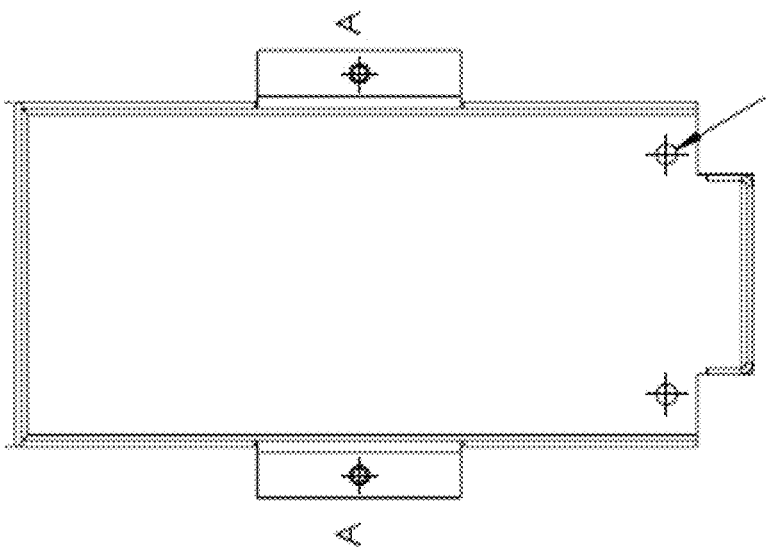

Automated and user-initiated updates based on goals/limitations and heart-rate data Trainer-user interaction via client data (1: many live classes) or camera (1:1 live training sessions v2)

REFLECTIVE VIDEO DISPLAY APPARATUS FOR INTERACTIVE TRAINING AND DEMONSTRATION AND METHODS OF USING SAME

CROSS-REFERENCE TO RELATED APPLICATIONS

This application claims priority to and the benefit of U.S. Provisional Patent Application No. 63/017,781, filed Apr. 30, 2020 and titled "Reflective Video Display Apparatus for Interactive Training and Demonstration and Methods of Using Same," and also claims priority to and the benefit of U.S. Provisional Patent Application No. 63/173,587, filed Apr. 12, 2021 and titled "Reflective Video Display Apparatus for Interactive Training and Demonstration and Methods of Using Same," the entire contents of each of which are incorporated by reference herein in their entireties.

BACKGROUND

Exercise is an important part of maintaining an individual's health and wellbeing. For many people, exercising is an activity that typically involves going to a gymnasium where they partake in a workout guided by an instructor (e.g., a fitness instructor, a personal trainer). However, dedicating a regular period of time to exercise at a gym can be a challenging endeavor due to other commitments in one's daily life (e.g., a person's job, family obligations). Oftentimes, a gym may be located at an inconvenient location and/or an instructor's availability is limited to certain periods of time during the day, thus limiting a person's ability to attend a workout at the gym. This inconvenience may also be detrimental to the instructor whose clientele may be restricted to people who are able to attend their workout at the gym at the prescribed period of time.

SUMMARY

An interactive exercise method includes streaming exercise content to an interactive video system for display via a mirror, the exercise content including a depiction of an instructor performing a repetitive movement. A video stream of a user performing the repetitive movement is received, via a camera of the interactive video system, and the user is detected in the video stream. The user or a body portion thereof is tracked in the video stream as the user performs the repetitive movement. The method also includes generating a measure of a difference between a form of the user performing the repetitive movement and a predetermined form for the repetitive movement. A corrective movement is displayed to the user, via the display and during the display of the instructor performing the repetitive movement, based on the measure, to conform the form of the user to the predetermined form for the repetitive movement.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 5B shows a front-side view of the outer shell of FIG. 5A.

FIG. 5C shows a side-side view of the outer shell of FIG. 5A.

FIG. 5D shows a top-side view of the outer shell of FIG. 5A.

FIG. 5E shows a bottom-side view of the outer shell of FIG. 5A.

FIG. 7B shows a front-side, flat representation of the wall mount bracket of FIG. 7A.

FIG. 7C shows a front-side view of the wall mount bracket of FIG. 7A.

FIG. 7D shows a side-side view of the wall mount bracket of FIG. 7A.

FIG. 10A shows a front-side view of an exemplary mirror glass, in accordance with some embodiments.

FIG. 10B shows a front-side view of an exemplary safety film.

FIG. 10C shows a front-side view of the safety film of FIG. 10B aligned to the mirror glass of FIG. 10A.

FIG. 11E shows a perspective view of the top bar of the stand of FIG. 11A.

FIG. 11F shows a top-side view of the top bar of FIG. 11E.

FIG. 16B shows a top-side view of the connector box of FIG. 16A.

FIG. 16C shows a bottom-side view of the connector box of FIG. 16A.

FIG. 16D shows a rear-side view of the connector box of FIG. 16A.

FIG. 16E shows a side-side view of the connector box of FIG. 16A.

FIG. 35A shows an exemplary instructor user interface on a web browser with a class schedule and an instructor dashboard of users attending the instructor's class, in accordance with some embodiments.

FIG. 35B shows an exemplary instructor user interface on a web browser of user information for a specific user in the class, in accordance with some embodiments.

FIG. 37 shows an example implementation in which a smart mirror counts and displays a repetition count for a movement that the user is performing, in accordance with some embodiments.

FIG. 38 is a flowchart showing an example method for identifying prioritized users from a plurality of users, in accordance with some embodiments,

DETAILED DESCRIPTION

All combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. Terminology explicitly employed herein that also may appear in any disclosure incorporated by reference should be accorded a meaning most consistent with the particular concepts disclosed herein.

Some aspects disclosed herein may be structurally and/or functionally similar to similarly named and/or referenced components in PCT Application No. PCT/US2019/034292 filed May 29, 2019 (sometimes referred to as the "'292 application"), the entire disclosure of which is incorporated herein by reference.

The concepts introduced discussed in greater detail below may be implemented in numerous ways. Examples of specific implementations and applications are provided primarily for illustrative purposes so as to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are useful for an understanding of the present implementations are described, and detailed descriptions of other portions of such known components are omitted so as not to obscure the present implementations.

An Exemplary Smart Mirror

Figure 1:
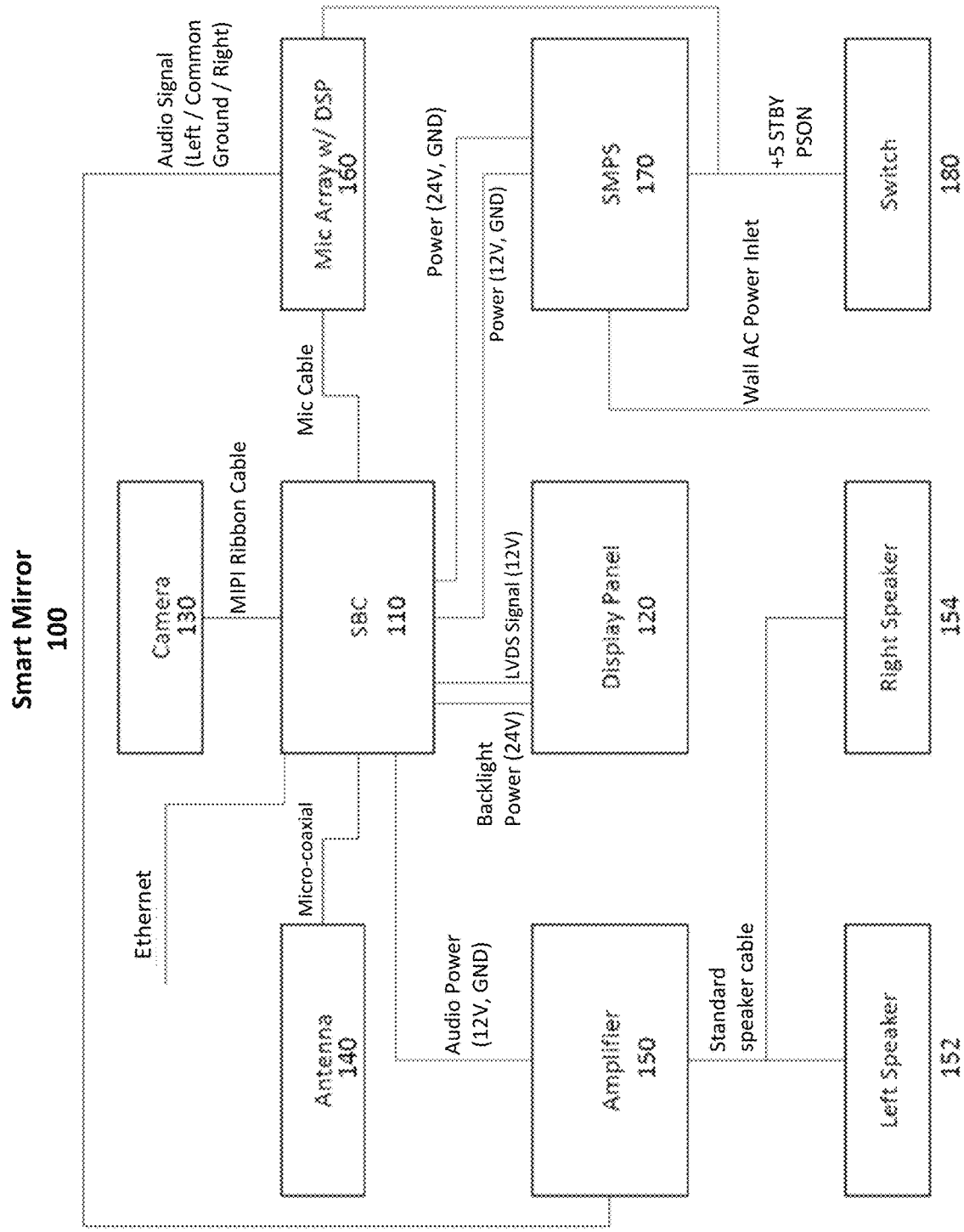
FIG. 1 shows a block diagram of an exemplary smart mirror, in accordance with some embodiments.

FIG. 1 shows an exemplary representation of a smart mirror 100. The smart mirror 100 may include a single board computer (SBC) 110 used to control, in part, the operation of various subcomponents in the smart mirror 100 and to manage the flow of content to/from the smart mirror 100 (e.g., video content, audio from the instructor or user, biometric feedback analysis). The smart mirror 100 may include a display panel 120 to show video content, a graphical user interface (GUI) from which the user may interact and control the smart mirror 100, biometric feedback data, and/or other visual content. A camera 130 may be coupled to the SBC 110 to record a video and/or images of a user (e.g., while the user is exercising during a workout). An antenna 140 may be coupled to the SBC 110 to provide data transmission and/or reception between the smart mirror 100 and another device (e.g., a remote control device, a biometric sensor, a wireless router). The antenna 140 may comprise multiple transmitters and receivers each tailored for a particular frequency and/or wireless standard (e.g., Bluetooth, 802.11a, 802.11b, 802.11g, 802.11n, 802.11 ac, 2G, 3G, 4G, 4G LTE, 5G). An amplifier 150 may be coupled to the SBC 110 to receive audio signals from the SBC 110 for subsequent sound output through a left speaker 152 and/or a right speaker 154. A microphone array 160 may also be used to enable a user to input voice commands and/or voice inputs to the smart mirror 100 (e.g., to start/stop a workout, to talk to the instructor). The microphone array 160 may also be coupled to the SBC 110 and include a digital signal processor (DSP).

Figure 18:
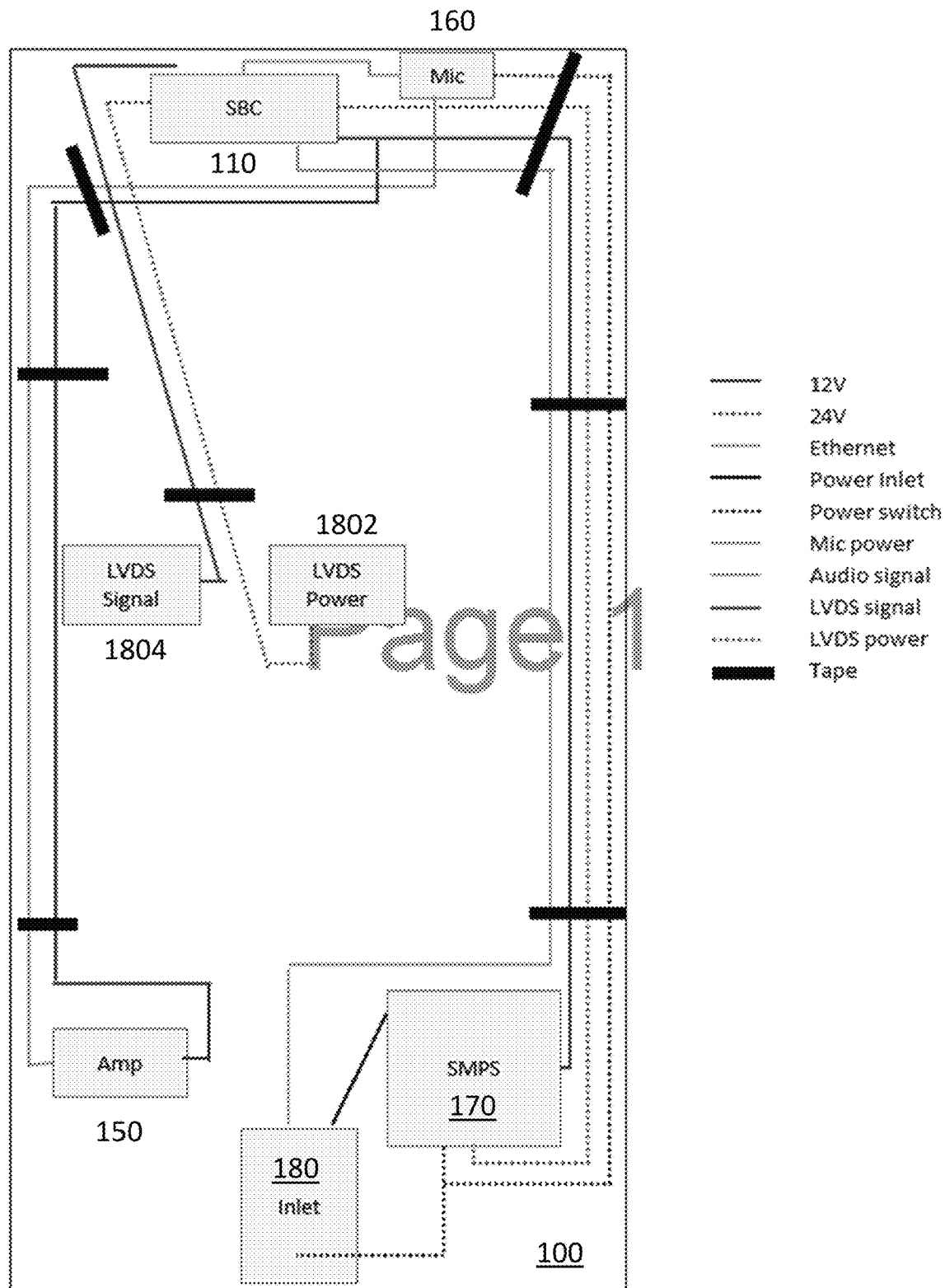
FIG. 18 shows a wiring diagram for various components of an exemplary smart mirror, in accordance with some embodiments.

A switched-mode power supply (SMPS) 170 may also be coupled to the SBC 110 to supply and manage electrical power to the various components of the smart mirror 100 from an external electrical power supply system (e.g., a wall outlet). A switch 180 may be coupled to the SMPS 170 and/or the microphone array 160 to switch the smart mirror 100 and the microphone array 160 on and off. FIG. 18 shows electrical and low-voltage differential signaling (LVDS) connections among these components and an LVDS power connection 1802 and signal connection 1804 for the display panel 120.

The smart mirror 100 may also include additional components not shown in FIG. 1. For example, the smart mirror 100 may include onboard memory and storage (nonvolatile and/or volatile memory) including, but not limited to a hard disk drive (HDD), a solid state drive (SDD), flash memory, random access memory (RAM), and a secure digital (SD) card. This onboard memory and/or storage may be used to store firmware and/or software for the operation of the smart mirror 100. As described above, the onboard memory and/or storage may also be used to store (temporarily and/or permanently) other data including, but not limited to video content, audio, video of the user, biometric feedback data, and user settings. In another example, the smart mirror 100 may include a frame 200, described in greater detail below with respect to FIG. 3B, to mount and support the various components of the smart mirror 100.

Figure 2A:
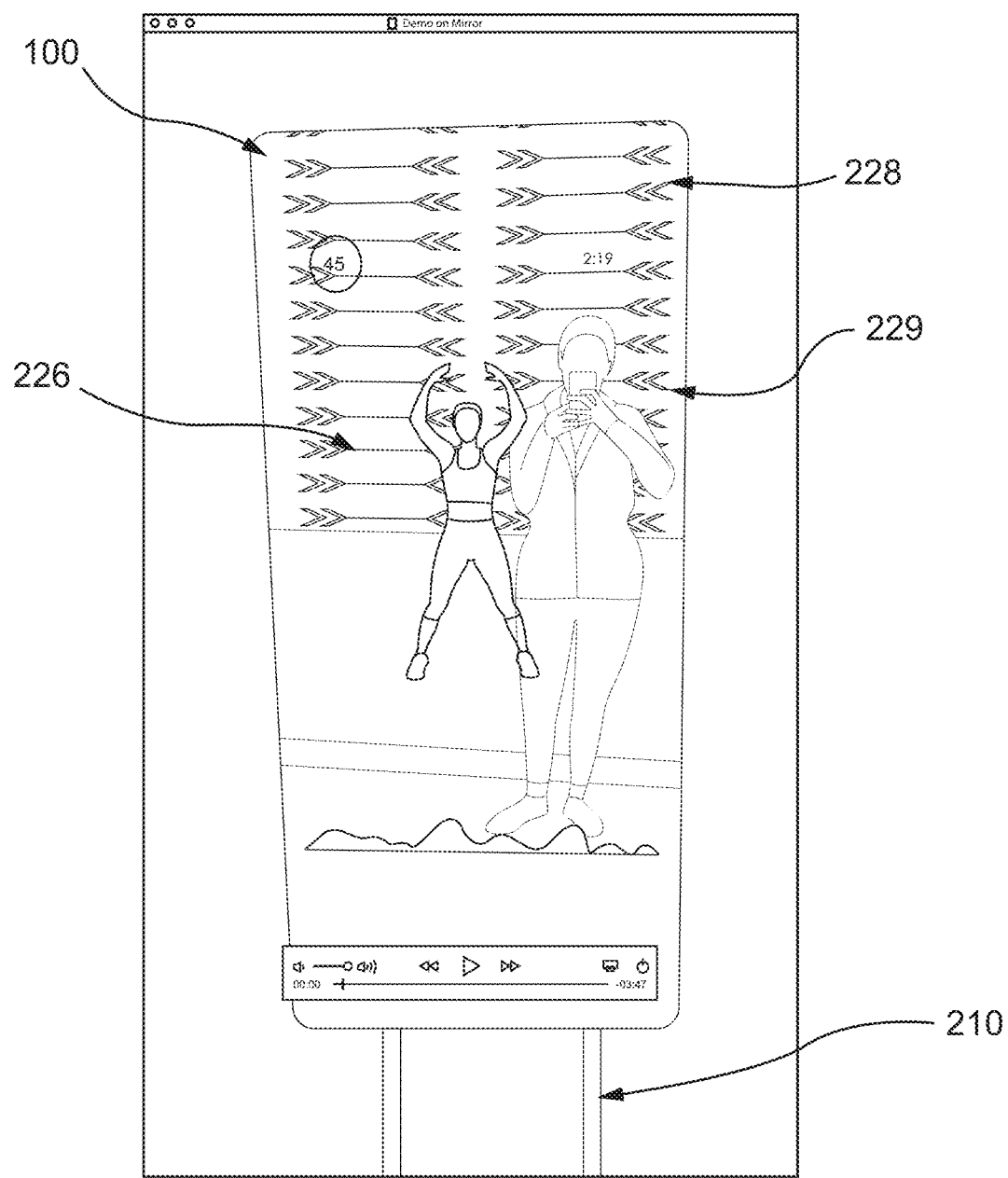
FIG. 2A shows an exemplary smart mirror with a stand disposed on the bottom, in accordance with some embodiments.
Figure 2B:
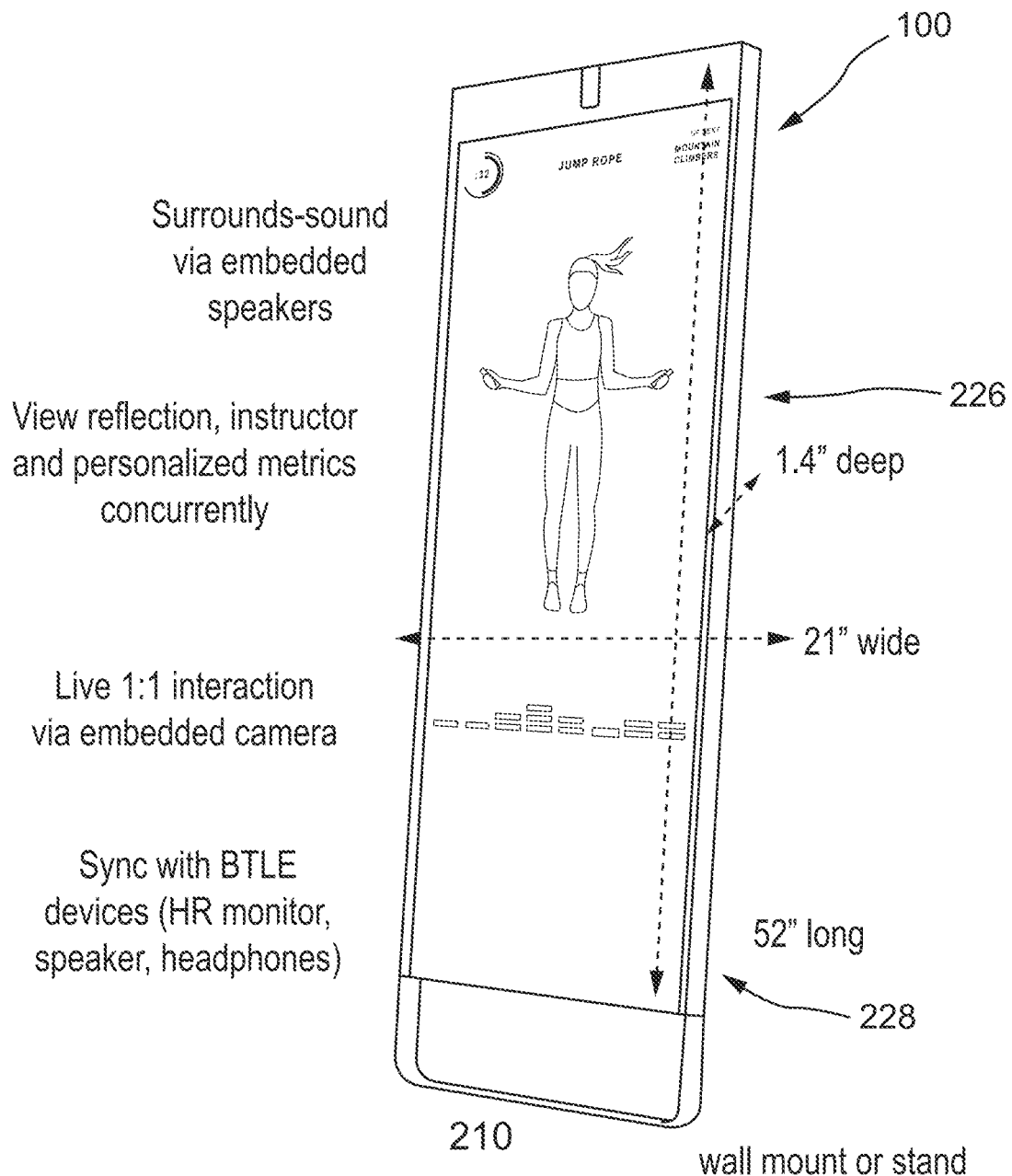
FIG. 2B shows another view of a smart mirror with a stand disposed on the bottom, in accordance with some embodiments.

The smart mirror 100 may be deployed in an environment (e.g., a user's home, a fitness studio) in several ways. For example, FIGS. 2A and 2B show the smart mirror 100 mounted to a stand 210 mounted to the bottom of the smart mirror 100. The smart mirror 100 reflects an image 229 of the user (here, taking a picture of the smart mirror 100 with a smart phone) and the surrounding environment. The smart mirror 100 also shows video content through a partially reflecting section 226, which blends nearly seamlessly with a fully reflecting section 228 to reflect the user's image 229 and the surrounding environment. The fully reflecting section 228 has a dark background and the partially reflecting section 226 is over a display panel 120 (FIG. 3B), which is dark when off to provide a nearly seamless reflection under ambient lighting.

The stand 210 is used, in part, to position the smart mirror 100 at some distance above the ground. The stand 210 may be used to support the smart mirror 100 along a vertical orientation (e.g., a plane of the display panel 120 is parallel to an adjoining wall). The stand 210 may also support the smart mirror 100 at a tilted orientation (defined by an angle relative to the wall) as shown in FIGS. 2A and 2B. The stand 210 may include a high friction base (e.g., a rubber foot) to prevent the smart mirror 100 from slipping along the floor when tilted. In some designs, the stand 210 may remain fixed relative to the frame 200 or may allow for articulation of the frame 200 relative to the stand 210 about some motion axis (e.g., a pivot axis). For instance, as the frame 200 is rotated, the stand 210 may remain unchanged in orientation and/or placement with respect to the floor.

Figure 2C:
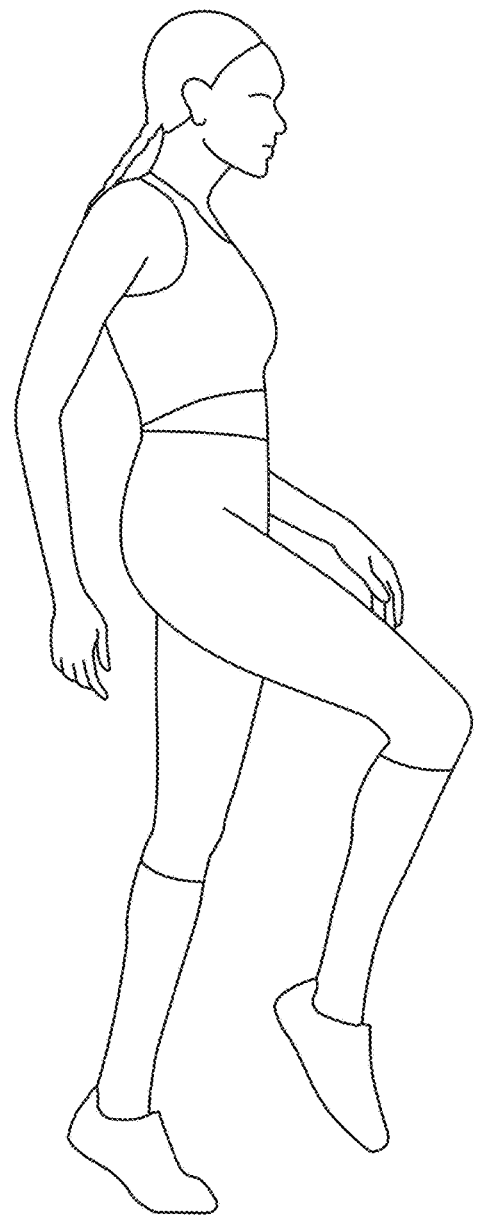
FIG. 2C shows an exemplary smart mirror mounted to a wall, in accordance with some embodiments.
Figure 2C:
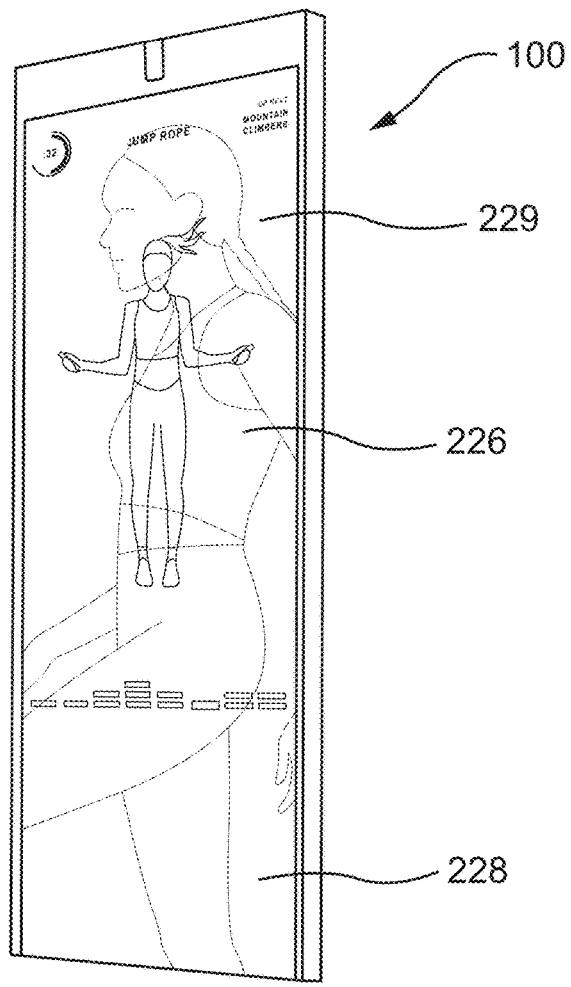

The smart mirror 100 may also be mounted to a wall directly, as depicted in FIG. 2C, or hung from a ceiling (not shown). Again, the smart mirror 100 appears completely reflective when the display is off. When the display is on, the display projects video imagery (e.g., of a trainer or exercise instructor) through the partially reflecting section 226 to the user, who may see a reflected image 229 of herself superimposed on the video imagery in the partially reflecting section 226. A fully reflecting section 228 bordering the partially reflecting section 226 also reflect the user's image. And when the display is off, the smart mirror 100 simply appears to be a plain mirror.

The smart mirror 100 may also be supported by a free-standing stand roughly vertically. Said in another way, the free-standing stand may sit on the ground or another horizontal surface and hold the smart mirror 100 so that it faces a user. The free-standing stand may be mounted to the bottom, the side, and/or the rear of the smart mirror 100. The free-standing stand may include one, two, three, or more legs to provide a stable platform for the smart mirror 100 (so the smart mirror 100 is unlikely to tip over). Each leg may have a high friction base (e.g., a rubber foot) to prevent the stand from slipping. In some designs, at least one leg may include a wheel to facilitate transport and/or adjustment of the smart mirror 100. Similar to the stand 210, the free-standing stand may also allow the smart mirror 100 to be tilted about a pivot axis.

FIGS. 3A-3D show several views of an exemplary smart mirror 100 with the stand 210 described above. As shown, the smart mirror 100 may be subdivided into several assemblies corresponding to the components described above. For instance, the smart mirror 100 may include a frame 200 comprising an inner frame 202 and an outer shell 204. The inner frame 202 may be used as a chassis onto which the other components described with reference to FIG. 1 are mounted to. The outer shell 204 may be used, in part, as an exterior housing to protect the inner frame 202 and the various components of the smart mirror 100 contained therein. The smart mirror 100 may include a display panel 120 mounted into the inner frame 202. The smart mirror 100 may include mirror glass 220 disposed over the display panel 120 to provide reflections of the user and the user's environment. The smart mirror 100 may also include various electronics separated into an upper electronics assembly 230 disposed towards the top of the inner frame 202 and a lower electronics assembly 240 disposed towards the bottom of the inner frame 202.

Figure 3A:
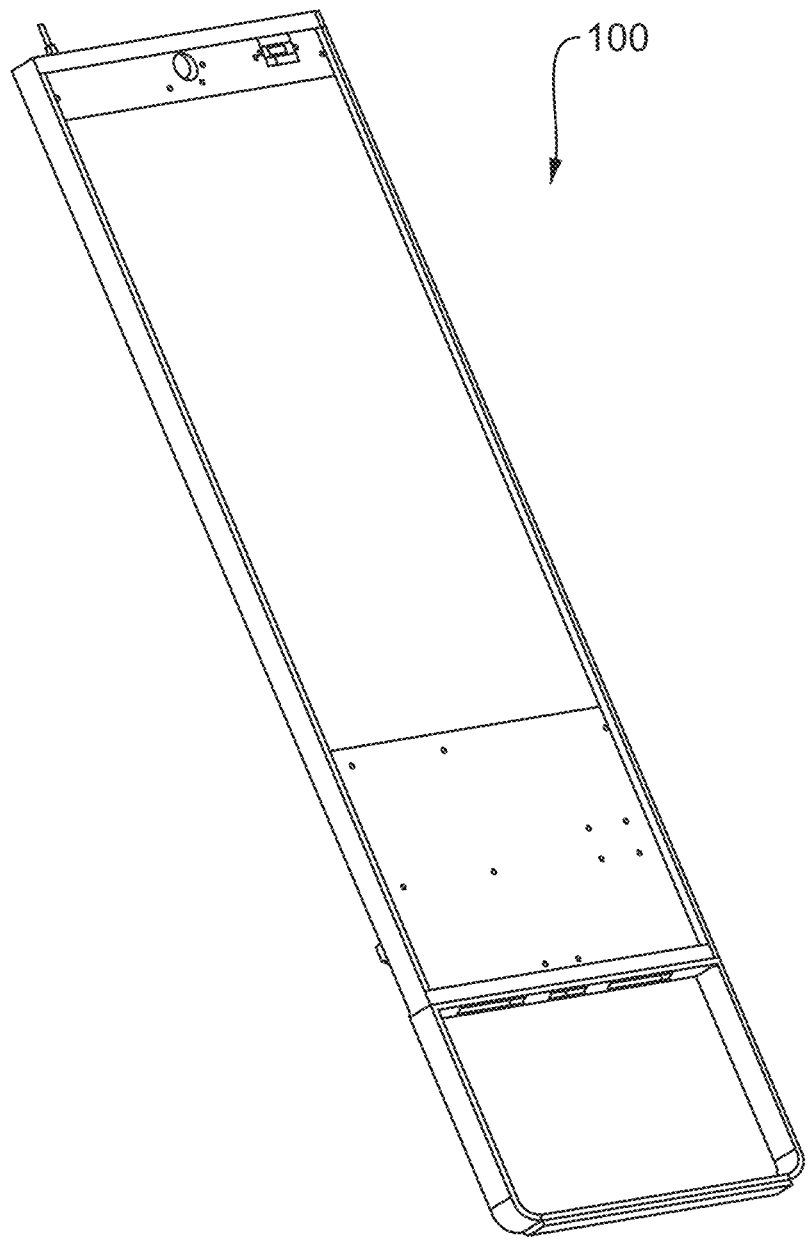
FIG. 3A shows a front, perspective view of an exemplary smart mirror, in accordance with some embodiments.
Figure 3B:
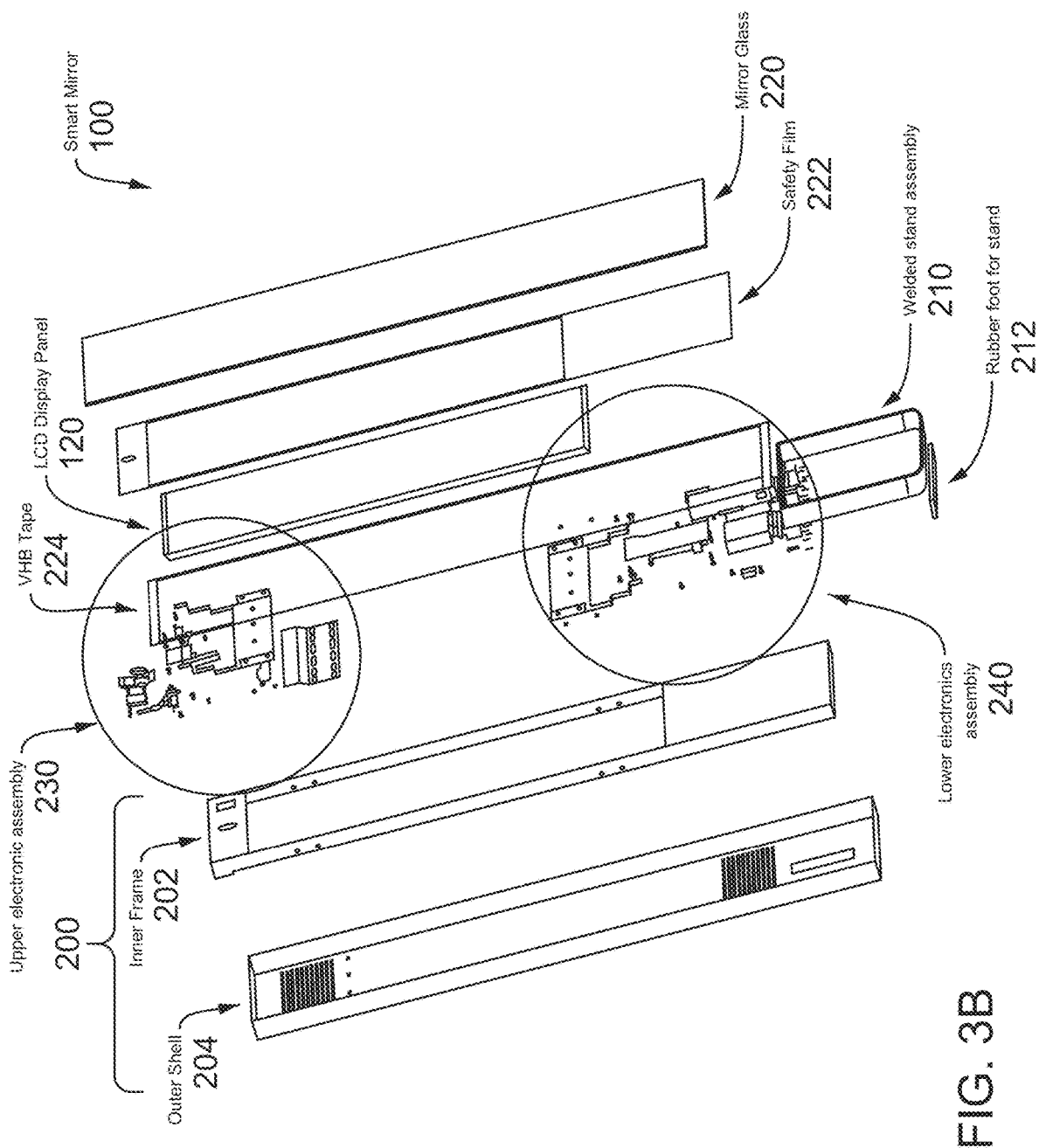
FIG. 3B shows an exploded view of the smart mirror of FIG. 3A.
Figure 3C:
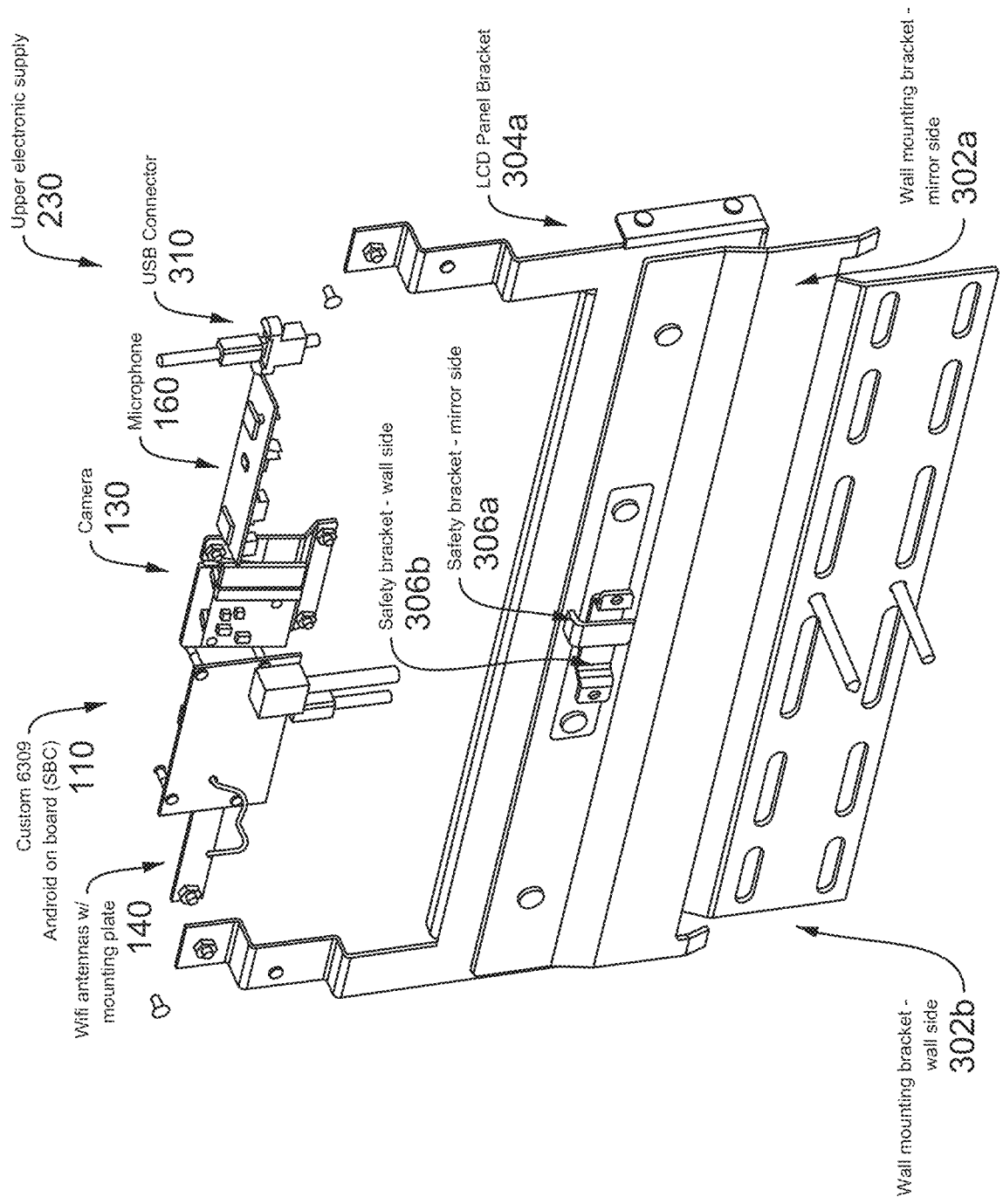
FIG. 3C shows an exploded view of an upper electronics assembly in the smart mirror of FIG. 3A.
Figure 3D:
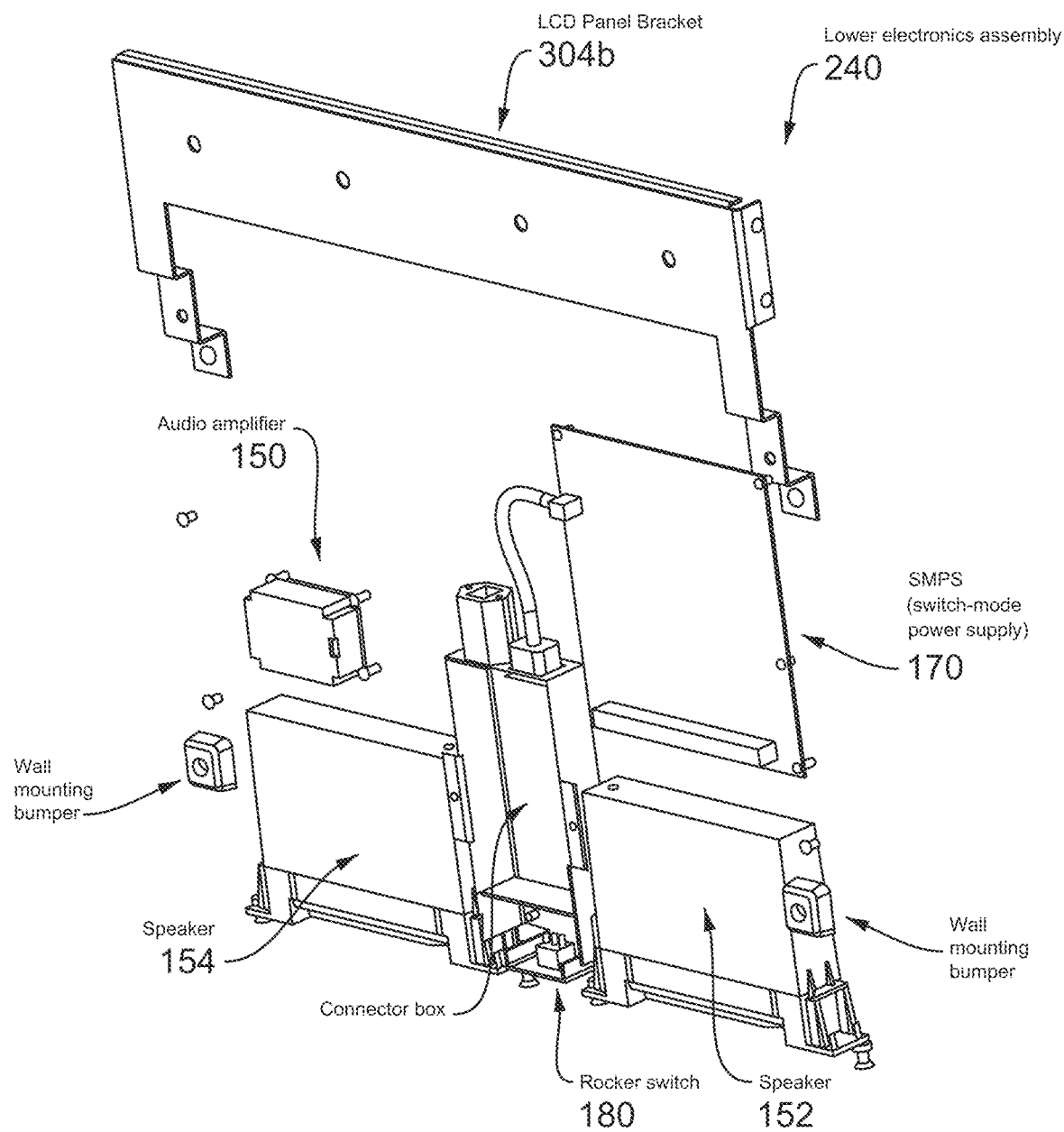
FIG. 3D shows an exploded view of a lower electronics assembly in the smart mirror of FIG. 3A.
Figure 4A:
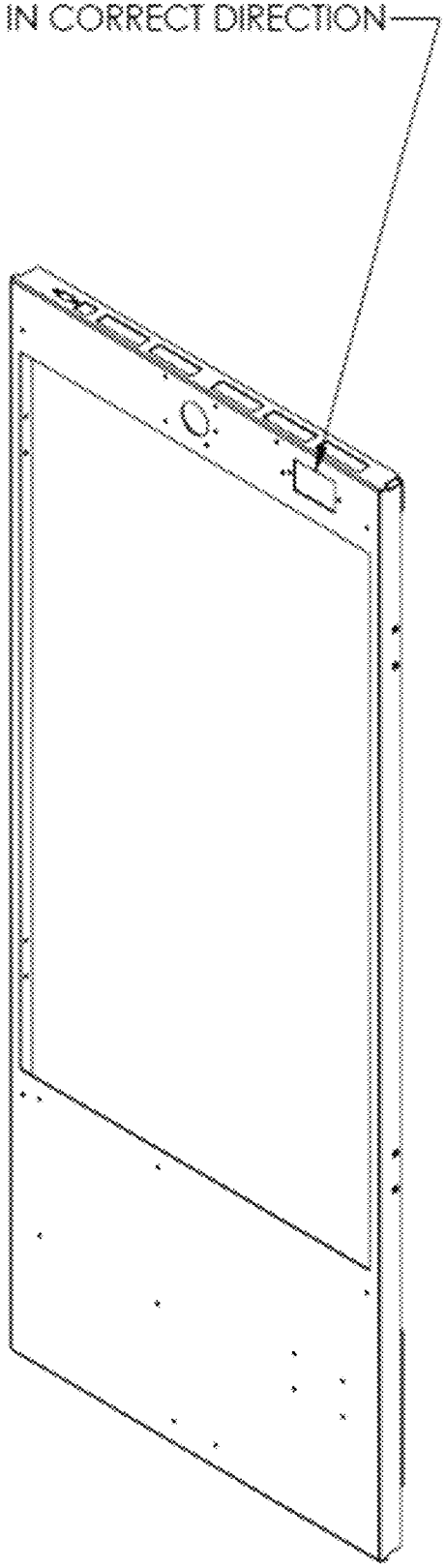
FIG. 4A shows a front, perspective view of an exemplary an inner frame, in accordance with some embodiments.
Figure 4B:
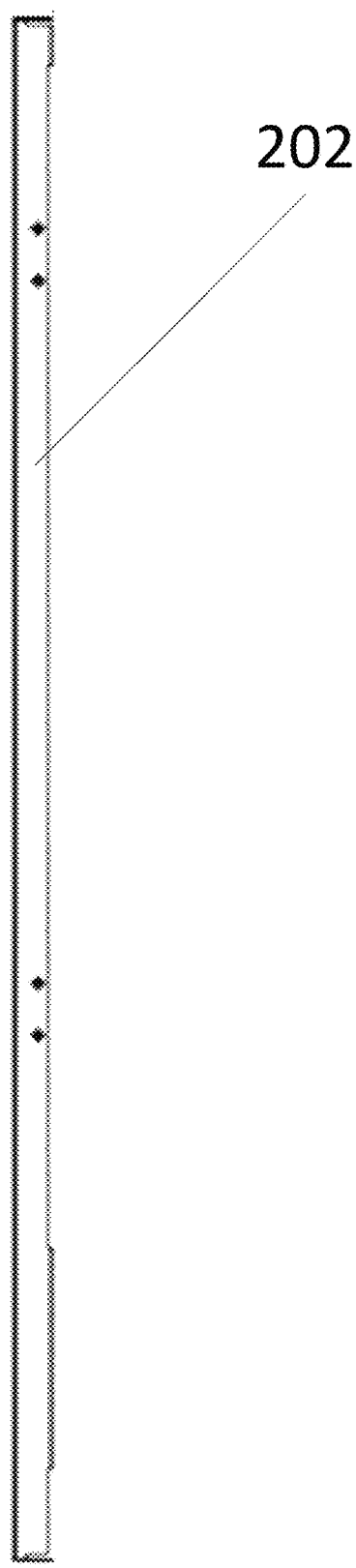
FIG. 4B shows a left-side view of the inner frame of FIG. 4A.
Figure 4C:
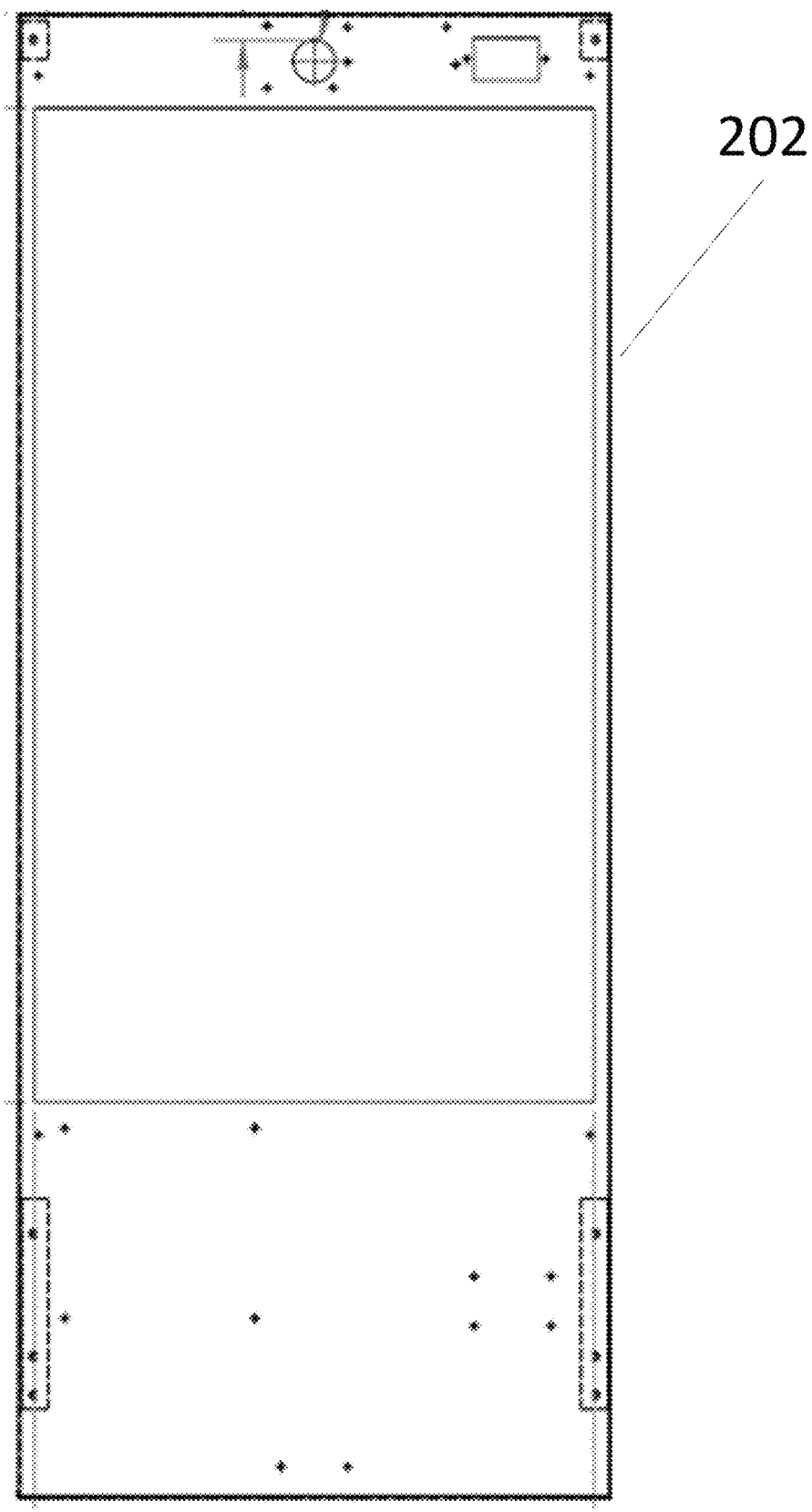
FIG. 4C shows a front-side view of the inner frame of FIG. 4A.
Figure 4D:
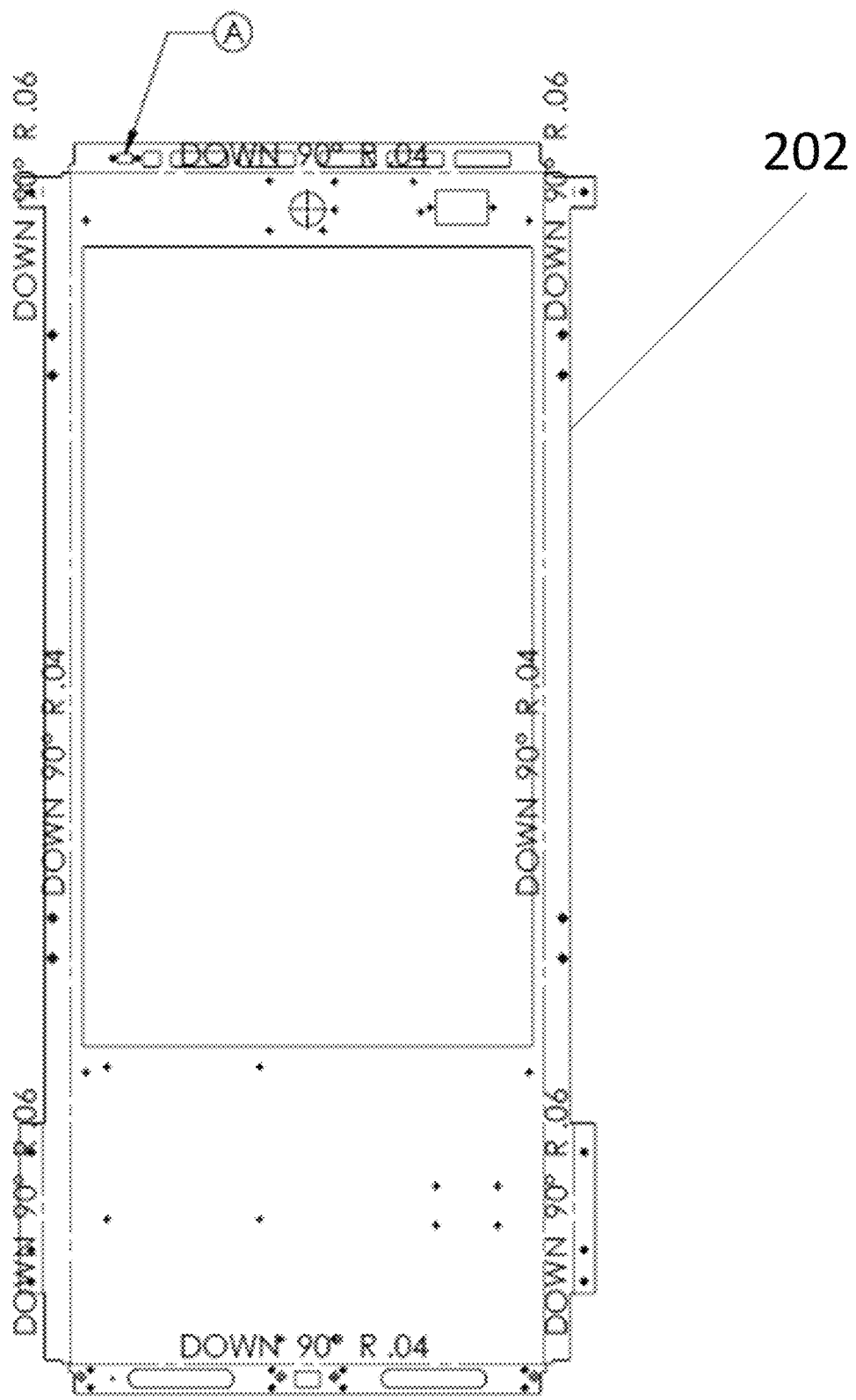
FIG. 4D shows a front-side, flat representation of the inner frame of FIG. 4A.
Figure 4E:
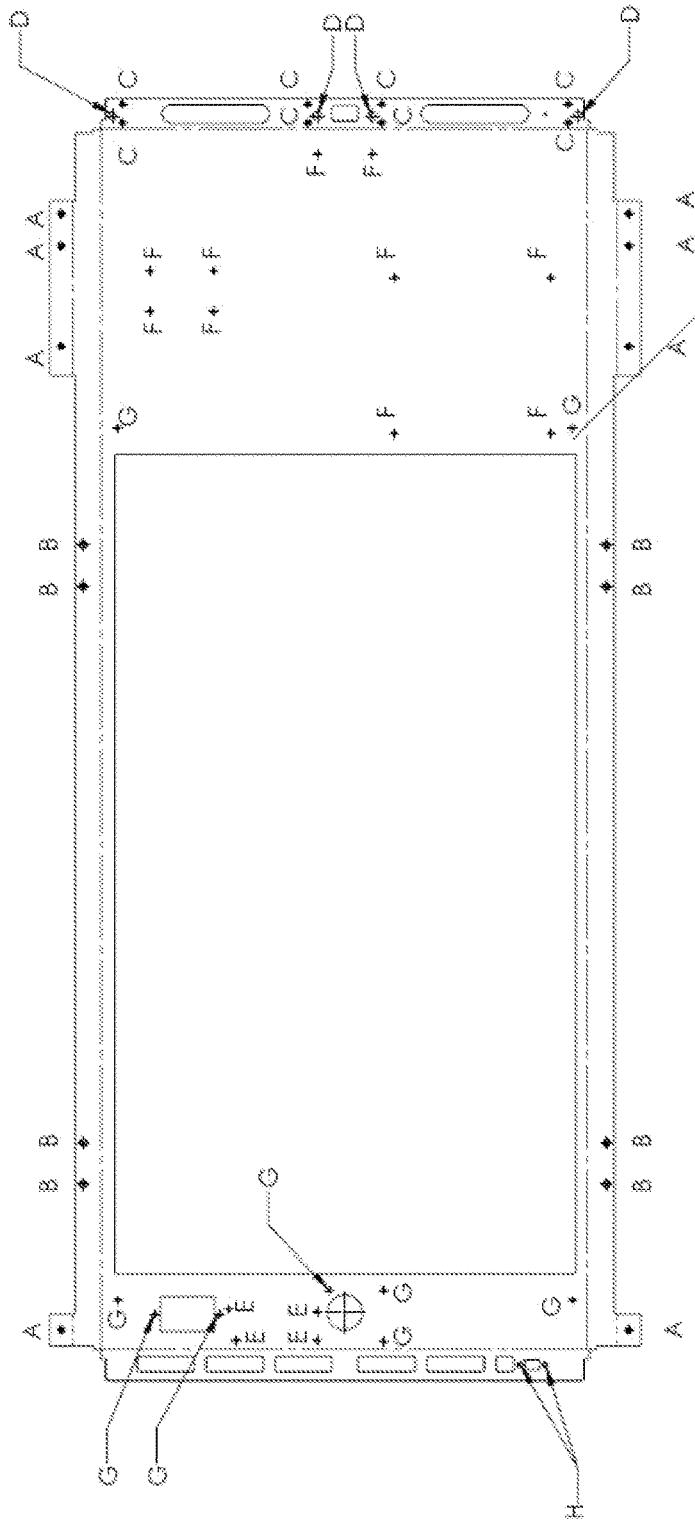
FIG. 4E shows a front-side, flat representation of the inner frame of FIG. 4A with various labeled holes for assembly.
Figure 5A:
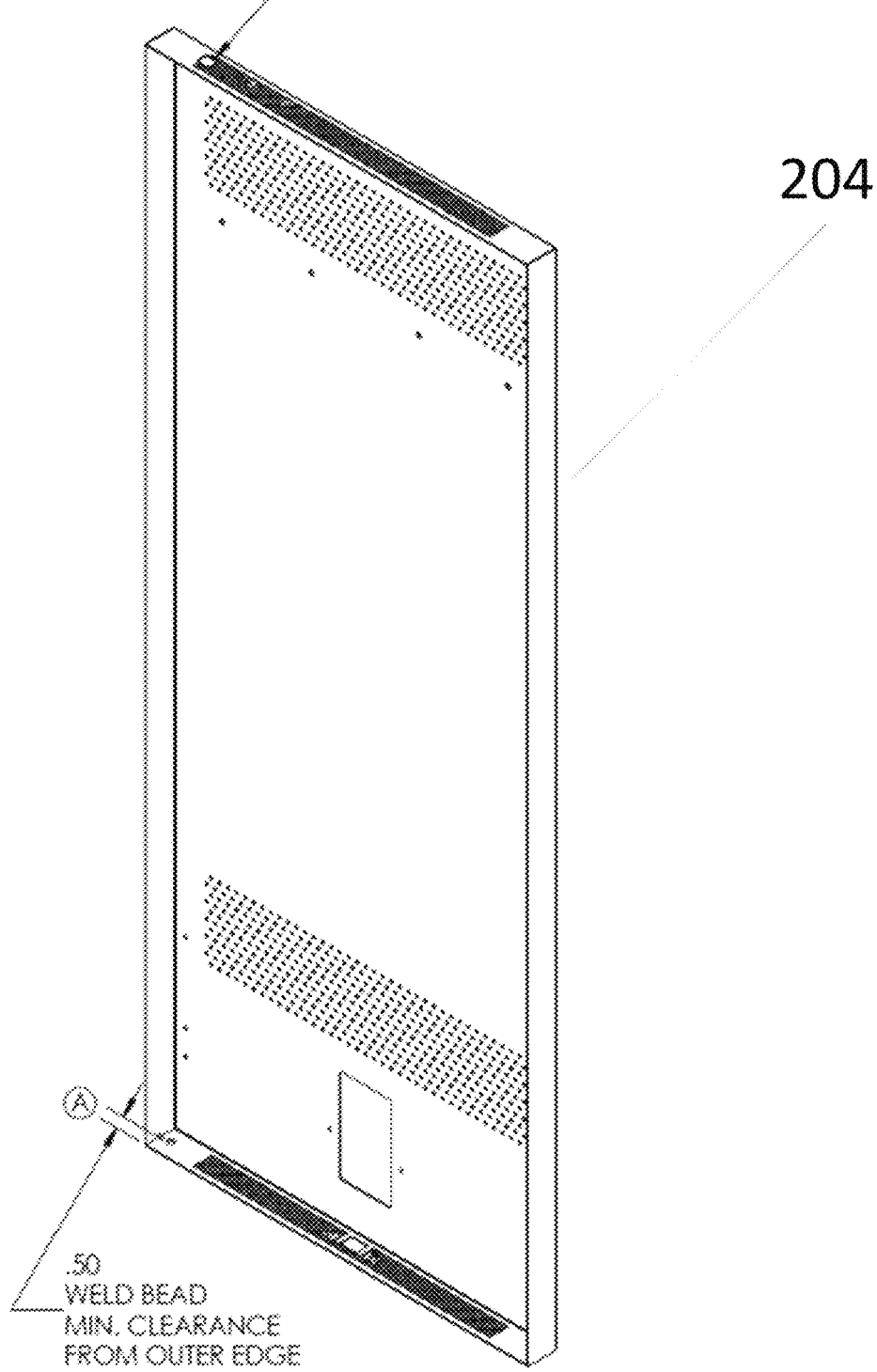
FIG. 5A shows a front, perspective view of an exemplary an outer shell, in accordance with some embodiments.
Figure 5F:
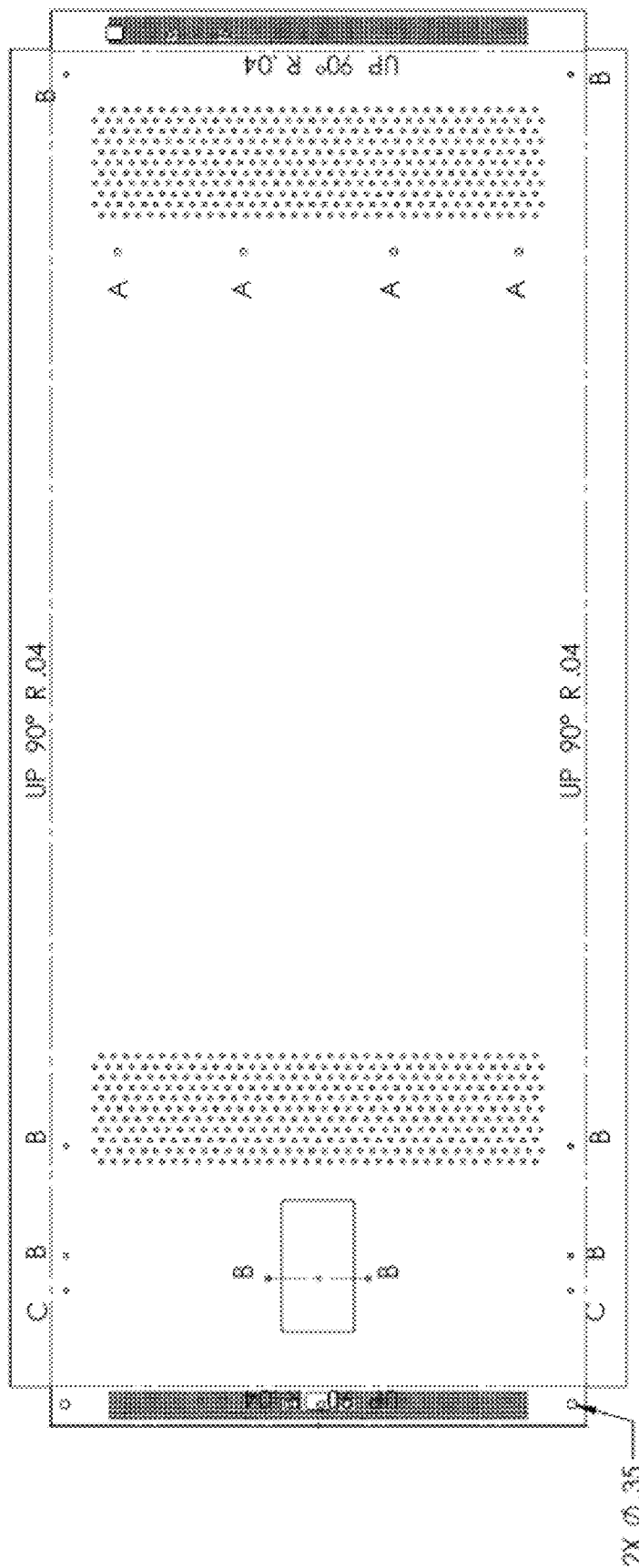
FIG. 5F a front-side, flat representation of the outer shell of FIG. 5A with various labeled holes for assembly.
Figure 6A:
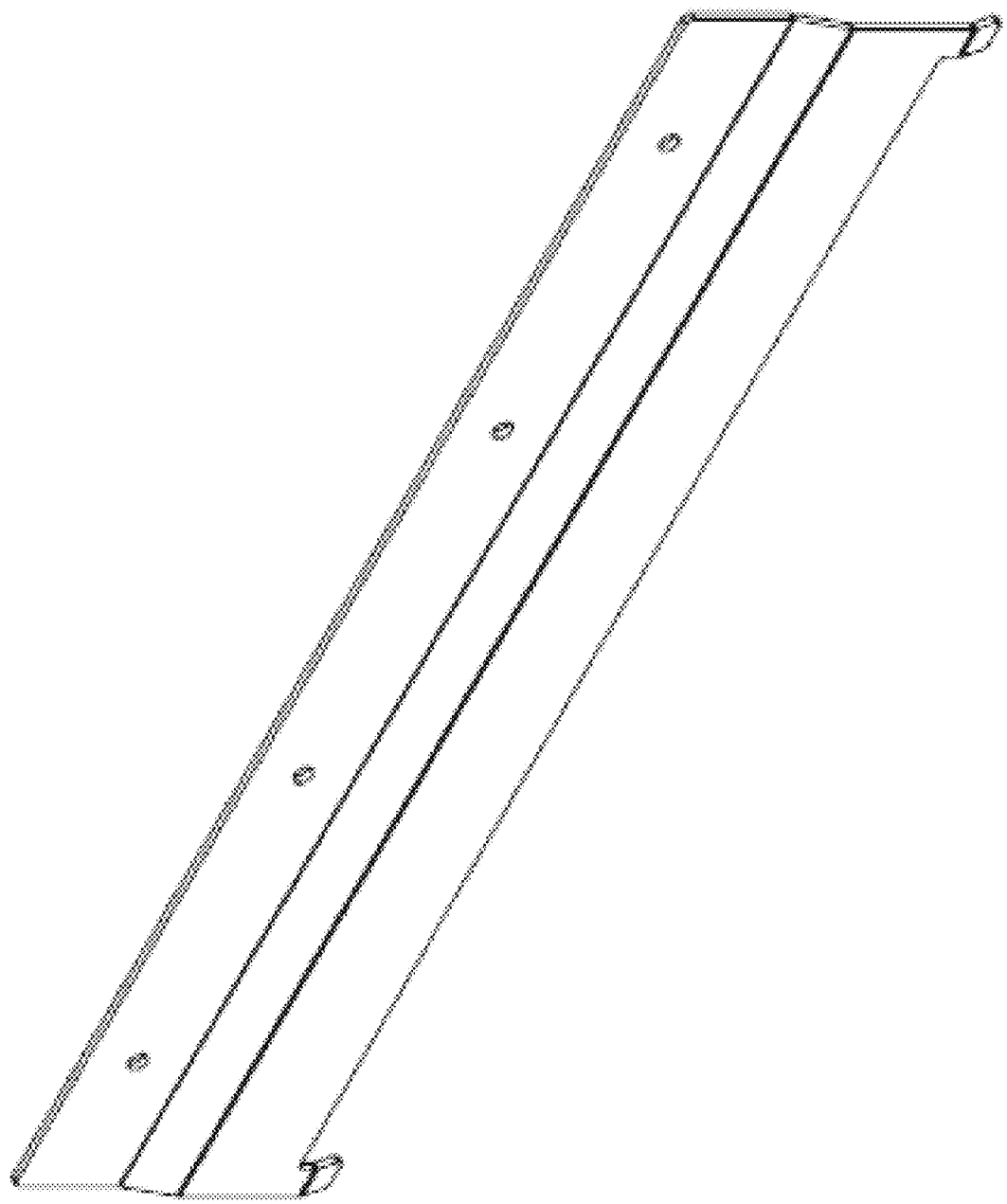
FIG. 6A shows a front, perspective view of an exemplary wall mount bracket on the smart mirror, in accordance with some embodiments.
Figure 6B:
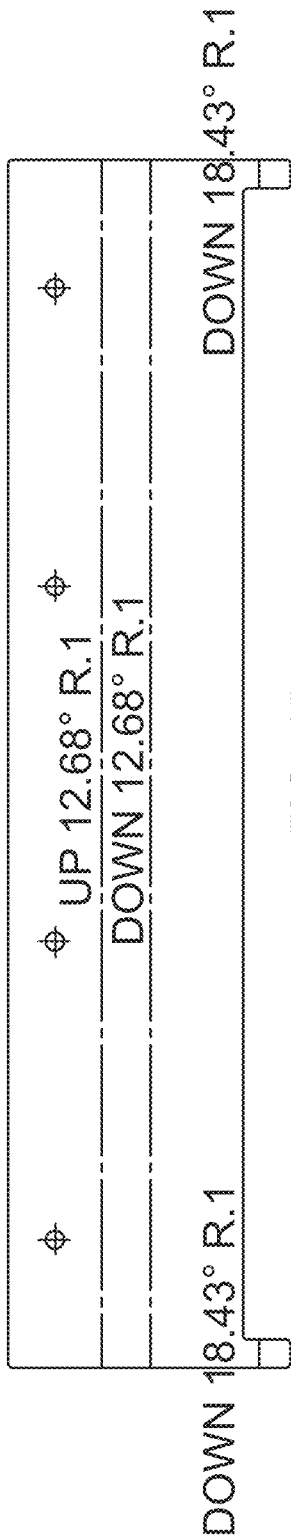
FIG. 6B shows a front-side, flat representation of the wall mount bracket of FIG. 6A.
Figure 6D:
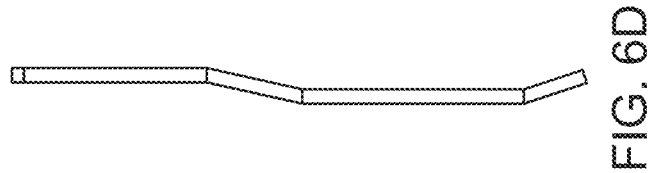
FIG. 6D shows a side-side view of the wall mount bracket of FIG. 6A.
Figure 6C:
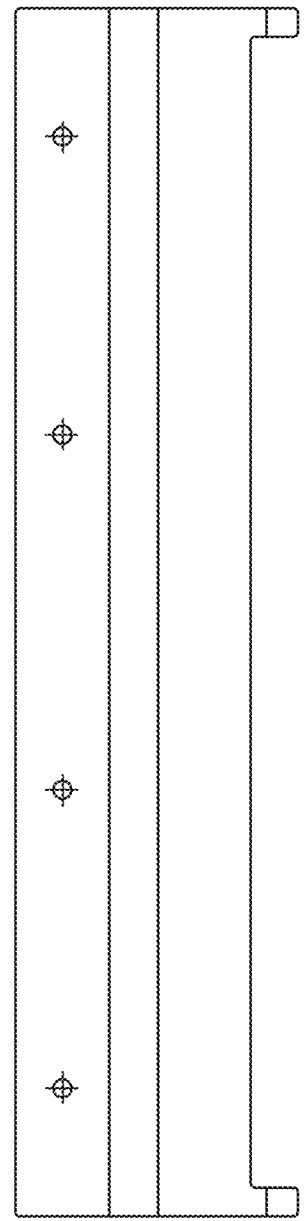
FIG. 6C shows a front-side view of the wall mount bracket of FIG. 6A.
Figure 7A:
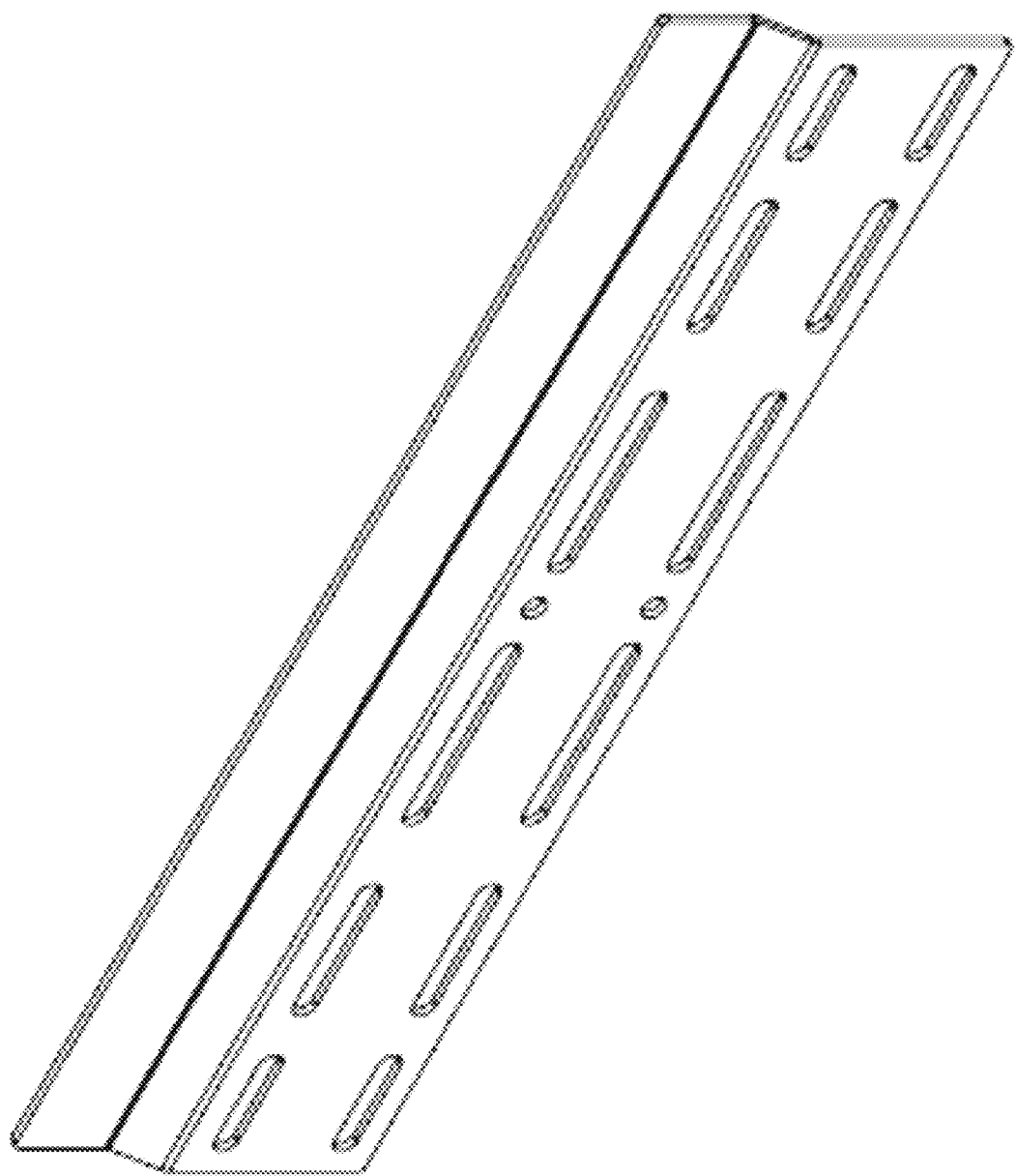
FIG. 7A shows a front, perspective view of an exemplary wall mount bracket on the wall side, in accordance with some embodiments.
Figure 8A:
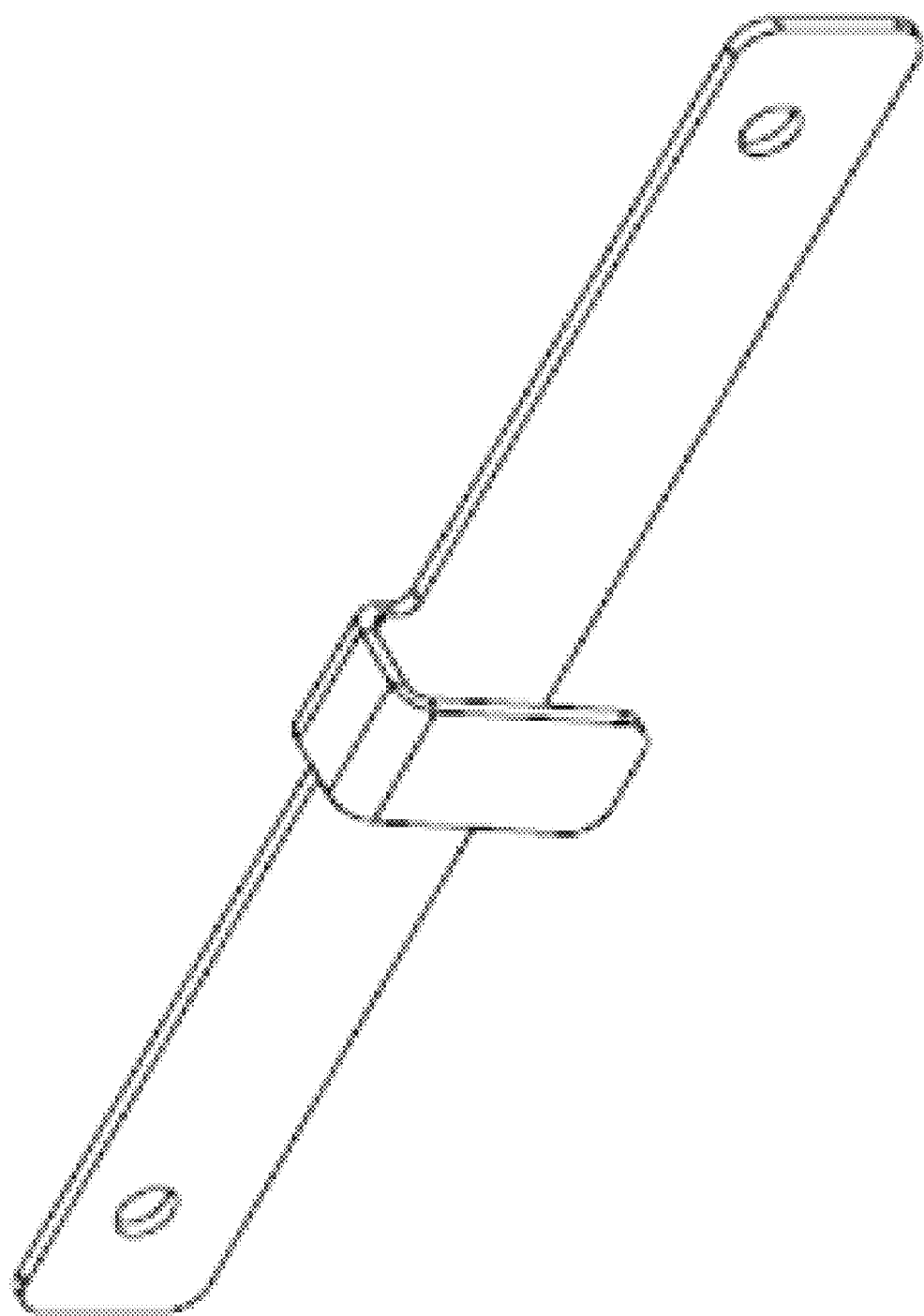
FIG. 8A shows a front, perspective view of an exemplary of a safety bracket on the smart mirror side, in accordance with some embodiments.
Figure 8D:
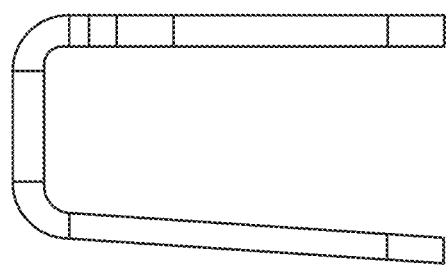
FIG. 8D shows a side-side view of the safety bracket of FIG. 8A.
Figure 8B:
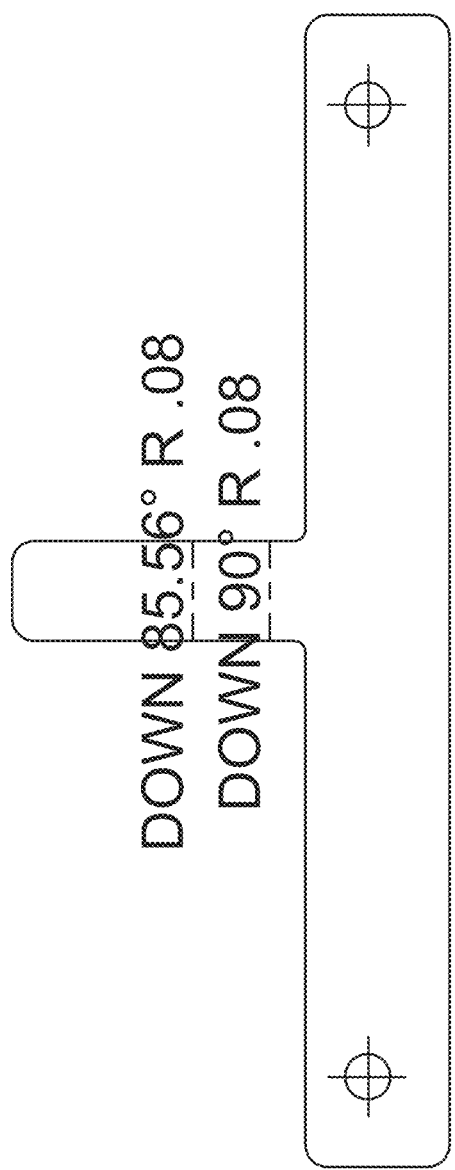
FIG. 8B shows a front-side, flat representation of the safety bracket of FIG. 8A.
Figure 8C:
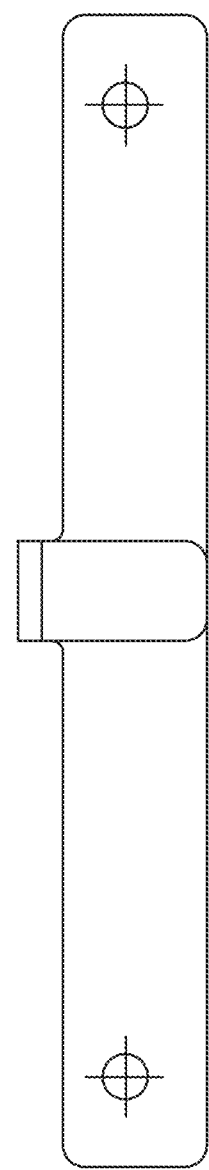
FIG. 8C shows a front-side view of the safety bracket of FIG. 8A.
Figure 9A:
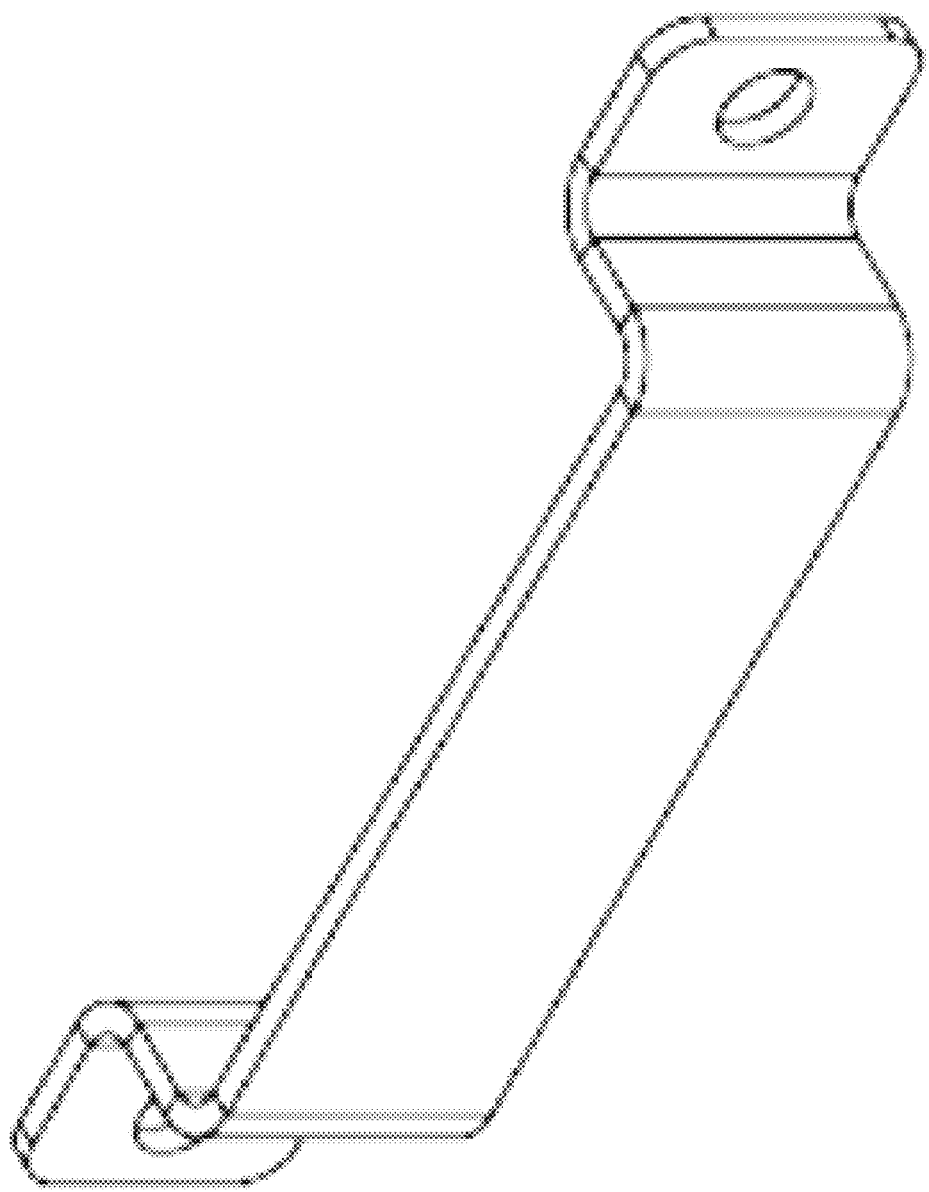
FIG. 9A shows a front, perspective view of an exemplary of a safety bracket on the wall side, in accordance with some embodiments.
Figure 9C:
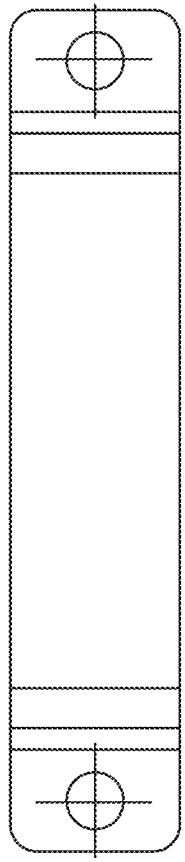
FIG. 9C shows a front-side view of the safety bracket of FIG. 9A.
Figure 9D:
FIG. 9D shows a side-side view of the safety bracket of FIG. 9A.
Figure 9B:
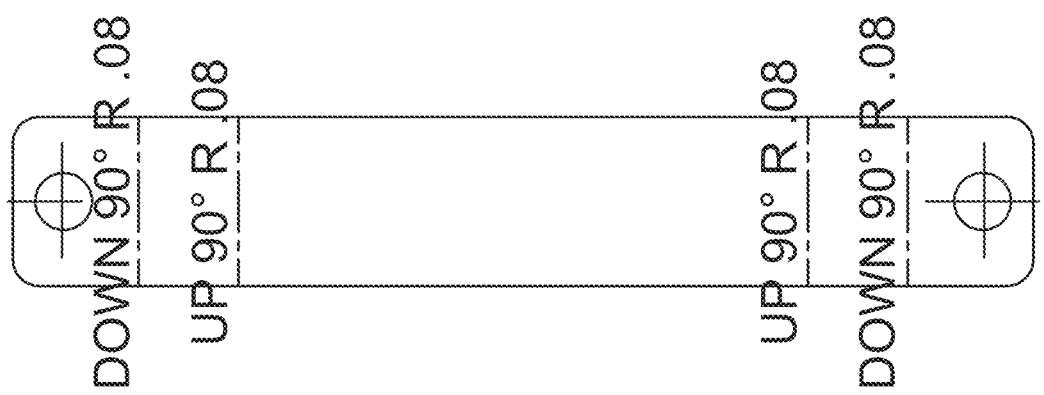
FIG. 9B shows a front-side, flat representation of the safety bracket of FIG. 9A.
Figure 10D:
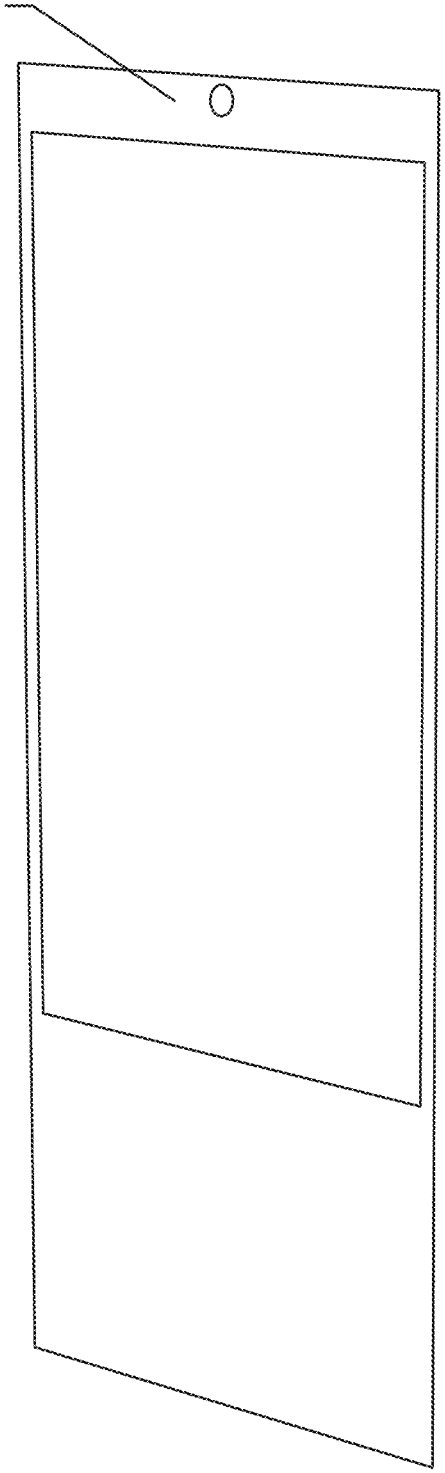
FIG. 10D shows a front, perspective view of the safety film of FIG. 10B.
Figure 11A:
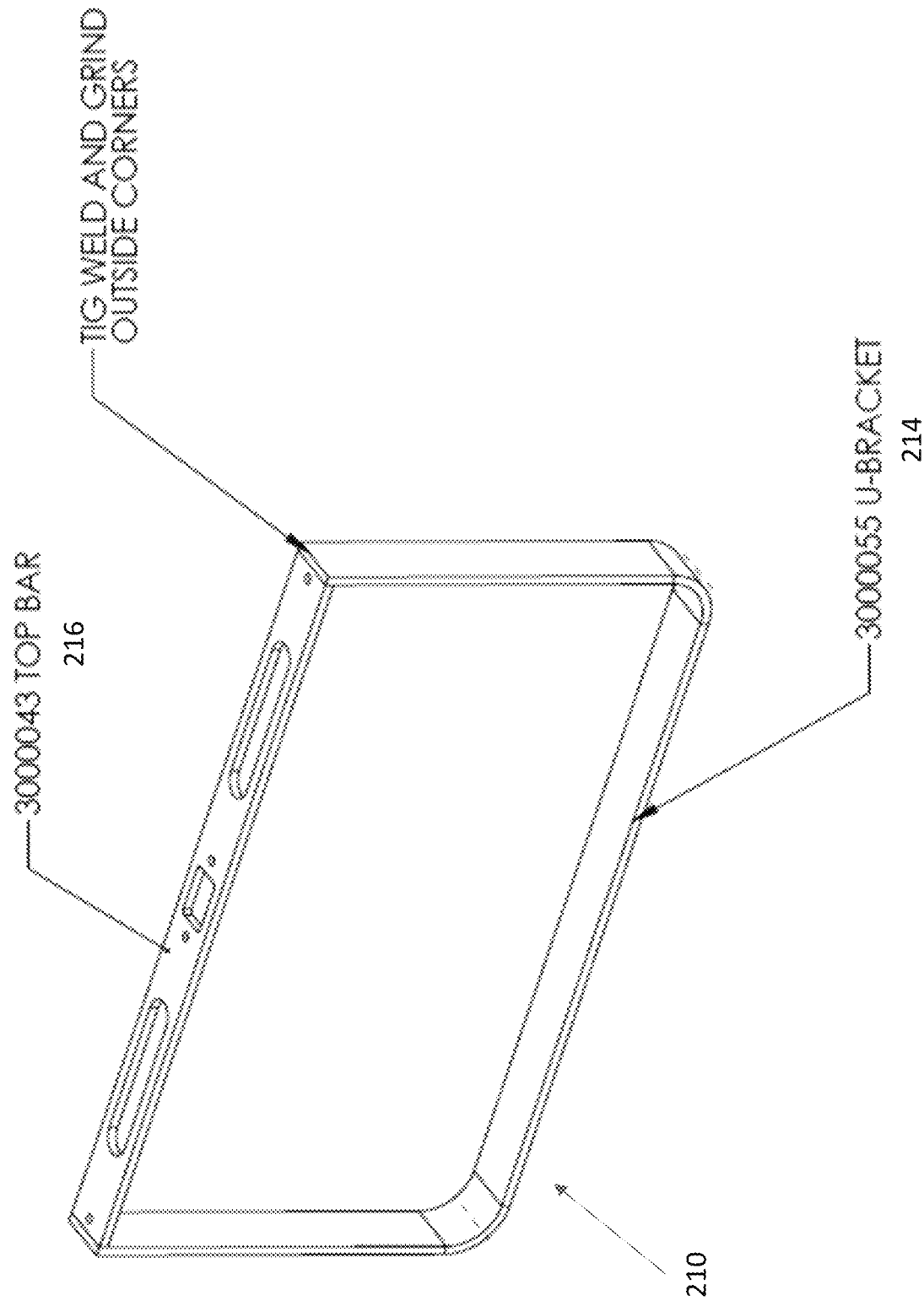
FIG. 11A shows a front, perspective view of an exemplary stand, in accordance with some embodiments.
Figure 11D:
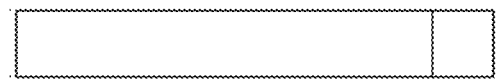
FIG. 11D shows a side-side view of the stand of FIG. 11A.
Figure 11B:
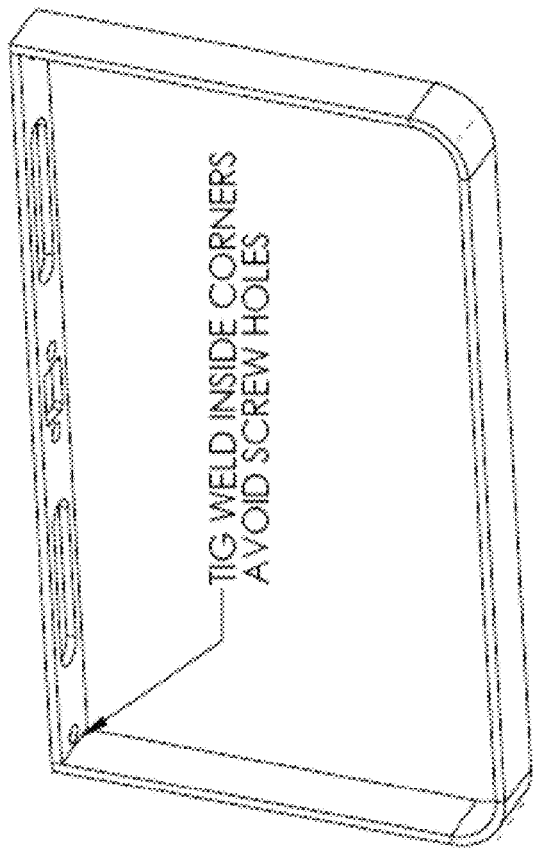
FIG. 11B shows another front, perspective view of the stand of FIG. 11A.
Figure 11C:
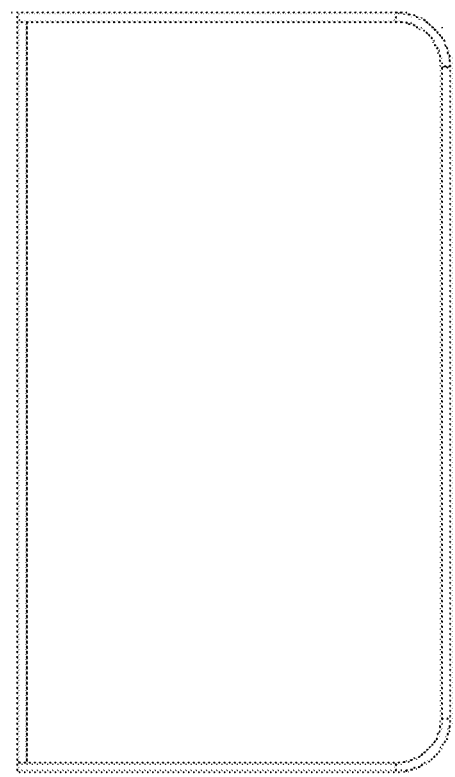
FIG. 11C shows a front-side view of the stand of FIG. 11A.
Figure 12A:
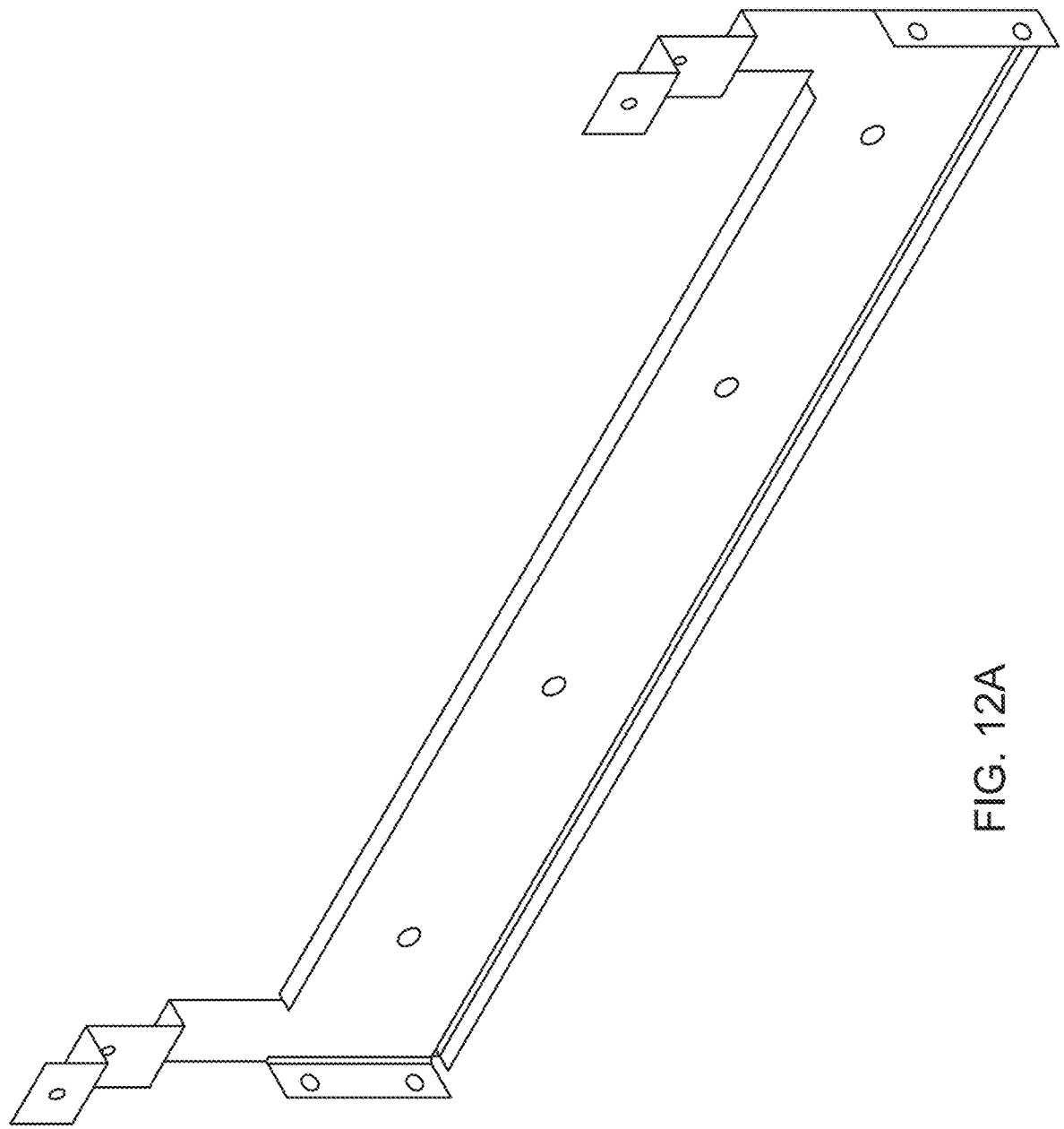
FIG. 12A shows a front, perspective view of an exemplary upper display panel bracket, in accordance with some embodiments.
Figure 12B:
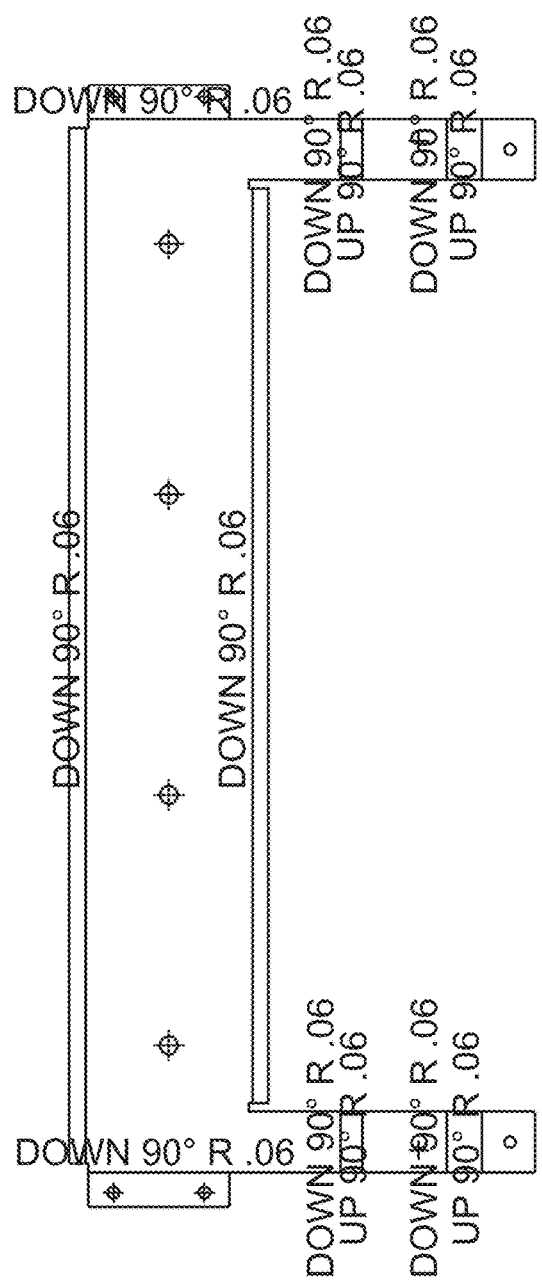
FIG. 12B shows a front-side, flat representation of the upper display panel bracket of FIG. 12A.
Figure 12C:
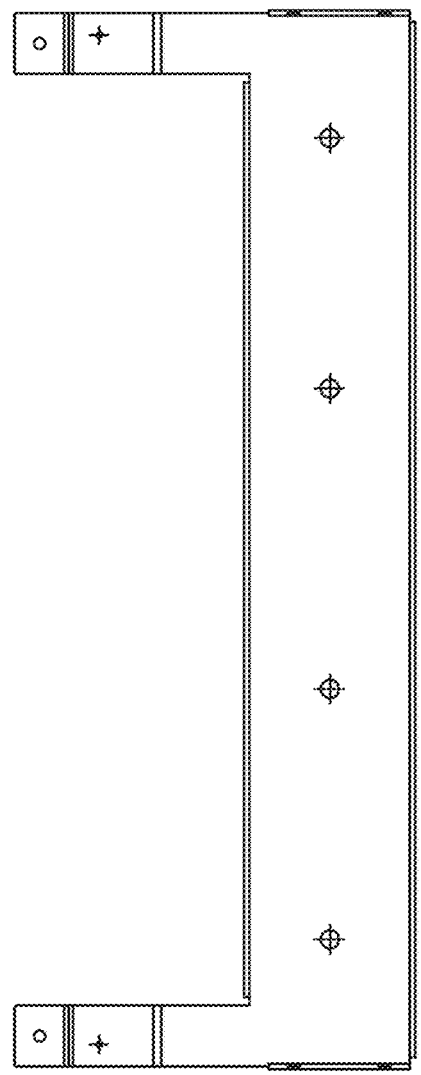
FIG. 12C shows a front-side view of the upper display panel bracket of FIG. 12A.
Figure 12D:
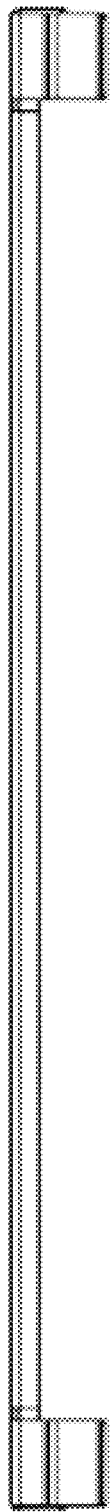
FIG. 12D shows a top-side view of the upper display panel bracket of FIG. 12A.
Figure 12E:
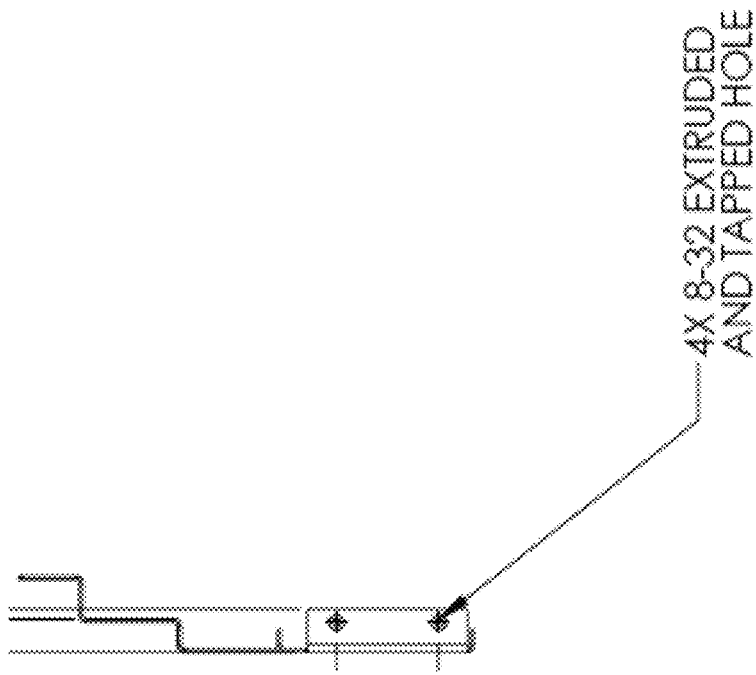
FIG. 12E shows a side-side view of the upper display panel bracket of FIG. 12A.
Figure 12F:
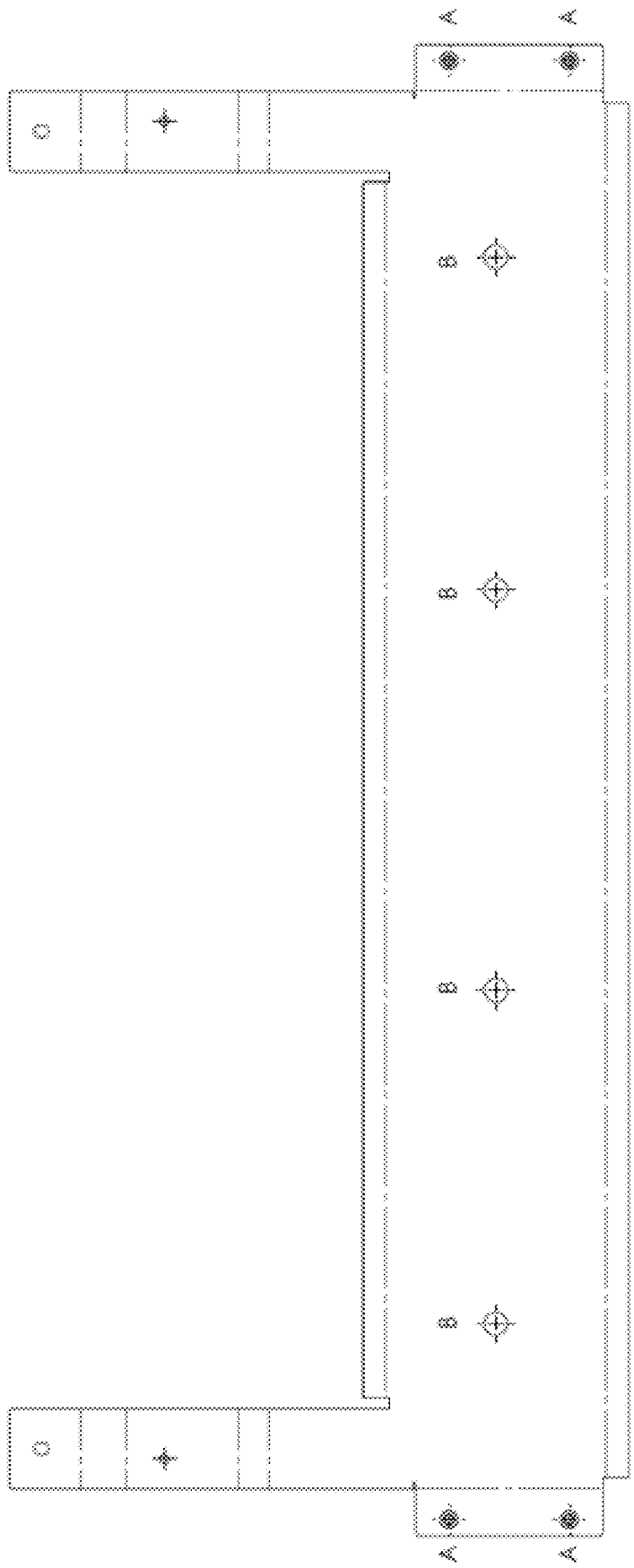
FIG. 12F shows a front-side, flat representation of the upper display panel bracket of FIG. 12A with various labeled holes for assembly.

As shown in FIG. 3C, the upper electronics assembly 230 may include the antenna 140, the camera 130, the microphone 160, and the SBC 110. FIG. 3D shows the lower electronics assembly 240 may include the SMPS 170, the switch 180, the amplifier 150, and the speakers 152 and 154. Additionally, the smart mirror 100 may include the stand 210 disposed on the bottom of the inner frame 202.

The smart mirror 100 in FIGS. 3A-3D represents one exemplary size and aspect ratio. The smart mirror 100, however, may generally be larger or smaller in size and/or have various aspect ratios. For example, a larger smart mirror 100 may be used to accommodate a taller user and/or multiple users. A smaller smart mirror 100 may be used to accommodate shorter users and/or to increase portability. Generally, the smart mirror 100 may have a height from about 24 inches to about 96 inches and a width from about 9 inches to about 120 inches. The aspect ratio of the smart mirror 100 may thus vary according to the respective ranges of the height and the width disclosed. FIGS. 4A-4E show several views of an exemplary inner frame 202. The inner frame 202 may be dimensioned and shaped to have an interior cavity within which contains the various components of the smart mirror 100 such as the SBC 110, the display panel 120, the camera 130, the antenna 140, the amplifier 150, the speakers 152 and 154, the microphone array 160, the SMPS 170, and the switch 180. The inner frame 202 may also include several mounting points to mount the aforementioned components to the inner frame 202 using various coupling members including, but not limited to screw fasteners, bolt fasteners, snap fit connectors, and adhesive. The inner frame 202 may also include apertures through which the camera 130 and the microphone 160 may record video and receive sound, respectively, from the user in the environment.

FIGS. 5A-5F show several views of an exemplary outer shell 204. The outer shell 204 may surround, at least in part, the inner frame 202. For example, FIG. 3B shows the outer shell 204 has an interior cavity that may contain therein the inner frame 202. The outer shell 204 may be used primarily to protect the inner frame 202 and the components contained therein. The outer shell 204 may include a plurality of ventilation holes or perforations to facilitate cooling of the various electronic components in the smart mirror 100. The outer shell 204 may also include a plurality of openings to transmit sound from the speakers 152 and 154 to the user. The outer shell 204 may also include an opening through which a port on a connector box is used to receive electrical power.

As shown in FIG. 2C, the smart mirror 100 may also be directly mounted to a wall for deployment. Various wall mounting mechanisms may be used including, but not limited to corresponding hooks on the wall and the smart mirror 100, a mounting bracket fastened to the wall and the smart mirror 100 via screw or bolt fasteners, and adhesive tape.

FIG. 3C shows an exemplary hook mechanism using a mounting bracket 302a on the smart mirror 100 and a corresponding mounting bracket 302b to be attached to the wall. FIGS. 7A-7D show additional views of the mounting bracket 302b. As shown, the mounting brackets 302a and 302b may have a width substantially similar to the width of the outer shell 204 to provide greater stability when hanging the smart mirror 100 from the mounting bracket 302b. As shown, the mounting bracket 302a may be coupled to the outer shell 204 using the same mounting points to mount an upper display panel bracket 304a disposed within the inner frame 202. The mounting bracket 302b may include multiple holes and/or slots to facilitate attachment to the wall. FIGS. 6A-6D show additional views of the mounting bracket 302a.

FIG. 3C shows a mirror-side safety bracket 306a and a wall-side safety bracket 306b. FIGS. 8A-8D show more views of the mirror-side safety bracket 306a. FIGS. 9A-9D show more views of the wall-side safety bracket 306b. These safety hooks 306a and 306b prevent the smart mirror 100 from tipping over when the smart mirror 100 is mounted to the stand 210. Similar to the wall mounting brackets 302a and 302b described above, the safety hook may also comprise a safety bracket 306a mounted to the outer shell 204 of the smart mirror 100 and a corresponding safety bracket 30b mounted to the wall. As shown in FIG. 3C, the safety brackets 306a and 306b may be positioned near a center line (e.g., a vertical axis) of the smart mirror 100 to increase stability.

FIG. 3C shows both the safety brackets 306a and 306b and the wall mounting brackets 302a and 302b. This is for showing where these respective components are placed with respect to the other components of the smart mirror 100. In practice, the smart mirror 100 may use just the safety brackets 306a and 306b or the wall mounting brackets 302a and 302b, but not both together.

The inner frame 202, the outer shell 204, the mounting brackets 302a and 302b, and the safety brackets 306a and 306b may be formed of various materials including, but not limited to steel, aluminum, fiberglass, carbon fiber, polyethylene terephthalate glycol (PETG), and plastic. For example, the inner frame 202, outer shell 204, mounting brackets 302a and 302b, and safety brackets 306a and 306b may be formed by patterning a flat sheet of metal, bending the sheet into the desired three-dimensional shape, and welding adjoining edges to form the finished component. Additional coatings (e.g., powder coatings, paint) may be applied to the inner frame 202, outer shell 204, mounting brackets 302a and 302b, and safety brackets 306a and 306b to reduce environmental contamination and/or for aesthetics.

The mirror glass 220 may be a two-way mirror or a two-way mirror film disposed on or in front of the display panel 120. The mirror glass 220 may thus be semi-reflective and semi-transparent to visible light. The mirror glass 220 may be substantially reflective when the display panel 120 is not active or in regions of the display panel 120 that show darker colors. The mirror glass 220 may be substantially transparent in regions of the display panel 120 that show brighter colors. Said in another way, the mirror glass 220 may appear reflective to the user when the intensity of light reflected by the mirror glass 220 (e.g., environmental light, natural light, light reflected off objects or the user in the environment) is greater than the intensity of light transmitted through the mirror glass 220 (e.g., light emitted by the display panel 120). Conversely, the mirror glass 220 may appear transparent to the user when the intensity of light reflected by the mirror glass 220 is less than the intensity of light transmitted through the mirror glass 220.

The mirror glass 220 may be coupled to the inner frame 202 using various coupling mechanisms including, but not limited to a tape, an adhesive, a clamp, a snap fit connector bonded to the mirror glass 220, and a screw fastener or a bolt fastener via a tab or pin bonded to the mirror glass 220. A safety film 222 may be attached directly to the mirror glass 220 to prevent the mirror glass 220 from shattering: if the mirror glass 220 breaks, the pieces of broken glass would remain affixed to the safety film 222. The safety film 222 may be transparent and can be patterned or printed with opaque (black) regions. For instance, the safety film 222 may be transparent over the partially reflecting section 226 of the smart mirror 100 and opaque over the fully reflecting section 228 of the smart mirror 100. Additionally, the safety film 222 may not fully cover the surface of the mirror glass 220. The patterning of the safety film 222 may be tailored to create a seamless appearance between the display panel 120 and the remaining portion of the mirror glass 220 when the smart mirror 100 is viewed from the front.

Double-sided adhesive tape 224 may be used to attach the mirror glass 220 to the inner frame 202 within the frame 200, as shown in FIG. 3B. On one side, the adhesive tape 224 is attached directly to the surface of the inner frame 202. On the other side, the adhesive tape 224 is attached to the safety film 222 or to the exposed mirror glass 220.

The mirror glass 220 may also be removable from the frame 200 after installation to allow replacement of the mirror glass 220 (as opposed to the entire smart mirror 100) in the event the mirror glass 220 is damaged. This may be accomplished by bonding the mirror glass 220 and safety film 222 to a set of pins or tabs that fit into a corresponding set of holes or slots in the frame 200. The number and distribution of pins and/or tabs may be tailored to reduce stress concentrations on the mirror glass 220 when assembled. The pins or tabs may be coupled to the frame 200 using a coupling member including, but not limited to a screw fastener, a bolt fastener, and a snap fit connector. The coupling member is configured to securely mount the mirror glass 220 to the frame 200 but may also allow a user to subsequently disassemble the smart mirror 100 to remove/replace the mirror glass 220.

The mirror glass 220 may be formed from various materials including, but not limited to glass, acrylic, mylar, plexiglass, a thermoplastic, polymethyl methacrylate (PMMA), or any other materials transparent to visible light. The reflective properties of the mirror glass 220 may be modified by a coating disposed by a partially reflective coating formed of various materials including but not limited to aluminum, silver, and dielectric coatings (e.g., a Bragg mirror). The safety film 222 may be formed from a flexible thin film polymeric material. The double-sided adhesive tape 224 may be various types of adhesive tapes including, but not limited to a very high bonding (VHB) tape, an ultra-high bonding (UHB), and an acrylic foam tape (AFT).

The smart mirror 100 may also be stylistically reconfigurable. For example, the smart mirror 100 may appear float when mounted to a wall. In this configuration, the edges of the mirror glass 220 may be fully exposed. The mirror glass's lateral dimensions may be equal to or larger than the lateral dimensions of the frame 210 located behind the mirror glass 220 as shown in FIGS. 10A-10D. As described above, the frame 200 may contain therein the various components of the smart mirror 100 (e.g., the SBC 110, the display panel 120, the camera 130, the antenna 140, the amplifier 150, the speakers 152 and 154, the microphone array 160, the SMPS 170, and the switch 180). Thus, a user directly facing the front of the smart mirror 100 may be unable to observe the frame 200 located behind the mirror glass 220, giving the impression that the smart mirror 100 is floating in space parallel to the wall.

Conventional floating mirror displays are typically two-piece assemblies where the mirror glass is positioned in front of the display. The mirror glass is typically hung from an elevated position, such as a ceiling or wall, and positioned in front of the display, which may also be hung from the ceiling or wall. This two-piece assembly increases installation complexity and limits the conventional mirror displays to environments where such mounting points are available. Other types of conventional mirror displays may be assembled in a framed configuration where a front side frame and a back side frame are joined together to hold the mirror glass in place. For this configuration, the edges of the mirror glass may be obscured by the front side frame and the front side frame may be observed by a user, thus affecting the aesthetic quality of the floating mirror configuration.

In contrast, the smart mirror 100 described herein may be constructed such that the mirror glass 220 is attached to a frame 200 thus forming a one-piece assembly. In the exemplary smart mirror 100 shown in FIG. 3A, the mirror glass 220 is bonded to a safety film 222. The safety film 222, in turn, is bonded to the inner frame 202 with double-sided adhesive tape 224. In this manner, the mirror glass 220 may be attached to the frame 200 such that the smart mirror 100 appears to float in space when mounted directly to a wall.

The smart mirror 100 may also allow for a decorative frame to be mounted on the front and/or side of the smart mirror 100. The decorative frame may be coupled to the outer shell 204 of the frame 200 located behind the mirror glass 220. The decorative frame may be coupled to the outer shell 204 using one or more coupling members including, but not limited to a screw fastener, a bolt fastener, and a snap fit connector. The decorative frame may also be coupled to the outer shell 204 using one or more magnets, thus increasing the ease of installation and reducing the assembly time. In some designs, the smart mirror 100 may include a decorative frame mounted on the edges of the mirror glass 220. If a user wishes to replace the decorative frame, the user may disassemble the smart mirror 100 using the pins or tabs described above to replace the mirror glass 220.

FIGS. 11A-11F show additional views of the stand 210 may be used to support the smart mirror 100 in a substantially vertical orientation (with or without tilt). The stand 210 is comprised of a U-shaped bracket 214 disposed beneath the inner frame 202 and the outer shell 204. The U-shaped bracket 214 is joined to a top bar 216. As shown, the U-shaped bracket 214 and the top bar 216 may be shaped and dimensioned to conform to the outer shell 204, thus providing a continuous surface around the sides of the smart mirror 100. The top bar 216 may include openings for the speakers 152 and 154. The top bar 216 may also include an opening through which the switch 180 may be accessed by the user. The stand 210 may also include a high friction base 212 (e.g., rubber feet) disposed on the bottom of the U-shaped bracket 214 as shown in FIG. 3B. The high friction base 212 may be used to prevent the smart mirror 100 from slipping along the floor, especially when the smart mirror 100 is partially tilted. The U-shaped bracket 214 and the top bar 216 may be formed of various materials including, but not limited to steel, aluminum, fiberglass, carbon fiber, polyethylene terephthalate glycol (PETG), and plastic.

The height of the mirror glass 220 and/or the display panel 120 of the smart mirror 100 may also be adjustable to accommodate different users with different heights. The smart mirror 100 may be designed to have a particular height range to accommodate a majority of users. If a user falls outside of this height range, the smart mirror 100 may be adjusted accordingly. Height adjustment may be accomplished in several ways. In one example, a slot-rail mechanism may be integrated into the smart mirror 100 using the frame 200 and the stand 210. For instance, the frame 200 may incorporate at least one slot between the outer shell 204 and the inner frame 202 to accommodate a rail on the stand 210. The rail on the stand 210 may thus be slidably adjustable along the slot in the frame 200. A locking mechanism may be included to secure the rail to the slot at a desired position. The locking mechanism may come in various forms including, but not limited to a ratcheting mechanism that allows motion along one direction (e.g., extension of the rail relative to the slot) and a release mechanism to allow motion in the opposite direction, a plurality of holes in the slot (or rail) with a spring-mounted pin in the rail (or slot) for securement, a clamping mechanism (e.g., a locking tab) to hold the rail against the slot via a frictional force.

The electronic components of the smart mirror 100 may be disposed in various locations on the inner frame 202 and the outer shell 204. In the exemplary smart mirror 100 shown in FIGS. 3A-3D, the electronic components are disposed primarily in the upper electronics assembly 230 and the lower electronics assembly 240 to simplify assembly and place respective components in preferred locations on the smart mirror 100 with respect to where a user may be located. Any wiring to electrically couple the electronic components may be routed along the inner frame 202 and/or the interior cavity of the outer shell 204.

The display panel 120 is primarily used to show video content to the user. The display panel 120 may be various types of displays including, but not limited to a liquid crystal display (LCD), a light emitting diode (LED) display, an organic light emitting diode (OLED) display. The display panel 120 may be configured to emit a lower light intensity when displaying darker colors (or may even turn off the respective pixels) in order to enhance the performance of the two-way mirror glass 220. In some instances, the display panel 120 may also be touch sensitive to provide additional interactive control of the smart mirror 100 to the user. For example, the display panel 120 may employ resistive touchscreen technology, surface acoustic wave (SAW) technology, a capacitive (e.g., surface capacitance, projected capacitance, mutual capacitance, self-capacitance) approach, an infrared-based approach (e.g., infrared grid, infrared acrylic projection, and/or the like), optical imaging using image sensors (e.g., CMOS sensors) placed around the edges of the display panel 120, dispersive signal technology, and/or acoustic pulse recognition. The touch sensitivity may be calibrated to account for the mirror glass 220 and any other intermediate components (e.g., the safety film 222) disposed between the display panel 120 and the environment. In some cases, the touchscreen capabilities described herein may be incorporated into the mirror glass 220 instead of, or in addition to, the display panel 120.

The entirety of the display panel 120 may be touch sensitive. Alternatively, some portions of the display panel 120 may be touch sensitive such as, for example, where controls are displayed to a user, while other portions of the display panel 120 may not be touch sensitive such as, for example, where the exercise instructor is typically displayed, where the user's reflection is expected to fall during a workout, and/or the like. In some cases, the portions of the display panel 120 that are touch sensitive may be dynamically re-configurable. For example, the entire display panel 120 may be touch sensitive when the user is browsing a large menu of selectable workouts, and a smaller portion of the display panel 120 may be touch sensitive during an ongoing workout, say corresponding to a displayed option to pause or stop the workout in a top right-hand corner of the displayed interface. In some cases, the displayed interface may include, as visual guidance to the user, a different color for such displayed options that correspond to the portion of the display panel 120 that is touch sensitive at that time. For example, an icon to end a workout may be surrounded by a grey border or halo that indicates the touch-sensitive region of the display panel 120 at that time.

As shown in FIGS. 3C and 3D, the display panel 120 may be mounted to the inner frame 202 using an upper display panel bracket 304a and a lower display panel bracket 304b. FIGS. 12A-12F show additional views of the upper display panel bracket 304a. The upper display panel bracket 304a and the lower display panel bracket 304b may be coupled to the inner frame 202 and the display panel 120 respectively using various coupling mechanisms including, but not limited to screw fasteners, bolt fasteners, snap fit connectors, or adhesive. The upper display panel bracket 304a and the lower display panel bracket 304b may be formed of various materials including, but not limited to steel, aluminum, fiberglass, carbon fiber, polyethylene terephthalate glycol (PETG), and plastic.

The antenna 140 may comprise multiple antennas that each function as a receiver and/or a transmitter to communicate with various external devices, such as a user's smart device (e.g., a computer, a smart phone, a tablet), a biometric sensor (e.g., a heart rate monitor), and/or a remote server or cloud server to stream or play video content. Once again, the antenna 140 may conform to various wireless standards including, but not limited to Bluetooth, 802.11a, 802.11b, 802.11g, 802.11n, 802.11ac, 2G, 3G, 4G, 4G LTE, and 5G standards.

Figure 13A:
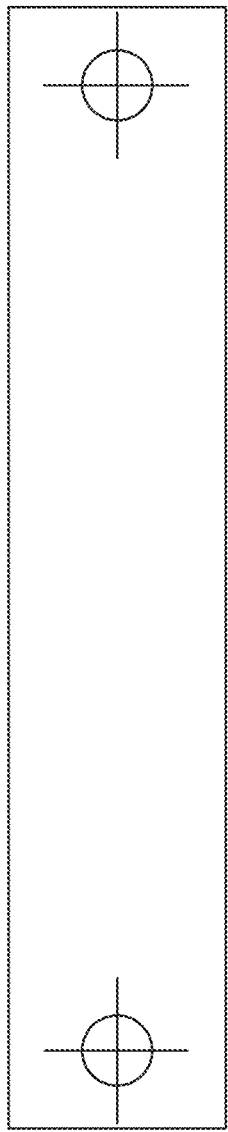
FIG. 13A shows a front-side view of an exemplary antenna mounting bracket, in accordance with some embodiments.
Figure 13B:
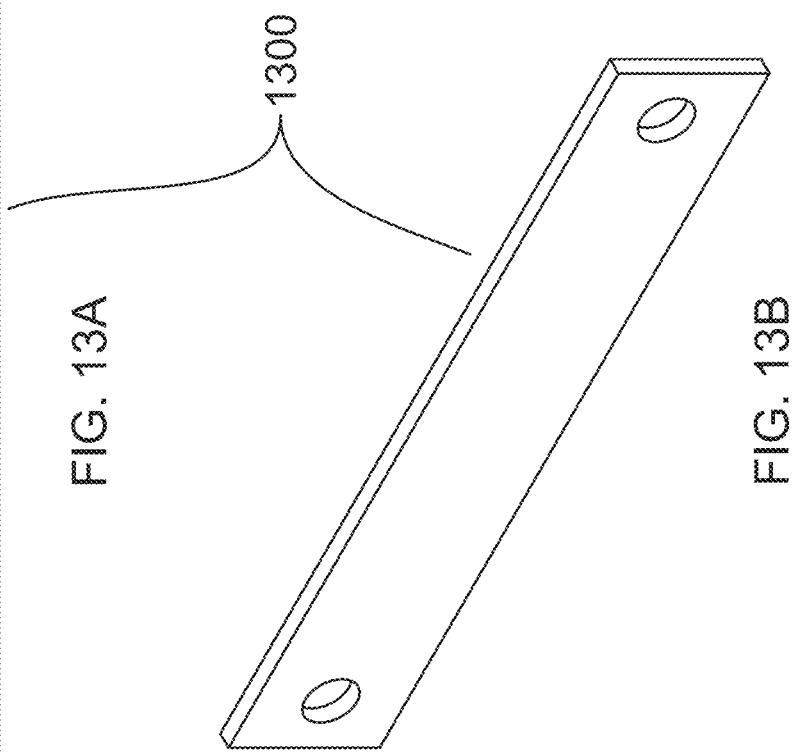
FIG. 13B shows a front, perspective view of the antenna mounting bracket of FIG. 13A.
Figure 14A:
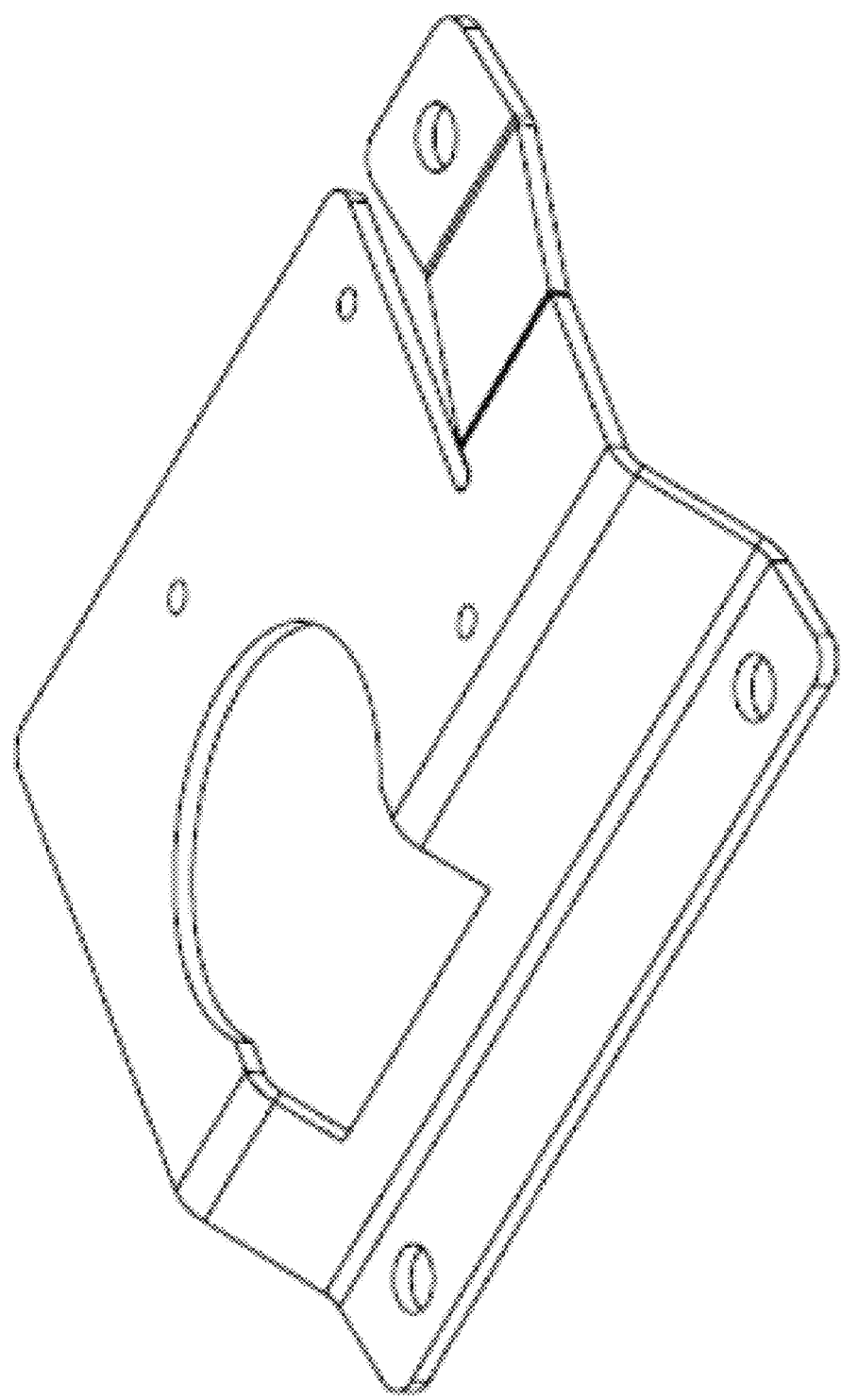
FIG. 14A shows a perspective view of an exemplary camera mount, in accordance with some embodiments.
Figure 14C:
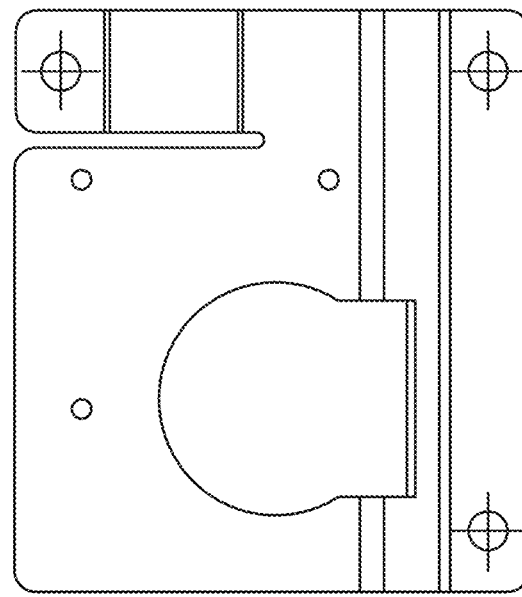
FIG. 14C shows a front-side view of the camera mount of FIG. 14A.
Figure 14E:
FIG. 14E shows a bottom-side view of the camera mount of FIG. 14A.
Figure 14B:
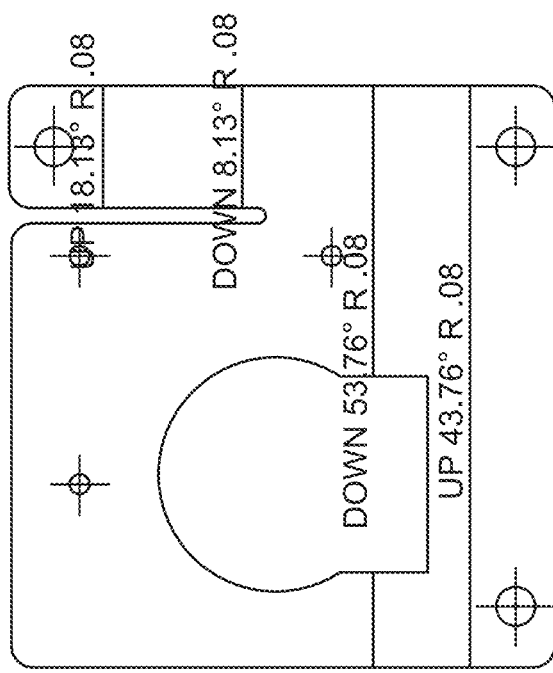
FIG. 14B shows a front-side, flat representation of the camera mount of FIG. 14A.
Figure 14D:
FIG. 14D shows a side-side view of the camera mount of FIG. 14A.
Figure 15A:
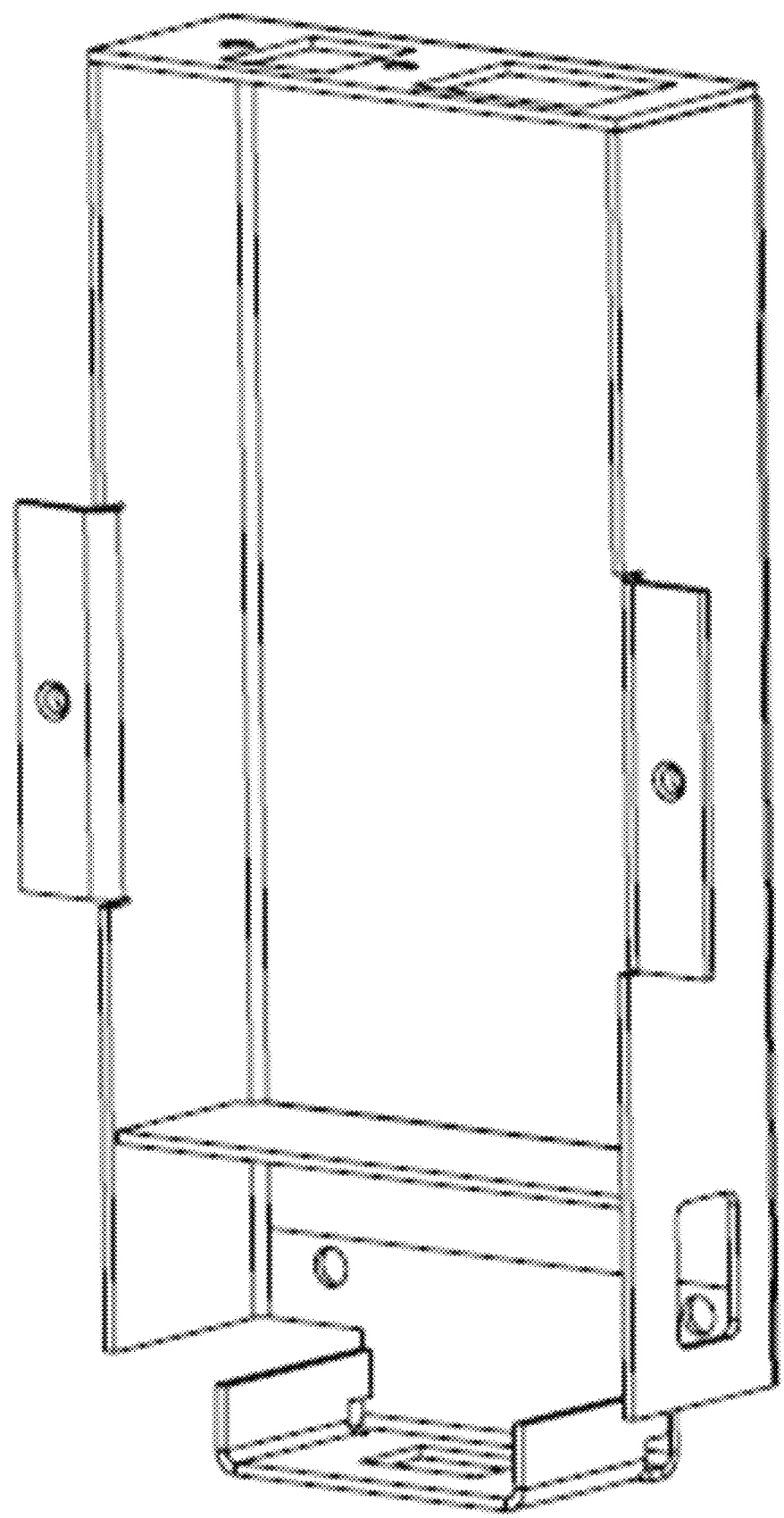
FIG. 15A shows a perspective view of an exemplary connector box with a L-bracket, in accordance with some embodiments.
Figure 15C:
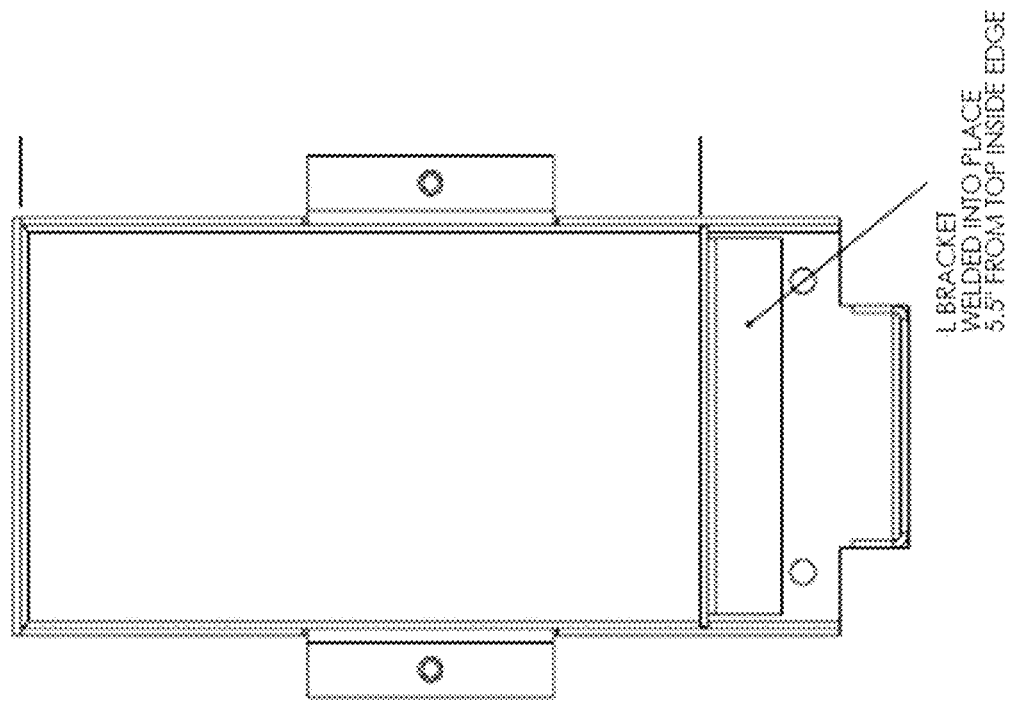
FIG. 15C shows a rear-side view of the connector box with a L-bracket of FIG. 15A.
Figure 15B:
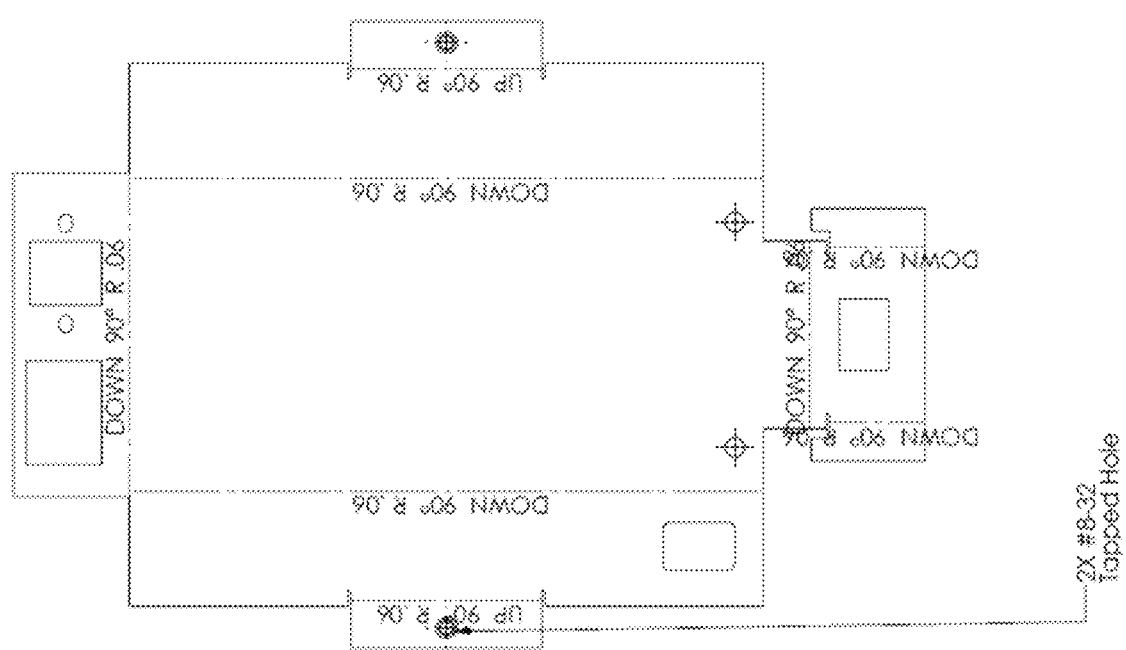
FIG. 15B shows a rear-side, flat representation of the connector box of FIG. 15A.
Figure 16A:
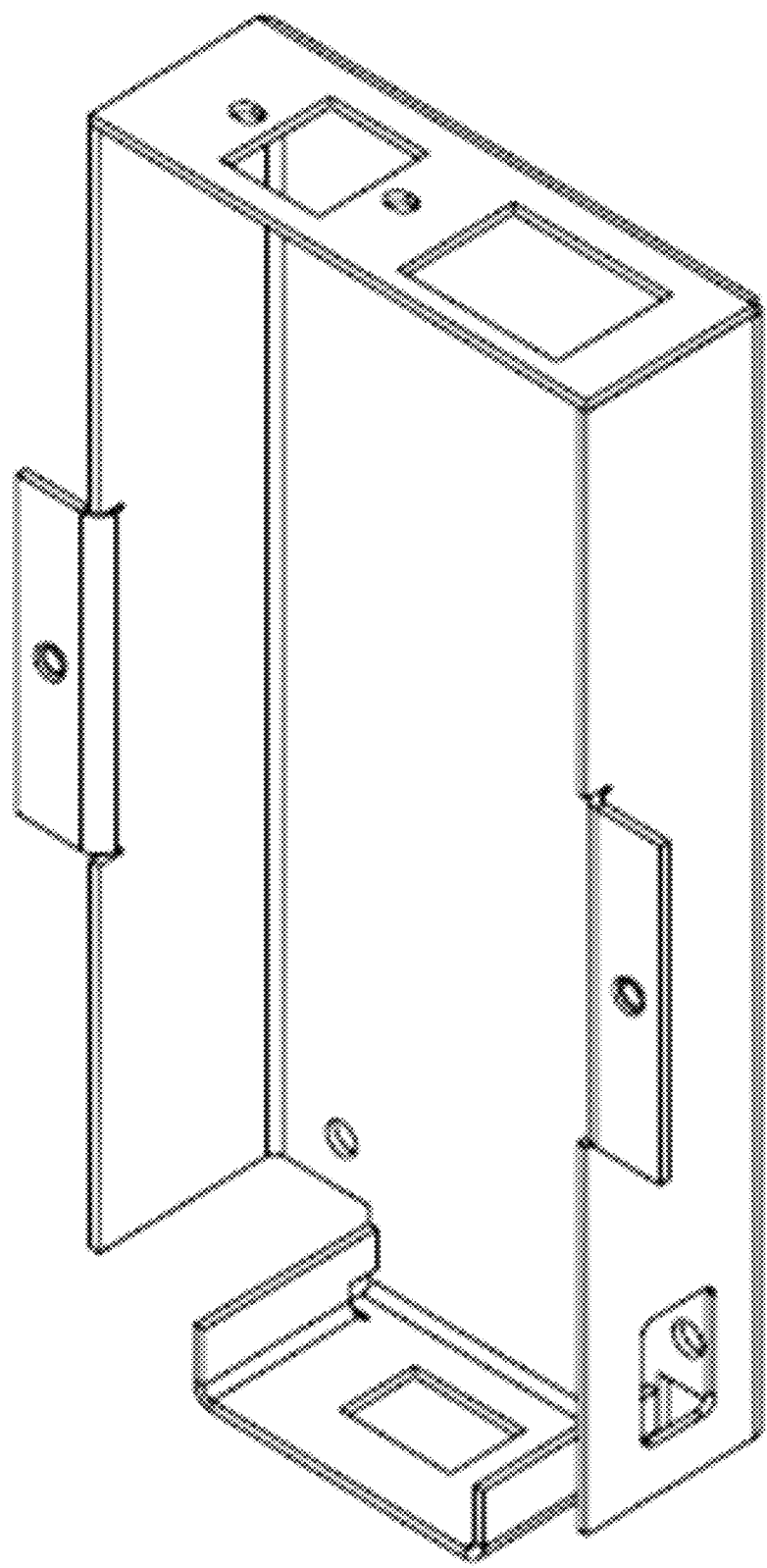
FIG. 16A shows a perspective view of the connector box of FIG. 15A.
Figure 17A:
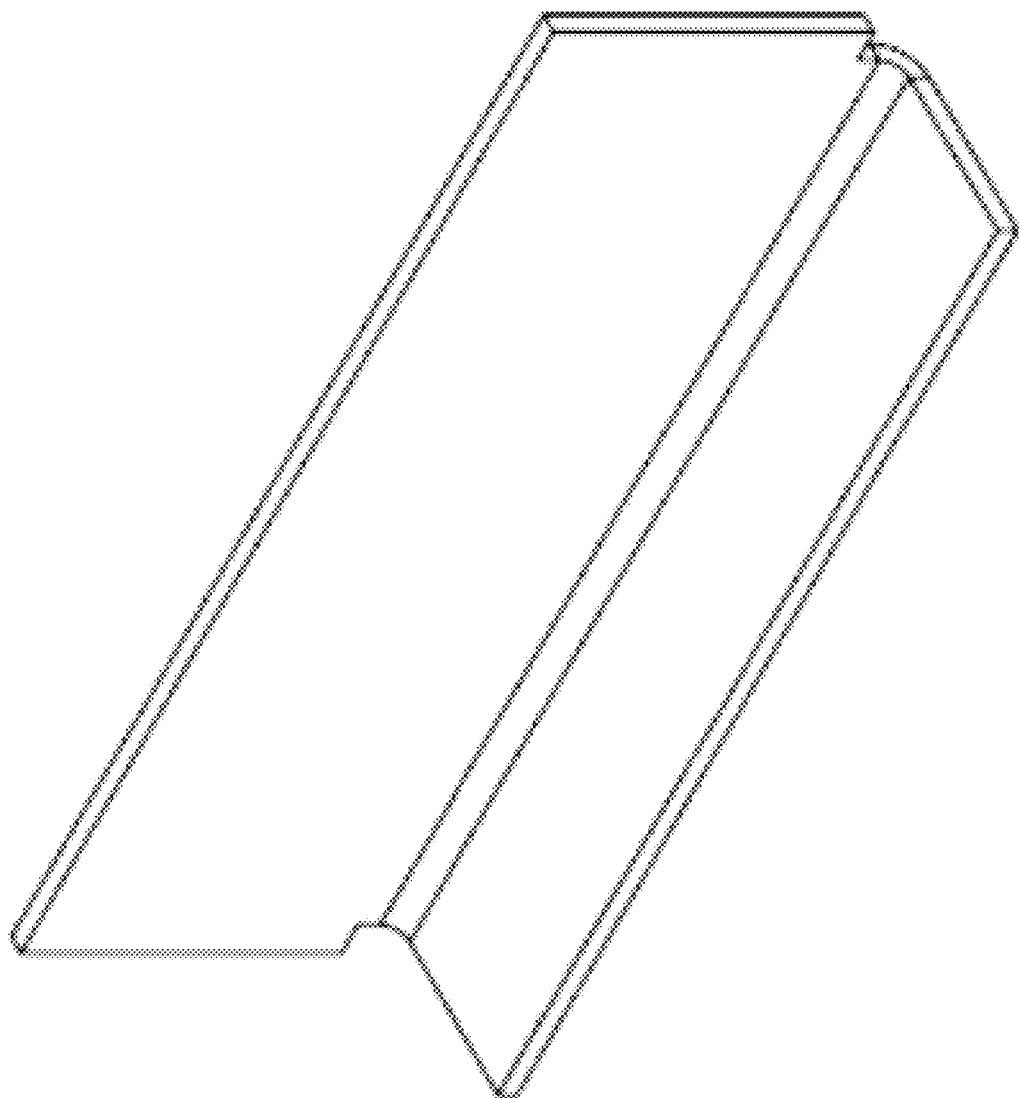
FIG. 17A shows a perspective view of the L-bracket of FIG. 15A.
Figure 17C:
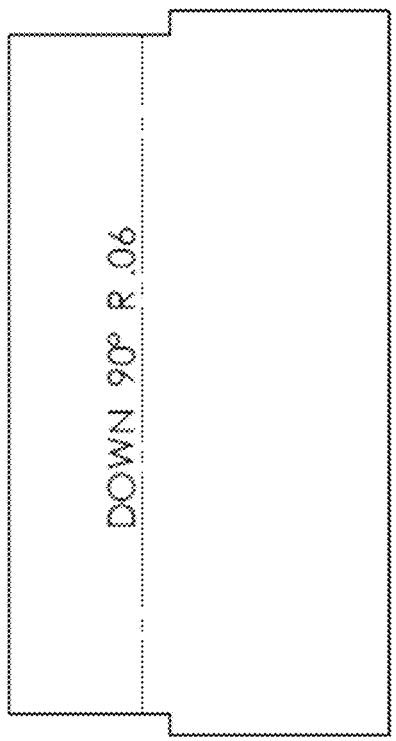
FIG. 17C shows a rear-side, flat representation of the L-bracket of FIG. 17A.
Figure 17E:
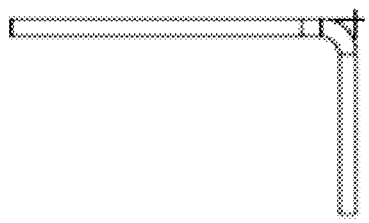
FIG. 17E shows a side-side view of the L-bracket of FIG. 17A.
Figure 17B:
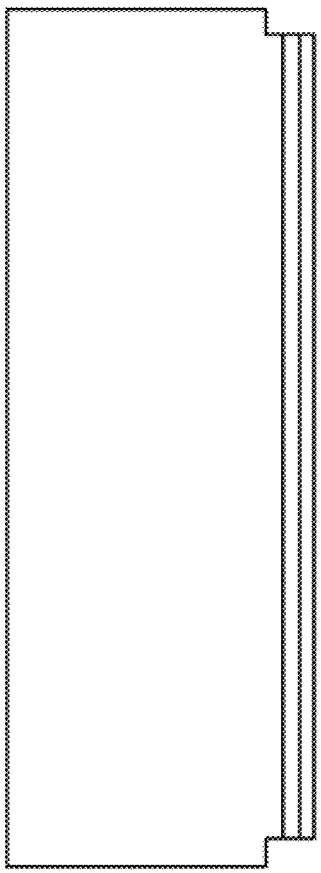
FIG. 17B shows a top-side view of the L-bracket of FIG. 17A.
Figure 17D:
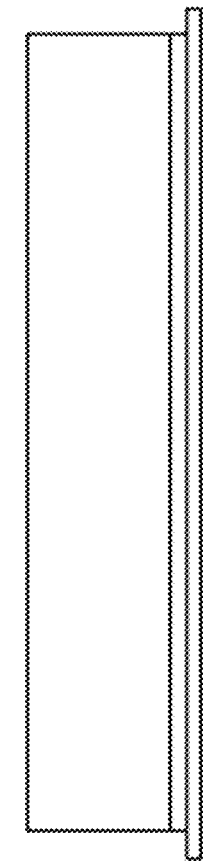
FIG. 17D shows a rear-side view of the L-bracket of FIG. 17A.

FIGS. 13A and 13B show an antenna mounting bracket 1300 that can be used to hold the antenna 140 in place. The antenna mounting bracket 1300 may be formed of various materials including, but not limited to steel, aluminum, fiberglass, carbon fiber, polyethylene terephthalate glycol (PETG), and plastic.

The microphone 160 may be used to record a user's voice and/or other ambient sounds. The microphone 160 may include a muffler to reduce unwanted ambient noise (e.g., a fan or street noise) from being acquired by the smart mirror 100. Similar to the camera 130, audio recorded by the microphone 160 may be shared with another person (e.g., an instructor or another user) in real-time or recorded for later playback. In one aspect, the audio may be acquired with the video of the user using timestamps that ensure the audio is synced to the video. The microphone 160 may also be coupled to the amplifier 150 to control the sound output from the speakers 152 and 154. For example, when a user speaks, the microphone 160 may send a signal to the amplifier 150 to reduce the sound output from the speakers 152 and 154 to avoid unwanted audio feedback. The microphone 160 may be used, in part, to enable voice control of the smart mirror 100. For example, a user may activate/deactivate the smart mirror 100 and navigate, start, and stop workouts with their voice. For example, the SBC 110 can provide for voice control, such as via a voice-user interface (VUI) and/or any other suitable approach, that permits the user to provide spoken command, via the microphone 160 for example, and/or via any other suitable interface. The voice control can be generally employed for providing user input for any aspect of operation of the smart mirror 100 such as, for example, control of the mirror 100 (e.g., "turn off"), for interaction with the mirror (e.g., "find a yoga workout under 30 minutes"), and/or the like. Voice control may be capable of recognizing the speaker for speaker identification, speaker verification (e.g., logging in the user via voice recognition), and/or the like (e.g., using pattern recognition techniques such as frequency estimation, hidden Markov models, Gaussian mixture models, pattern matching algorithms, neural networks, matrix representation, vector quantization, decision trees, and/or the like), enabling multiple users to use the same mirror 100 at the same time (e.g., as described below for user groups) or at different times.

The left and right speakers 152 and 154 may be used to output sound to the user (e.g., instructions from the instructor, music, sound effects). The speakers 152 and 154 may be low profile and configured to emit sound in one or more desired frequency bands. In some designs, the speakers 152 and 154 may be oriented to emit sound in a direction transverse to the front of the mirror glass 220 (e.g., towards the floor or the ceiling) to reduce the thickness of the smart mirror 100 as shown in FIG. 3B. In some designs, the speakers 152 and 154 may be oriented to emit sound in a direction towards a user located in front of the mirror glass 220. In this configuration, sound may be emitted through openings on the front of the smart mirror 100 (e.g., openings in the mirror glass 220). The mirror glass 220 may also vibrate with the speakers 152 and 154 to produce sound emitted towards the user. The mirror glass 220 may thus be tuned to emit sounds at frequencies that may be otherwise unavailable in a front-facing, low-profile speaker. The sound output may be controlled, in part, by the amplifier 150.

As described above, the camera 130 in the smart mirror 100 may be used to acquire video and/or still images of the user while the user performs an activity (e.g., a workout). The video of the user may then be shared with an instructor to allow the instructor to observe and provide guidance to the user during a workout. The video may also be shared with other users of other smart mirrors for comparisons or competition. The video of the user may also be shown on the display panel 120 in real-time or stored for subsequent playback. For example, the video of the user may be used for self-evaluation during or after a workout by providing a visual comparison of the user to the instructor. Stored video may also allow user to evaluate their progress or improvement when performing similar exercises over time.

The video may also be processed, in real-time during a workout or after a workout is finished, to derive biometric data of the user based on the movement and motion of the user. For example, image analysis techniques may be used to determine various aspects of a user's workout including, but not limited to a user's breathing rate as a function of time, a user's performance in reproducing a proper form or motion of a particular exercise, the number of repetitions performed by the user during a workout, stresses on a user's limbs or joints that may lead to injury, and a user's stamina based on deviations of a particular exercise over time. This biometric data derived from the video may be used in combination with biometric data acquired by a biometric sensor worn by the user to provide a user additional analysis on their workout.

The camera 130 may be one of several cameras mounted in or on the smart mirror 100, where each camera may be configured to image different aspects of a user. The camera 130 may include a standard web camera. In another example, the camera 130 may include a spatial motion sensing camera (e.g., a Microsoft Kinect) capable of tracking a user's motion within a three-dimensional (3D) space. The motion sensing camera may have sufficient spatial resolution to track individual extremities (e.g., arms, legs, hands, feet, fingers, toes). This data may be used to reconstruct a high fidelity 3D model of the user that is animated in accordance to the user's movement as a function of time. The 3D model of the user may thus provide additional information to the user and/or the instructor to assess a user's performance in executing a workout and to guide the user on proper form and technique. For example, the 3D model may be displayed to the user with a comparison to a second 3D model of another person (e.g., the instructor) performing an exercise with a correct form and technique. The motion sensing camera may also be used to identify and track the motion of multiple users.

In yet another example, the camera 130 may include a thermal camera (e.g., a forward-looking infrared (FLIR) camera) to generate temperature maps of the user's skin. These temperature maps may be used to track spatial and temporal changes to a user's skin temperature during a workout (e.g., resting, exercising, recovering after a workout), which may provide additional biometric data such as a user's hydration levels.

As yet another example, user detection/recognition and motion tracking may be carried out by the SBC 110 as follows. The SBC 110 may be configured for real-time and/or near real-time motion tracking of a user of the mirror 100, such as during a workout, via the video stream acquired by the camera 130. The video stream can be analyzed in real-time using approaches for user detection/recognition such as machine learning and/or deep learning. Non-limiting examples of machine learning approaches for user recognition can include those of the Viola-Jones object detection framework, Scale-Invariant Feature Transform (SIFT), Histogram of Oriented Gradients (HOGs), and/or the like. Non-limiting examples of deep learning approaches can include You Only Look Once (YOLO), Convolutional Neural Networks (CNNs), Region-based Convolutional Neural Networks (RCNN), Fast RCNN, Faster RCNN, Mask RCNN, Single Shot Multibox Detector, and/or the like. In some cases, where the camera 130 can include an infrared camera, the user's body temperature can be the basis for user recognition.

The user detection/recognition can be applied to the user's entire body, and/or a body part such as, for example, limbs of the user. The user recognition that is performed can be specific to the exercise class and/or workout that the user is performing. For example, recognition for the user's arms can be performed for an upper body workout or for an upper body portion of a workout, while recognition for the user's legs can be performed for a running-in-place workout/portion of a workout. In this manner, the SBC 110 can efficiently analyze the relevant portions of the user's body as required or desired for a specific workout without engaging in a potentially computationally-intensive whole-body analysis.

The video stream can also be analyzed in real-time for motion tracking of the user and/or any portion of the user's body, such as limbs. For example, once the arms of the user are detected as explained above, their motion can be tracked to determine whether the user is correctly performing the workout, as described in more detail later. Motion tracking can include both a) target representation and localization, and b) filtering and data association. Example target representation and location techniques can include Kernel-based (mean shift) tracking, contour/boundary tracking, and/or the like. Example filtering and data association techniques can include the Kalman filter, the Particle filter, and/or the like.

The SBC 110 may be configured to track the user's motion during a workout to generate a user movement pattern, which can generally be characterized as any spatio-temporal data/data structure that involves objects (i.e., the user's body, or a body portion) moving over time, and can include trajectory information for the object(s). The user movement pattern can then generally be characterized as the tracked motion of the user, or body part(s) thereof, over some period of time. The period of time may be a predefined period, associated with the duration of a workout within an exercise class, with the entire exercise class, with multiple exercise classes in a class sequence, and/or the like.

The user's movement pattern can be compared against that of a predetermined movement pattern (sometimes also referred to simply as an 'exercise movement pattern') such as, for example, an 'ideal' movement pattern for that movement. The predetermined movement pattern can be defined in any suitable way such as, for example, computationally, by averaging movement patterns generated by multiple instructors presumably performing the movement correctly (e.g., an average generated from videos of five different instructors performing a squat), and/or the like. In some cases, the movement of the instructor themselves, during a workout/exercise class, can be used to generate the predetermined movement pattern. Generation of the predetermined movement pattern based on one or more instructors performing the movement can be done, for example, using user recognition and motion tracking as described above on the instructor(s) performing the movement.

This comparison between the user's movement pattern and the predetermined movement pattern can be used to generate a score based on how well the user performs the movement and/or follows the instructor, provide corrective feedback to the user to improve their form during or after an exercise class, and/or the like. As a non-limiting example, the comparison can be generally be performed as follows. User recognition and motion tracking can be employed to generate the user movement pattern. In some cases, the exercise video is one that was previously archived and already includes (e.g., as metadata) the exercise movement pattern for at least a portion of the exercise class.

The comparison between the user movement pattern and the exercise movement pattern can be performed in any suitable manner. For example, when a user is asked to perform a set of ten squats, then the degree of bend in the user's knee on the first squat, which is tracked and captured in the user movement pattern, can be compared to the estimated knee bend per the exercise movement pattern. If the user does not squat to at least the same degree, or within some predetermined tolerance (e.g., within 5 degrees of knee bend), the comparison can include a quantitative and/or qualitative calculation of a difference, e.g., a delta measure for that movement, such as difference in squat angle, simply an indication that the user has not achieved the desired form (here, squat depth), and/or the like. Generally, the tolerance can be characterized in any suitable manner, such as in angle, degree, length/distance, percentage (e.g., within 5% of vertical alignment, within 5% of horizontal alignment, and/or the like), and/or the like. As another example, when a user is instructed to perform jumping jacks, the motion of the user's arms and legs can be tracked to ensure full extension. As yet another example, when the user is instructed to perform a plank, the entire body of the user can be monitored to ensure correct posture/form.

The SBC 110 can use the comparison as a basis for selecting a corrective movement pattern to present to the user, so as to inform the user on how to correct their form. Each movement may have associated with it a set of corrective movement patterns that can be presented to the user, depending on the error in the user's form. Corrective patterns can be established, for example, manually, based on machine learning techniques (e.g., trained on such manually created data), and/or the like.

For example, one set of corrective movement patterns may be to ask the user to go lower on a squat, another set of corrective movement patterns may be to ask the user to keep their heels on the ground during a squat, and/or the like. So when the delta measure indicates that the user did not squat to the same degree as specified by the exercise movement pattern (and accounting for any tolerances), the SBC 110 can select the corrective movement pattern that asks the user to go lower on a squat.

FIG. 34 illustrates how such a corrective movement pattern can be displayed to the user 3410 via a smart mirror 3400, which may be structurally and/or functionally similar to the mirror 100. Illustrated for the example where the user 3410 is performing alternating shoulder presses, the corrective movement pattern can include illustrating, via the arrows 3420a and 3420b, to move one arm up to a greater degree (as indicated by the arrow 3420a), and the other arm back down to a greater degree (as indicated by the arrow 3420b). When the user 3410 is performing multiple shoulder presses, the motion can be detected and analyzed for the first few repetitions, and result in the illustration of the corrective movement pattern of FIG. 34. If/when the user 410 attains the correct form (e.g., for at least 2 repetitions), the indication of the corrective movement pattern may be removed from the display. In some cases, the user can elect to view corrective patterns during an exercise class irrespective of their own form, which can serve as an additional (to the instructor) guide to the user towards attaining the correct form.

The display of the corrective movement pattern can include displaying, in real-time an animated image of the user on the display panel 120 such as, for example, a stick figure, an avatar of the user, and/or the like. The animated image can be sized to be similar to the size of the instructor or similar to the size of the reflected image of the user (e.g., as estimated by projection analysis of the video stream of the user). In some cases, the animated image can represent the actual form of the user, so that the user can visualize how their form is improving response to the corrective movement pattern.

The animated image can be generated based on user recognition and tracking as explained earlier, and responsive to determining that the user's form needs correction. In some cases, the animated image can be displayed for the duration of a workout, an entire exercise class, and/or an entire class sequence. The user may be able to manually toggle the display of the animated image to be ON/OFF for a specific workout/class/class sequence, or globally (e.g., via user account settings).

The SBC 110 can additionally and/or alternative use the comparison or delta measure as a basis for repetition counting for a movement that the user is performing, for repetitive exercises. Referring again to the example exercise class where the user is asked to perform a set of squats, if the delta measure for a single squat is within some predetermined threshold (e.g., the user's knee angle is evaluated to be within 10 degrees of that of the instructor), that squat can be determined to be a valid repetition of the movement. As illustrated in FIG. 35 for a user 3510 performing a squat exercise in front of a smart mirror 3500, such counting 3520 can be displayed to the user in real time in any suitable manner such as, for example, a single number that is updated with each repetition, a series of numbers that sequentially light up as the user accomplishes those number of repetitions (e.g., a series of 1, 2, 3 . . . , a series of 5, 10, 15 . . . and/or the like), a progress bar, a bubble filling up with each repetition, and/or the like. In some cases, the SBC 110 can use the comparison/delta measure as a basis for timing the user. For example, if the user is instructed during a yoga class to hold a pose for 10 seconds, the comparison information can be used to count for how long the user correctly maintains the pose.

While generally described herein for real-time analysis, it is understood that the user recognition, tracking, repetition counting, and/or the like can be performed on previously acquired video as well such as, for example, an archived video of a user acquired during an exercise class. In this manner, a user can review, at their leisure, their form, how well they were able to perform the desired number of repetitions, and/or the like. In some cases, the comparison information is also stored and presented to the user such as, for example, during playback of the archived video, as an indication of a percentage of time during the exercise class that the user had the correct form, and/or the like.

While described herein with respect to the SBC 110, it is understood that one or more of user recognition, motion tracking, form correction, repetition counting can be performed remotely such as, for example a cloud platform associated with remote storage, with a content provider, and/or the like. For example, an archived or live streamed exercise video can be analyzed in real-time on the cloud platform to generate the exercise movement pattern. As another example, video captured of the user during an exercise class can be transmitted to the cloud platform and be analyzed for form correction and/or repetition counting on the cloud platform itself. In this manner, more computationally intensive algorithms one or more of user recognition, motion tracking, form correction, repetition counting, as well as relatively more complex analysis, can be performed without necessarily incorporating the complex hardware that may be required to do so into every user's mirror 100.

FIGS. 14A-14E show several views of an exemplary camera mount 1400 that can be used to mount the camera 130 to the inner frame 202. The camera mount 1400 may be a mechanical component designed to orient the camera 130 such that the field of view of the camera 130 captures the user under most use cases. For example, FIG. 3C shows the camera mount 1400 has bent shape to tilt the camera 130 downwards. The camera mount 1400 may be formed of various materials including, but not limited to steel, aluminum, fiberglass, carbon fiber, polyethylene terephthalate glycol (PETG), and plastic.

The smart mirror 100 may be configured to receive electrical inputs from an alternating current (AC) source or a direct current (DC) source. The SMPS 170 may be compatible with both AC and DC input sources. The SMPS 170 may be used, in part, to convert the electrical input into a desired form for subsequent dissemination to other components of the smart mirror 100. For example, the SMPS 170 may be used to convert AC to DC or DC to AC. The SMPS 170 may also be used to adjust the voltage and/or current of the input to desired values (e.g., increase the voltage from 120 V to 240 V, decrease the voltage from 240 V to 120 V).

The SMPS 170 may be configured to receive electrical inputs via a power cord coupled to the smart mirror 100 or a wireless power transfer system (e.g., the smart mirror 100 has a receiver that receives wireless power from a transmitter mounted to a wall via an inductive or capacitive coupling mechanism). In one example, a standard International Electrotechnical Commission (IEC) cable may be used to connect the SMPS 170 directly to a standard wall outlet (e.g., a 120-240V/60 Hz outlet). In some designs, the SMPS 170 may be partially or wholly disposed outside the frame 200 of the smart mirror 100 (e.g., an AC adapter for a laptop) to reduce the overall size of the smart mirror 100.

The smart mirror 100 may also include a battery (not shown) to provide greater portability. Thus, the deployment of the smart mirror 100 may be less constrained by the location of a power source (e.g., a wall outlet) within a particular room. The battery may be various types of rechargeable or disposable batteries including, but not limited to a lithium-ion battery, a nickel cadmium battery, and a nickel metal hydride battery. A rechargeable battery may be charged by connecting the smart mirror 100 to a power source (e.g., connecting an IEC cable to a wall outlet). The smart mirror 100 may also be configured to operate while charging.

The smart mirror 100 may also be turned on or off using a switch 180 disposed on the smart mirror 100. The smart mirror 100 may also be activated or deactivated remotely using another remote control device, such as a computer, a smart phone, or a tablet connected to the smart mirror 100.

FIGS. 15A-17E show several views of an exemplary connector box that may also be incorporated into the smart mirror 100. The connector box may be used to house wiring and wiring ports to connect the smart mirror 100 to an external power source (e.g., via an IEC cable). The connector box may also house wiring between the SMPS 170 and other electronic components in the smart mirror 100. The connector box may be formed of various materials including, but not limited to steel, aluminum, fiberglass, carbon fiber, polyethylene terephthalate glycol (PETG), and plastic.

The smart mirror 100 may also include additional connectors to connect the smart mirror 100 to other devices, such as a smart phone or a tablet. For example, FIG. 3C shows the smart mirror 100 may include a USB connector 310 disposed towards the top of the smart mirror 100. In some applications, this connector may be used to provide a wired connection for software updates, firmware updates, and diagnostic tests of the smart mirror 100. The connector may also be used to transfer power from the smart mirror 100 to another device (e.g., charging a smart phone).

Biometric Devices and the Smart Mirror

A biometric sensor worn by the user may also be communicatively coupled to the smart mirror 100 to provide biometric data of the user during a workout. As described below, the smart mirror 100 may display raw and/or processed biometric data to the user via the display panel 120. This biometric data may be used for subsequent analysis to evaluate the user's overall health and for recommending subsequent workouts to the user. The biometric data may also be used to compare a user's activity level or performance to that of other users. Various types of biometric data may be measured by one or more biometric sensors including, but not limited to a user's heart rate, a user's step count, the motion of the user's various extremities, the user's skin temperature, and the user's perspiration rate. (A user may operate the smart mirror 100 without wearing any biometric sensor, in which case biometric data normally acquired and displayed to the user may be replaced by a blank or a dashed mark on the display panel 120 indicating that no biometric data is being acquired.)

Figure 19:
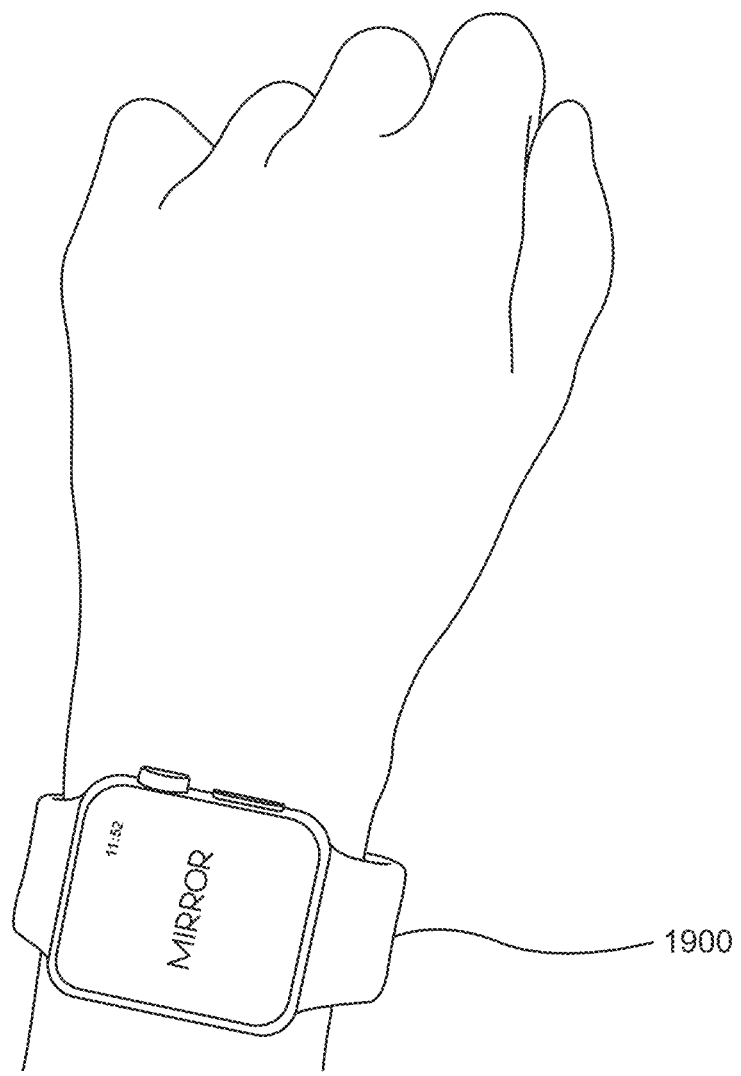
FIG. 19 shows an image of an exemplary biometric sensor worn on a user's wrist, in accordance with some embodiments.
Figure 20:
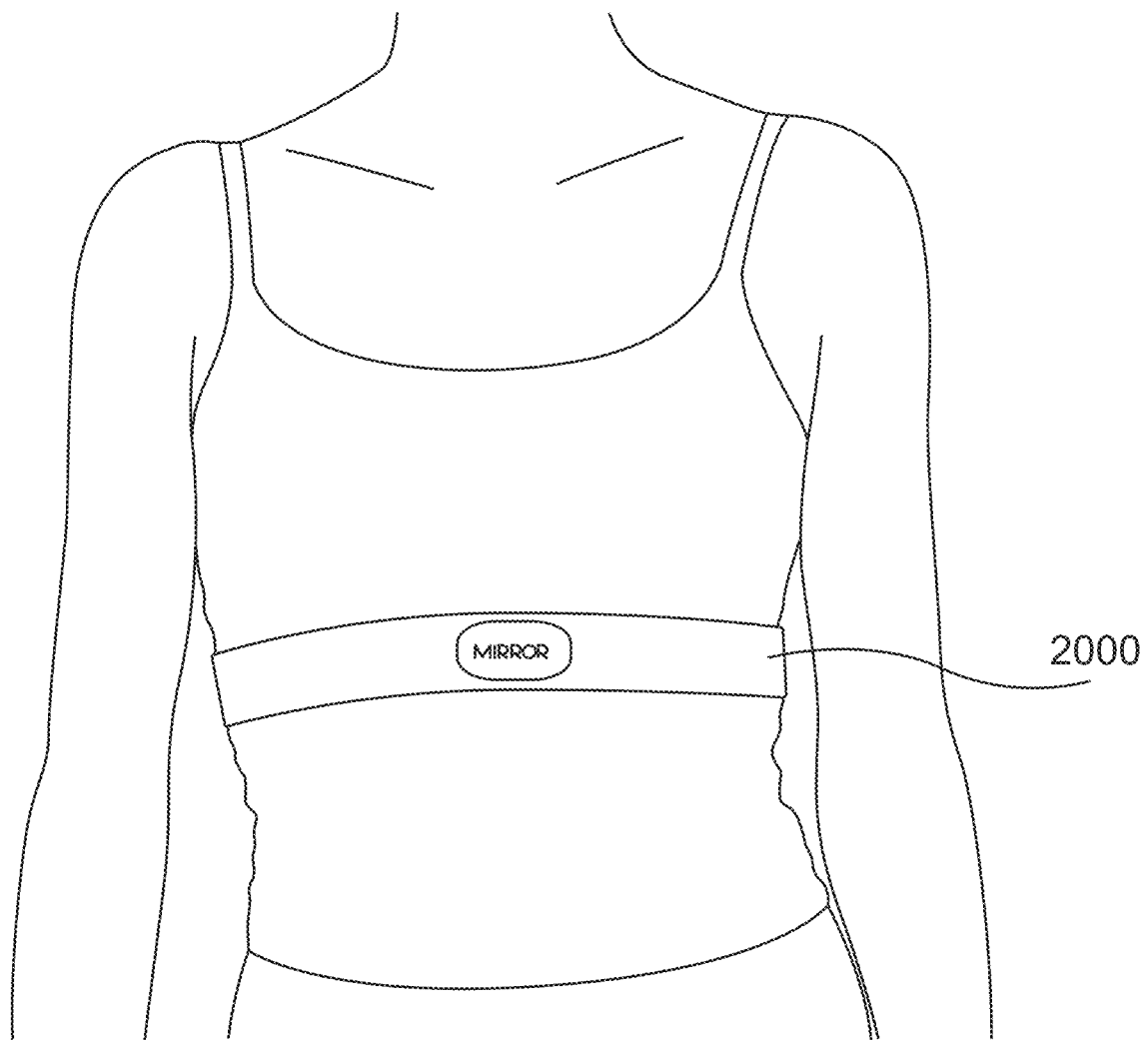
FIG. 20 shows an image of an exemplary biometric sensor worn around a user's ribcage, in accordance with some embodiments.

The biometric sensor may be worn by the user in various ways. For example, FIG. 19 shows the user wearing a biometric sensor 1900 on her wrist. FIG. 20 shows another example of the user wearing a biometric sensor 2000 around her waist. A user may wear multiple biometric sensors, which, in some instances, may be tailored to measure certain biometric data at certain locations on the user's body. Either biometric sensor may be coupled to the smart mirror 100 wirelessly using various communication protocols including, but not limited to Bluetooth, 802.11a, 802.11b, 802.11g, 802.11n, and 802.1 lac, either directly or via a smart phone or wireless router.

Using a Smart Mirror

The smart mirror 100 may be coupled to various devices and controlled, in part, using these devices. For example, the smart mirror 100 may be connected to a smartphone, a smartwatch, a tablet, a dedicated remote for the smart mirror 100, a smart exercise equipment (e.g., a treadmill, an exercise bike, a smart dumbbell), or a personal computer. These devices may be networked and/or a web-enabled and thus used to access various fitness-based features in a software application configured to work with the smart mirror 100 (e.g., an app for a Google Android, an Apple iOS, or Microsoft Windows device).

The smart mirror 100 may also be used without connection to any device. For example, a user may control the smart mirror 100 using voice control via the microphone 160, such as via voice control as explained above. The smart mirror 100 may also be controlled using gesture commands in cases where the camera 130 includes a motion sensing camera or by applying image analysis techniques to video of the user acquired by the camera 130, as explained above with respect to motion and position tracking. For example, user arm movement in a video stream acquired by the camera 130 can be tracked to identify if/when the user makes a predetermined gesture command with their hand, arm, eyes (e.g., eye tracking), and/or the like. The smart mirror 100 may also be controlled using touch commands in cases where the display panel 120 is touch sensitive in full or in part, as described above.

Figure 21:
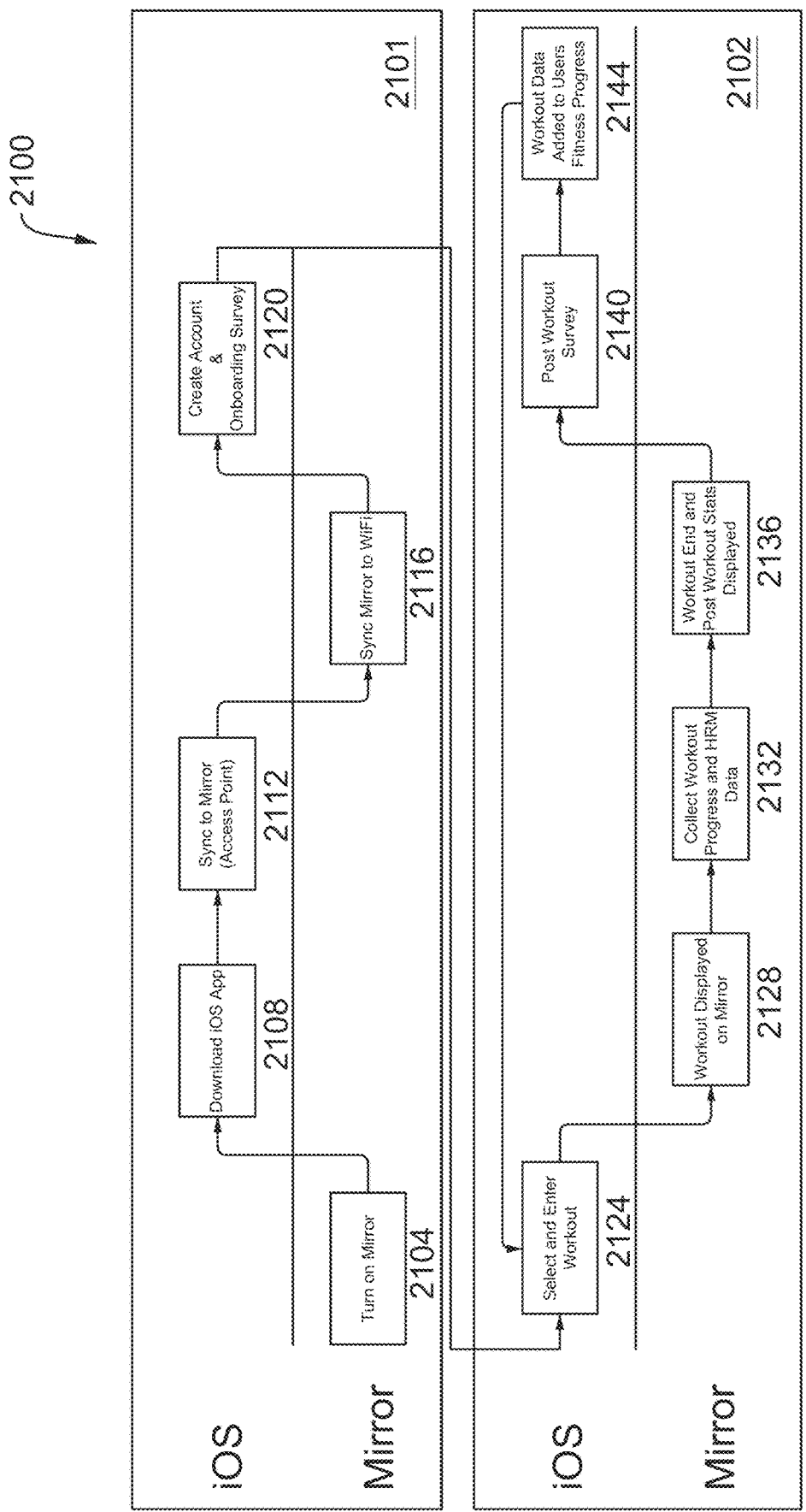
FIG. 21 shows a flowchart of an exemplary method of setting up and a smart mirror in conjunction, in accordance with some embodiments.

FIG. 21 shows an exemplary method 2100 of using the smart mirror 100 generally comprising a setup process 2101 followed by a use process 2102. The setup process 2101 may be comprised of the following steps: (2104) turning on the mirror, (2108) downloading the app on a user's smart device, (2112) syncing the smart device to the smart mirror 100 via an access point, (2116) syncing the smart mirror 100 to a network, and (2120) creating an account and filling out an onboarding survey. The use process 2102 may be comprised of the following steps: (2124) selecting and entering a workout, (2128) displaying the workout on the smart mirror 100, (2132) collecting the workout progress and biometric data from a biometric sensor, (2136) displaying post workout statistics after the workout ends, (2140) posting a workout survey, and (2144) adding the workout data to a user's fitness progress. Following the use process 2102, the smart mirror 100 may include the step of (2148) querying the user to select and enter another workout, which if selected, leads to a repeat of steps (2128) through (2148). The following description elaborates upon the various steps shown in FIG. 21.

Connectivity Between the Smart Mirror and Other Devices

As described above, the smart mirror 100 may be connected to various devices during operation. To maintain operation, the connection between any pair of devices (including the smart mirror 100) should be monitored. The connection between a specific pair of devices may be represented as a "connection state." Thus, multiple connection states may be monitored during use of the smart mirror 100.

Figure 22:
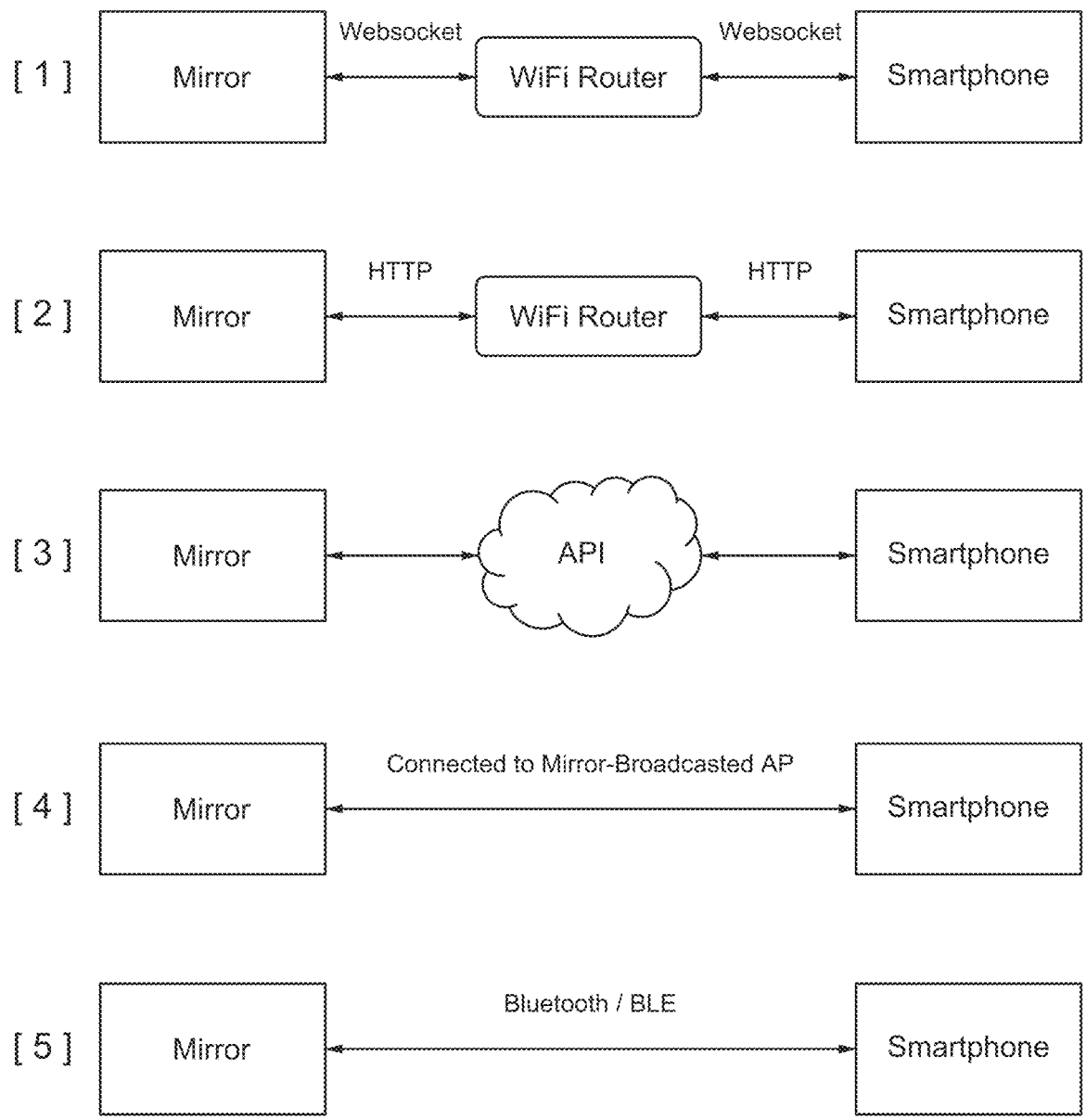
FIG. 22 shows a summary of the various wireless connections used to communicatively couple a smart mirror to a smart device, in accordance with some embodiments.

FIG. 22 shows a partial summary of connectivity options and states between a smart mirror and one or more other devices. These connections include but are not limited to between: (1) a user's smart device (e.g., the client) and the smart mirror 100 (e.g., the server), which may be monitored using a WebSocket protocol and may have values of 'connected' and 'closed'; (2) a user's smart device and a Bluetooth low energy (BTLE) device, which may have values of 'connected' and 'disconnected'; (3) a Bluetooth audio device (e.g., the client) and the smart mirror 100 (e.g., the server), which may have values of 'paired-connected', 'paired-disconnected', and 'unpaired'; (4) a user's smart device and an application programming interface (API) server, which may be in communication via a hypertext transfer protocol (HTTP) where the connection is configured to be on demand with a request/response structure such that data is sent as a request and the server responds with data; (5) the smart mirror 100 and an API server, which may be in communication via HTTP where the connection is configured to be on demand with a request/response structure such that data is sent as a request and the server responds with data; (6) the smart mirror 100 and a streaming service, which may be in communication via a HTTP live streaming (HLS) protocol and may have values of 'connected/streaming', 'buffering', and 'disconnected'; and (7) the smart mirror 100 and a publish/subscribe service, which may be in communication via Websocket and may have values of 'connected' and 'disconnected.'

In the event that one device (e.g., the smart mirror 100, a smart device, a biometric sensor, a server, a network router) is disconnected from another device, a healing process is used to re-establish and maintain connection between the devices (also referred to herein as "device healing"). The healing process should preferably be transparent to the user such that when a connectivity problem arises, the workout is not interrupted.

Generally, a user may connect a smart device (e.g., a smart phone or tablet) to the smart mirror 100 and a biometric sensor (e.g., a heart rate monitor (HRM) via Bluetooth) when installing and/or configuring the smart mirror 100. The user may also connect other devices, such as a Bluetooth audio device (e.g., a speaker or a microphone). The smart mirror 100, biometric sensor, and other accessory devices may be treated as three distinct categories of devices from the perspective of the user's smart device. The smart mirror 100 may automatically determine the points in time and the appropriate length of time for the user's smart device to attempt to connect with the previously paired smart mirror 100 and the Bluetooth devices. This process should preferably be performed without using excessive amounts of the smart device's battery.

Figure 23A:
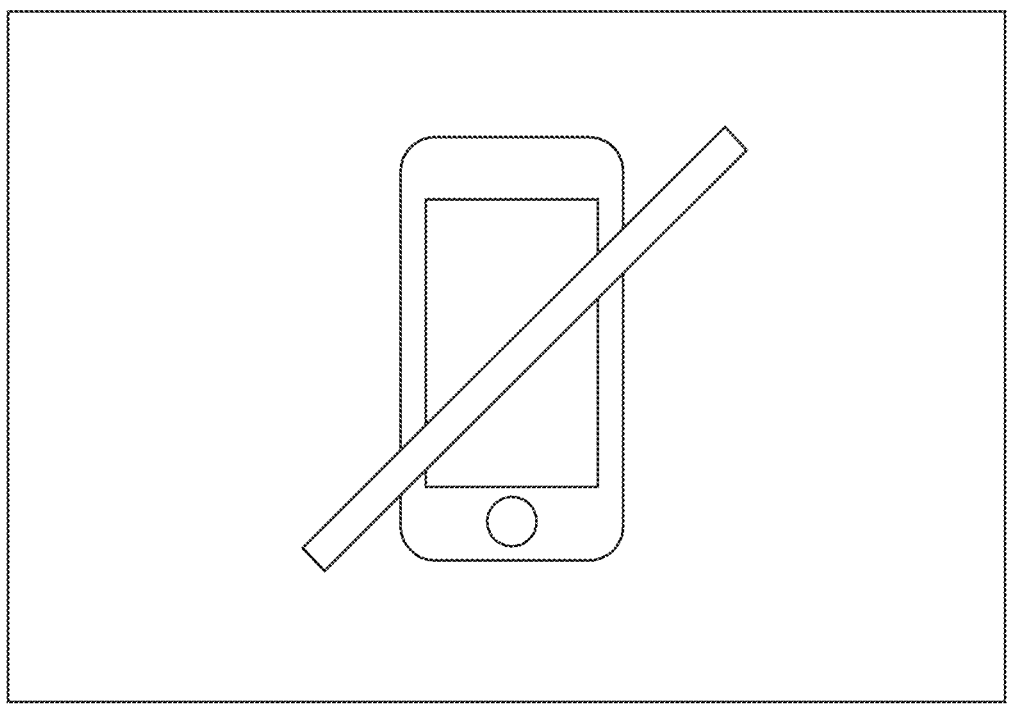
FIG. 23A shows an exemplary icon displayed on the smart mirror to indicate the smart mirror is disconnected from the smart device, in accordance with some embodiments.
Figure 23B:
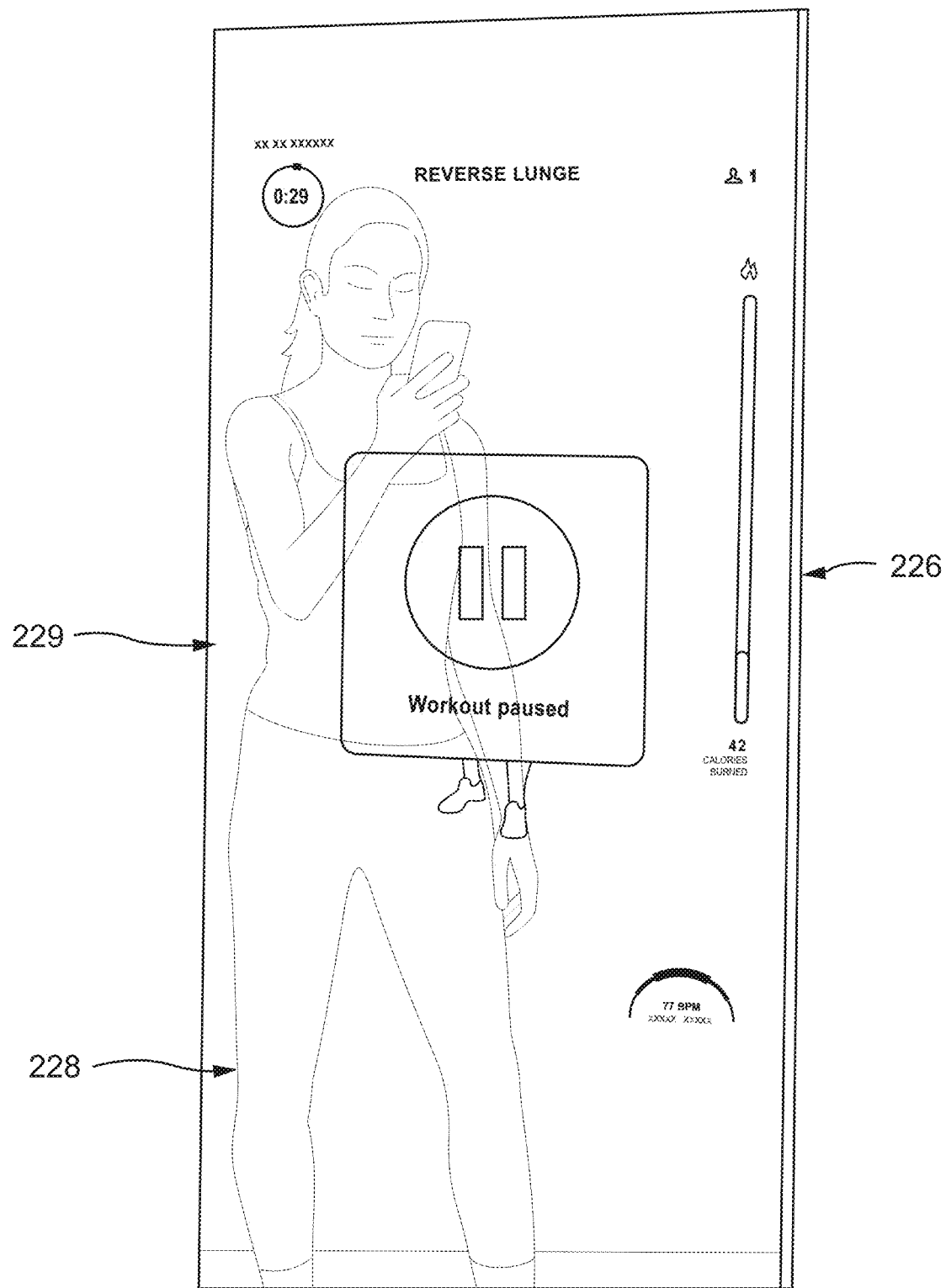
FIG. 23B shows a pause notification displayed on the smart mirror when the application is closed, minimized, or the smart device enters sleep mode, in accordance with some embodiments.

Before a healing process is attempted, the user should pair their smart device to at least one device in a particular category via a "settings" interface on the application installed on the user's smart device. Thus, a healing process should only be attempted when (1) no devices in a particular category are connected and (2) at least one device was previously paired device is present, but disconnected. The display panel 120 of the smart mirror 100 may show an icon when the smart device is disconnected from the smart mirror 100. An exemplary icon is shown in FIG. 23A, which may be displayed at the top right of the smart mirror 100. When the app is closed, minimized, or the smart device enters a sleep mode, the workout may be paused as shown in FIG. 23B.

Figure 24A:
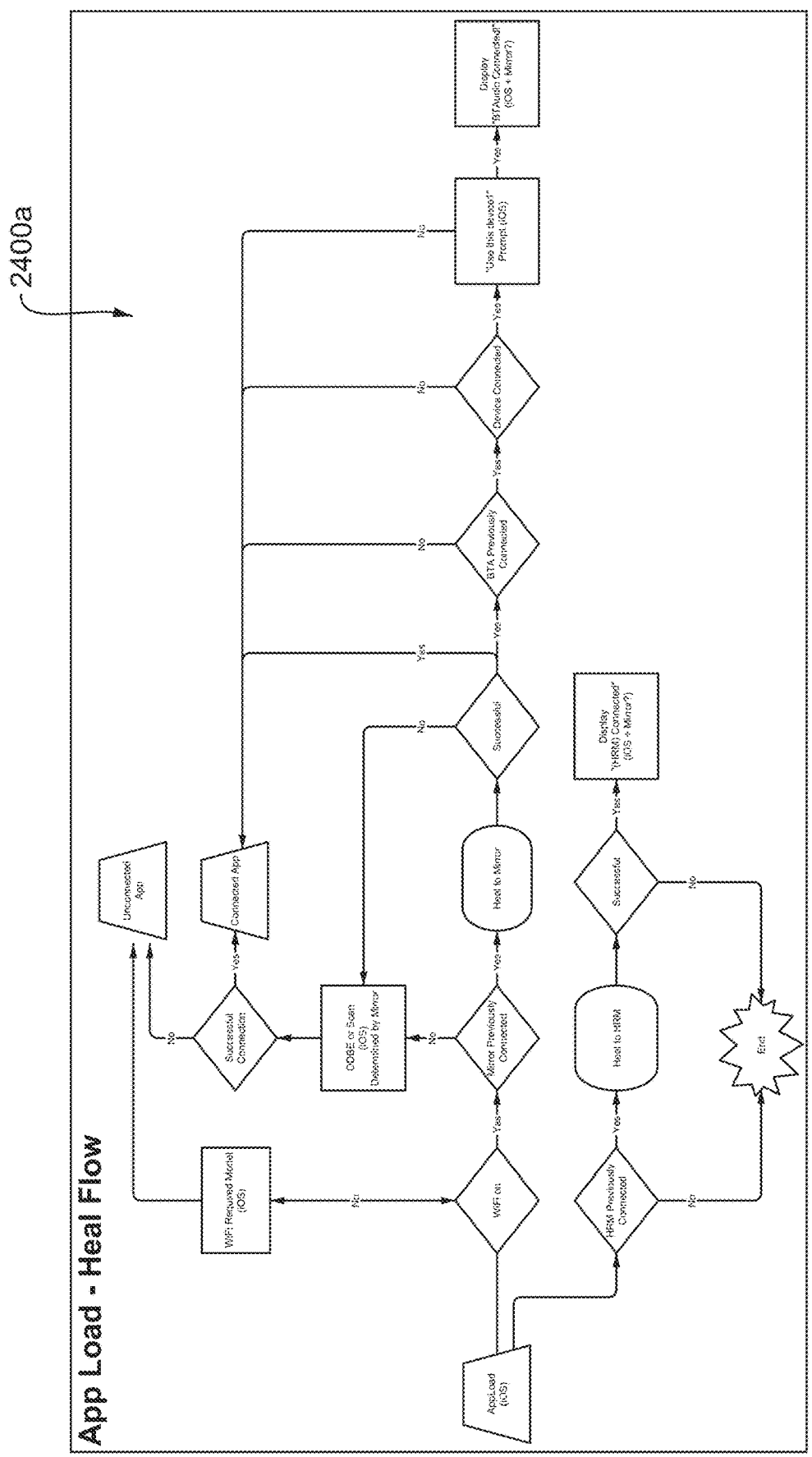
FIG. 24A shows a flowchart of an exemplary healing process when loading the application, in accordance with some embodiments.
Figure 24B:
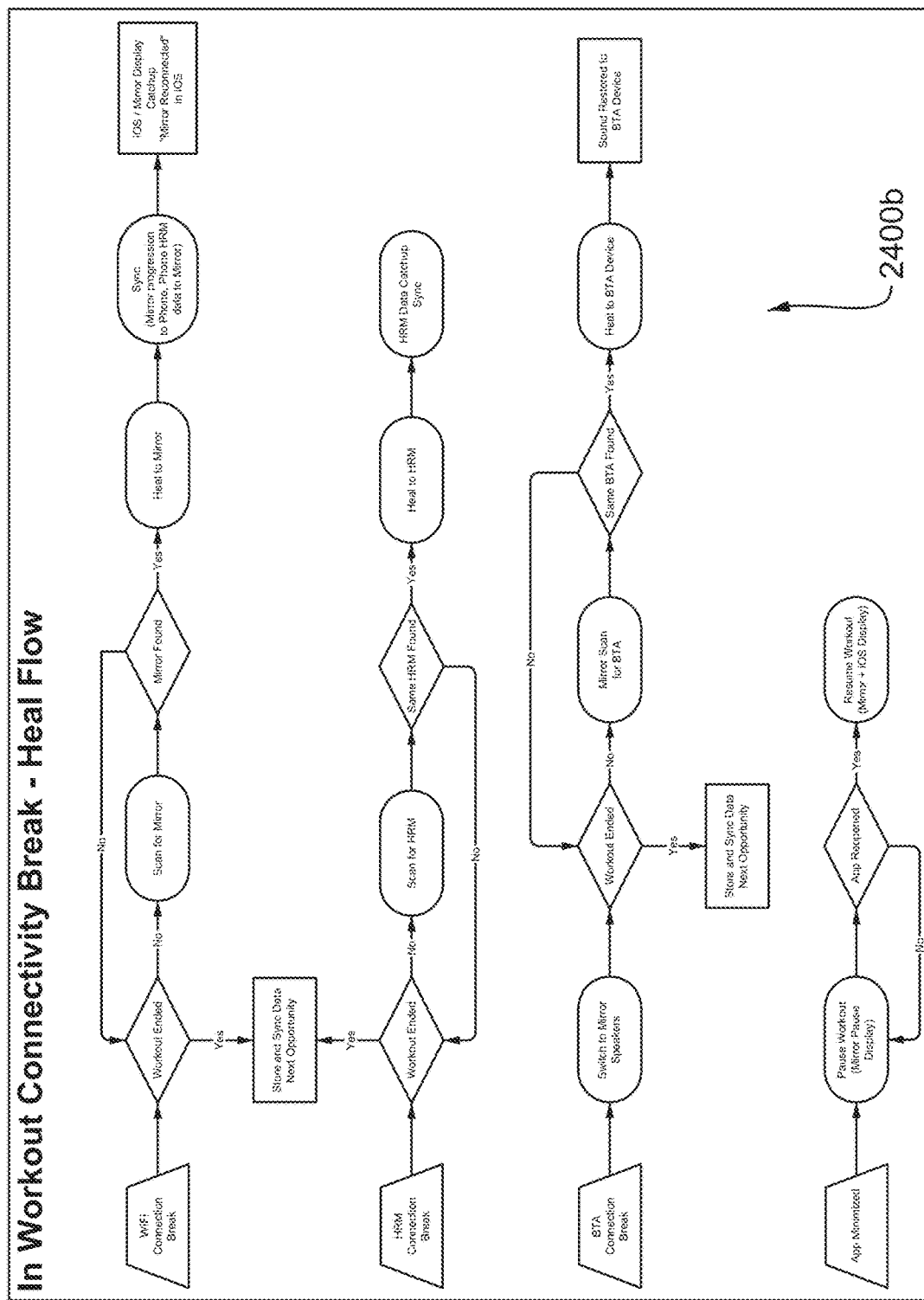
FIG. 24B shows a flowchart of an exemplary healing process when a connectivity break occurs during a workout, in accordance with some embodiments.
Figure 24C:
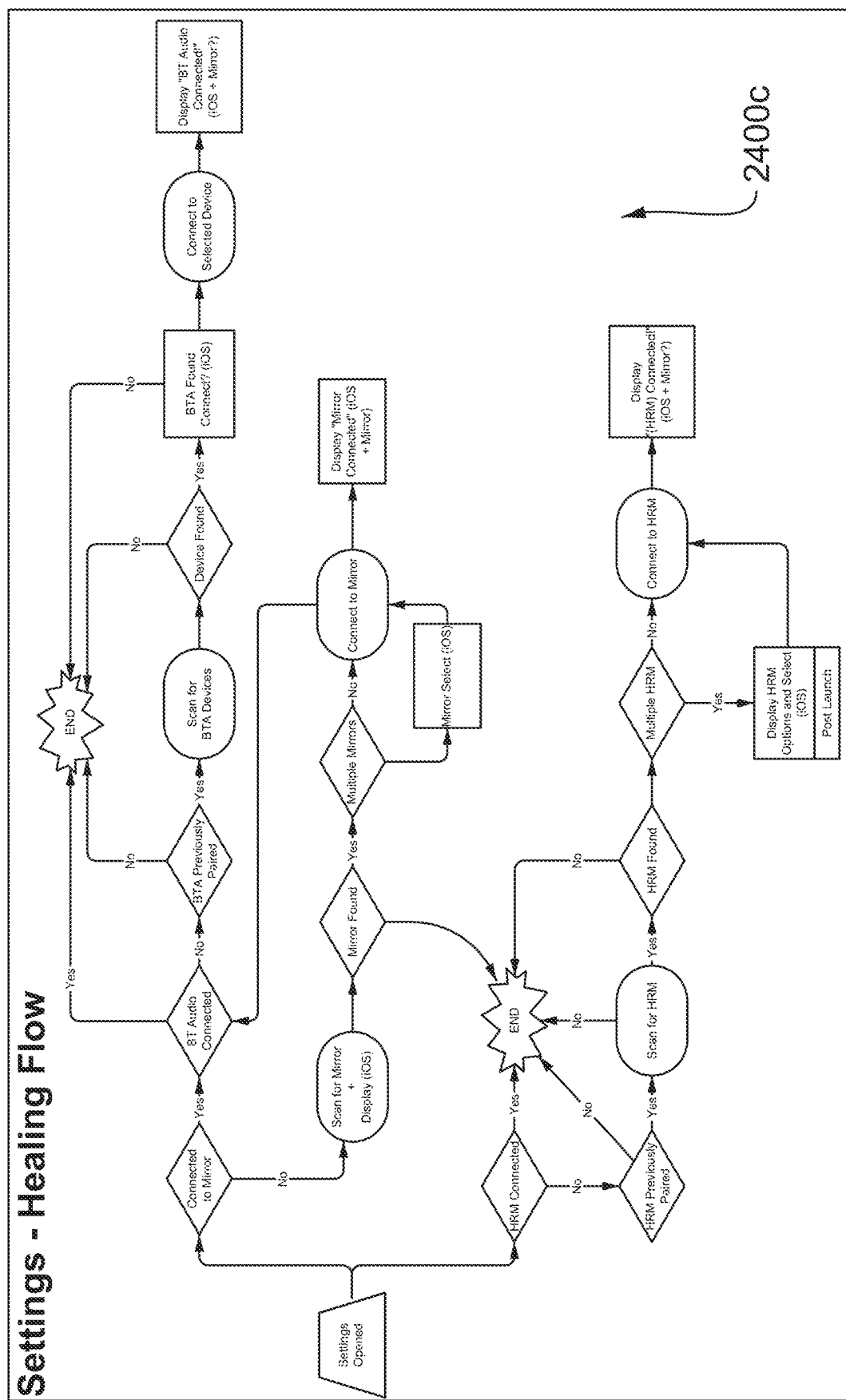
FIG. 24C shows a flowchart of an exemplary healing process when a user accesses the application settings, in accordance with some embodiments.

FIGS. 24A, 24B, and 24C show exemplary healing processes for situations where the user is loading the application on their smart device, a connectivity break occurs during a workout, and a user accesses the application settings, respectively. As shown in FIG. 24A, the healing process 2400a may be configured such that the user's smart device attempts to connect to the smart mirror 100 and any previously paired Bluetooth devices (e.g., a biometric sensor or an audio device). This healing process 2400a may be aborted after a scan time of about 30 seconds followed by a message to the user indicating failure to connect to a device. If the smart mirror 100 and/or other devices are discovered, the user's smart device should automatically connect to these devices. In the event more than one Bluetooth device is found, the healing process 2400a may connect to the most recently found device and/or may allow the user to select between multiple connected devices. The healing process 2400a may be repeated under other conditions, such as when the user is opening a preview of a workout (e.g., Workout Preview) in the application on their smart device. Again, the healing process 2400a may run for about 30 seconds before the connection attempt is aborted.

FIG. 24B shows a healing process 2400b for situations where any one of the devices described above is disconnected from the user's smart device during a workout. For instance, when the user opens "Workout Options," which include several settings for configuring the workout, the healing process 2400b may be performed if a previously paired device other than the smart mirror 100 is no longer connected to the user's smart device. Again, this process may run for about 30 seconds before the connection attempt is aborted. If a user's smart device disconnects from the smart mirror 100 and/or the biometric sensor during a workout, the workout should preferably continue on the smart mirror 100 unless the user is requested to pause the workout. Once the connection state between the user's smart device and the smart mirror 100 and/or the biometric sensor is healed, the timers and workouts on the user's smart device should sync to the smart mirror 100. In this manner, the smart mirror 100 should dictate where the workout user interface and/or the user's smart device should jump to once healing occurs. After the workout is finished, the user's profile should be updated with any relevant workout data regardless of whether a connectivity issue occurred. If a user's smart device disconnects from another device, such as a Bluetooth audio device, the smart mirror 100 should output audio in the interim until the audio device is healed. Again, this process may run for about 30 seconds before the connection attempt is aborted.

FIG. 24C shows a healing process 2400c configured for situations where the user opens the "Settings" interface on the smart device. The healing process 2400c may occur when a previously connected Bluetooth device or the smart mirror 100 is no longer connected. Again, this process may run for about 30 seconds before the connection attempt is aborted.

Data Transfer Using Bluetooth

The smart mirror 100, the user's smart device, and/or other Bluetooth connected devices may transfer data in a serial manner (e.g., from a client to a server, from a server to a client) using various wireless technologies, such as Bluetooth Low Energy. Depending on the wireless technology used, a scheme may be devised for various aspects of data transfer including, but not limited to an initial connection setup, chunking of messages for transfer, message reassembly, and connection teardown. In the case where Bluetooth Low Energy is used, the scheme may be used with or without Bluetooth Low Energy security features.

Figure 25:
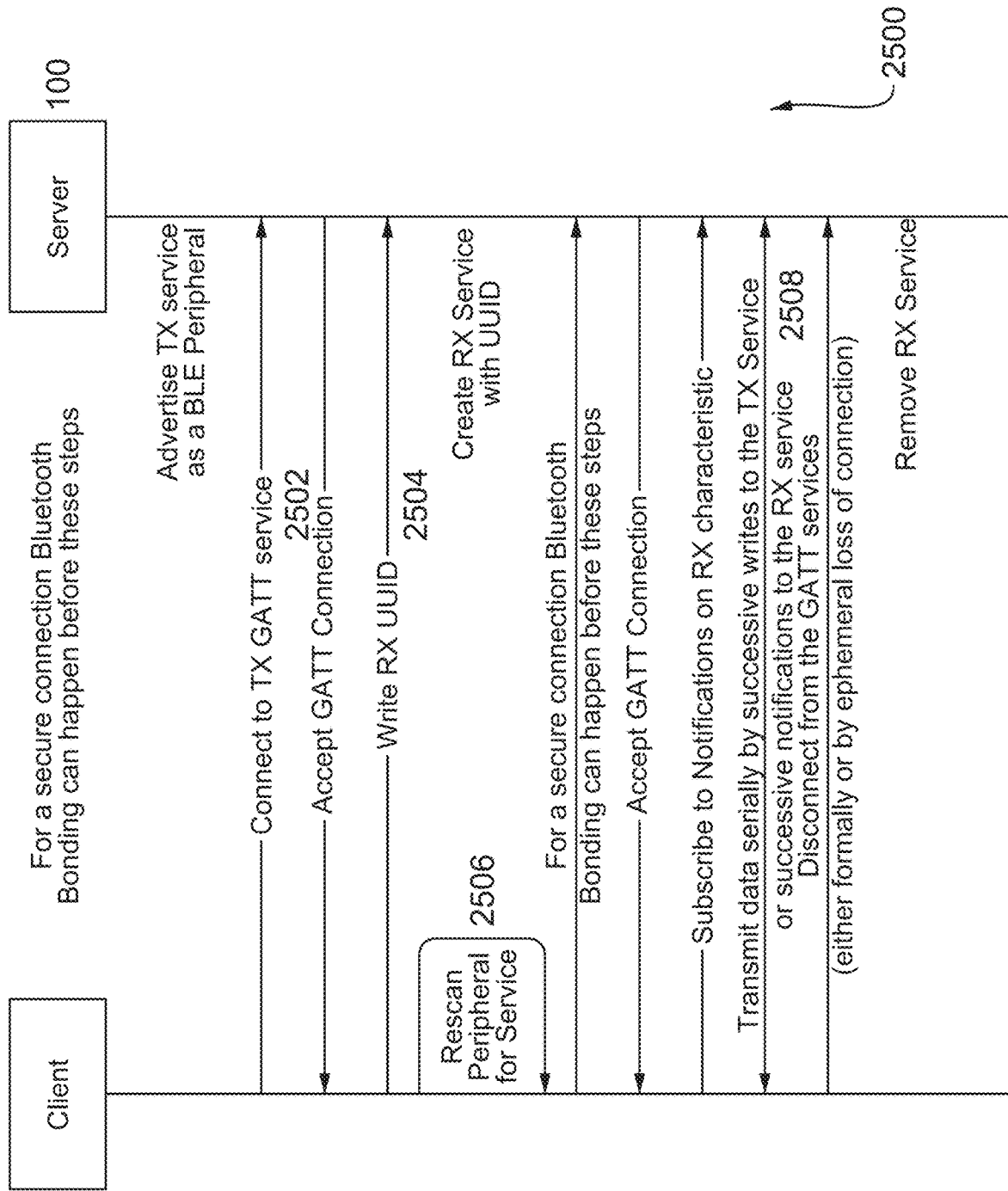
FIG. 25 shows a flowchart diagram describing how the smart mirror is communicatively coupled to another device via a Bluetooth Low Energy connection, in accordance with some embodiments.

FIG. 25 shows an exemplary process 2500 to connect and transfer data over Bluetooth Low Energy. Bluetooth Low Energy was included to enable for low energy transfer of finite amounts of data. Many data profiles are ubiquitously supported by major implementations, but these data profiles typically do not support the transfer of stream data. Generally, stream data is sent over a SPP (Serial Port Profile) connection, but in some situations these connections may be unsupported by the device manufacturer and/or may only be allowed by the device manufacturer under specific use cases due to excess consumption of power, which limits the use of such connections for practical use. Instead, the smart mirror 100 may use Bluetooth Low Energy using Generic Attributes (GATT) characteristics as the client-server communication protocol. The server may accept connections from multiple devices simultaneously. The communication of messages larger than what the hardware can support may still be sent using a data-chunking process built into the protocol, allowing a theoretically unlimited message size.

The initial connection setup may start with the server (e.g., the smart mirror 100) advertising as a Bluetooth Low Energy peripheral. The server may advertise a GATT service with a single GATT write characteristic. Clients scanning for peripherals (e.g., a user's smart device) may locate and connect to the available GATT service if the client is within range of the server (2502). For Bluetooth Low Energy in particular, a client connected to the server may be identified by its media access control (MAC) address either (1) ephemerally without bonding where the MAC address is intentionally modified for security purposes or (2) concretely with bonding where a returning client resolves to the same unique MAC address. The client may be responsible for ensuring that the first data written into the characteristic after connection is a 128-bit unique user identification (UUID) in common readable form, base-10 representation separated into sections by dashes with 8, 4, 4, 4, and 12 digits respectively (2504). Upon a successful write of the UUID, the server may advertise another GATT service with the written UUID as its identifier and a single GATT read characteristic set up to allow notifications. The client may rescan the server's GATT services and complete the connection by subscribing to notifications on the read characteristic (2506).

Once a connection is established between the client and the server, data may be sent in both directions (i.e., from the client to the server, from the server to client) using a simple chunking scheme (2508). The data exchange may include protocol agnostic raw data thus allowing an application developer to set up their own messaging over the available connection. To accomplish chunking, each full message is split into parts that fit within the Bluetooth Low Energy Minimum Transfer Unit (MTU) size, which is determined by the Bluetooth Low Energy connection setup and the platform being used.

The chunking process works as follows: (1) the length of the message to be sent is computed in units of bytes, (2) a preamble of a fixed byte length that denotes the size of the total message is prepended to the original message, (3) the message with the preamble prepended is split into chunks such that they fit within the MTU, (4a) in the case of client to server messaging, the chunks may be written sequentially into the servers write characteristic, with confirmation as per the Bluetooth Low Energy specification, (4b) in the case of server to client messaging, the chunks may be written sequentially into the servers read characteristic for the intended recipient, triggering a notification on the client as per the Bluetooth Low Energy specification, (5) the recipient (i.e., the server or the client) may read the preamble from the first chunk to determine the length of the following message, (6) the recipient may fill a buffer with data from successive chunks until the expected number of bytes is received, and (7) the message may then be parsed/decoded as needed followed by the recipient continuing to listen for the next preamble.

Connectivity Using a HostAP Mode

In some configurations, the smart mirror 100 may be configured to use a HostAP mode (also referred to in the art as the "Chromecast mode" due to use in the Google Chromecast device), which is a method of setting up an Internet of things (IoT) device where the IoT device acts as an access point for other devices using the same interface as a standard wireless router. The HostAP mode may provide several benefits: (1) uses well known and field tested/proven methodologies, (2) allows application code to support one path for messaging, (3) prevents the use of other interfaces (i.e., there is no need to use Bluetooth or near-field communication (NFC)), and (4) allows the application layer to use multicast Domain Name Systems (mDNS) to discover devices on the network instead of other approaches such as Bluetooth scanning, which is typically slow and error prone.

Depending on the operating system of the smart device, a user may manually change the device's settings to connect to the IoT network. For example, a user using a smart device with an iOS operating system, such as an iPhone or an iPad, should go to the settings of their device to connect to the IoT devices network for initial setup and/or error recovery when the network goes out.

Figure 26A:
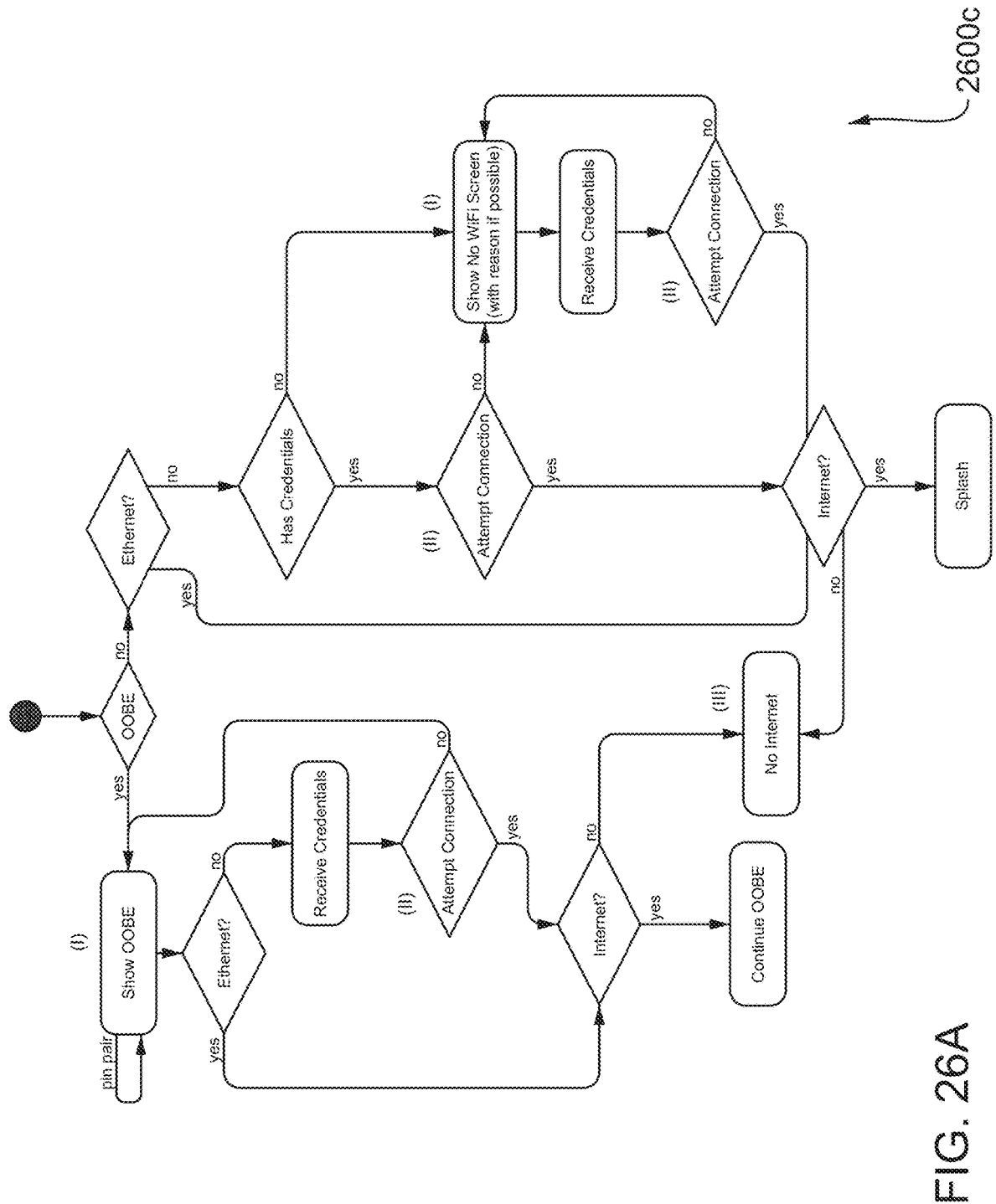
FIG. 26A shows a flowchart describing an exemplary method of using a smart mirror with a HostAP mode, in accordance with some embodiments.
Figure 26B:
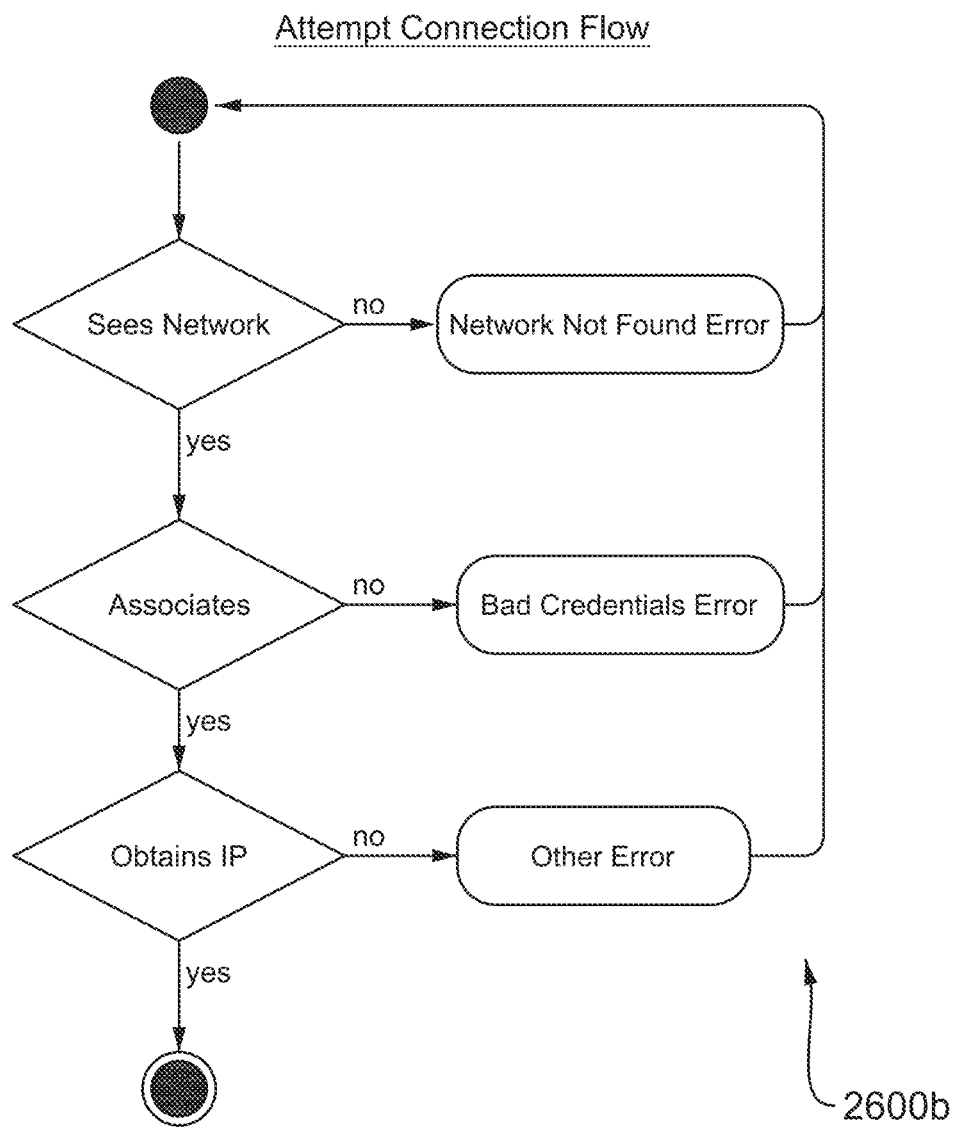
FIG. 26B shows a flowchart for the 'Attempt Connection' process of FIG. 26A.
Figure 26C:
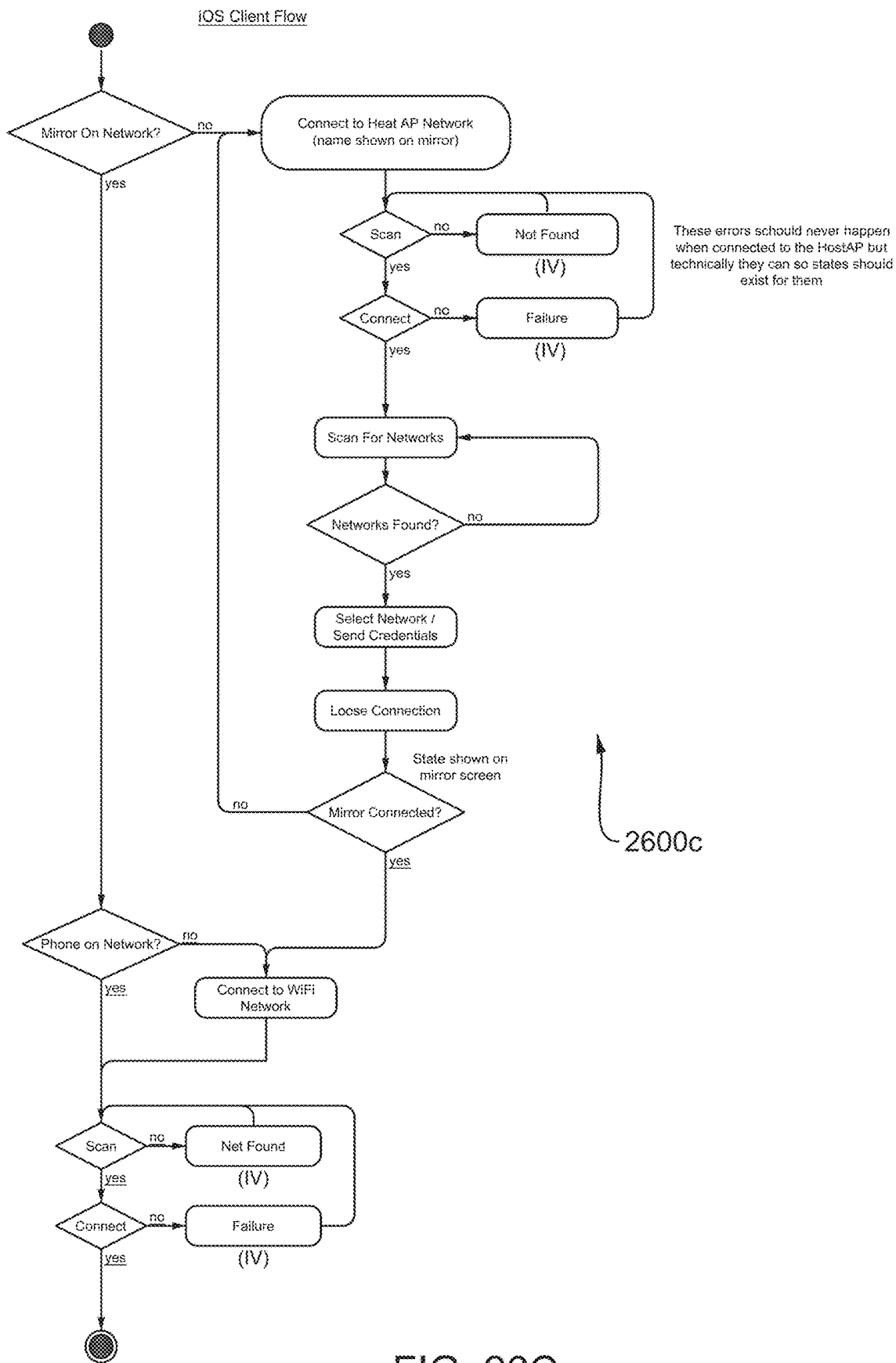
FIG. 26C shows a flowchart describing an exemplary method of connecting a device with an iOS operating system to the smart mirror and/or setting up a network connection, in accordance with some embodiments.

The smart mirror 100 may also be configured to operate the HostAP/mDNS mode. FIGS. 26A-26C show exemplary flow charts of the smart mirror 100 integrating the HostAP/mDNS functionality. Specifically, FIG. 26A shows a process 2600a describing the various states of operation for the smart mirror 100 and the applicable actions for each state. State (I) represents the smart mirror 100 broadcasting its HostAP network. State (II) represents the 'Attempt Connection Flow' process 2600b, which is depicted in FIG. 26B. If the smart mirror 100 loses connection to the local network over Ethernet or Wi-Fi, the network issue and/or setup prompt screen should be displayed on the display panel 120 of the smart mirror 100. State (III) represents the smart mirror 100 being connected to the network (Ethernet or Wi-Fi) with no internet access, which is shown to the user in the form of a message. In this case, the message may be a full screen blocker on the smart mirror 100. Additionally, if an unknown client device (e.g., a new user id since the smart mirror 100 was installed and configured) connects to the smart mirror 100, the unknown client device should be pin-paired to the smart mirror 100 first.

FIG. 26C shows a process 2600c for a smart device running the iOS operating system to connect to the smart mirror 100 and/or to setup a network connection. The various states of operation and the applicable actions for each state are shown. In particular, state (IV) represents recoverable error state. As shown, the error states are unlikely to occur while the smart device is connected to the smart mirror's HostAP, but a user interface/contingency process may be included in the event such a failure does occur.

Live Streaming Content

As described above, the smart mirror 100 is configured to show video content on the display panel 120 from a studio (e.g., a fitness studio, a classroom). The video content may be streamed as live content or as on-demand content. For example, live content may be recorded and stored on a central repository such that users may later request and play the video content, hence becoming on-demand content. For example, after the video content is recorded, the video files may be uploaded to Amazon's S3 storage and transcoded into moving pictures experts' group dynamic adaptive streaming over HTTP (MPEG-DASH) files. This enables rebroadcast of high-quality, adaptive streaming video to the smart mirror 100. The smart mirror 100 may also be configured to receive and/or have access to multiple live streams that are broadcast simultaneously from multiple studios and/or sound stages. A user may thus have access to multiple live streams and through the user interface, may browse and/or select the desired live stream. In some configurations, the smart mirror 100 may use the Google Android operating system and may thus have access to the Android Exoplayer library to connect the smart mirror 100 to HTTP live stream (HLS) streams for a user to view a live workout. The live-streaming content may also be set to be publicly viewable and/or accessible or private (limited to select individuals).

In some applications, the smart mirror 100 may be connected to an online streaming service that provides users with third-party video content streamed from a server (e.g., directly through a network router or indirectly through a user's smart device). Third party content may be provided to users on a subscription basis. The third party may provide content to a centralized distribution platform, which communicates with the smart mirror 100 over a network. One benefit of a centralized distribution platform is that the distribution of content to the smart mirror 100 is simpler. Alternatively, the third party may develop a separate distribution platform, which may use separate software applications on the smart device for users to access content.

The smart mirror 100 may be configured to provide video content in accordance to industry-accepted standards, particularly when handling variations in network bandwidth. For video streaming, the smart mirror 100 may adhere to the HLS authoring specification, which specifies conditions for changing the video stream quality in real-time to adapt to a user's network bandwidth. For on-demand video content and encore workouts, the smart mirror 100 may adhere to the MPEG-DASH specification, which also provides conditions for changing video quality in real-time to adapt to a user's bandwidth. For non-video related functionalities, the smart mirror 100 may be configured to operate in accordance to industry-standard mobile development methods, including, but not limited to HTTP request retry logic and user interface (UI)/user experience (UX) prompts to the user that handle various network connectivity and latency issues.

Data Storage and Privacy

The smart mirror 100 may also store user information locally on the smart mirror 100 and/or a remote storage device (e.g., a cloud service) depending on the amount of storage space used. For example, user information that uses little storage space may be stored locally on the smart mirror 100, including but not limited to the user's name, age, height, weight, and gender. Additionally, video content (e.g., a fitness routine) may also be stored the smart mirror 100 to reduce the impact of network latency, which may affect the video streaming quality. This amount of video content stored may be limited by the storage capacity of the smart mirror 100. In some configurations, the video content may only be stored temporarily on a daily or weekly basis or depending on the percentage of the smart mirror's capacity being used. User information that uses a substantial amount of storage space may be stored on a remote storage device including, but not limited to biometric data, such as the user's heart rate and breathing rate and video recordings of the user captured during a workout. The smart mirror 100 may retrieve this information for subsequent analysis and display.

The transfer of data between the smart mirror 100 and a remote storage device may be secured (e.g., encrypted) in various ways to prevent unwanted loss or theft of user information. For example, the Bluetooth Low Energy protocol includes built-in security features that may be used by devices leveraging this protocol. However, these security features may only be used when a Bluetooth bonding step is completed before establishing a connection with encryption. In some cases, various security mechanisms may not be implemented or may malfunction, at which point application level security may be implemented in combination with the chunking specification of data described above. For example, Advanced Encryption Standard (AES) encryption of the message may be applied before prepending the preamble of a message. In some respects, the Bluetooth Low Energy protocol performs a similar process via built-in security features at a firmware level and may provide similar protection against a person from reading the communications between a client and a server.

When a client disconnects from a server, the GATT service added for the client to read/notify messages may be removed from the service record on the server's device. This ensures that no connections are left open and the system does not accidentally leak information to nefarious snoopers. This termination of the connection may be triggered by either the server or the client and relies on the Bluetooth Low Energy stack to provide a notification to both sides that the connection has closed. If Bluetooth bonding was used in the initial connection setup to provide firmware level encryption security, the bond information may be stored on each device such that bonding does not need to be repeated following subsequent connections between the client and the server.

A User Interface for the Smart Mirror

A user may control the smart mirror 100 using a smart phone or tablet or by interfacing directly with the smart mirror 100 (e.g., a voice control command, a gesture command via the camera 130, a touch command via the display panel 120). A graphical user interface (GUI) may be provided to facilitate user interaction with the smart mirror 100. The GUI may be adapted to conform to different user inputs dependent on the manner in which a user interfaces with the smart mirror 100. For example, a GUI on a user's smart phone may allow the user to change settings of the smart mirror 100, select/browse various fitness classes, and/or change settings during a workout.

Figure 27:
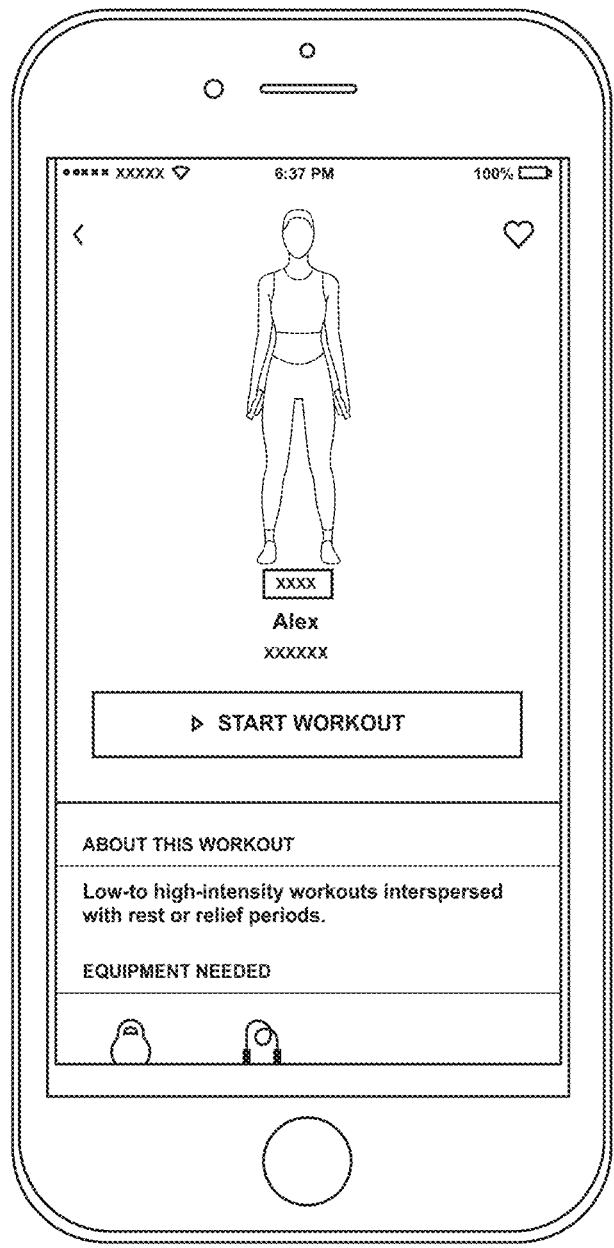
FIG. 27 shows an exemplary graphical user interface (GUI) on a smart phone, in accordance with some embodiments.

FIG. 27 shows an exemplary GUI displayed on a user's smartphone. The GUI may support touch commands and may be designed to accommodate the size of the display on the user's smart phone. In another example, a GUI on a user's computer may provide a more conventional user interface that relies upon inputs from a keyboard and/or a mouse. In yet another example, a GUI on the smart mirror 100 may provide voice or gesture prompts to facilitate user-provided voice commands and gesture commands, respectively. The GUI for the smart mirror 100 may be adapted to support multiple types of user inputs (e.g., a controller, a remote, a voice command, a user command).

The following description provides several exemplary GUI-related features to facilitate user interaction with the smart mirror 100. These GUI-related features are categorized according to the following categories: settings, browsing and selecting a class, class interface, social networking, and background processes. These categories are used merely for illustrative purposes and that certain features may be applied under several situations that may fall under multiple categories and/or use cases. One or more of these features may be adapted and/or modified to accommodate certain user input types. The GUI may extend to multiple devices including, but not limited to the smart mirror 100, a smart phone, a tablet, a computer, and a remote control.

Smart Mirror Settings

Figure 28A:
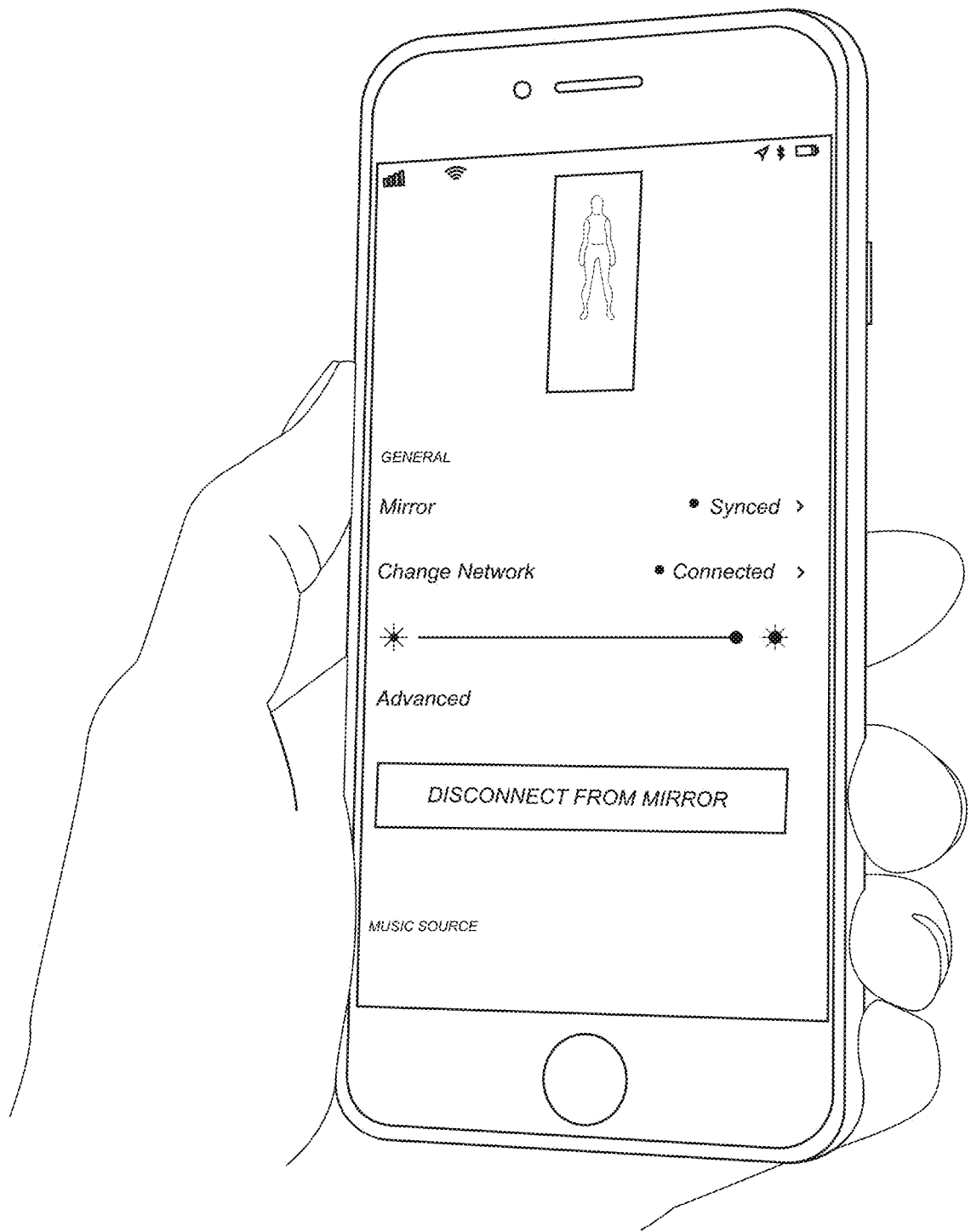
FIG. 28A shows an exemplary GUI on the smart device to control connectivity of a smart device to a smart mirror and/or a network connection, in accordance with some embodiments.
Figure 28B:
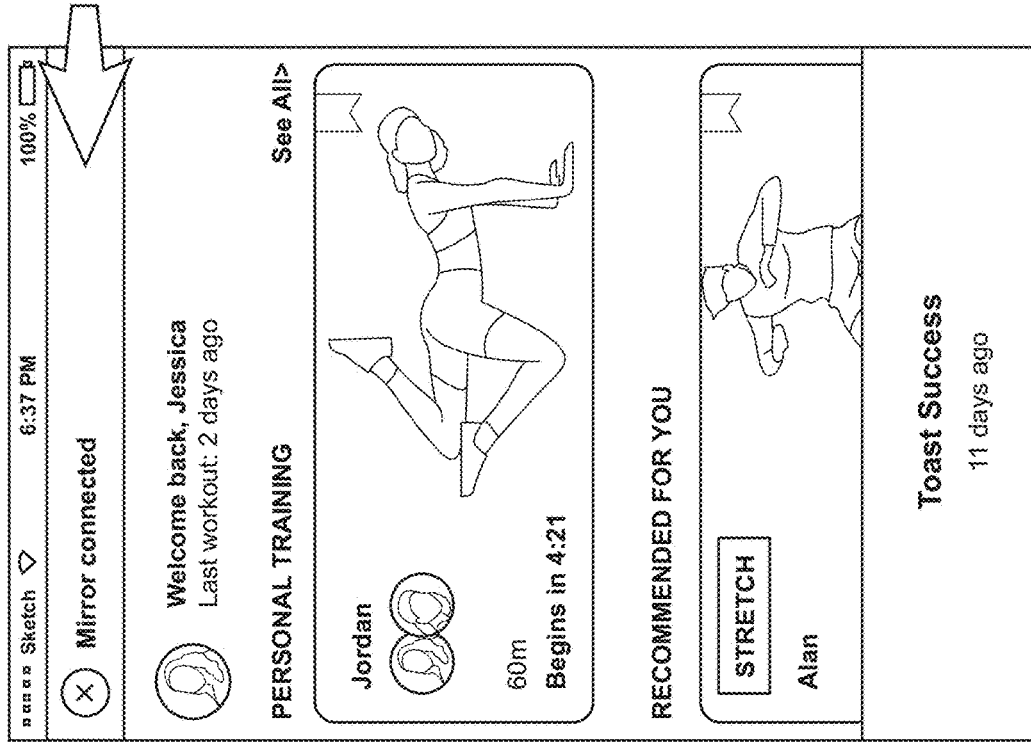
FIG. 28B show an exemplary GUI on the smart device showing notifications whether the smart mirror is connected to the smart device, in accordance with some embodiments.
Figure 28B:
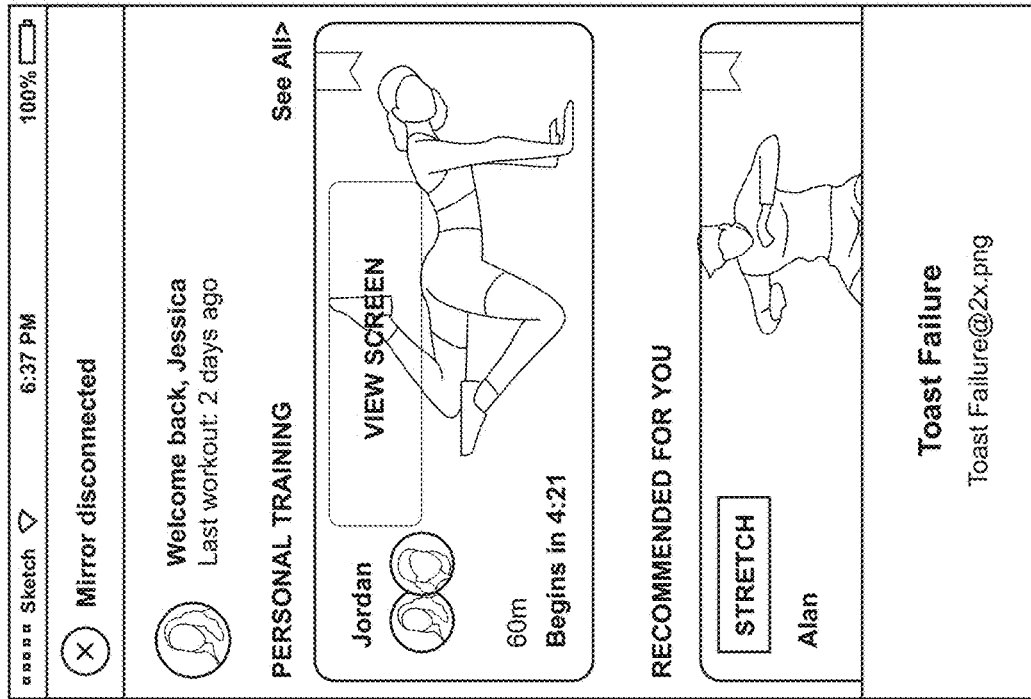

The GUI may allow the user to modify and choose various settings related to the operation of the smart mirror 100. For example, the GUI may be used to initially setup a connection between a user's smart device and the smart mirror 100 (or the smart mirror 100 and a network). FIG. 28A shows an exemplary GUI screen used to sync a user's smart phone to the smart mirror 100 and to connect the smart phone and/or smart mirror 100 to a network. As shown in FIG. 28A, the GUI may indicate the status of the connection of the smart phone and the smart mirror 100 under a settings screen. FIG. 28B shows the GUI may also show the connection status of the smart mirror 100 and brightness of the smart mirror display 120 while using the GUI to navigate and browse for content. Additionally, the GUI may provide prompts to instruct the user the steps to connect the user's smart device to the smart mirror 100. Generally, the GUI may enable the user to manage the connectivity between the smart mirror 100, the user's smart device, a network router, and any peripheral devices (e.g., a biometric sensor or a Bluetooth audio device).

The GUI may also enable the user to create a user account when first using the smart mirror 100. The user account may be used, in part, to manage and store user information including, but not limited to the user's name, age, gender, weight, height, fitness goals, injury history, location, workout history, social network blog, contact list, group memberships, ratings/reviews of fitness classes, and leaderboard scores. The user account may also be used to store user preferences and account settings. In this manner, the user's information may be stored remotely (e.g., on a server or a cloud service), reducing the risk of accidental data loss due to failure of the user's smart device or the smart mirror 100. The GUI may be configured to have the user log into their account before using the smart mirror 100. The user information may be stored without creation of a user account. For example, the user information may be stored locally on the user's smart device or the smart mirror 100. Depending on the user's settings, the user information may be shared with other users and/or instructors without the use of a user account.

The GUI may further include several settings to customize the smart mirror 100 based on the user's preferences. For example, the brightness, contrast, and color temperature (e.g., a warmer hue, a cooler hue) of the display panel 120 of the smart mirror 100 may be manually changed in the GUI. In some cases, these display parameters may be adjusted automatically depending on ambient lighting conditions and/or user preferences. For example, the smart mirror 100 may include an ambient light sensor that monitors ambient lighting conditions, which may be used to adjust the display parameters according to a particular criteria. For instance, the smart mirror 100 may adjust the display's brightness, contrast, color balance, and/or hue, e.g., for increasing visibility of the video content in bright ambient light or decreasing blue/green light to reduce eye fatigue and/or disruptions to sleep quality during evening hours.

Figure 28C:
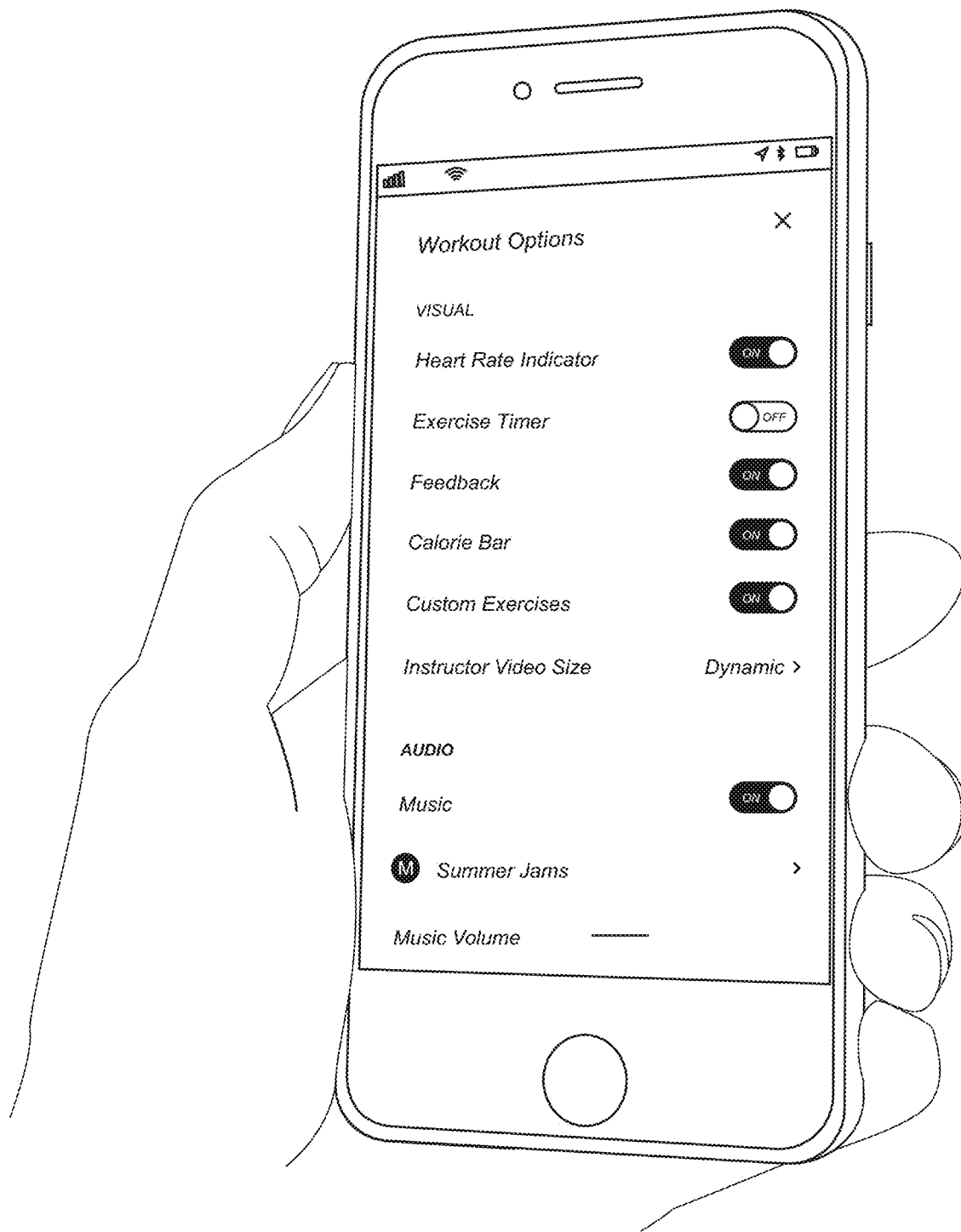
FIG. 28C shows an exemplary GUI on the smart device to customize the user interface of the smart mirror and/or the smart device, in accordance with some embodiments.

The GUI may enable the user to change the user interface (UI) layout. For example, the GUI may enable the user to toggle the display of various items during a workout including, but not limited to various biometric data (e.g., heart rate, step count, etc.), an exercise timer, a feedback survey for a fitness class or each exercise, and a calorie bar (indicating number of calories burned). Some of these options are shown in the exemplary GUI of FIG. 28C. Additionally, the GUI may enable the user to change the color or theme of the UI including a different background image, font style, and font size. The layout of the GUI during a workout may also be modified. For example, the size of the video content (e.g., the size of the instructor shown on the display panel 120) may be changed based on user preferences. In some cases, the size of the instructor may also be dynamically varied, in part, to accommodate exercises captured at different viewing angles and/or different levels of magnification.

The GUI may also include options for the user to change their privacy settings. For example, the user may select the type of information and/or content that is shared with other users. The privacy settings may allow users to set the level of privacy (e.g., the public, the group, the subgroup, designated contacts, or the user themselves may have access) for different information and/or content. The privacy settings may also include what type of information may be stored remotely (e.g., on a server, a cloud service) or locally on the user's smart device or the smart mirror 100.

The GUI may also allow the user to adjust various audio settings on the smart mirror 100 (and/or a speaker peripheral connected to the smart mirror 100/the user's smart device). The audio settings may include, but is not limited to the volume of music, the volume of an instructor's voice, the volume of another user's voice, and the volume of sound effects. Additionally, the GUI may allow the user to select language options (e.g., text and audio) and to display subtitles or captions during a workout. The GUI may also allow the user to configure a prerecorded voice, which may be used to provide narration, instruction, or prompts. The gender, tone, and style of the prerecorded voice may be adjusted by the user via the GUI.

Figure 28D:
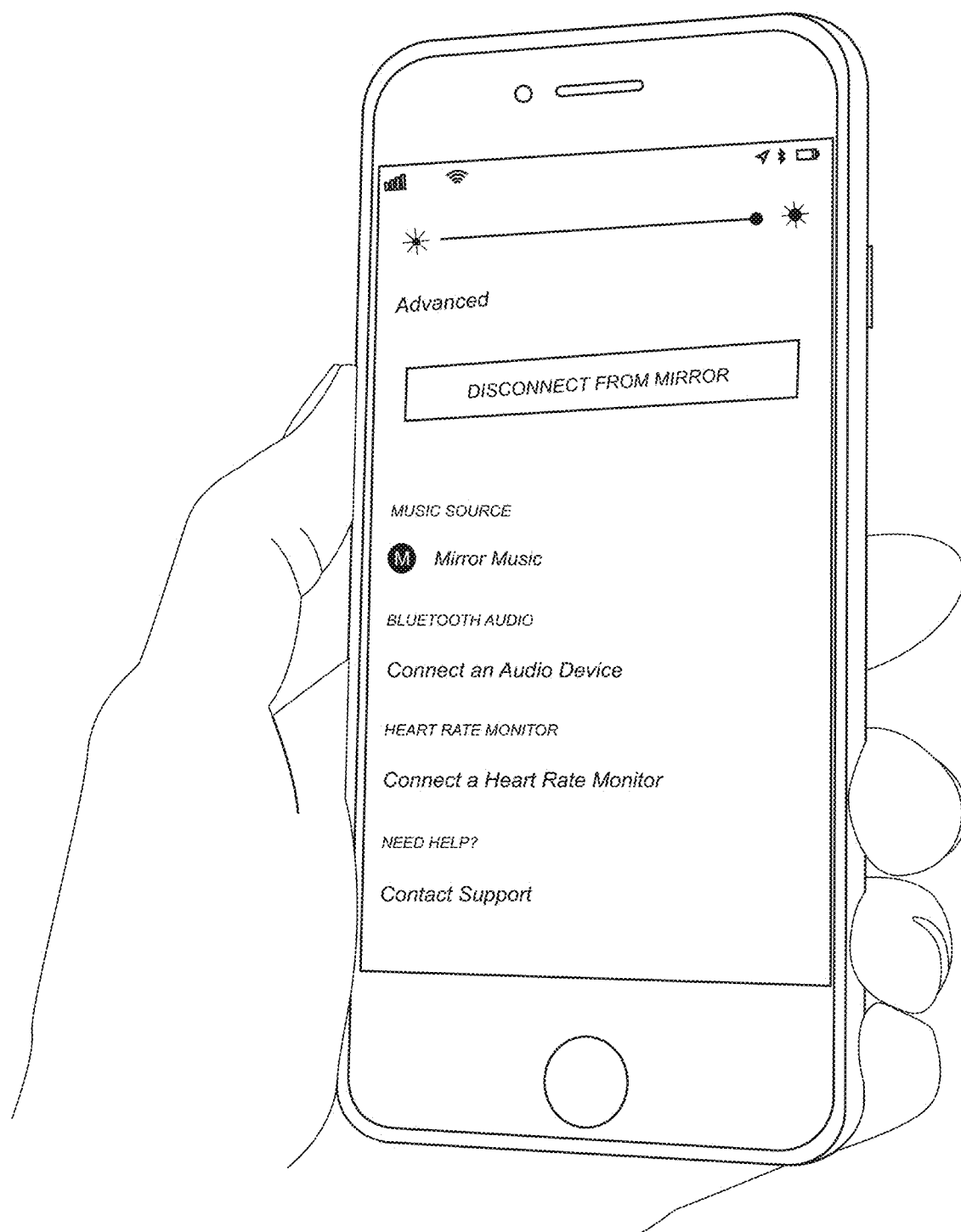
FIG. 28D shows an exemplary GUI on the smart device to manage connection of the smart device to various peripheral device such as an audio device or a biometric sensor, in accordance with some embodiments.
Figure 28E:
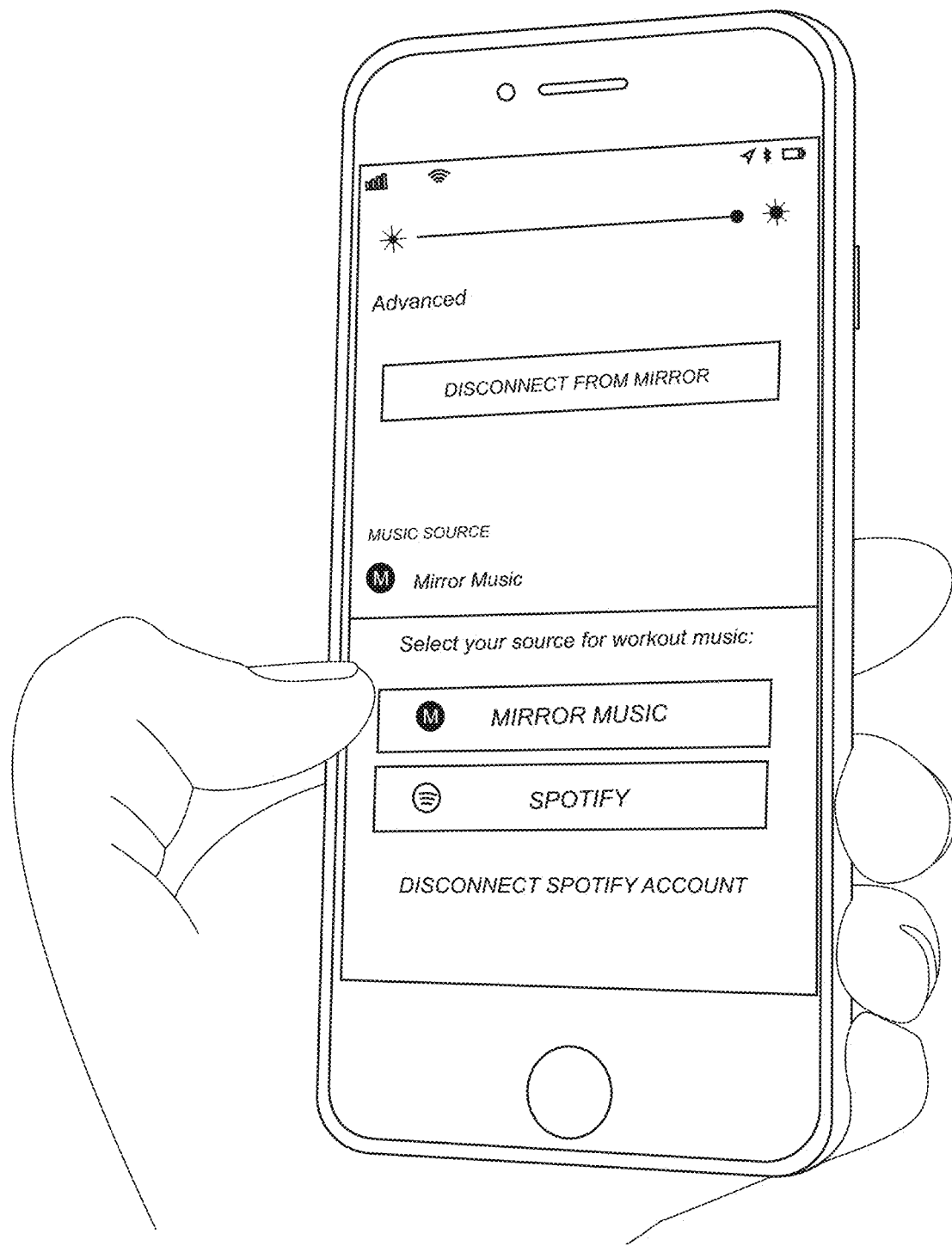
FIG. 28E shows an exemplary GUI on the smart device to select a music source such as the local device or a third party service, in accordance with some embodiments.
Figure 28F:
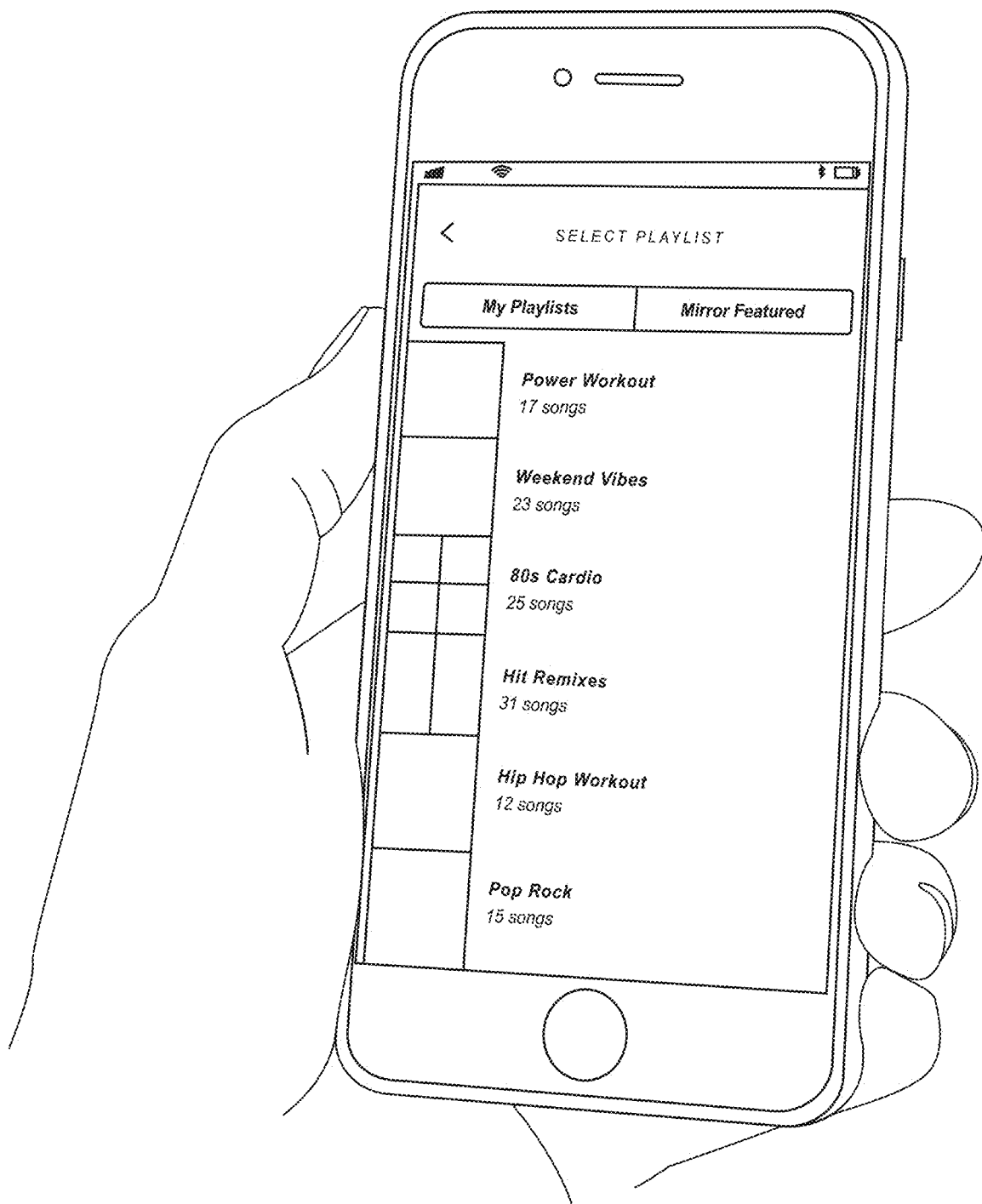
FIG. 28F shows an exemplary GUI on the smart device of music playlists, in accordance with some embodiments.

FIGS. 28D-28F show how the GUI can be used to select and play music with the smart mirror 100, such as while exercising during a fitness class or while the display is off. FIGS. 28D and 28E show the GUI used to connect to and select a music source. The smart mirror 100 may also support music downloaded locally (e.g., onto onboard storage in the smart mirror 100) and/or streamed from external sources and third party services, such as Spotify. The music may also be stored on a remote device (e.g., a smart phone) and transferred to the smart mirror or speaker via a wireless or wired connection. The music may be selected independently from the activity and may be played by the smart mirror 100 or a speaker connected to the smart mirror 100 (e.g., Bluetooth speaker). Additionally, the music may be arranged and organized as playlists. The playlist may be defined by the user, another user, or an instructor. FIG. 28F shows the GUI may support multiple playlists for the user to select during a given session with the smart mirror 100.

Browsing and Selecting Smart Mirror Classes (Video Content)

The GUI may also enable the user to navigate and browse various content available to be downloaded and/or streamed to the smart mirror 100. The GUI may generally provide a list of available fitness classes (including individual exercises) a user can select. Various types of content may be included, such as live streams, recorded video content, and/or customized fitness classes. The content may be arranged such that pertinent information for each class is displayed to the user including, but not limited to the class name, instructor name, duration, skill level, date and time (especially if a live stream), user ratings, and a picture of the instructor and/or a representative image of the workout. Once a particular fitness class is selected, additional information on the class may be displayed to the user including, but not limited to the class timeline, the class schedule (e.g., types of exercises), names of other users registered for the class, biometric data of users who previously completed the class, a leaderboard, and user reviews. In some cases, a preview video of the class may be shown to the user either within the list of fitness classes and/or once a particular fitness class is selected.

If the content selected by the user is on-demand, the content may be immediately played on the smart mirror 100 or saved for later consumption. If the content is instead a live stream, an integrated calendar in the GUI may create an entry indicating the date and time the live fitness class occurs. The calendar may also be configured to include entries for on-demand content should the user wish to play the content at a later date. The GUI may show the calendar to provide a summary of reserved fitness classes booked by the user. The calendar may also be used to determine whether a schedule conflict would occur if the user selects a class due to an overlap with another class. The GUI may also be linked to a user's third party calendar (e.g., a Microsoft Outlook calendar, a Google calendar, etc.) to provide integration and ease of scheduling particularly with other appointments in the user's calendar.

The GUI may initially list the fitness classes together as a single list. The GUI may provide several categories for the user to select in order to narrow the listing of classes. The GUI may also include one or more filters to help a user narrow down a selected listing of fitness classes to better match the user's preferences. The filter may be based on various attributes of the user and/or the fitness class including, but not limited to the exercise type, duration, skill level, instructor name, number of registered users, number of openings available, an average user score based on registered users and previous users who completed the class, injury, location, age, weight, demographic, height, gender, user rating, popularity, date and time, and scheduling availability.

The GUI may also be configured to provide a listing of the fitness classes the user previously attended. This listing may be further subdivided between fully completed fitness classes and partially completed fitness classes in case the user wishes to repeat or finish a fitness class. The GUI may also provide a listing of the fitness classes that the user has designated as favorites. Generally, a fitness class may be favorited before, during, or after the class by selecting an interactive element configured to designate the content as the user's favorite. The GUI may also provide a listing of featured fitness classes to the user. A fitness class may be featured under various conditions including, but not limited to being selected by a moderator or editor, the popularity (e.g., the number of hits for a certain period of time), and the user rating.

Fitness classes may also be recommended to the user. A listing of recommended fitness classes may be generated using a combination of the user's profile and their social network. For example, recommendations may be based on various attributes including, but not limited to the user's age, weight, height, gender, workout history, ratings, favorited classes, group membership, contact lists, skill level, workout performance, recommendations from other users and/or instructors, and other users that are being followed via the social network component. The recommendations may be updated and further refined based on feedback provided by the user. For example, an initial listing of recommended fitness classes may be shown to the user. The user may then select a subset of the classes that match the user's interest (or don't match the user's interest). Based on the selection, an updated listing of recommended fitness classes may be presented to the user that more closely match the selected classes.

Figure 29A:
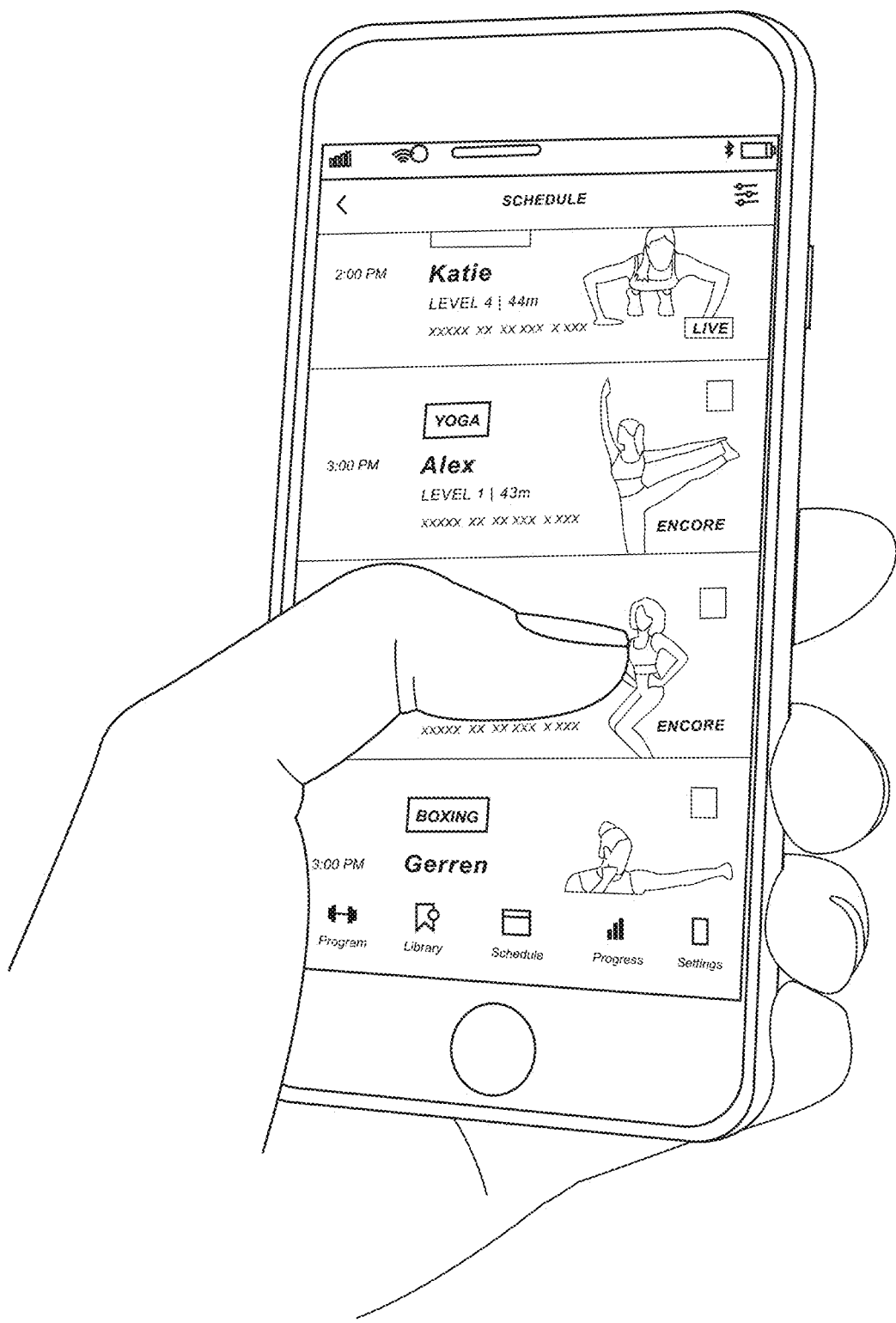
FIG. 29A shows an exemplary GUI on the smart device to browse and select a fitness class from a listing of fitness classes, in accordance with some embodiments.
Figure 29B:
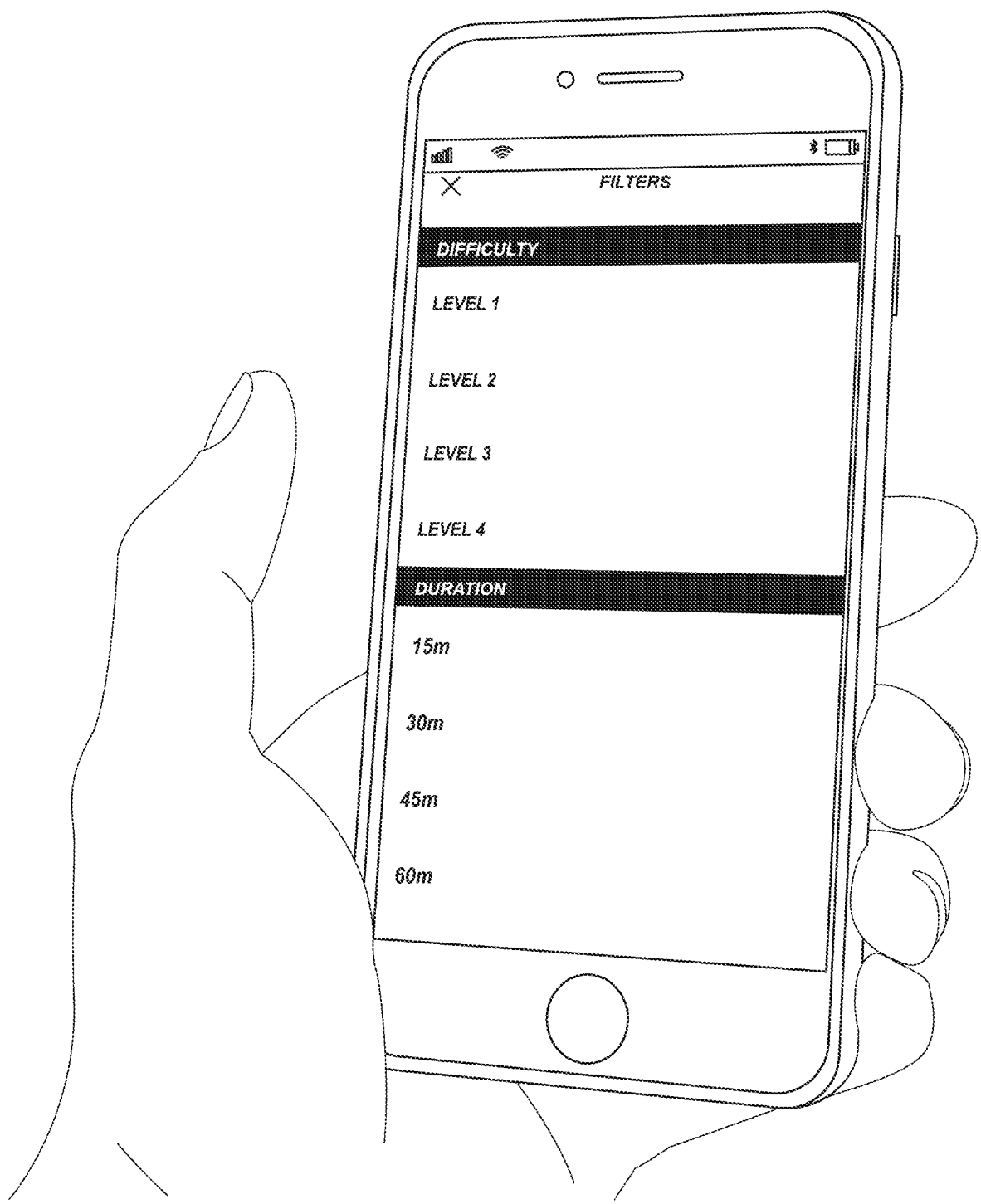
FIG. 29B shows an exemplary GUI on the smart device of filters used to narrow down a listing of fitness classes, in accordance with some embodiments.
Figure 29C:
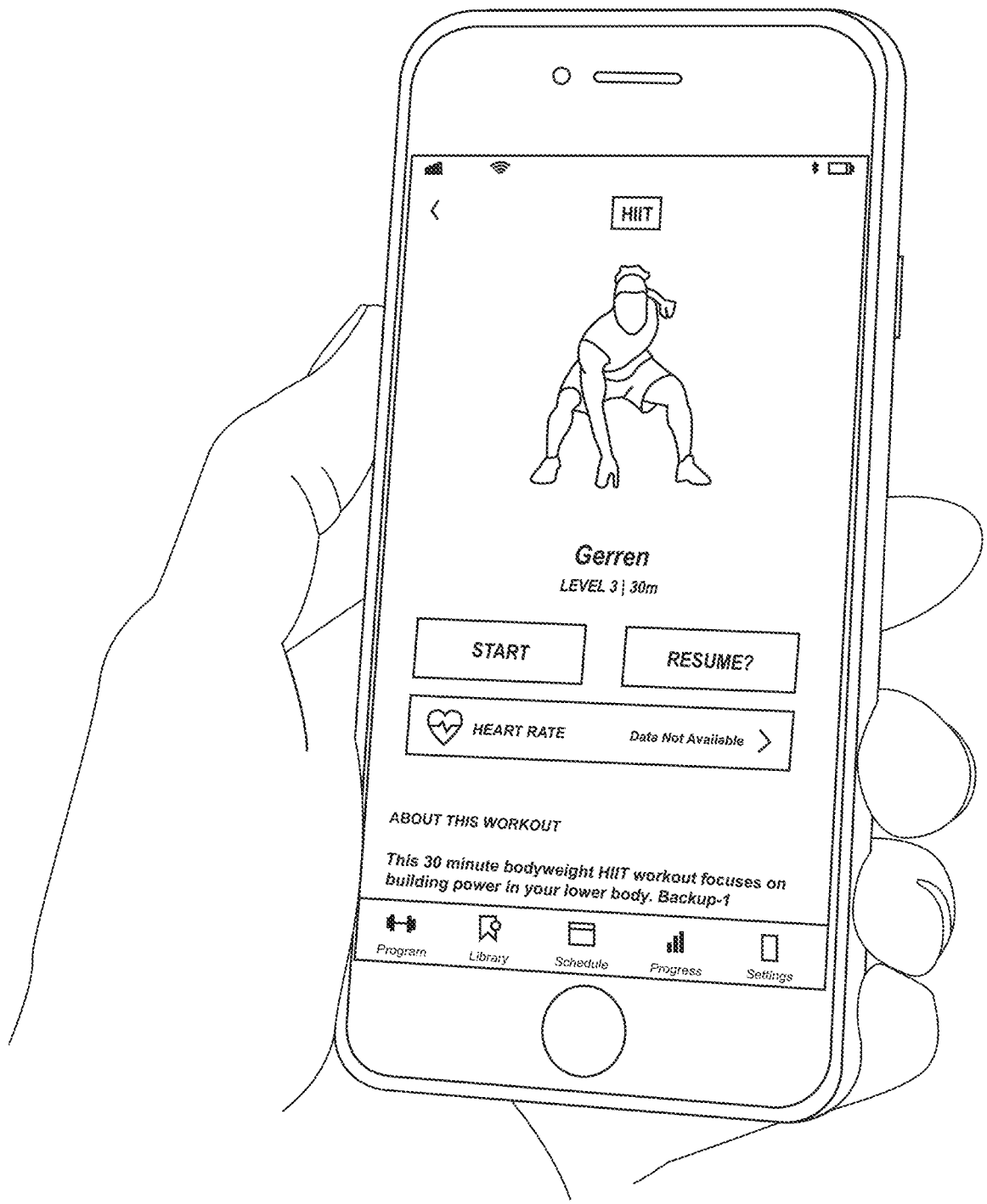
FIG. 29C shows an exemplary GUI on the smart device of an exemplary selection of a fitness class, in accordance with some embodiments.

FIGS. 29A-29C show an exemplary GUI for the user to browse and select a fitness class. FIG. 29A shows a representative listing of fitness classes on the user's smart phone. As shown, the class listing may include the time, instructor name, exercise type, and duration. FIG. 29B shows an exemplary GUI for selecting one or more filters. As shown, the filters may include workout skill level, duration, instructor, and exercise type. Once a particular class is selected, the GUI may present additional information for the class as depicted in FIG. 29C. For example, a brief description of the fitness class may be provided. Additionally, biometric data of the user and/or other previous users attending the class may be displayed to the user to provide an indication of the workout intensity. The GUI may also include interactive elements to start and/or resume the fitness class (e.g., in the event the user previously started the class, but did not finish).

The GUI may also provide the ability to generate customized fitness classes designed to better match user preferences. A customized fitness class may be constructed from individual exercises extracted from multiple fitness classes. The type of exercises included may depend on various user information including, but not limited to the user's fitness goals, age, weight, skill level, biometric data, past performance, and the types of exercise chosen by the user (e.g., cardio, strength, stretching exercises). Each exercise may also be modified according to various aspects including, but not limited to the duration, the number of repetitions, and the exercise conditions (e.g., resistance, weight, incline angle). Additionally, the order of the exercises may be arranged based on the desired pace of the workout. For example, a higher intensity workout may place more difficult exercises together within the workout. A lower intensity workout may include more rest breaks distributed throughout the workout. The total duration of the customized workout may also depend on user preferences including, but not limited to a user-defined duration, the number of calories the user wishes to burn, and biometric data to determine a preferred duration for the user to meet their fitness goal while reducing the risk of injury (e.g., due to overexertion, dehydration, muscle strain).

Queued Classes and Playlists

The GUI may also provide the ability to generate chain, concatenate, and/or otherwise combine multiple, entire fitness classes into a class sequence (e.g., a "playlist") for a user and/or a group of users. An example class sequence could include a 15-minute yoga class for warmup, followed by a 30-minute high intensity interval training (HIIT) class, and followed by a 10 minute abdominal workout class. The selected fitness classes in the class sequence, the duration of the class sequence, as well as the ordering of the selected fitness classes within the class sequence, may independently be user-specified or automated such as, for example, as a recommendation of a class sequence for a user or a group of users. The fitness classes included in the class sequence may depend on various user information and/or user group information including, but not limited to the user's fitness goals, age, weight, skill level, biometric data, past performance, injury, the types of exercise chosen by the user (e.g., cardio, strength, stretching exercises), the user group's fitness goals, group preferences, average group skill level, group biometric data, past group performance, past exercise class selections by the user group, and/or the like. The fitness classes within a class sequence can 'auto-play', i.e., as soon as one fitness class in the sequence ends, the next fitness class in the sequence begins, and so on, until the last fitness class is finished, without requiring any user input. In some cases, a predetermined waiting period may be inserted between adjacent classes within the sequence (e.g., 30 seconds, to permit the user to pause or stop the class sequence, to take a hydration break without having to pause or stop the class sequence, etc.). Alternatively, transition from any fitness class to another fitness class can require user input. Given this ability of a user to assemble a fitness class or program from individual workouts, and to concatenate entire fitness classes as well, a wide variety of customized exercise routines are available to the user and to user groups.

In some embodiments, a "build your workout" method includes a user creating a listing or queue of workout "modules" or segments that can be chained together (e.g., using stitching, optionally interspersed with interstitial content such as a transition video or a time delay) to form a playlist compilation (also referred to herein as a "customized interactive video playlist") that can subsequently played (e.g., with each module or segment played in sequence, or on shuffle, or rearranged by the user) on a smart mirror and/or smart device (e.g., mobile device) of the present disclosure. As used herein, "interstitial content" can refer to video (whether live or pre-recorded), graphic imagery, or animation that is included within a customized interactive video playlist at any location within the associated data file (e.g., before the first video segment of the customized interactive video playlist, between any two adjacent video segments of the customized interactive video playlist, or after a final video segment of the customized interactive video playlist). The playlist compilation can be named, labelled, stored, replayed, broadcast to other users, shared as a file with other users, posted via social media, etc. Each workout module or segment can include live video of an instructor, live video of another user from a networked plurality of users, pre-recorded video, interactive video or other media (e.g., advertising content), etc. The workout modules or segments may, collectively, be of a common workout type (e.g., all running or all strength training), or may include multiple different workout types.

In some embodiments, a customized interactive video playlist is stored in a data file that includes a plurality of data fields. The data fields can include (but are not limited to) any combination of the following: playlist duration, segment duration, number of segments, segment workout type, interstitial content start time, interstitial content end time, adjacent interstitial content identifier, instructor identifier, user location identifier, instructor location identifier, scenery identifier, user identifier, user setting(s), user permission(s), friend identifier(s), volume adjustment data, display adjustment data, biometric sensor status(es) (ON/OFF), target device type, target device identifier, segment historical performance score, segment historical biometric data, playlist rating(s) (e.g., average playlist rating), segment rating(s) (e.g., average segment rating(s)), number of historical playlist plays, number of historical segment plays, an indication of whether the segment is a live video segment or a pre-recorded segment, a live segment start time, a live segment end time, a storage location for a pre-recorded segment, a storage location for an interstitial content, etc. Any of the foregoing data fields can be set to a desired value by a user, via interaction with a GUI of an app running on a smart mirror and/or smart device. Alternatively or in addition, any of the foregoing data fields can be set to a designated value automatically by the app itself.

At least a subset of the data fields can be organized or grouped, for example, in a row within associated records each representing a segment from a plurality of segments of the customized interactive video playlist. For example, a record for a first segment from a plurality of segments of a customized interactive video playlist for a user may specify that the segment workout type is a warmup run, having a duration of ten minutes, with a target device being a smart mirror of the user having serial number XX123, the segment may be shared with user A246 and user B468, the biometric sensor(s) should be OFF (or that any biometric data is not captured), and the volume should be increased 20% relative to a baseline volume. A record for a second segment from the plurality of segments of the customized interactive video playlist for the user may specify that the segment workout type is a sprint run, having a duration of three minutes, with a preceding transition video (video XX4) of duration 45 seconds, a target device being a mobile device of the user having serial number MM55, the segment may be not be shared with user A246 and user B468, the biometric sensor(s) should be ON, and the volume should be set to a baseline volume. A record for a third segment from the plurality of segments of the customized interactive video playlist for the user may specify that the segment workout type is a strength training segment, having a duration of twenty minutes, with no adjacent transition video, a target device being the mobile device of the user having serial number MM55, the segment may be shared with user B171 and the instructor, the biometric sensor(s) should be ON, and the volume should be muted.

In some embodiments, during user creation of a customized interactive video playlist, the user selects video segments by interacting with a GUI of an app running on a smart mirror and/or a smart device of the user, and once the user has completed selecting the video segments (e.g., once a user selects "Done" via the GUI), the app stores the customized interactive video playlist in a data file in local memory and/or remote memory, and modifies the customized interactive video playlist (optionally based on stored user settings and/or preferences) by one or more of: adding interstitial content, adjusting a volume setting associated with one or more video segments of the customized interactive video playlist, adjusting a display setting associated with one or more video segments of the customized interactive video playlist, cropping a portion of one or more video segments of the customized interactive video playlist (e.g., such that the customized interactive video playlist has a duration less than or equal to a maximum duration threshold), removing one or more video segments from the customized interactive video playlist (e.g., such that the customized interactive video playlist has a duration less than or equal to a maximum duration threshold), etc.

In some embodiments, a customized interactive video playlist is generated and/or modified, based on the selected video segments and using stitching or other methods of joining/concatenating the video segments. The modification of the customized interactive video playlist can include modifying one or more of the selected video segments of the customized interactive video playlist. The modifying the one or more of the selected video segments of the customized interactive video playlist can be dynamic and/or performed in real-time. For example, the app can automatically, iteratively or periodically (e.g., in response to a detected event and/or according to a schedule), determine, during a given video segment or before the first video segment in the customized interactive video playlist, an appropriate duration for a next video segment of the customized interactive video playlist, for example based on: biometric data associated with the user and determined prior to that next video segment, a user modification to a user preference, a change to an itinerary, duration, or workout plan of that next video segment, a change to an itinerary, duration, or workout plan of a video segment subsequent to that next video segment, etc.

In one example, if a user has performed a first video segment of a customized interactive video playlist, the first video segment directed to a warmup, and the user is currently performing a second video segment of the customized interactive video playlist, the second video segment directed to a "cardio" workout, the app may determine, based on sensor data received by the app, that the user's heartrate is higher than a predefined threshold. Based on the heartrate being higher than the predefined threshold, the app may adjust a duration of the next (third) video segment, directed to a "cooldown," such that the cooldown segment is longer. Alternatively, the app may identify a substitute video segment to replace the user-defined third video segment, optionally based on one or more of: a similarity between the type of workout depicted in the third video segment and the type of workout depicted in the substitute video segment, a difference in intensity between the workout depicted in the second video segment and the workout depicted in the substitute video segment, an instructor being common to the third video segment and the substitute video segment, a threshold number of "friends" of the user being registered participants for the substitute video segment, a historical rating of the user for the substitute video segment, a historical rating of at least one friend of the user for the substitute video segment, or heartrate data (e.g., a slope of a heartrate curve, a time to reach a predefined heartrate value, etc.) detected by one or more sensors and received by the app during the first video segment. Alternatively, the app may identify an additional video segment to insert before or after the user-defined third video segment within the customized interactive video playlist, the identification of the additional video segment optionally based on one or more of: a similarity between the type of workout depicted in the third video segment and the type of workout depicted in the additional video segment, a difference in intensity between the workout depicted in the second video segment and the workout depicted in the additional video segment, an instructor being common to the third video segment and the additional video segment, a threshold number of "friends" of the user being registered participants for the additional video segment, a historical rating of the user for the additional video segment, a historical rating of at least one friend of the user for the additional video segment, or heartrate data (e.g., a slope of a heartrate curve, a time to reach a predefined heartrate value, etc.) detected by one or more sensors and received by the app during the first video segment.

In another example, if a user has performed a first video segment of a customized interactive video playlist, the first video segment directed to a warmup, and the user is currently performing a second video segment of the customized interactive video playlist, the second video segment directed to a "weightlifting" workout, the app may determine, based on sensor data received by the app, that the user's heartrate is lower than a predefined target value. Based on the heartrate being lower than the target value, the app may adjust a duration of the next (third) video segment, directed to a "cooldown," such that the cooldown segment is shorter. Alternatively, the app may identify a substitute video segment to replace the user-defined third video segment, optionally based on one or more of: a similarity between the type of workout depicted in the second video segment and the type of workout depicted in the substitute video segment, a difference in intensity between the workout depicted in the second video segment and the workout depicted in the substitute video segment, an instructor being common to the third video segment and the substitute video segment, a threshold number of "friends" of the user being registered participants for the substitute video segment, a historical rating of the user for the substitute video segment, a historical rating of at least one friend of the user for the substitute video segment, or heartrate data (e.g., a slope of a heartrate curve, a time to reach a predefined heartrate value, etc.) detected by one or more sensors and received by the app during the first video segment. Alternatively, the app may identify an additional video segment to insert before or after the user-defined third video segment within the customized interactive video playlist, the identification of the additional video segment optionally based on one or more of: a similarity between the type of workout depicted in the second video segment and the type of workout depicted in the additional video segment, a difference in intensity between the workout depicted in the second video segment and the workout depicted in the additional video segment, an instructor being different between the second video segment and the additional video segment (e.g., selecting a more motivating instructor, optionally based on a machine learning model associated with the user), a threshold number of "friends" of the user being registered participants for the additional video segment, a historical rating of the user for the additional video segment, a historical rating of at least one friend of the user for the additional video segment, or user heartrate data (e.g., a slope of a heartrate curve, a time to reach a predefined heartrate value, etc.) for example as detected by one or more sensors and received by the app during the first video segment.

Figure 30:
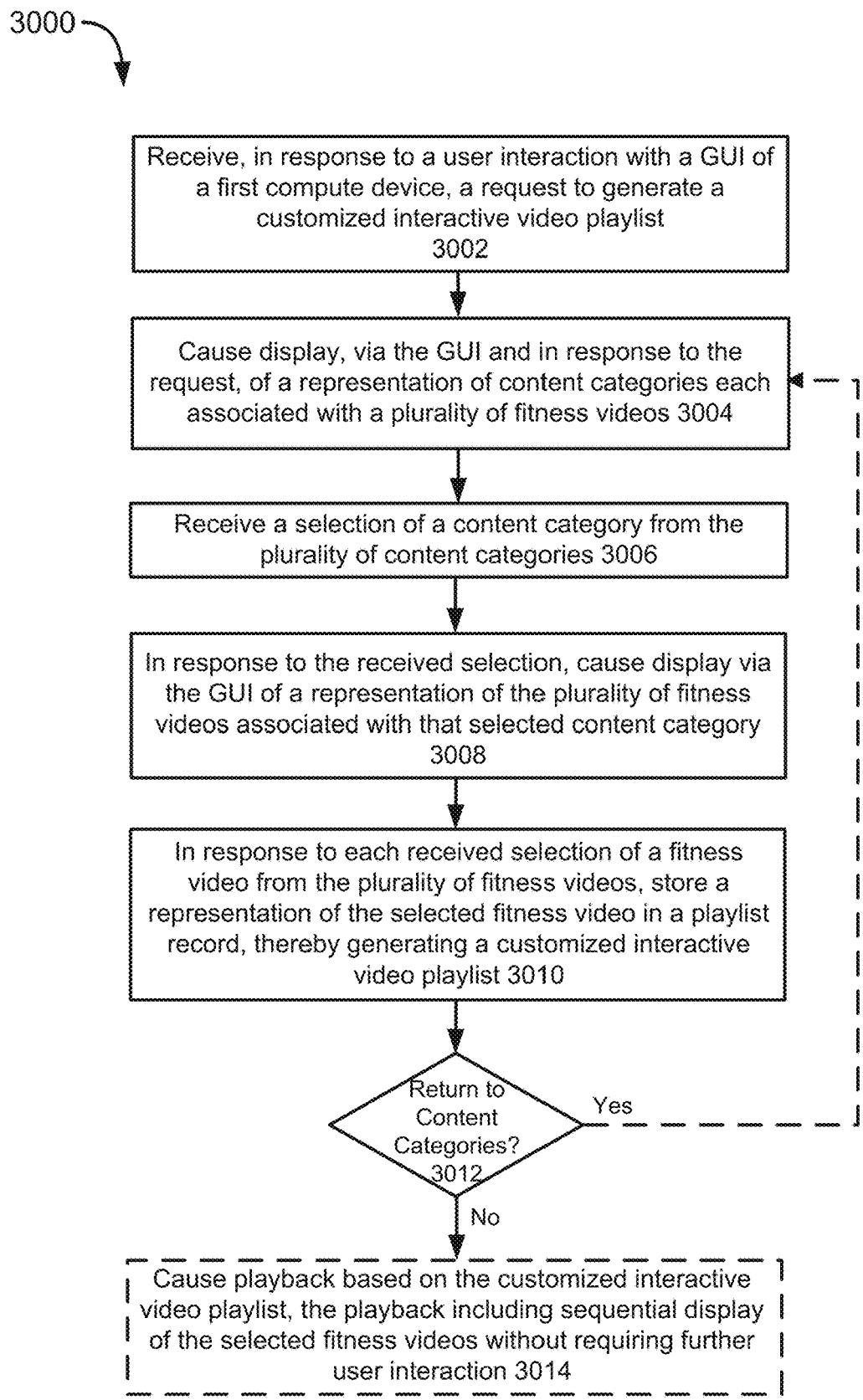
FIGS. 30-31 are flowcharts showing example methods for generating customized interactive video playlists, in accordance with some embodiments.
Figure 31:
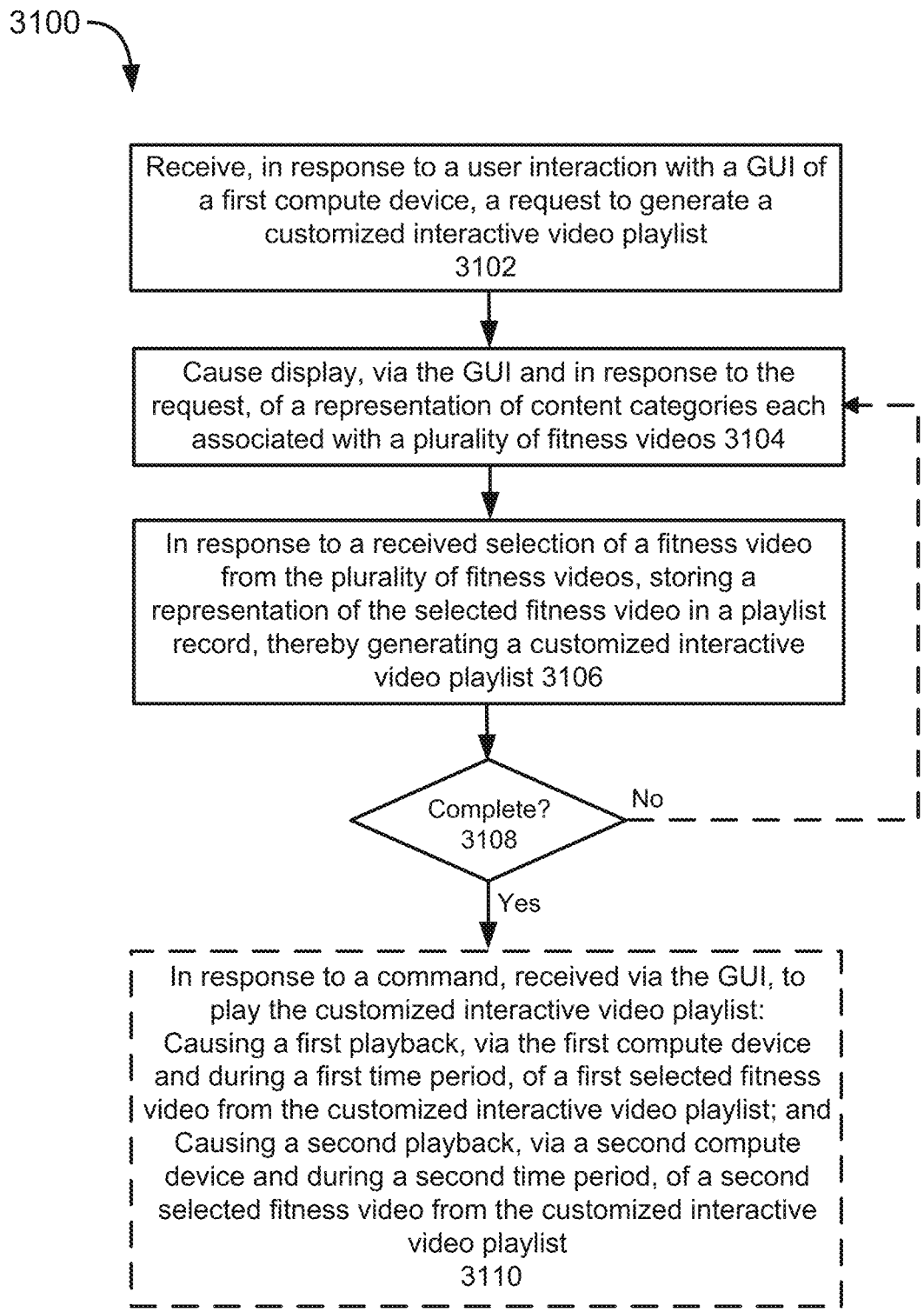

FIGS. 30-31 are flowcharts showing example methods for generating customized interactive video playlists, in accordance with some embodiments.

As shown in FIG. 30, the method 3000 includes receiving, at 3002, at a processor running an app, and in response to a user interaction, by a user, with a graphical user interface (GUI) of a first compute device of the user, a request to generate a customized interactive video playlist. The method 3000 also includes causing display, at 3004, via the GUI and in response to the request, of a representation of a plurality of content categories, each content category from the plurality of content categories being associated with a plurality of fitness videos. The plurality of content categories can include at least one of a warm-up category, a cardio category, a strength training category, or a cool-down category. At 3006, an indication of a selection of a content category from the plurality of content categories is received via the GUI in response to a user interaction with the GUI. The method 3000 further includes, at 3008 and in response to the received selection indication, causing display, via the GUI, of a representation of the plurality of fitness videos associated with that selected content category. The method 3000 further includes, at 3010, in response to each selection indication, received from the first compute device of the user, of a fitness video from the plurality of fitness videos for a selected content category from the plurality of content categories, storing a representation of the selected fitness video in a playlist record of a database accessible via the processor, to produce the customized interactive video playlist, the customized interactive video playlist including a plurality of selected fitness videos. If, at 3012, a request is received via the GUI from the user to return to the content categories, the method 3000 loops back to step 3004, and the user can continue to navigate to different content categories (3006) and select additional fitness videos (3008, 3010) for the customized interactive video playlist. If, at 3012, a request is not received (e.g., within a predefined time period) via the GUI from the user to return to the content categories, or if a user indicates, via the GUI, that the customized interactive video playlist is complete, the method 3000 terminates or, optionally, includes causing playback, at 3014, via at least one of the first compute device of the user or a second compute device of the user, based on the customized interactive video playlist, the playback including sequential display of the selected fitness videos from the plurality of selected fitness videos of the customized interactive video playlist without requiring further user interaction. The playback can be performed in response to a user request received via the GUI of the first compute device of the user (e.g., a smart mirror, a mobile device, etc.) or via a GUI of a second compute device of the user (e.g., a smart mirror, a mobile device, etc.).

In some embodiments, the method 3000 also includes receiving, from the first compute device of the user, a selection of a filter, and modifying, based on the filter, at least one of the representation of the plurality of content categories or the representation of the associated plurality of fitness videos for the selected content category. The filter can include one of: a length filter, a difficulty filter, a trainer filter, a muscle group filter, a fitness objective filter, an equipment type filter, an equipment category filter, an equipment make filter, or an equipment model filter.

As discussed above, in some embodiments a method for generating customized interactive video playlists includes the sequenced selection of a first (single) content category, followed by the selection of one or more fitness videos from that first content category, followed by the optional selection of a next (second) content category, followed by the selection of one or more fitness videos from that second content category, etc., until the customized interactive video playlist is complete. In other embodiments, however, a method for generating customized interactive video playlists can include receiving an indication of selections of multiple content categories from the plurality of content categories, via a GUI and in response to a user interaction with the GUI. Subsequent to the user's selection of the multiple content categories, the user may be presented with a collection of fitness videos covering all of the multiple content categories and select (by interacting with the GUI) the desired fitness videos from the collection of fitness videos, either in a desired playback sequence/order or in a first sequence/order that the user can subsequently rearrange/reorder via the GUI. Alternatively, and subsequent to the user's selection of the multiple content categories, the user may navigate to each of the selected content categories from the multiple content categories, in any order, and make selections of fitness video from each of the selected content categories in turn.

In some embodiments, a selected fitness video from the plurality of selected fitness videos of the customized interactive video playlist is a live-streamed fitness video, and playback commences at a time such that the live-streamed fitness video one of: begins after another selected fitness video from the plurality of selected fitness videos ends, or ends before another selected fitness video from the plurality of selected fitness videos begins.

In some embodiments, the method 3000 also includes receiving, from the first compute device of the user, a command to reorder the selected fitness videos from the plurality of selected fitness videos, and modifying the playlist record, in response to the command, to reflect an updated order of the plurality of selected fitness videos.

In some embodiments, the method 3000 also includes receiving, from the first compute device of the user, one of: a command to remove a selected fitness video from the plurality of selected fitness videos, or a command to add another fitness video to the plurality of selected fitness videos, and modifying the playlist record, in response to the command, to reflect a modified plurality of selected fitness videos.

In some embodiments, the first compute device of the user is a smart mirror, the second compute device of the user is a mobile device, and the playback includes: (1) displaying a first selected fitness videos from the plurality of selected fitness videos via the smart mirror during a first time period, and (2) displaying a second selected fitness videos from the plurality of selected fitness videos via the mobile device during a second time period different from the first time period.

In some embodiments, the displaying the first selected fitness videos from the plurality of selected fitness videos via the smart mirror during the first time period is in response to detecting that a location of the user is within a predetermined range of the smart mirror.

In some embodiments, the displaying the second selected fitness videos from the plurality of selected fitness videos via the mobile device during the second time period is in response to detecting that a location of the user is outside a predetermined range of the smart mirror.

In some embodiments, the user is a first user, and the method 3000 also includes receiving, from the first user and via the GUI, a command to share the customized interactive video playlist with a second user associated with a third compute device, and causing display, in response to the command and via a compute device or the second user, of a notification that the customized interactive video playlist of the first user is accessible via the third compute device.

In some embodiments, the method 3000 also includes causing display, during playback and via at least one of the first compute device of the user or a second compute device of the user, of a user-selectable object representing an option to modify a duration of a selected fitness video from the plurality of selected fitness. The method 3000 also includes, in response to an indication received from the at least one of the first compute device of the user or the second compute device of the user of an interaction with the object, causing display of a representation of a plurality of recommended fitness videos.

In some embodiments, the method 3000 also includes causing display, to the user via the GUI and at the end of a workout segment playback or at the end of a customized interactive video playlist playback, of a message presenting options to the user as to how to proceed (e.g., to continue exercise, cool down, discontinue exercise, etc.). Similarly, the method 3000 can include causing display, to the user via the GUI and during a workout segment playback or during a customized interactive video playlist playback (e.g., in response to detecting that the user's heartrate was higher than a predefined threshold during the workout segment or customized interactive video playlist, or if the user's heartrate exhibits a recovery rate that is slower than a predefined recovery rate during the workout segment or customized interactive video playlist) of a message presenting options to the user as to how to proceed (e.g., to continue exercise, cool down, discontinue exercise, etc.).

In response to a user reply, input, or selection of an option to continue exercise, a set of exercise classes, workout segments, and/or customized interactive video playlists may be identified, and representations of the set of exercise classes, workout segments, and/or customized interactive video playlists may be presented to the user for selection via the GUI. In some implementations, the app identifies the set of exercise classes, workout segments, and/or customized interactive video playlists based on one or more of: the workout segment or customized interactive video playlist most recently played back (e.g., if a legs class was just completed, a leg-based stretch class may be identified as a candidate for selection), biometric data associated with the user (e.g., associated with the workout segment or customized interactive video playlist most recently played back), one or more user settings, one or more user preferences, etc. For example, if a user's heartrate was higher than a predefined threshold during the workout segment or customized interactive video playlist most recently played back, or if the user's heartrate exhibits a recovery rate that is slower than a predefined recovery rate during the workout segment or customized interactive video playlist most recently played back, a lower-intensity workout segment or a lower-intensity customized interactive video playlist may be identified.

In some embodiments, the method 3000 also includes receiving, during playback, sensor data (e.g., including biometric data) associated with the user, and identifying at least one replacement fitness video based on the sensor data. The method 3000 also includes displaying, during playback and via at least one of the first compute device of the user or a second compute device of the user, of a user-selectable representation of the at least one replacement fitness video.

In some embodiments, the method 3000 also includes, in response to an indication, received from the at least one of the first compute device of the user or the second compute device of the user, of an interaction with the user-selectable representation of the at least one replacement fitness video, modifying the customized interactive video playlist to include the at least one replacement fitness video.

In some embodiments, the interaction with the user-selectable representation of the at least one replacement fitness video is a first user interaction, and the playback includes displaying, via the at least one of the first compute device of the user or the second compute device of the user, a second selected fitness video from the plurality of selected fitness videos of the customized interactive video playlist after a first selected fitness video from the plurality of selected fitness videos of the customized interactive video playlist has completed, in response to a second user interaction.

In some embodiments, fitness videos can be associated with environments (e.g., indoor or outdoor). A customized interactive video playlist can include one or more fitness videos having an associated environment, and includes a prompt (e.g., implemented as interstitial content), preceding each of the one or more fitness videos, for the user to indicate that he/she is ready to physically move to the next environment (e.g., "Ready to go outside?" or "Ready to go inside?"). The prompt(s) can be displayed to the user via the GUI, and the playing of the next fitness video may be triggered by the user affirmatively indicating, by interacting with the GUI to respond to the prompt, that he/she is ready to move to the indicated environment.

In some embodiments, the producing the customized interactive video playlist further includes combining the selected fitness videos from the plurality of selected fitness videos such that there are substantially no gaps between contiguous pairs of the selected fitness videos from the plurality of selected fitness videos during playback.

As shown in FIG. 31, a method 3100 includes receiving, at a processor and in response to a user interaction, by a user, with a graphical user interface (GUI) of a first compute device of the user, a request to generate a customized interactive video playlist (3102). At 3104, the method 3100 includes causing display, via the GUI and in response to the request, of a representation of a plurality of content categories, each content category from the plurality of content categories being associated with a plurality of fitness videos (e.g., tens, hundreds, or thousands of fitness videos). Each fitness video can be used as a video segment. The plurality of content categories can include at least one of a warm-up category, a cardio category, a strength training category, or a cool-down category. At 3106, in response to a selection indication, received from the first compute device of the user, of a fitness video from the pluralities of fitness videos, a representation of the selected fitness video is stored in a playlist record of a database accessible via the processor, to produce the customized interactive video playlist, the curated interactive video playlist including a plurality of selected fitness videos. At 3108, the method 3100 includes receiving an indication as to whether the user has completed making their selections for the customized interactive video playlist. For example, a prompt of "Complete?" may be presented to the user via the GUI, in which case, if the user selects "No," the method 3100 loops back to the display of the content categories at 3104 and proceeds as discussed above. Conversely, in other embodiments not shown, a prompt of "Make Further Selection(s)?" may be presented to the user via the GUI, in which case if the user selects "Yes," the method loops back to the display of the content categories, and if the user selects "No," the method terminates or proceeds to a step similar to step 3110 of FIG. 31, discussed below.

Returning to FIG. 31, if at 3108 an indication is received that the user has completed making their selections for the customized interactive video playlist, the method 3100 terminates, or optionally proceeds, at 3110 and in response to a command received via the GUI to play the customized interactive video playlist, with: (1) causing a first playback, via the first compute device (e.g., a smart mirror) of the user and during a first time period, of a first selected fitness video from the plurality of selected fitness videos of the customized interactive video playlist; and (2) causing a second playback, via a second compute device (e.g., a smart/mobile device) of the user different from the first compute device of the user, and during a second time period different from the first time period, of a second selected fitness video from the plurality of selected fitness videos of the customized interactive video playlist. The method 3100 optionally also includes determining a location of the user in response to the command to play the customized interactive video playlist, and selecting the first compute device for the first playback based on the location of the user.

In some embodiments, the second selected fitness video is displayed via the first compute device concurrently with the second playback via the second compute device.

In some embodiments, the method 3100 also includes receiving, from the first compute device of the user, an indication of a selection of a filter; and modifying, based on the filter, the representation of the plurality of content categories.

In some embodiments, the user is a first user, and the method 3100 also includes receiving, from the first user and via the GUI, a command to share the customized interactive video playlist with a second user associated with a third compute device, and causing display, in response to the command and via a compute device of the second user, of a notification that the customized interactive video playlist of the first user is accessible via the third compute device.

In some embodiments, the method 3100 also includes receiving, from the user and via the GUI, one of: a command to remove a selected fitness video from the plurality of selected fitness videos, or a command to add another fitness video to the plurality of selected fitness videos, and modifying the playlist record, in response to the command, to reflect a modified plurality of selected fitness videos.

In some embodiments, the method 3100 also includes receiving, from the user and via the GUI, a command to reorder the selected fitness videos from the plurality of selected fitness videos, and modifying the playlist record, in response to the command, to reflect an updated order of the plurality of selected fitness videos.

In some embodiments, the first time period is contiguous with the second time period.

In some embodiments, the method 3100 also includes detecting a change in location of the user during the first playback. In response to detecting the change in location of the user, the method 3100 also includes at least one of: stopping the first playback via the first compute device of the user, or continuing the first playback via the second compute device of the user for a remainder of the first time period.

In some embodiments, the GUI includes functionality (e.g., objects with which the user can interact) for searching and/or filtering the content categories and/or the fitness videos. Filtering can be based on a specified duration (or range thereof), difficulty rating (or range thereof), instructor/trainer name, trainer type, workout type, focus area (e.g., upper body, running, deep breathing, etc.), and/or environment (e.g., indoor or outdoor). As discussed above, the content categories and the fitness videos can have associated environments (e.g., indoor or outdoor). In some embodiments, a user can select no more than a predefined maximum number of fitness videos for a given customized interactive video playlist.

Class Interface

Once the user selects the fitness class and the class begins, the GUI may be configured to display various information and/or controls to the user. As described above, the smart mirror 100 is used primarily to show video content via the display panel 120 and audio outputs via the speakers 152 and 154. In some cases, the display panel 120 may also be configured to show GUI-related features that are more informational rather than a control input. The portion of the GUI with control inputs may instead be shown on the user's smart device. Therefore, the GUI, as described herein, may be split between the smart mirror 100 and another device. Of course, the smart mirror 100 may be configured to be used without the aid of another device as described above. In such cases, the information and control inputs provided by the GUI may be displayed entirely on the display panel 120.

Figure 32A:
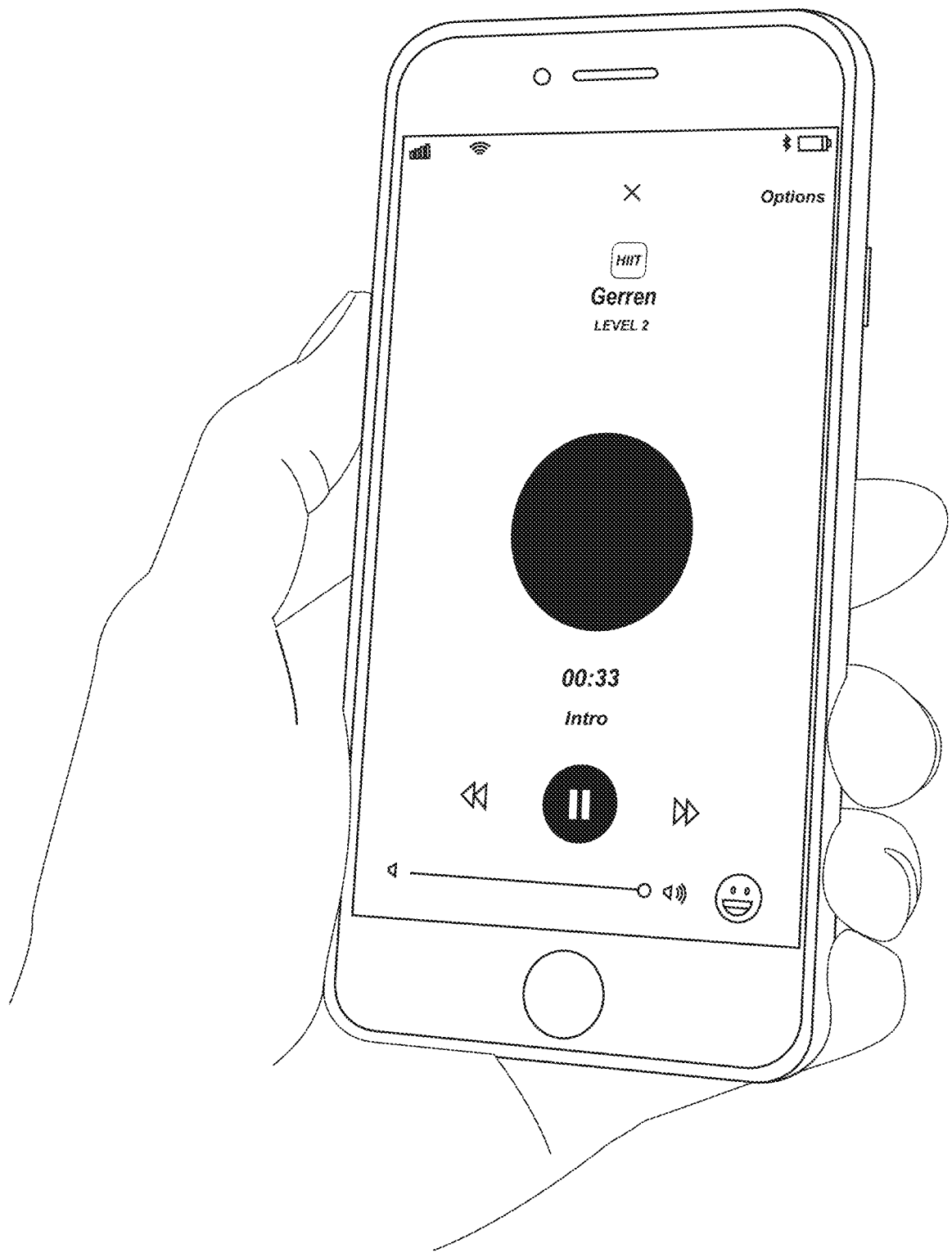
FIG. 32A shows an exemplary GUI on the smart device to control a fitness class played on the smart mirror, in accordance with some embodiments.
Figure 32B:
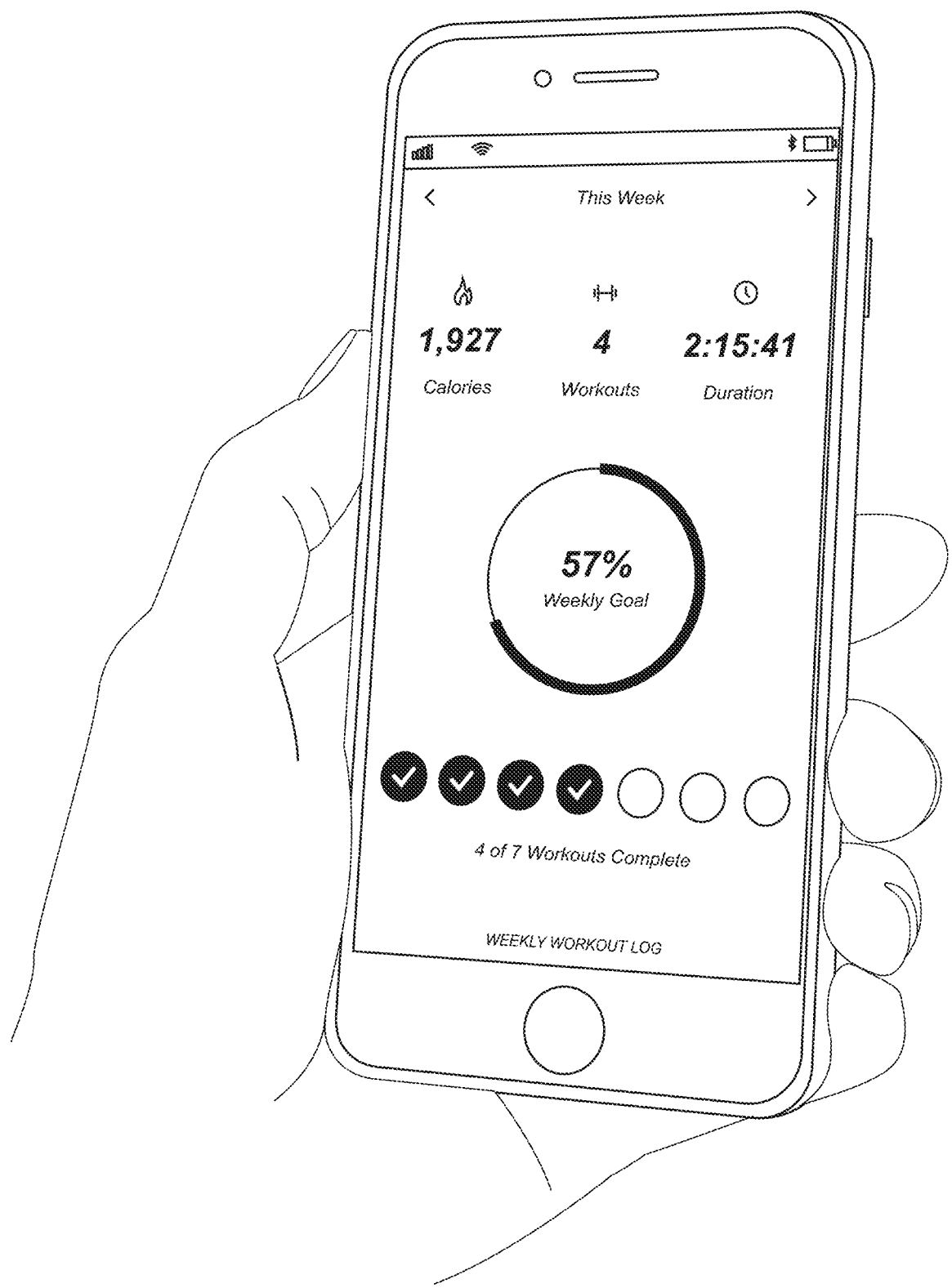
FIG. 32B shows an exemplary GUI on the smart device of a workout log, in accordance with some embodiments.
Figure 32C:
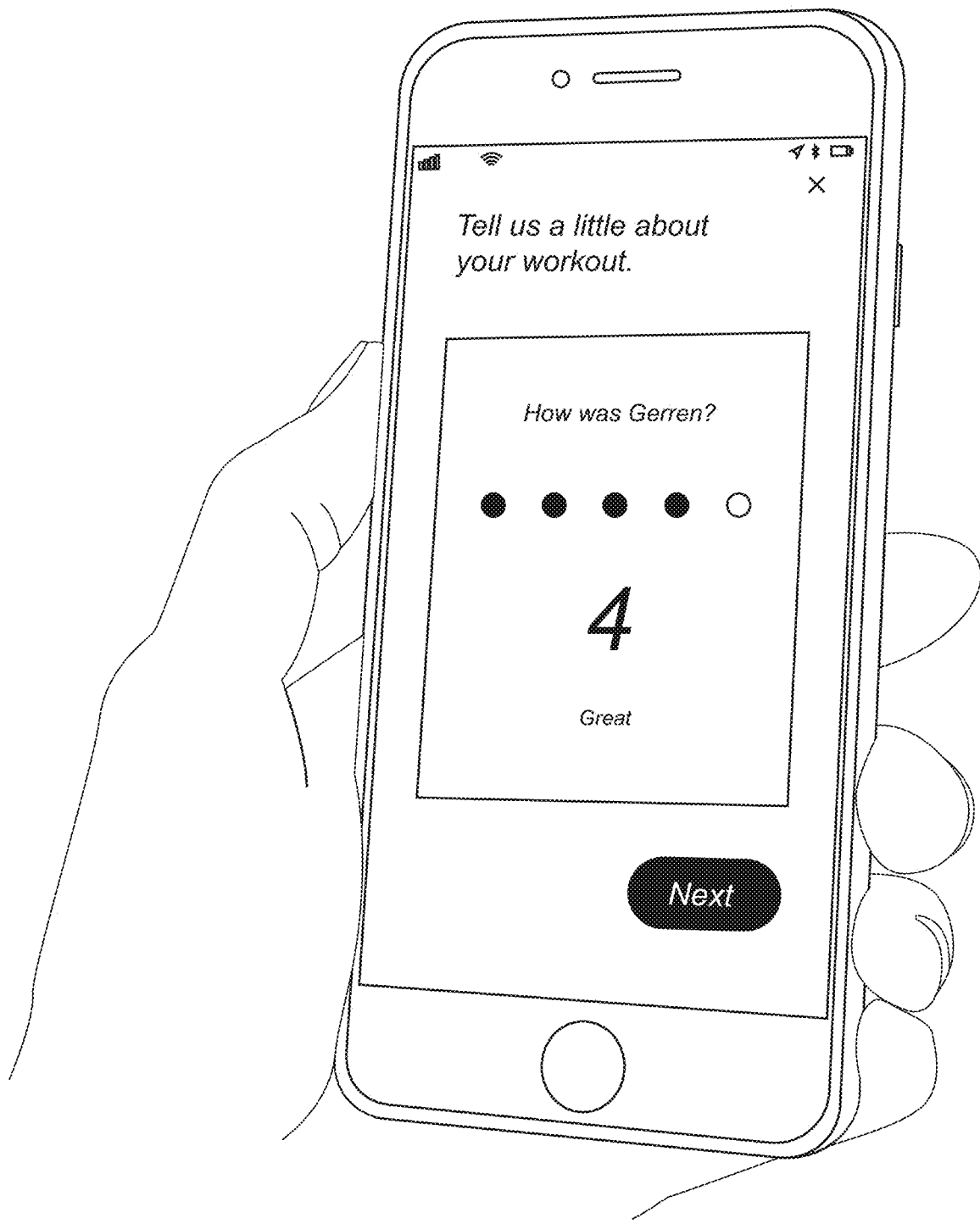
FIG. 32C shows an exemplary GUI on the smart device to provide user feedback on an instructor and/or a fitness class, in accordance with some embodiments.

FIGS. 32A-32C show an exemplary GUI on the user's smart phone used, in part, to control the fitness class and to provide user input. FIG. 30A shows the GUI on the user's smart phone may give the user the ability to play, pause, rewind, fast forward, or skip certain portions of the workout. The GUI may also include controls for the user to adjust the volume of the output sound (e.g., from the smart mirror 100 or a Bluetooth speaker) and to rate the exercise and/or fitness class. The GUI on the user's smart phone may also display the current exercise, the skill level, the instructor name, and the duration of the routine. FIG. 32B shows an exemplary GUI of a workout log of the user. This workout log may be accessed before, during, or after the workout. As shown, the workout log may contain various information including the total calories burned, the total number of workouts, the total duration the user was exercising, the user's progress in meeting a fitness goal (e.g., a weekly goal), and the number of workouts completed relative to the number of workouts to meet the weekly goal. FIG. 32C shows an exemplary GUI of a survey for the user to provide feedback on the instructor and/or the fitness class.

Figure 33A:
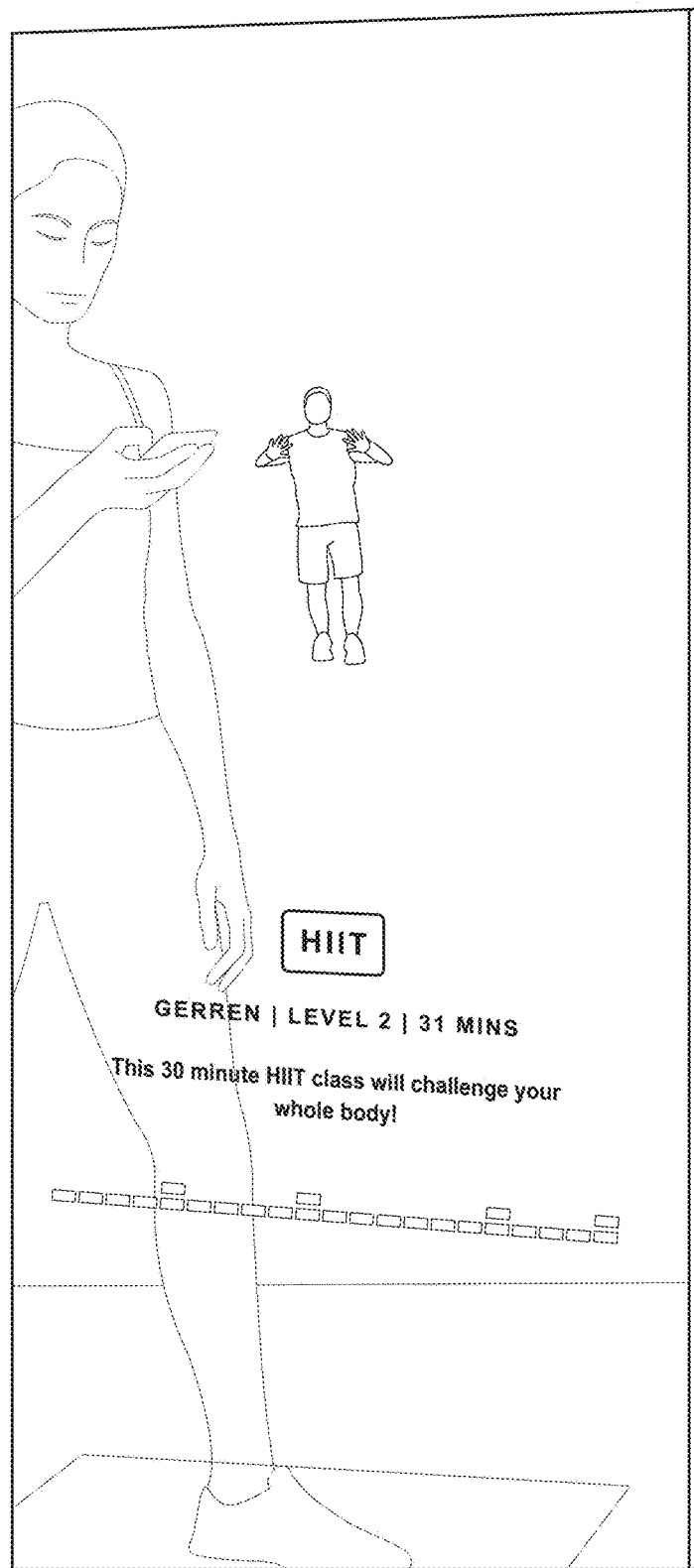
FIG. 33A shows an exemplary GUI on the smart mirror of a fitness class overview, in accordance with some embodiments.

As described above, the smart mirror 100 may also show various GUI-related features during the workout. For example, FIG. 33A shows an overview of the fitness class prior to the start of the workout including video of the instructor, instructor name, skill level, duration, name of the class, brief summary of the class, and timeline. The timeline may be used to indicate the pace and/or intensity level of class. For instance, the timeline in FIG. 33A indicates four periods (each represented by two parallel bars) corresponding to a higher intensity workout. In some cases, the timeline may be displayed throughout the workout on the smart mirror 100 and/or the user's smart device. The timeline may also be interactive (on either the smart mirror 100 via a touch command or the user's smart device) to allow the user to select and jump to different sections of the class.

Figure 33B:
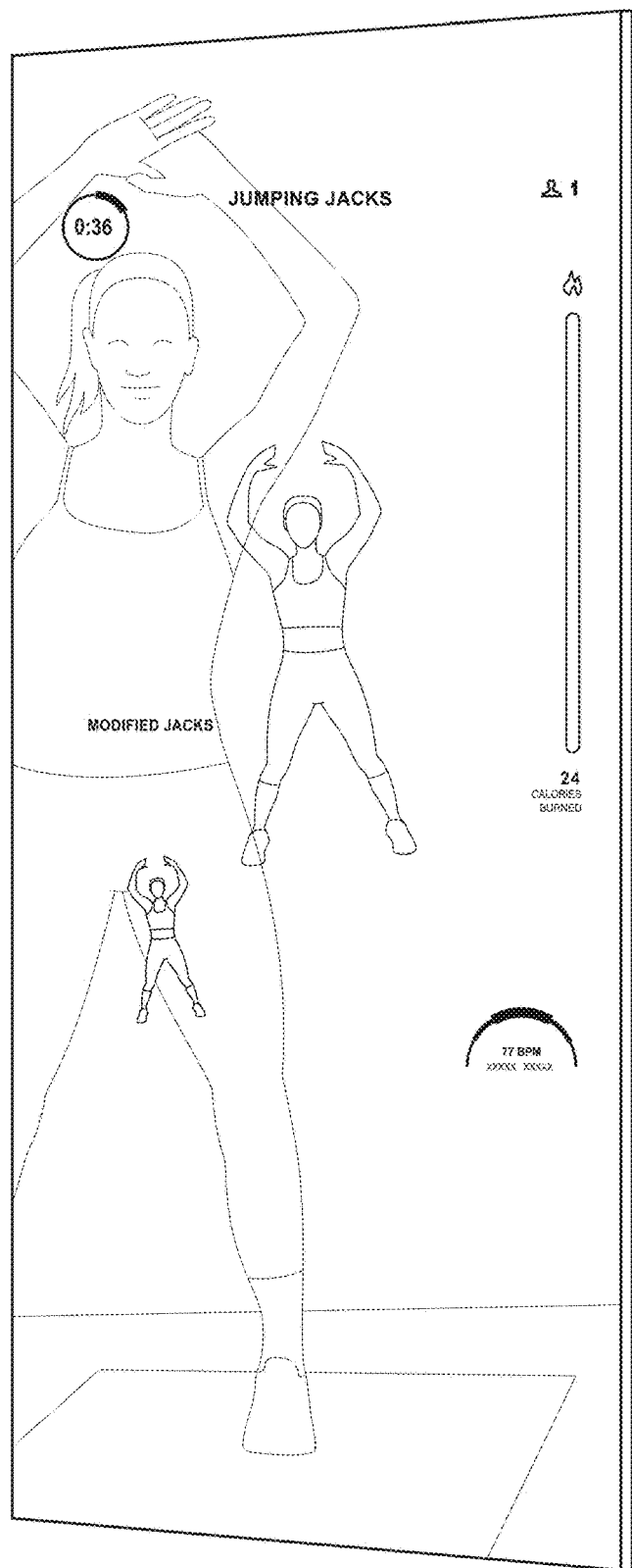
FIG. 33B shows an exemplary GUI on the smart mirror of an exemplary user interface during a workout, in accordance with some embodiments.

Once the class begins, various GUI-related features may be shown to indicate the status and progress of the user's workout in conjunction with the video content. FIG. 33B shows one exemplary GUI on the smart mirror 100 during a workout. As shown, the GUI may include a timer indicating the amount of time passed and a progress bar (e.g., represented as a circle around the timer) to show the user's progress for a particular exercise. Depending on the exercise, a counter may instead be shown to represent the number of repetitions for the exercise. The GUI also shows the name of the exercise and the number of users actively participating in the same fitness class. The GUI may also show the next exercise in the workout. If the user is wearing a biometric sensor, such as a heart rate (HR) monitor, the GUI on the smart mirror 100 may also display real-time biometric data, such as the user's heart rate. Additional information derived from the biometric data may also be displayed, such as the number calories burned based on the user's heart rate. In some cases, the video content may be augmented by additional notes from the instructor. For example, FIG. 33B shows the instructor performing the exercise and a miniaturized representation of the instructor performing the same exercise using an alternative form and/or movement. The alternative form may present a more challenging version of the exercise to the user.

Figure 33C:
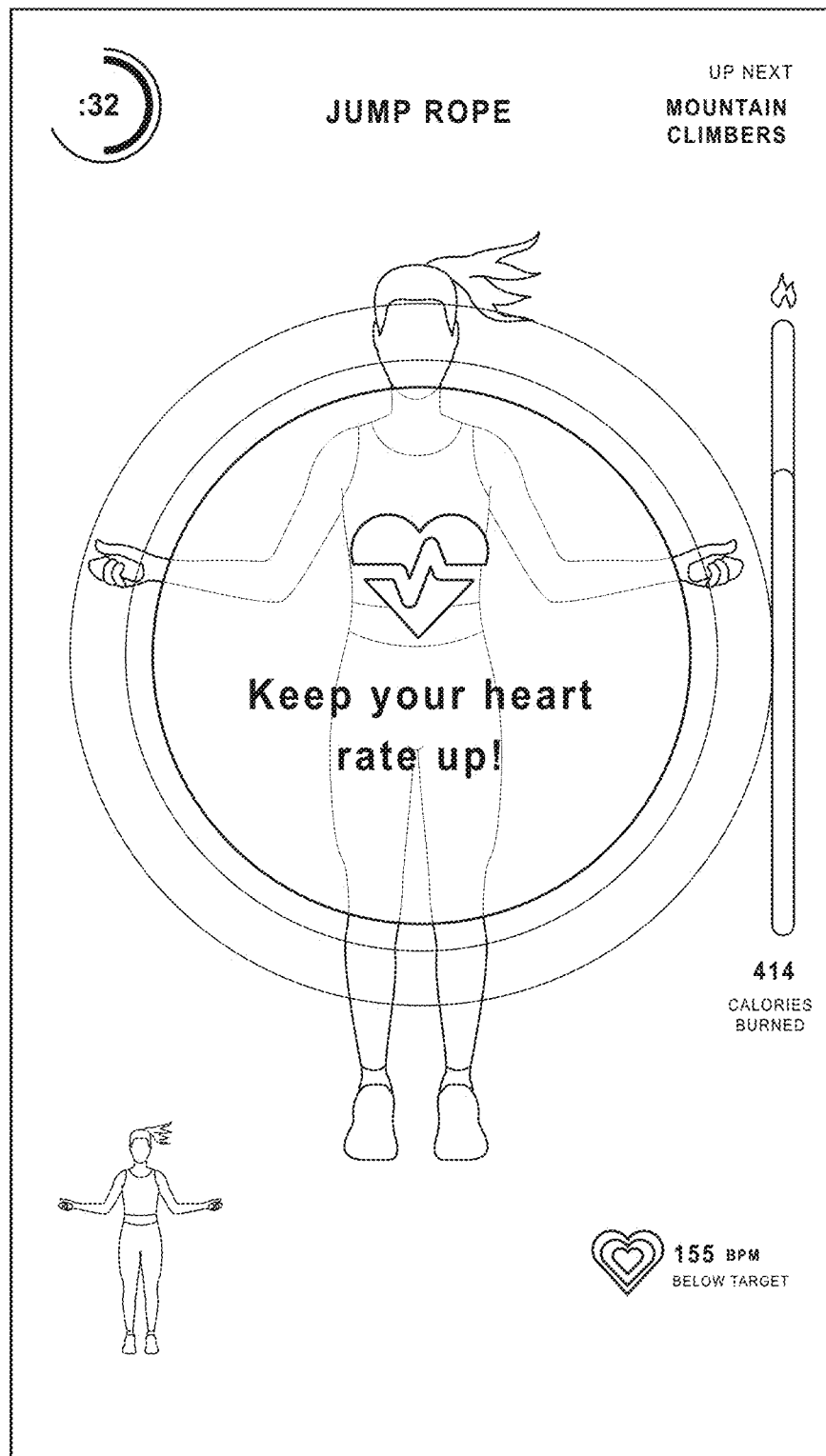
FIG. 33C shows an exemplary GUI on the smart mirror of a message displayed to a user based on the user's biometric data, in accordance with some embodiments.
Figure 33D:
FIG. 33D shows an exemplary GUI on the smart mirror of a message displayed to a user showing adaptation of the workout based on the user preferences, in accordance with some embodiments.
Figure 33E:
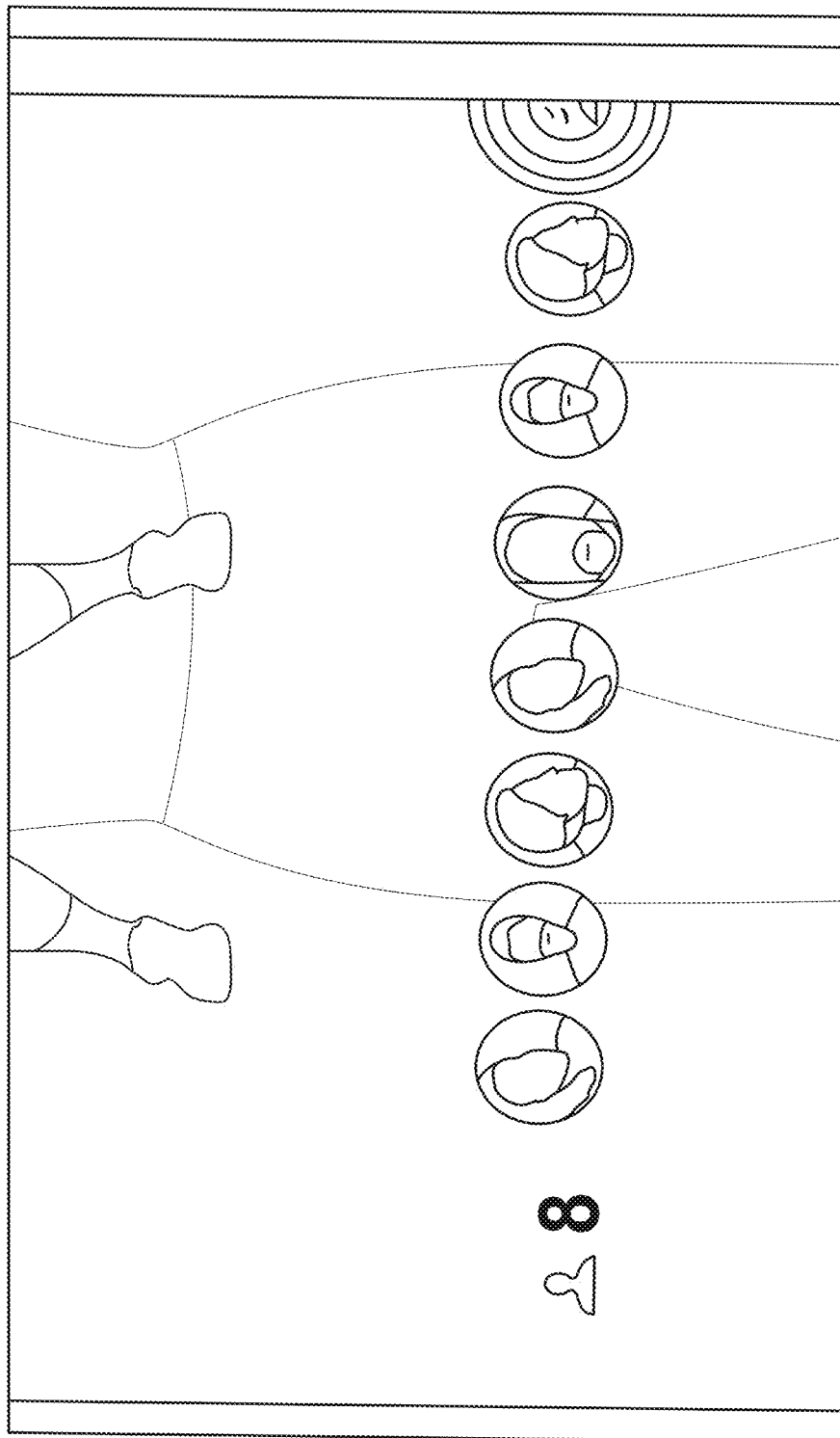
FIG. 33E shows an exemplary GUI on the smart mirror of avatars of other user's in the same fitness class, in accordance with some embodiments.
Figure 33F:
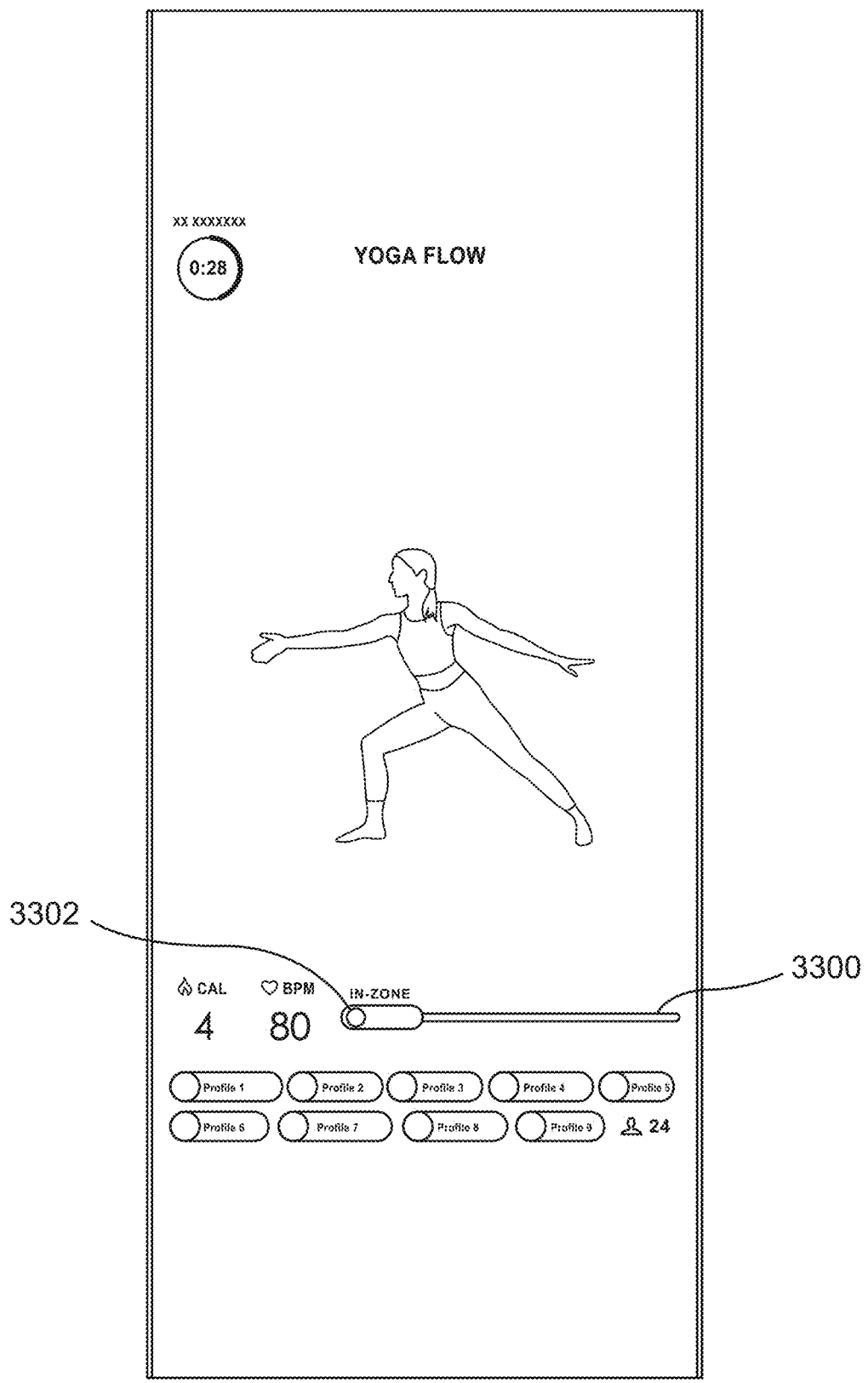
FIG. 33F shows an exemplary GUI on the smart mirror with the user's heart rate displayed on a target heart rate zone, in accordance with some embodiments.
Figure 33G:
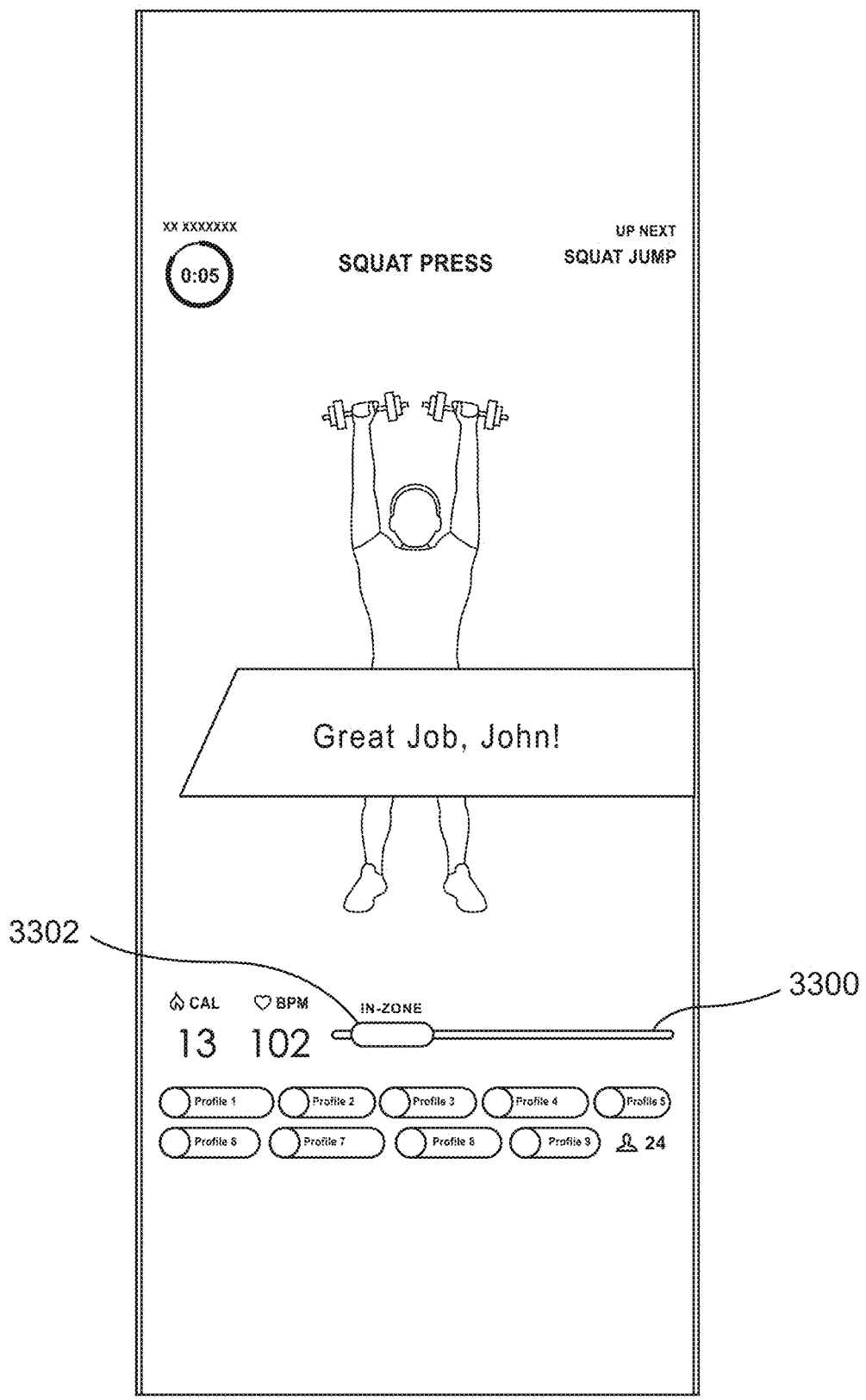
FIG. 33G shows an exemplary GUI on the smart mirror with a message indicating the user's heart rate meets a target heart rate zone, in accordance with some embodiments.
Figure 33H:
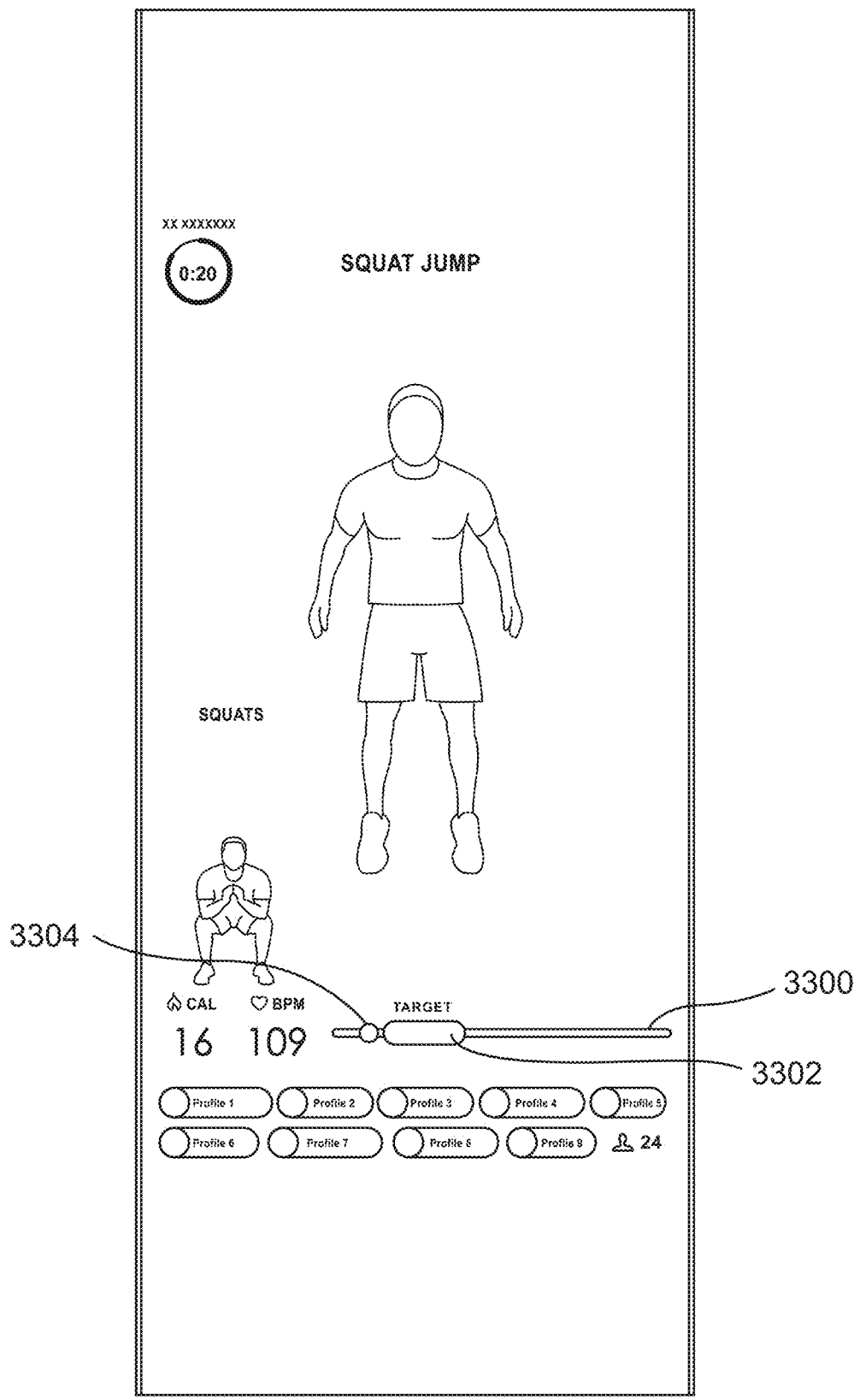
FIG. 33H shows an exemplary GUI on the smart mirror with the user's heart rate falls outside a target heart rate zone, in accordance with some embodiments.

In some cases, the smart mirror 100 may actively monitor the user's biometric data to provide additional guidance to the user. For example, FIG. 33C shows the smart mirror 100 may display a message indicating the user's heart rate has dropped below a desired threshold. Thus, the smart mirror 100 may indicate to the user to increase their intensity in order to increase their heart rate. In another example. FIG. 33D shows the smart mirror 100 may inform the user the exercise is modified to accommodate a user's injury and/or to reduce the risk of injury. In other cases, the GUI may provide a message containing other information derived from the biometric data including, but not limited to the user's heart rate relative to a target heart rate zone, the number of steps relative to a target number of steps, the user's perspiration rate, the user's breathing rate, and the extent to which the user is able to properly emulate the form and movement of a particular exercise (e.g., qualified using feedback such as 'poor', 'good', 'great').

The smart mirror 100 may also show avatars corresponding to at least a portion of the other users attending the same fitness class. The avatar may be an image of each user, an icon, or a graphic. For example, the smart mirror 100 may acquire an image of the user to display as an avatar during the initial creation of the user's account. The image may be modified or replaced thereafter. FIGS. 33E-33K show several exemplary representations of other users' avatars, names, and locations. Additional information from other users may also be shown including, but not limited to the other users' scores during the workout, skill level(s), and biometric data (e.g., heart rate, heart rate relative to a target heart rate zone, step count).

Figure 33I:
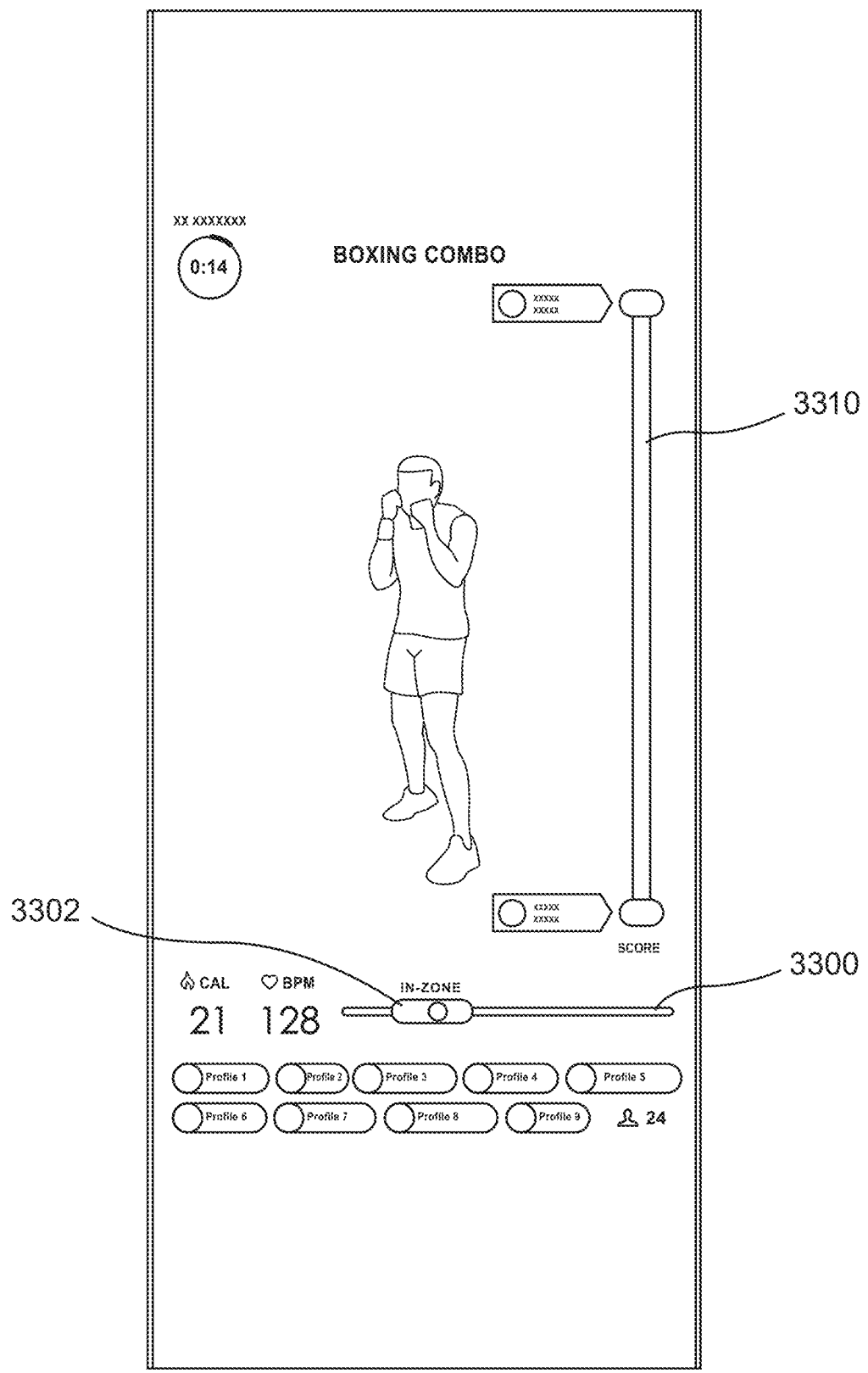
FIG. 33I shows an exemplary GUI on the smart mirror with the user's score and a target score, in accordance with some embodiments.
Figure 33J:
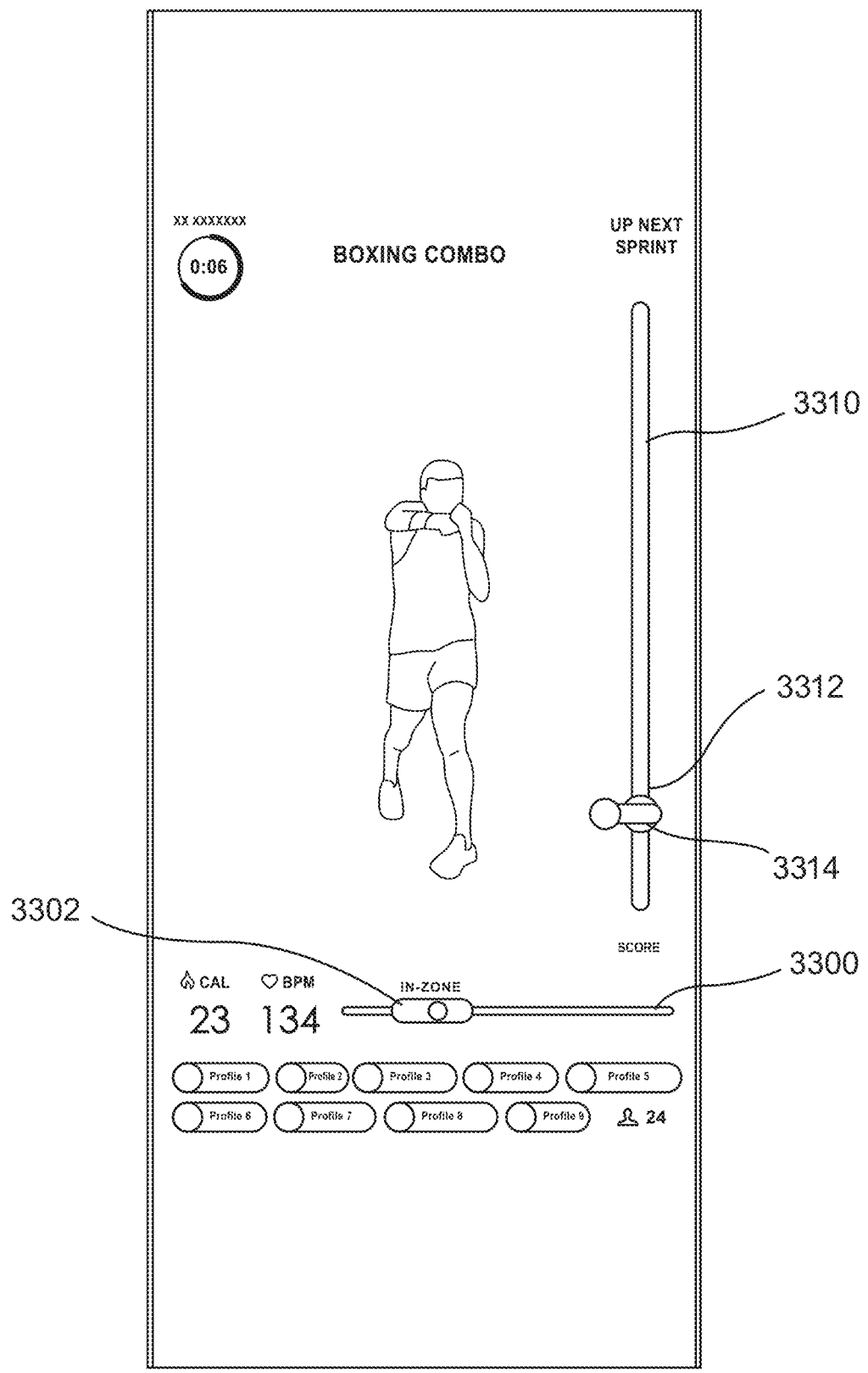
FIG. 33J shows an exemplary GUI on the smart mirror with the user's score and a target score at a later period of time in the workout relative to FIG. 33I.
Figure 33K:
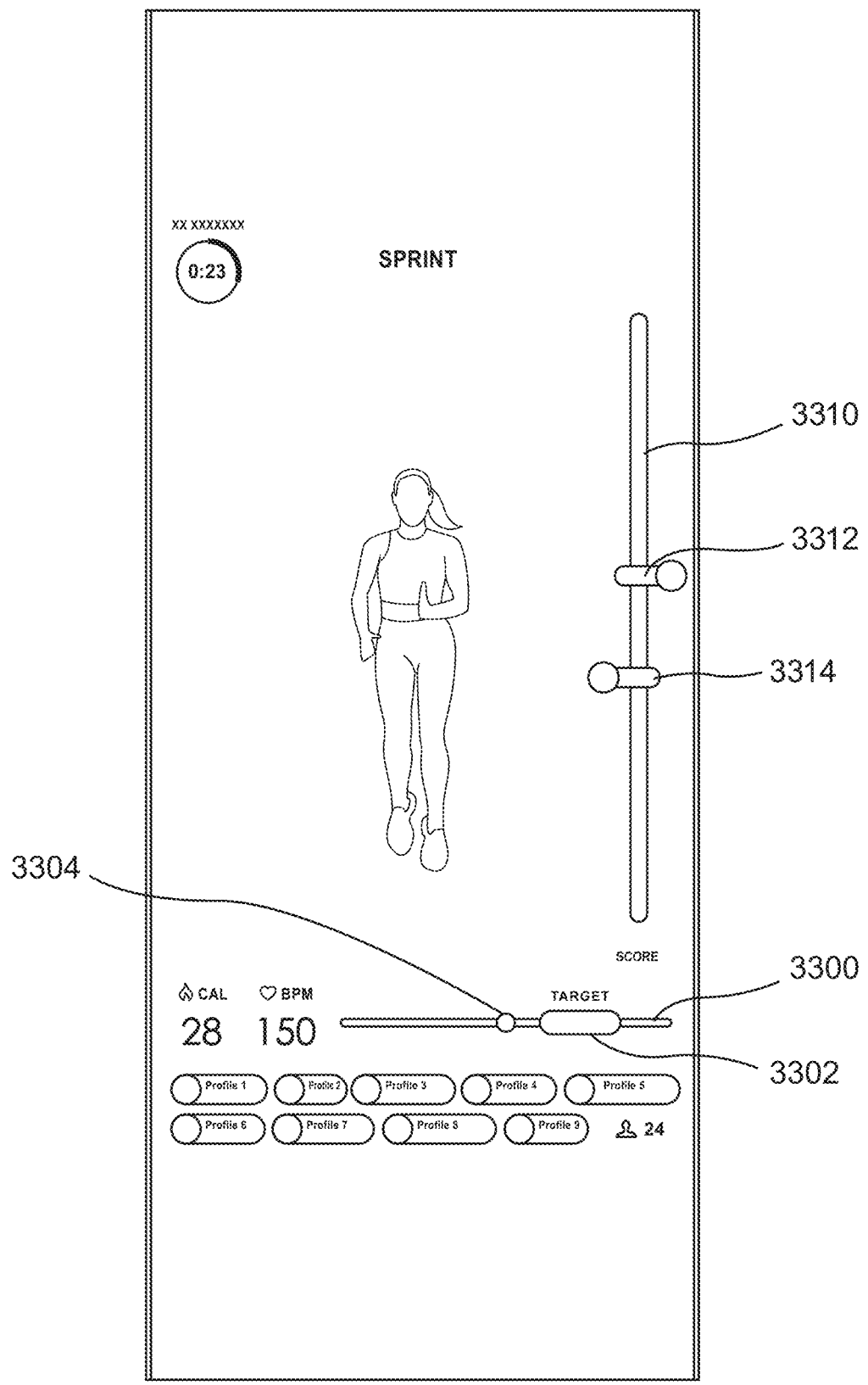
FIG. 33K shows an exemplary GUI on the smart mirror with the user's score and a target score at a later period of time in the workout relative to FIG. 33J.

Other information displayed on the smart mirror 100 may include the user's heart rate relative to a target heart rate zone. FIGS. 33F-33K show a horizontal heart rate range bar 3300 representing a heart rate range. The user's heart rate is shown on the bar in combination with a target heart rate zone 3302 on the heart rate range bar 3300. This information may visually indicate whether the user is exerting the appropriate level of intensity during the workout. This heart rate information may also be used to compute a score for the user to indicate their performance during the workout. For example, FIGS. 33I-33K show a score bar 3310 indicating the real-time score 3314 of the user relative to a target score 3312, such as a predetermined score, another user's score, the user's previous score when performing the same exercise and/or workout. The user's score 3314 may change as the exercise or workout progresses based on the number of points awarded for satisfying certain criteria, as discussed below. In some cases, a leaderboard may be displayed during or after the workout. The leaderboard may rank the users based on their respective scores.

Figure 33L:
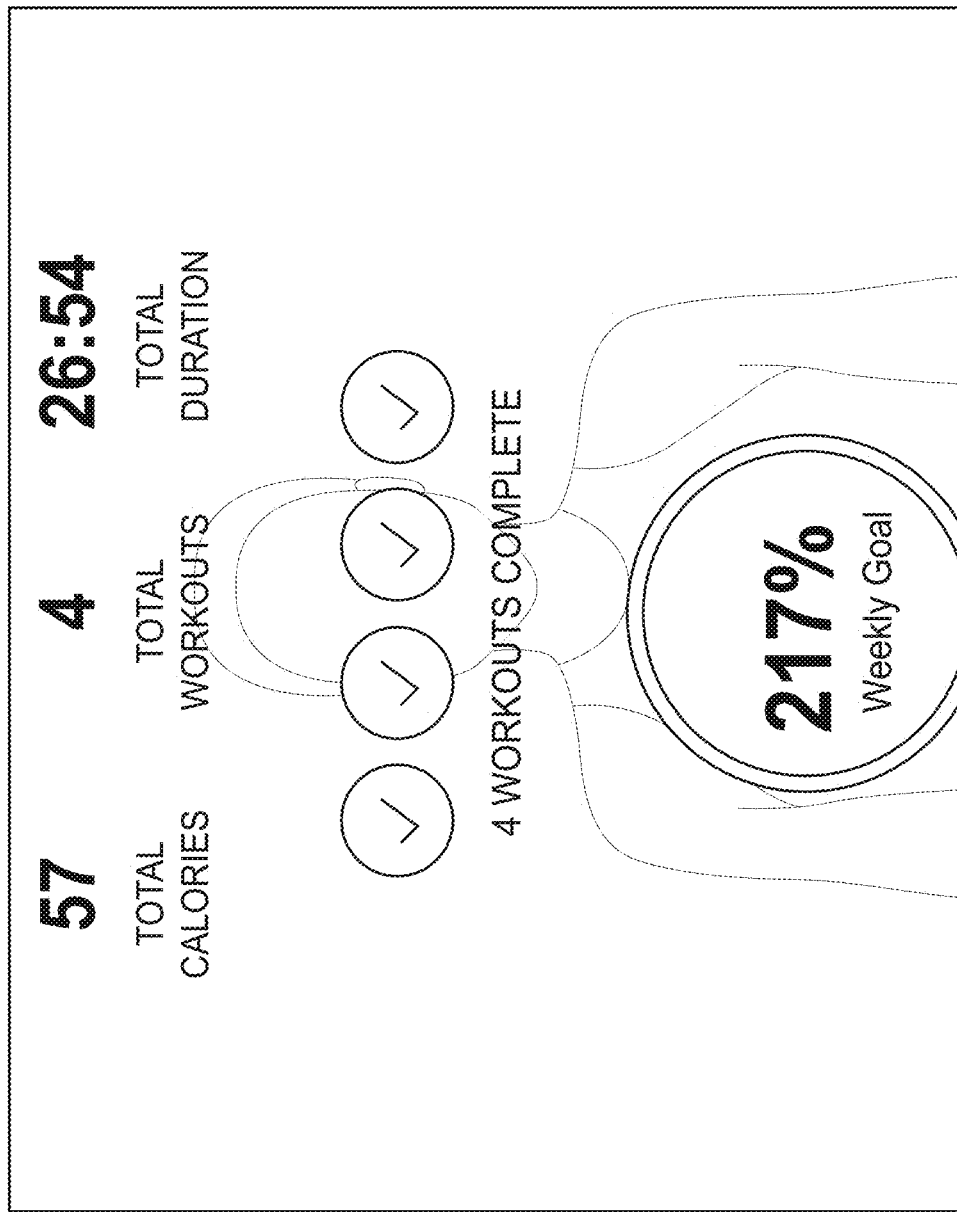
FIG. 33L shows an exemplary GUI on the smart mirror of a user's workout log, in accordance with some embodiments.
Figure 33M:
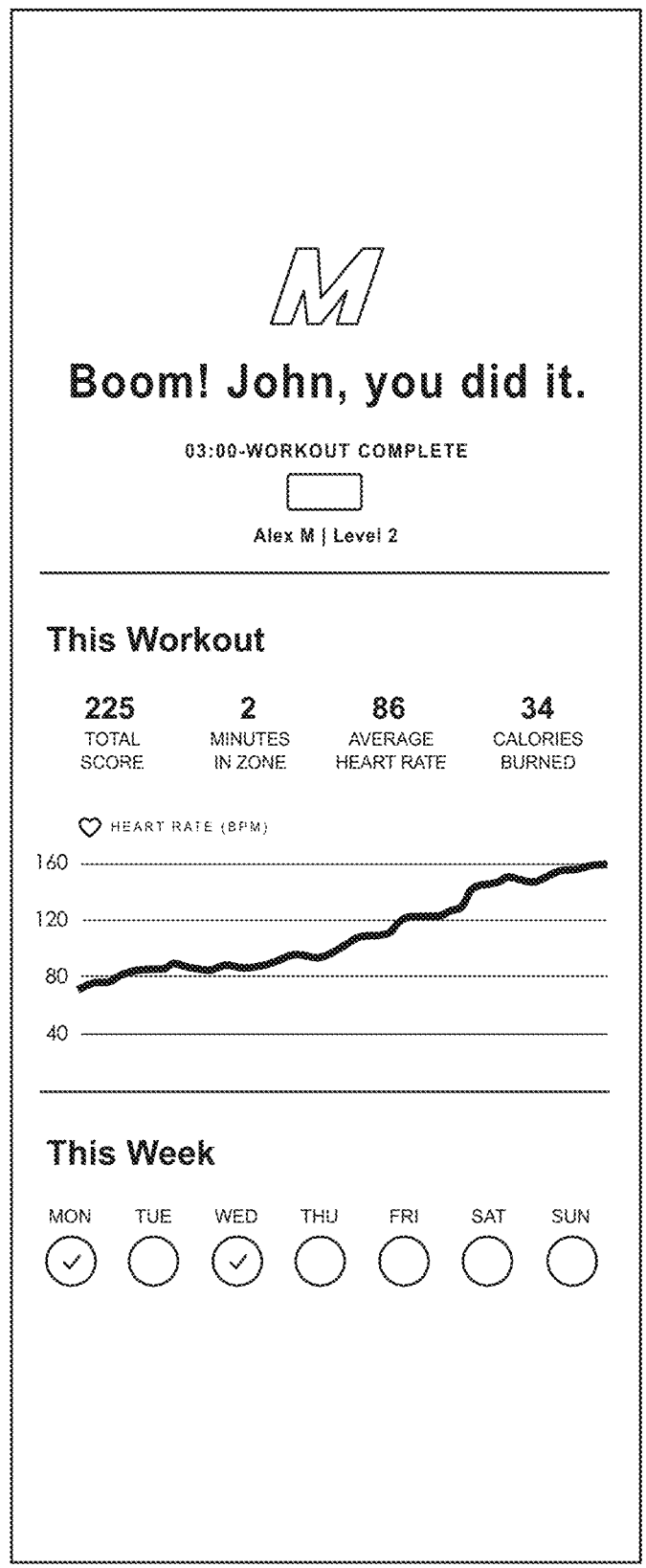
FIG. 33M shows an exemplary GUI on the smart mirror of a user's performance after a particular workout, in accordance with some embodiments.

Once the workout is complete, the GUI may display a summary of the workout and the weekly exercise log described above. For example, FIG. 33L shows the workout log on the smart mirror 100 as previously described with reference to the GUI shown on the user's smart phone in FIG. 32B. FIG. 33M shows a summary of the workout. As shown, the GUI may provide the user's score, the duration the user's heart rate was within the target heart rate zone, the user's average heart rate, the number of calories burned, and a chart showing the change in the user's heart rate during the workout. The GUI in FIG. 33M may also show the days of the week the user met their daily exercise goals.

In some cases, the user may receive achievements during or after the workout. These achievements may be awarded when the user satisfies certain criteria, as described below. The achievements may also be shared with other users in the fitness class immediately after receipt or after the workout is complete. Similarly, the user may see another user's achievements during or after the workout. The display of achievements may be toggled on or off in the settings depending on user preferences.

As described above, the smart mirror 100 may display a miniaturized representation of the instructor. In some cases, the miniaturized representation of the instructor may be overlaid with a corresponding representation of the user captured using the camera 130. Each representation may be semi-transparent to enable the user to compare their form and movement to the instructor. In some cases, the representation of the instructor or the representation of the user may be displayed as a stick model to provide greater visual clarity when comparing the two representations with respect to one another. In some applications, the GUI may enable the user to download representations of other users and/or instructors for guidance when performing a particular exercise. Furthermore, the smart mirror 100 and the GUI may enable the user to display multiple representations for comparison. For example, representations of each user in a fitness class may be displayed on the smart mirror 100.

The various GUI-related features shown on the smart mirror 100 may be toggled on or off via the settings GUI described above. The layout, color, and size of these GUI-features may also be customizable. For example, the user may wish to show as little information as possible (e.g., only the timer, exercise type, and the progress bar) such that the video content and the user's reflection appear less cluttered and/or less obstructed during the workout.

The smart mirror 100 may also be configured to dynamically adjust and adapt content in real-time during a workout. Such adjustments may depend on a combination of user preferences and instructor recommendations. For example, the user may specify preferences on various types of fitness routines (e.g., cardio workouts, strength training, stretching, upper body workouts, core workouts, lower body workouts, current injuries, and past injuries). Based on these preferences, the instructor may recommend a particular set of fitness routines and past user ratings of these fitness routines.

The recommended fitness routines may be then be streamed to the user and updated in real-time based on user feedback (e.g., preferences on intensity level of exercise, preferences on exercising certain areas of the body). Biometric data (e.g., heart rate, breathing rate) may also be monitored to adjust the intensity of the fitness routines. For example, the instructor (or the user) may specify a target range for the user's heart rate during the workout. If the user's heart rate is out of the target range, the smart mirror 100 may first warn the user and then adjust the content to either bring the user's heart rate into the target range or modify the target range if the fitness routine is no longer preferred. Dynamic adaptation of content may be achieved by analyzing user feedback or biometrics data using a processor with a decision tree, neural network, or another machine learning method.

Sharing Social Media Using a Smart Mirror

The smart mirror 100 may also have a social networking component that allows the user to connect to another person (e.g., another user, an instructor) and a group/community of people. The user may connect to another person using a search feature integrated into the GUI. The search feature may enable the user to search for another person based on various attributes including, but not limited to their legal name, username, age, demographic, location, fitness interests, fitness goals, skill level, weight, height, gender, current injuries, injury history, and type of workout music. In one example, once the user selects another person with which they want to connect to, a request may be send to the other person for subsequent confirmation/approval. If the other person approves, the user may be connected to the other person and may see the person on a list of contacts. In some cases, the user may configure their account to automatically accept requests from other users. This may be an option selected under the settings portion of the GUI.

The GUI may also provide other methods for the user to connect to another person. For example, the user may connect to other users based on their attendance of a particular fitness class. For example, the user may register for a fitness class. Before the class begins, the user may be able to view other users attending the same class. The GUI may enable the user to select another user and send a connection request. A connection request may also be sent during or after the fitness class. The GUI may also recommend people to connect with based on the attributes described above (e.g., the attributes may be combined to form a representation of the user) as well as other attributes including but not limited to a similar workout history, similar workout performance or progression, similar scores on a leaderboard, geographic proximity (e.g., based on a user's defined location, an Internet Protocol (IP) address), and/or shared connections with other users (e.g., $1^{st}$ degree, $2^{nd}$ degree, $3^{rd}$ degree connections). The GUI may also enable the user to browse through a leaderboard and select another user shown on the leaderboard. Once the other user is selected, a connection request may again be sent.

The GUI may provide a list of contacts to the user, which may be grouped and/or organized according to the user's preferences. For example, the list of contacts may be arranged based on the user's immediate family, friends, coworkers, list of instructors, people sharing similar interests, demographic, and so on. The list of contacts may also include a filter that enables the user to select and display one or more groups.

Additionally, the GUI may enable the user to join another group and/or community of users. For example, a user may create a group for users interested in cycling. Another group may be created for users interested in other interests such as boxing, running, weightlifting, and/or yoga. The group may be set to be a public group where any user may see the group via the GUI and may send a connection request to join the group. The group may also be set to be a private group that may not be available via the GUI and only allows users to join by an invitation. The group may be created by a user or an instructor. Other users may join the group upon approval by the creator or another user with appropriate administrative rights. In some cases, the group may be configured to accept all connection request automatically.

The group may be used, in part, to provide users a forum to communicate and share information with one another. For example, a user may provide recommendations for various fitness classes to other users. In another example, an instructor may send a message on a new or upcoming fitness class they are teaching. In another example, a user may send a message indicating they are about to begin a fitness class. The message may provide an interactive element that enables other users to join the fitness class directly, thus skipping the various navigational screens previously described to select a fitness class. Additionally, a user may post a message containing audio and/or video acquired by the smart mirror 100 to share with other users in the group. For example, a user may post a video showing their progress in losing weight. In another example, the user may show video of the instructor and/or other users participating in the fitness class. A user in the group may also generate a group-specific leaderboard to track and rank various members of the group.

In some cases, the GUI may also enable at least a portion of the users within a group to join a particular fitness class together. For example, the users within a group may form a subgroup where a designated leader of the subgroup may then select a fitness class, using similar processes described above, thus causing the other members of the subgroup to automatically join the same fitness class. In some cases, two or more users of the group may join the same fitness class via the same smart mirror 100, i.e., at the same physical location. The mirror 100 may be able to recognize and distinguish different users based on video and/or imagery acquired via the camera 130 and analyzed as described above for user recognition and tracking, based on voice input acquired via the microphone 160 and analyzed as described above for voice recognition, via each user expressly identifying themselves (e.g., by logging into their profile via the same mirror 100), and/or the like.

The GUI may also provide live audio and/or video chat between users within the same group and/or subgroup. For example, when a subgroup of users joins a fitness class together, the GUI may allow the users of the subgroup to communicate with one another during the workout. This may include audio and video (e.g., a frame showing the other user's head, face, or body) streams from other users overlaid onto the exercise displayed on the display panel 120. It should be appreciated the subgroup may also be formed based on the user's selection of one or more contacts on their list of contacts (as opposed to being restricted to users within a group).

The GUI may also enable the user to create a social network blog to include various user-generated content and content automatically generated by the smart mirror 100. User-generated content may include, but is not limited to ratings or reviews of various fitness classes, audio messages generated by the user, video messages generated by the user, interactive elements linking to one or more fitness classes. Automatically generated content may include, but is not limited to updates to the user's score on a leaderboard, achievements by the user (e.g., completing a fitness goal), and attendance to a fitness class. The content shown on the user's social network blog may be designated as being public (e.g., any user may view the content) or private (e.g., only select group of users designated by the user may view the content).

The GUI may also enable the user to "follow" another user. In this description, "follow" is defined as the user being able to view another user's information that is publicly accessible including, but not limited to the other user's social network blog, workout history, and score(s) on various leaderboards. The option of following another user may be presented as another option when the user is assessing whether they want to connect to other user. Therefore, the GUI may enable the user to follow another user using similar methods described above in the context of connecting to other users.

Figure 34A:
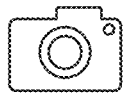
FIG. 34A shows an exemplary GUI on the smart mirror notifying the user take an image of themselves, in accordance with some embodiments.
Figure 34B:
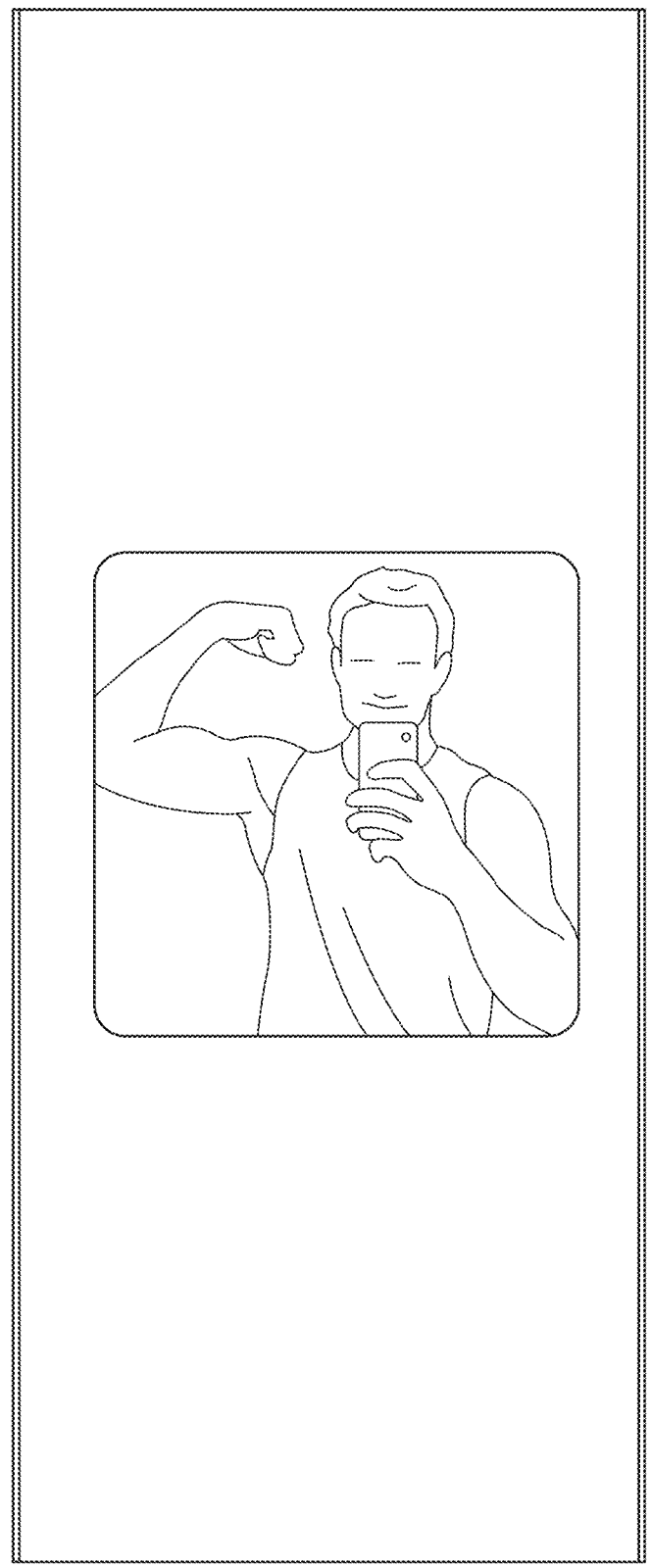
FIG. 34B shows an exemplary GUI on the smart mirror of the user's image acquired by the camera of the smart mirror, in accordance with some embodiments.
Figure 34C:
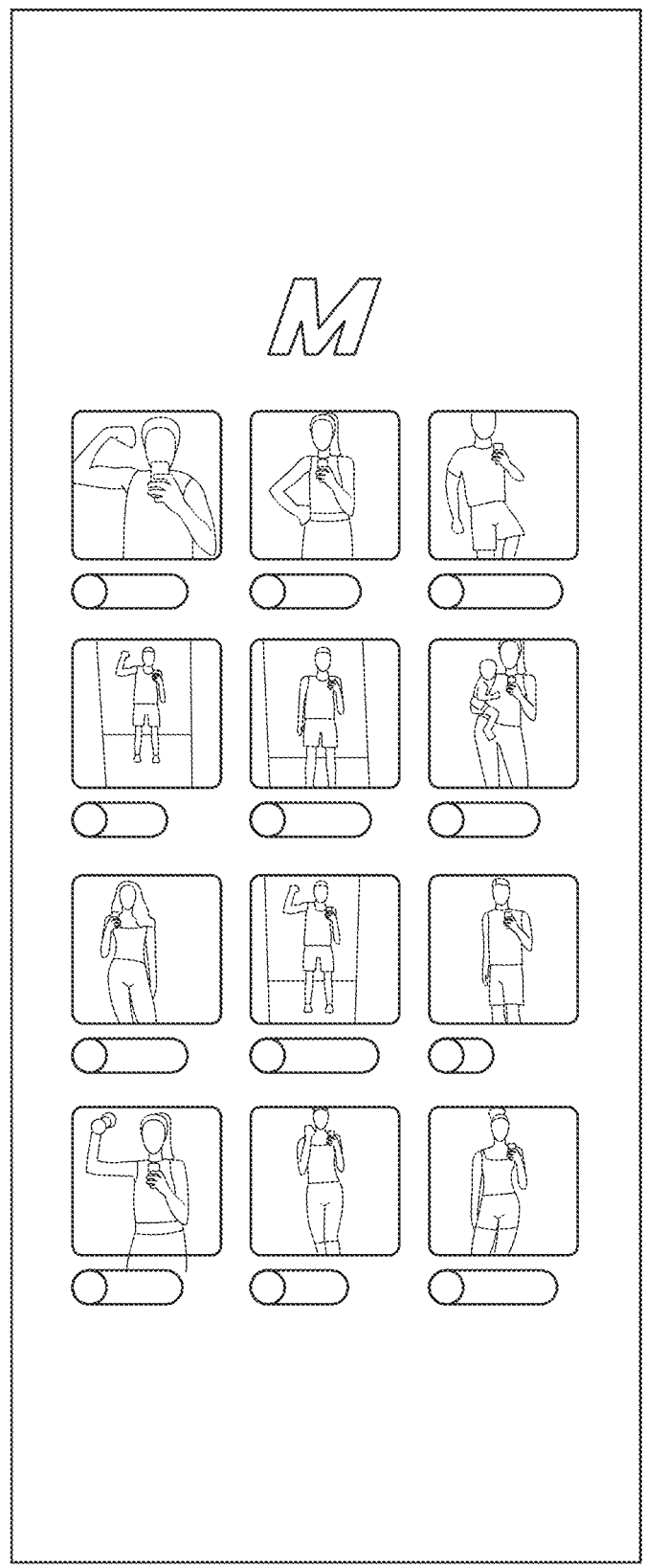
FIG. 34C shows an exemplary GUI on the smart mirror of multiple user's images, in accordance with some embodiments.

As described above, the smart mirror 100 may be used to share various user information with other users including, but not limited to the user's profile, social network blog, achievements, biometrics, activity selection, a video recording, and feedback. For example, user A may share their progress on a fitness routine to user B, who can then provide feedback (e.g., an emoji, an audio message, a video message, etc.) to user A. In another example, the GUI on the smart mirror 100 or on the user's smart phone may prompt the user to take a selfie image, either with the smart mirror's camera 130 or the smart phone, following the completion of a workout as shown in FIG. 34A. The camera 130 and the display panel 120 may then be configured to show a live video of the user to create a desired pose. An image of the user may then be acquired (e.g., after a preset period of time or based on an input command by the user) as shown in FIG. 34B. The image of the user may then be shared with other users (e.g., in the same fitness class, in the user's list of contacts, in the user's group) as shown in FIG. 34C. The user may also view other user's images.

In another example, the camera 130 may record a video of user A during a workout, which may then be shared with user B. As user B performs the same workout, the video of user A may be overlaid onto the display panel 120 with a live video of user B. The respective video recording of user A and the live video of user B may be semi-transparent such that user B may compare their form and/or movement to user A during the workout. In some cases, the smart mirror 100 may enable the user to download video recordings of other users and/or instructors to display onto their respective smart mirror 100 whilst performing the workout. In this manner, the smart mirror 100 may support a "ghost mode" that allows users to compare their performance during a workout to other people. For example, the user may download a video recording of multiple experts performing the same workout. The user may then display the video recording of each expert (individually or in combination) to evaluate the user's progression in the workout.

The smart mirror 100 may also support achievements. Achievements are defined as rewards given to the user upon satisfying certain criteria for the achievement. The rewards may include, but is not limited to a badge (e.g., a visual graphic the user can share with others), a number of points contributing to a user's leaderboard position, and access or a discount to premium content. Achievements may be given for various reasons including, but not limited to exercising several days in a row, meeting an exercise goal, completing certain types of workouts and/or exercises, completing a certain number of workouts and/or exercises, and advancing to more difficult skill levels. A summary of the achievements may be shown on the GUI to the user.

Information may be shared between users in several ways. In one example, smart mirrors may share data directly with one another via local, direct connections when the smart mirrors are connected to the same network (e.g., multiple smart mirrors at a gym, hotel, or home). In another example, information may be shared via the application installed on each user's smart device through a remote network connection (e.g., a wireless network, wireless internet, a telecommunication network). Information may also be stored remotely on a server, which may then be distributed between users (e.g., with or without authorization of the user depending on the settings of the smart mirror 100 and/or the user's account).

Leaderboards, Heart Rate, and Transitions Between Target Heart Rate Zones

As described above, the GUI may also include one or more leaderboards to rank users according to a user's score. For example, a leaderboard may be generated for each fitness class to rank the participant's performance during and after the class. In another example, one or more global leaderboards may be used to rank many, if not all, users based on the type of exercise or a combination of different exercises.

The leaderboard may be used, in part, to provide a competitive environment when using the smart mirror 100. Users may use their scores to evaluate their progress at a workout by comparing their current scores to their own previous scores recorded by the smart mirror 100. Additionally, one user may compete against one or more other users (e.g., globally, within the same group, within the same subgroup) to attain higher scores in a live setting (e.g., users within the same fitness class) or with respect to previous scores recorded by the other user(s). The user may configure the leaderboard to show other users exhibiting similar attributes including, but not limited to demographic, gender, age, height, weight, injury, location, skill level, and fitness goal. These attributes may be dependent on the user (e.g., the leaderboard includes users similar to the user) or may be entirely independent (e.g., the leaderboard includes users dependent solely on the criteria specified by the user).

The user's score on a leaderboard may be calculated in various ways. In one example, the user's score may be determined based on how quickly the user's hear rate (HR) moves between different target hear rate zones. A target hear rate zone may be defined as some percentage range of a user's peak heart rate. Various heart rate zones may thus be defined including, but not limited to a rest zone, a fitness zone, an aerobic zone, an anaerobic zone, a fat burn zone, and a cardio zone. There may be a different target heart rate zone for each section of an exercise video (e.g., a warm-up heart rate zone to start, alternating rest and anaerobic heart rate zones during intervals, and a warm-down heart rate zone to end). Depending on the definition of these zones, some zones may overlap in the range of the percentage of the user's peak heart rate.

A HR accuracy percentage may be used to determine the number of points given to the user during a workout. The HR accuracy percentage represents how quickly the user's hear rate (HR) moves between the different target hear rate zones. A higher score may correspond to the HR changing instantaneously. However, this situation may be unrealistic and/or may result in an exceedingly challenging condition imposed on the user resulting in biased scores. In some cases, the score may instead be computed by comparing the user's heart rate to a HR curve representing the transitions between different HR zones. The HR curve may include a smoothing effect between each HR zone transition to provide a more realistically attainable HR accuracy percentage. The smoothing effect may depend on various metrics including, but not limited to the user's historical HR data, the HR data of a community of user's, the user preferences, the user demographic, the exercise and/or workout structure.

In one use case, a single smart mirror 100 may support multiple users performing a workout. During the workout, the scores for each user may be displayed on the display panel 120. In this manner, the users may compare their scores against one another during the workout, which may provide an incentive for the users to achieve a greater workout performance compared to the case where each easer exercises on their own separately.

In another example, the user's score may be computed based on other factors of a user's workout performance (which may depend on the type of biometric data collected) including, but not limited to the user's step count, number of repetitions for each exercise, distance traveled (e.g., if running or walking), calories burned, the period of time the user's HR is in a particular HR zone, the user's form and/or movement when performing a particular exercise routine. In some cases, the user's score may be modified based on conditions that render a particular exercise more difficult or easier including, but not limited to the weight being lifted, the incline angle of a treadmill, the resistance setting of an exercise bike, and/or the use of supporting blocks during yoga. These modifications may be in the form of a multiplier applied to the user's score to rewards and penalize the user based on the relative difficulty of the conditions of the exercise.

The user's score may be a combination of one or more of the factors described above. In some cases, the user's score may further include weights applied to particular exercises to intentionally bias the user's score. For example, more points may be awarded to the user for cardio-related exercises compared to strength-related exercises to correspond to the user's fitness goal of increasing stamina. The user's score may also be computed where strength-related exercises are given more points than cardio-related exercises to provide the user a score representative of their fitness goal of increasing their strength. Multiple scores may thus be generated based on the user's biometric data and workout history to convey to the user a quantitative metric representing their progress for various fitness attributes.

Smart Mirror Background Processes

In addition to the GUI providing users the ability to access and control the operation of the smart mirror 100 and/or the content shown on the display panel 120 of the smart mirror 100, various background processes may also provide user's additional information when not actively using the smart mirror 100. A background process may be a process that performs certain functions that, depending on the output of the function, results in the generation and transmission of a message to the user with a representation of the output. The background process may be substantially automated. This allows, for instance, a user to run other applications on their smart device while the background process is running. These background processes may run locally on a user's smart device (e.g., a smart phone) or remotely on a device (e.g., a server) with communication access to the smart mirror 100 and/or the user's smart device. A background process may be controlled, in part, via an application installed on the user's smart device, the smart mirror 100, and/or a remote device.

The background process may be configured to send various types of messages (also treated as notifications) to the user including, but not limited to a text message, an email, a voicemail, or a post on a user's social network account. The frequency of the messages may vary depending on the content of the message. For example, a message containing a reminder for the user to exercise may be sent every other hour of each day. In another example, a message from another user or an instructor may be sent to the user immediately after submission or may be stored and aggregated with other messages to be sent as a digest (e.g., an email digest containing multiple messages). In yet another example, recommendations for fitness classes may be sent to a user on a weekly or monthly basis. Generally, the message may be sent to the user at various frequencies (e.g., ranging between immediately after the message is generated to months or even years) depending, in part, on user preferences. The background process may also be configured to reduce power consumption, thus prolonging a device that operates using a battery (e.g., a user's smartphone or tablet).

In some cases, the message sent by a background process may include an interactive element (e.g., a web link, a button) for a user to provide input. For example, a message containing a recommendation for a class may include one or more options a user can select (e.g., 'register for class', 'not interested'). If the user selects the option to register for the class, a web page or an application may open to a screen that allows the user to review the class and finalize registration. In another example, a message containing a status update of another user (e.g., a user's friend) may provide options for the user to send an emoji to indicate their response. For instance, if the user's friend successfully meets one of their fitness goals, the user may send a smiley face or a thumbs up. In yet another example, a message may indicate a user's friend is attending a particular fitness class and may include an option to enable the user to join the fitness class without navigating through other screens of the GUI.

Generally, various content may be included in a message generated by a background process. For example, a background process may monitor the duration of time since a user previously used the smart mirror 100. After exceeding a predefined threshold (e.g., an hour, a day, a week), a message may be generated to remind the user to exercise. The message may also contain a user's progress towards meeting one or more fitness goals. The smart mirror 100 may also send status updates to the user including, but not limited to when a new software update is available for installation, connectivity issues between a user's smart device and the smart mirror 100 or the smart mirror 100 and a network, an unauthorized login into a user's account, and when another user is using the smart mirror 100 (e.g., a family member).

A background process may also relay messages from an instructor (or another user) sent directly to the user or posted on the user's social network blog. The message may include, but is not limited to updates on the status of a fitness class (e.g., cancellation, change of schedule), feedback from an instructor following a particular fitness class, feedback from a personal trainer providing guidance to the user on a regular basis, recommendations for a fitness class, messages posted to a community forum, a digest of messages from other users, and/or requests for connection on a user's social network. A background process may also monitor updates of other user's (e.g., a friend, a person followed by the user) and send messages in an automated manner when certain updates occur. The message may contain various content including, but not limited to the other user completing one or more fitness goals, the other user registering and/or participating in a new fitness class, the other user liking or providing a high rating to a particular fitness class, a change in the other user's position on a leaderboard, updated pictures of the other user (e.g., after completing a fitness class), and birthday wishes.

Generating Content for a Smart Mirror

The smart mirror 100 is configured to provide a flexible platform that allows video content generated by instructors (or other users) to be readily disseminated to a user. The various networking capabilities of the smart mirror 100 described above may enable video content to be live streamed directly to a user's smart mirror 100 or stored on a centralized distribution platform (e.g., a remote server, a cloud service) for subsequent consumption by the user. In some cases, the video content may be distributed through use of a software application connected to the smart mirror 100 (e.g., a first party app from the manufacturer of the smart mirror 100 or a third party app from a streaming service compatible with the smart mirror 100).

Video content may be generated in various settings, such as a fitness studio or a user's home. In one example, an instructor may generate video content of a fitness class using a studio. The studio may use a standard, one-camera setup or a more sophisticated setup (e.g., multiple cameras to acquire video at multiple viewing angles) to acquire video of a fitness class. A producer may be used to monitor and/or control the audio-visual equipment used to stream the class. The fitness class may be defined as a single continuous shot from beginning to end of the instructor performing the workout.

The studio may be setup to stream one class at a time. The video/audio of the class is captured and transcoded via a hardware encoder (e.g., Epiphan Pearl). The class may be live streamed by uploading the video content to a low-latency cloud server (e.g., a Wowza cloud server) where the content is transcoded and broadcast to an HLS stream (private or public). The content may also be recorded at a high resolution for subsequent re-use or playback (e.g., as on-demand content).

The studio may include a room with a trainer wall where video is recorded. The room may have dimensions of approximately 18 feet wide, 30 feet long, and 12.3 feet high. The camera recording the video may be positioned approximately 15 feet from the trainer wall. The camera may be configured to have a field of view of the trainer area with dimensions approximately 8 feet wide, 9 feet deep, and 9 feet high, corresponding to a recorded area. Other studio arrangements with different room dimensions and camera placement may be used depending on the desired viewing and field of view of the instructor.

The recorded area may be configured to be a 'black box', where the walls of the recorded area are covered in a dark colored material (e.g., a matte black paint) and the floor is covered with a high grip, dark colored material (e.g., a black rubber floor with little texture). The recorded area may be illuminated by side lighting devices disposed at various heights and assembled to form a small semi-circle on either side of the instructor. Overhead lighting may result in reflections and the scattering of light off the floor. In order to maintain a 'black void' configuration, the presence of overhead lighting should be reduced. The lighting systems may also be configured to emit light with various colors and lighting effects (e.g., highlights, wash effects).

In other settings, the recorded area may be configured to have surfaces with various colors, patterns, and/or surface finishes including, but not limited to one or more green screens for picture in picture videos, an all-white backdrop, a black Plexiglas floor, and a grey concrete floor. The studio may also be configured to have one or more cameras to record video at various angles. For example, two cameras with a B-roll for a master video or a picture in picture configuration may be used. Two cameras that record video at various angle changes may also be used.

The camera may be configured to record video at various resolutions for live streaming and/or recording (e.g., 1080p, 1080i, 2K, ultra-high definition (UHD), 4K, 8K). The video recorded by the camera may be in various formats including, but not limited to H.264 and MPEG formats. The video may be recorded at various framerates (e.g., 24 frames per second). For example, a single fixed camera (Sony FS5K) may be mounted on its side to record video with a portrait view. A look up table (LUT) may be applied to the video feed before being passed to the encoder in order to reduce the amount of color correction processing during post processing of the recorded video. Other various settings on the camera may be adjusted including, but not limited to International Standards Organization (ISO) settings (e.g., ISO 3200), and white balance (WB) settings (e.g., WB 6300K).

For sound recording, one or more microphones may be used. For example, the studio may include two highly directional Audix Miniature shotgun mics mounted on a 50" gooseneck boom supported by a simple floor-standing microphone stand. In this manner, environmental noise, such as traffic and external room noise, may be reduced without having to attach a microphone directly to the instructor. A plurality of microphones may be used to facilitate sound recording when the instructor changes position. For example, one microphone may be configured for instructors in a standing position and another microphone may be configured for instructors in a crouching/prone position. An automixer may be coupled to the microphones to ensure the sound recorded by multiple microphones is properly balanced. Hands-free microphones, such as a lavalier microphone, may also be used for sound recording and to reduce environmental noise during recording. Audio may be recorded at various qualities (e.g., AAC 48 kHz stereo 320 kpbs).

The quality of the live stream and the recorded video may be substantially similar or intentionally different. For example, the studio may be configured to stream video at a 1080 by 1920 pixel resolution, 24 frames per second, and 23 megabits per second for the highest bandwidth configuration. Adaptive streaming may also be applied when streaming video to adapt to variabilities in a user's network bandwidth. The smart mirror 100 may adjust video quality by detecting the user's bandwidth in real-time.

The fitness class may be recorded in various configurations. For example, the fitness class may include only the instructor or the instructor with one or more students to depending on which configuration provides improved user immersion and/or a better approach to teaching an exercise technique. This may depend, in part, on user preferences as well. The video content may be recorded at variable framerates (e.g., a high frame rate per second recording may facilitate slow motion playback). The video content may also be recorded with up to a 360 degree format to allow users to change views of the fitness class during a workout. This effect may also be achieved through use of multiple cameras as well. Furthermore, video content recorded in the studio may be annotated with exercise specific notes and/or lines drawn on the instructor to provide greater clarity to the form and movement of a particular exercise. In some cases, a talking head may also be included to provide users with narration during the class.

Instructor Interface for Smart Mirror Classes

An instructor user interface may also be provided to assist the instructor in managing the fitness class in real-time. The instructor user interface may be shown on the display of various devices including, but not limited to a computer, a smart phone, a tablet, a smart watch, and a television. Furthermore, the instructor user interface may be accessed using a dedicated software application installed locally on the instructor's device and/or via a web application using a web browser. In some cases, the instructor may also use the smart mirror 100 to record video content using the camera 130 and the microphone 160 and/or to manage the fitness class using the smart mirror 100 directly or a smart device coupled to the smart mirror 100.

The instructor user interface may include various information on the fitness class and the users attending the class including, but not limited to a class itinerary, a class timeline, user information of each user, user scores, a leaderboard of users, and user feedback on each exercise and/or the overall class. The instructor may use the instructor user interface to select and modify a class plan or timeline before or during the fitness class. The timeline of the class may be adjusted dynamically in real-time based on the instructor's progress in executing the class plan. For example, the instructor may decide to shorten or remove a particular exercise in favor of prolonging another exercise. In another example, user feedback during the class may indicate to the instructor the users are getting tired more quickly than anticipated, thus the instructor may change the class plan in favor of less physically intense routines.

The instructor user interface may devote one section of the instructor's device display to show the class plan and the class timeline. Another section of the instructor user interface may show an instructor dashboard with user information of each user. The user information may include, but is not limited to each user's biometric data, user feedback (e.g., emoji's, ratings for each exercise), age, weight, gender, height, injury history, previous fitness classes attended, desired goals for the workout (e.g., losing weight, building muscle). The instructor dashboard may also include a summary of the user's attending the class, which may be updated in real-time. The summary may also include a representative score of each user as the fitness class progresses. In this manner, the instructor may determine users who are exceeding or falling behind the pace of the exercise.

The instructor dashboard may also enable the instructor to provide individual messages and/or feedback to each user in various formats including, but not limited to emojis (e.g., a thumbs up, a thumbs down), audio directed specifically to a particular user or group of users, and video directed specifically to a particular user or group of users. The instructor may also be able to provide instructions or displays showing how to perform modified versions of exercises for users who are injured or who have other physicals limitations. For instance, the instructor may display a main exercise and a modified exercise (e.g., "Squat Jumps" and "Squats" as in FIG. 33H) for those who choose not to perform the main exercise. These versions can be displayed to all users or to only affected users.

As described above, the instructor user interface may be shown on the display panel 120 of the smart mirror 100. The camera 130 and the microphone 160 of the smart mirror 100 may be used to enable the instructor to provide the aforementioned feedback to a user or group of users. Additionally, the speakers 152 and 154 may be used to receive audio feedback from a user or group of users during the fitness class. For example, the instructor may ask how the users are feeling after each exercise and the users may respond by verbally telling the instructor the pace is too fast, too slow, or satisfactory.

Figure 35A:
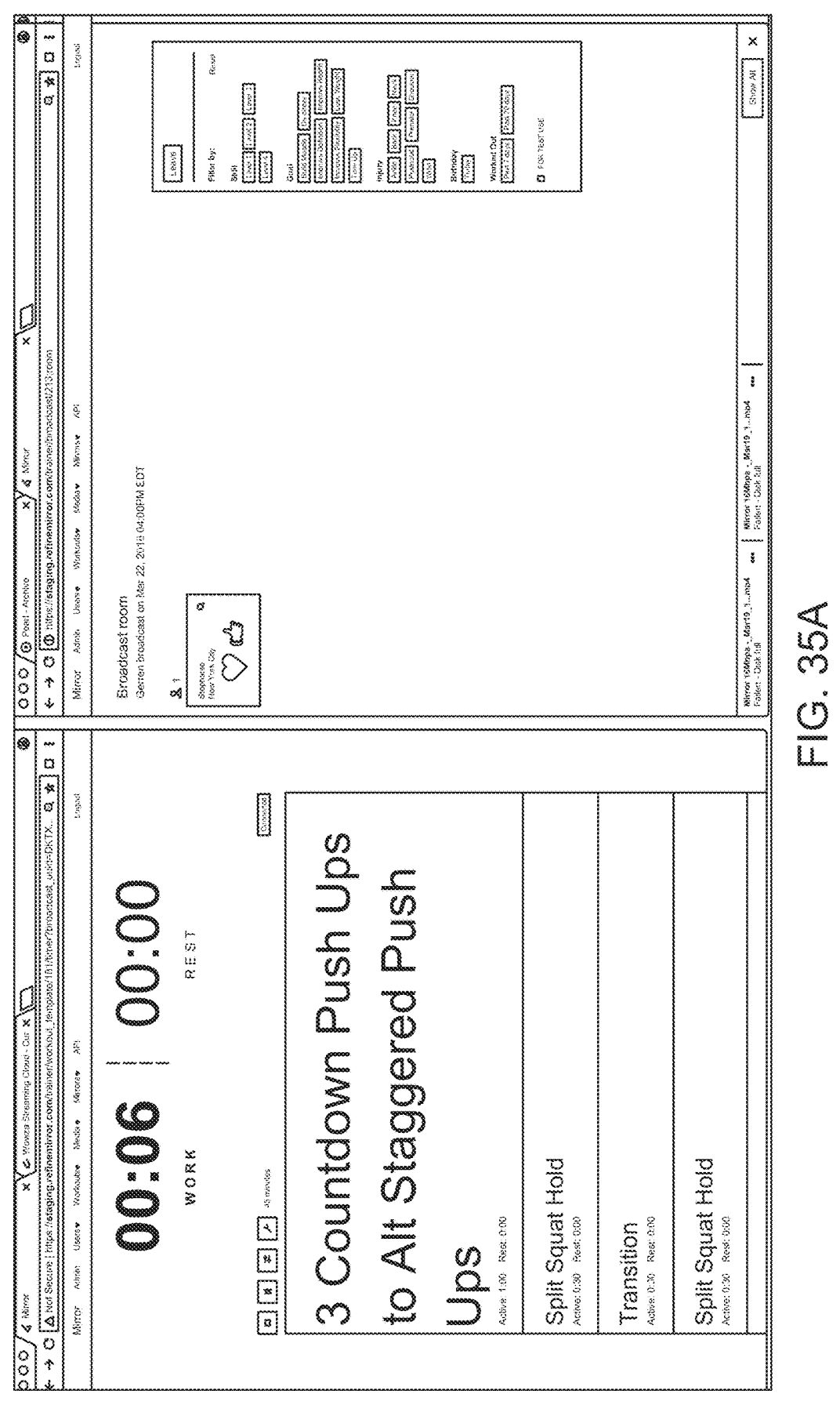
Figure 35B:
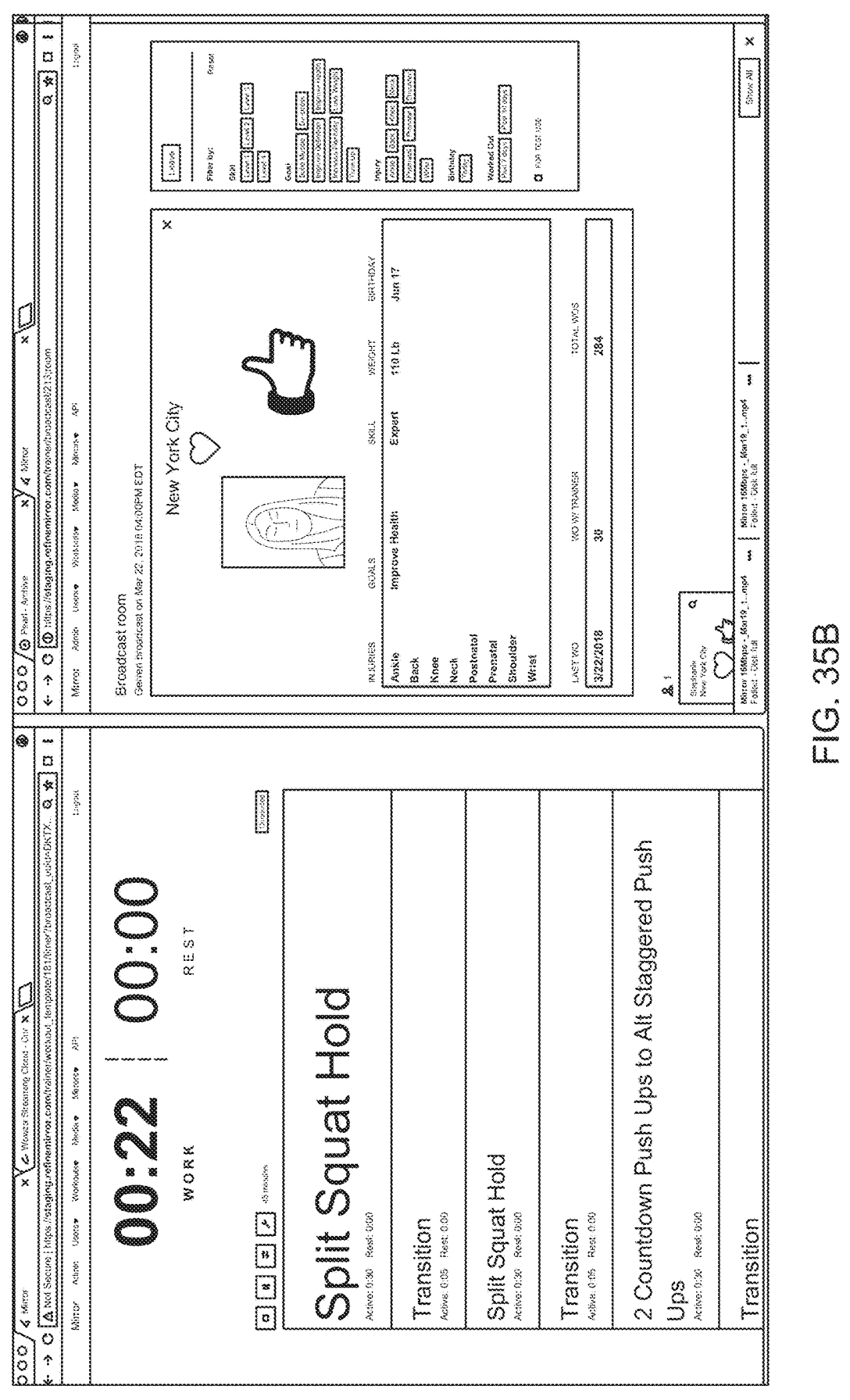
Figure 35C:
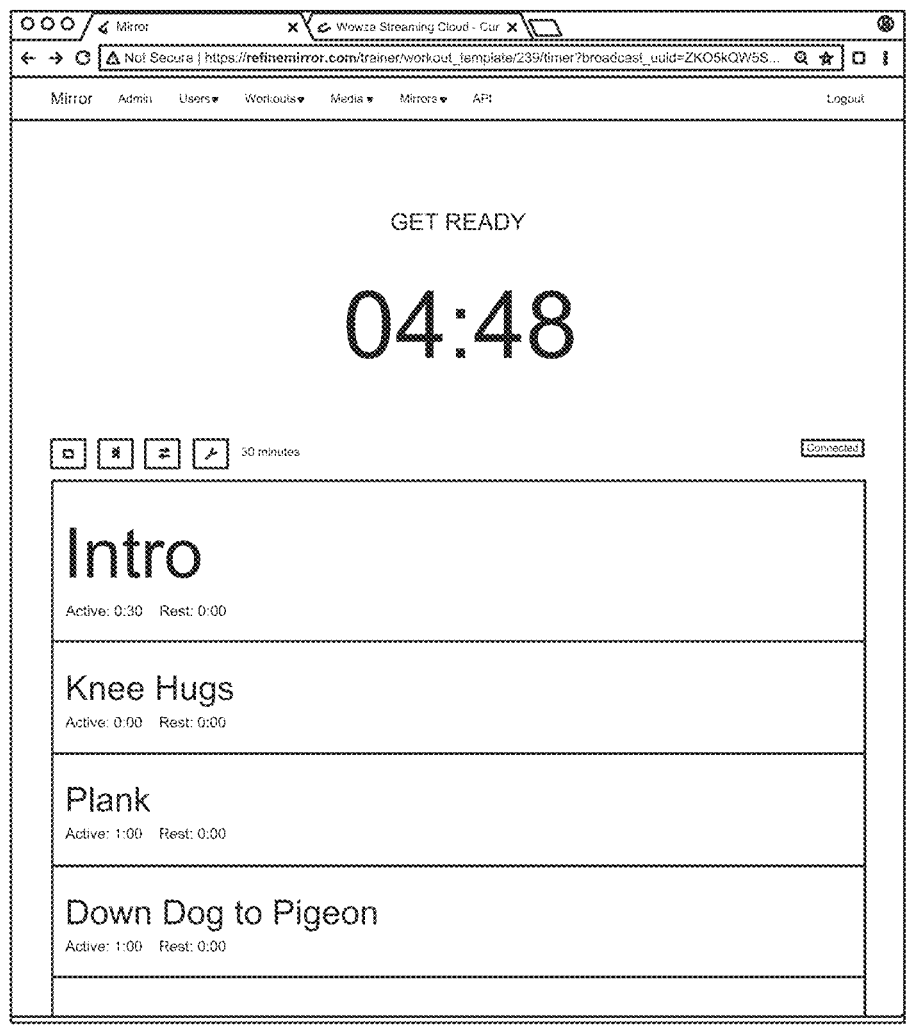
FIG. 35C shows an exemplary instructor user interface on a web browser of another class schedule, in accordance with some embodiments.

FIGS. 35A-35C show an exemplary instructor user interface accessed through a web browser via an instructor's device, such as a computer. FIG. 35A shows the instructor user interface may include a class schedule with a summary of each exercise and the projected period of time of each exercise. The class schedule may be configured to show the current exercise, which may be updated in real-time as the fitness class progresses. The workout schedule in FIG. 35A may also provide controls to the instructor to pause/resume timers for each exercise, to skip particular exercises, or to go back and repeat particular exercises. FIG. 35C shows another exemplary class schedule with a magnified view of the aforementioned controls available to the instructor.

The instructor user interface may also include a summary of the users streaming the fitness class via their respective smart mirror 100. The summary may include each user's name, location, and current status based on one or more emojis. The instructor user interface may include filters to organize and display users according to various parameters including, but not limited to skill level, fitness goals (e.g., build muscle, de-stress, improve health, improve flexibility, improve definition, lose weight, tone up), current and/or past injuries (e.g., ankle, back, knee, neck, postnatal, prenatal, shoulder, wrist), the user's birthday, the duration of time since a user last worked out (e.g., past 7 days, past 30 days).

An instructor may also select individual users in the class to show additional information for each user as shown in FIG. 35B. Various user information may be displayed including, but not limited to the user's picture, the user's name, the user's location, current and past injuries, fitness goals, skill level, weight, birthday, frequency of user workouts, workouts with a trainer (e.g., specific to name or type of trainer), total number of workouts, and user ratings for the class.

Figure 36:
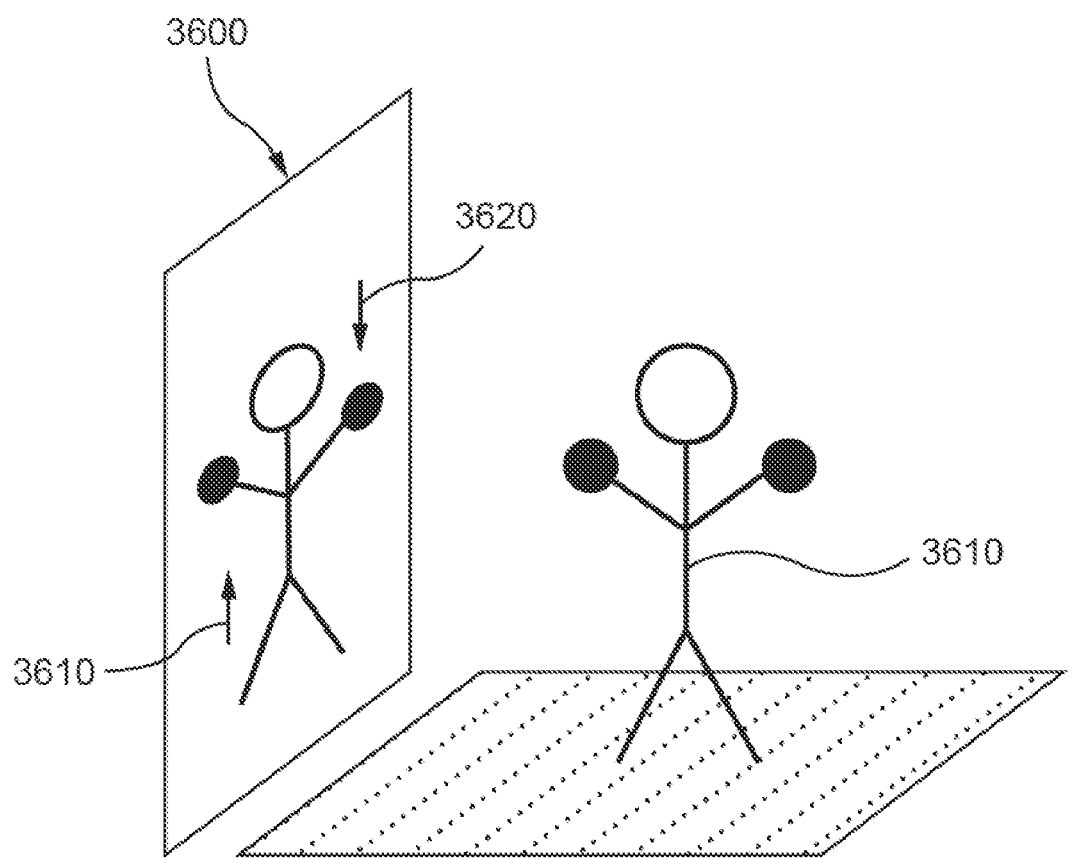
FIG. 36 shows an example implementation in which a user is provided corrective feedback on exercise form by a smart mirror, in accordance with some embodiments.

FIG. 36 shows an example implementation in which a user 3610 is provided corrective feedback on exercise form by a smart mirror 3600, in accordance with some embodiments. The corrective feedback includes a graphical prompt or indication ("up" arrow 3610) that the user 3610 should raise his/her left arm higher, and a graphical prompt or indication ("down" arrow 3620) that the user 3610 should lower his/her left arm. In some such implementations, a length of the arrow can be proportional to the amount of recommended adjustment.

Figure 37:
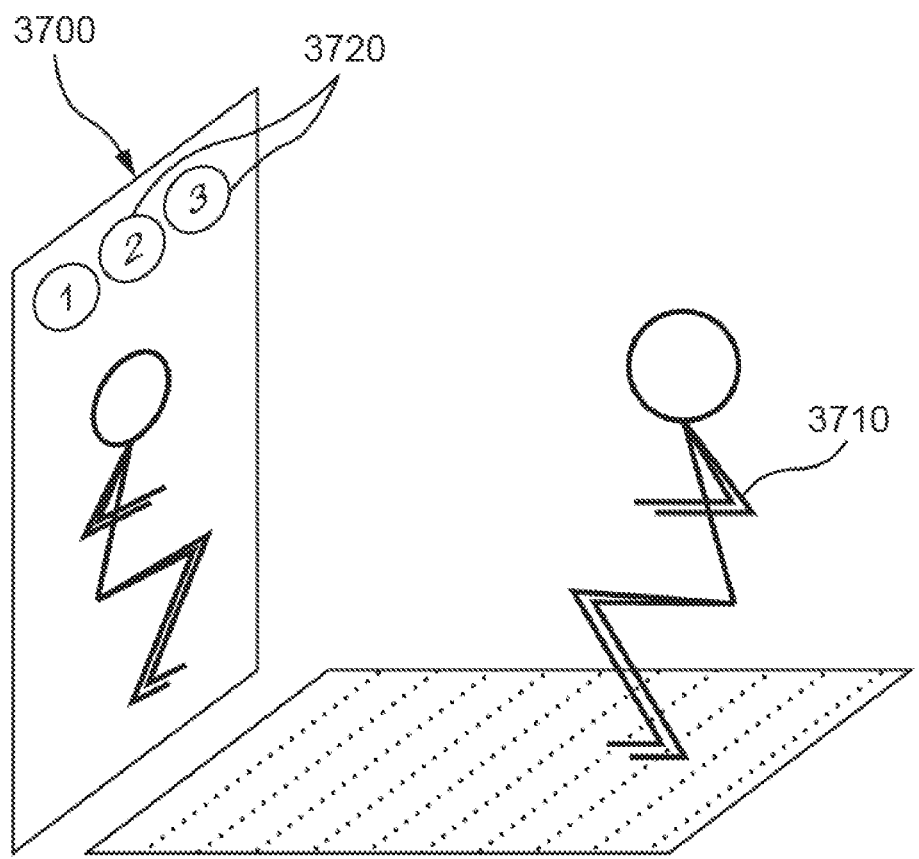

FIG. 37 shows an example implementation in which a smart mirror 3700 counts and displays a repetition count 3720 for a movement (e.g., squats or lunges) that a user 3710 is performing, in accordance with some embodiments.

Figure 38:
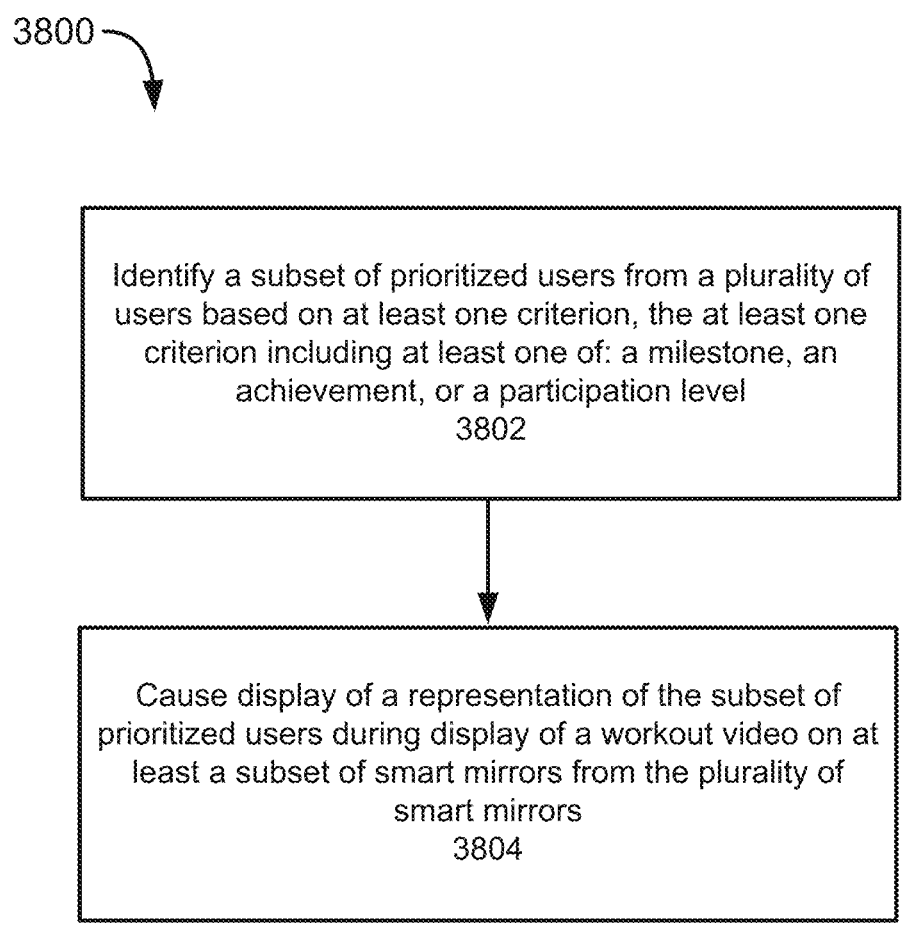

FIG. 38 is a flowchart showing an example method for identifying prioritized users from a plurality of users, in accordance with some embodiments, As shown in FIG. 38, the method 3800 includes identifying, at 3802, via a processor and based on at least one criterion, a subset of prioritized users from a plurality of users. The at least one criterion can include (but is not limited to) at least one of: a milestone (e.g., a birthday, an anniversary, a new membership, an updated member status, etc.), an achievement (e.g., an award), a geographic location, a demographic attribute, a social media related score, a social media related statistic (e.g., number of followers/friends, number of comments on a given post, number of new followers/friends within a predefined time period, etc.), a virtual group membership, a participation level (e.g., a historical participation level, for example as determined for a predefined historical period of time), or a machine-learning model based prediction (e.g., of user motivation, user confidence, user engagement, user enthusiasm, user energy level, user emotion(s), user physical performance, or user participation). For example, the prioritized users can include users who have met a predetermined level of interaction with their associated smart mirror and/or a predetermined level of participation within a smart mirror network or a smart mirror community (e.g., three classes per week for a month of a given class type, trainer, time, etc.), or users who are regular participants ("regulars") of a particular class (e.g., attending at least a predetermined threshold minimum number of times per predefined time period), or users who are regular attendees of a particular instructor (e.g., attending at least a threshold minimum number of unique classes instructed by the particular instructor for a given time period), etc. Each user from the plurality of users is associated with a smart mirror from a plurality of smart mirrors forming the smart mirror network, and the plurality of users can be referred to as the smart mirror community.

In some embodiments, the at least one criterion is generated automatically via one or more servers in communication with the smart mirror network and/or via one or more of the smart mirrors within the smart mirror network. The at least one criterion can be generated according to a predefined or user-defined schedule (e.g., daily, weekly, monthly), in response to a user request received via a compute device of the user, and/or according to predefined or user-defined rules (e.g., generate criterion in response to detecting that a predefined number of classes have been completed within a predefined period of time, generate criterion when a predefined type of class has been scheduled, etc.). In some embodiments, the at least one criterion is generated based on and/or in response to one or more of: a detected pattern of user activity, a detected achievement of a milestone, a detected change in the absolute performance or the relative performance of the user(s), a detected achievement of a predefined number of milestones, a detected change in membership status, or a detected social connection between a given user and at least one other users from the smart mirror community.

At 3804, the method 3800 includes causing display of a representation of the subset of prioritized users during display of a workout video on at least a subset of smart mirrors from the plurality of smart mirrors, each smart mirror from the plurality of smart mirrors configured such that both the workout video and a reflected image of a user associated with that smart mirror are viewable via that smart mirror by the user associated with that smart mirror when the user associated with that smart mirror is positioned in front of the smart mirror during display of the workout video. For example, the workout video can appear superimposed on, directly adjacent to (e.g., within a predetermined number of pixels of), or adjacent to a portion of the reflected image of the user.

The representation of the subset of prioritized users can include a panel or tile rendered at the top, bottom, or either side of the display. Alternatively or in addition, users from the subset of prioritized users can be rendered within the display as virtual "presences" in the background behind a live or prerecorded instructor. For example, an instructor may appear in the foreground of the display during presentation of a workout video, and a live image of a first user from the subset of prioritized users can be inserted in the background behind and slightly to the left of (and optionally partially overlapping with) the instructor. Similarly, a live image of a second user from the subset of prioritized users can be inserted in the background behind and slightly to the right of (and optionally partially overlapping with) the instructor. In this manner, the display can be populated with live or pre-recorded video of users from the subset of prioritized users such that the instructor appears to be leading a class with the users from the subset of prioritized users present in the room with the instructor. The display of such virtual "presences" may change over time during the workout video (e.g., in response to a change in prioritization of users, in response to a real-time change in the composition of the subset of prioritized users, etc.) and/or may only occur during a predefined time period within the workout video. In some such implementations, a studio camera may "pan" around an instructor during a live class, and additional virtual views of users from the subset of prioritized users may be shown (e.g., such that the users from the subset of prioritized users who are virtually "behind" the instructor are more fully in view).

The method 3800 optionally also includes designating each user from the subset of prioritized users as a regular participant in response to the participation levels exceeding the predefined threshold participation level. The designation can be an "internal" designation that includes storing, in memory, a record including an identifier of the user, an indication that the user is a regular participant, and optionally a representation of the class for which the user is a regular participant. Alternatively or in addition, the designation of a user as a regular participant can include annotating a visual representation of that user within a GUI of the display of the smart mirror and/or associated compute device(s) to visually show (e.g., graphically or via a textual representation) that the user is a regular participant. The method 3800 optionally also includes causing display of a reminder, to each user from the subset of prioritized users and an associated smart mirror from the plurality of smart mirrors, of an upcoming workout (optionally without providing similar notifications to users who are not within the subset of prioritized users).

The method 3800 optionally also includes modifying a news feed of the smart mirror network such that a prominence of data associated with the subset of prioritized users is increased relative to a prominence of data associated with the remainder of users from the plurality of users. For example, the prominence of the data associated with the subset of prioritized users can be increased relative to the prominence of data associated with the remainder of users from the plurality of users in one or more (including any combination) of the following ways: the data can be rendered in a distinctive color, the data can be rendered in a distinctive font, the data can be rendered in a distinctive size, the data can have a distinctive shape, the data can have a distinctive associated graphic, the data can have a distinctive brightness, the data can have a distinctive character length, the data can be animated, etc.

In some embodiments, one or more users from the subset of prioritized users may have a "spotlight" applied to a representation of the one or more users during the display of the workout video. A "spotlight" can refer to one or more of: a visual user interface (UI) representation, a graphic image (e.g., a halo effect or illumination), a video, or an animation (e.g., a strobe or flashing illumination).

In some embodiments, a plurality of smart mirror sub-networks can be identified for a given smart mirror network and/or a plurality of smart mirror sub-communities can be identified for a given smart mirror community. In such embodiments, the spotlighting of one or more users and/or the identification and display of a subset of prioritized users can be different for each sub-network from the plurality of sub-networks and/or for each smart mirror sub-community from the plurality of smart mirror sub-communities. For example, if there are 100 smart mirrors within a smart mirror network, four smart mirror sub-networks (A, B, C, and D), including 25 smart mirrors each, may be identified for that smart mirror network. Within smart mirror sub-network A, a first set of one or more users may be selected for spotlighting and/or a first subset of prioritized users may be identified and made prominent within the display during display of the workout video. Within smart mirror sub-network B, a second set of one or more users (different from the first set of one or more users) may be selected for spotlighting and/or a second subset of prioritized users (different from the first subset of prioritized users) may be identified and made prominent within the display during display of the workout video. Within smart mirror sub-network C, a third set of one or more users (different from the first and second sets of one or more users) may be selected for spotlighting and/or a third subset of prioritized users (different from the first and second subsets of prioritized users) may be identified and made prominent within the display during display of the workout video. Within smart mirror sub-network D, a fourth set of one or more users (different from the first, second, and third sets of one or more users) may be selected for spotlighting and/or a fourth subset of prioritized users (different from the first, second, and third subsets of prioritized users) may be identified and made prominent within the display during display of the workout video.

Alternatively or in addition to the multiple sub-networks described above, four smart mirror sub-communities (P, Q, R and S) can be identified for a given smart mirror community of users associated with the 100 smart mirrors within the example smart mirror network. Each of the smart mirror sub-communities P, Q, R and S can include users that are one or more of: connected to one another (e.g., "friended") within a social networking platform, located within a common predefined or user-defined geographic region, having associated performance metrics within a predefined or user-defined range, having one or more milestones meeting a predefined or user-defined criterion, etc. Within smart mirror sub-community P, a first set of one or more users may be selected for spotlighting and/or a first subset of prioritized users may be identified and made prominent within the display during display of the workout video. Within smart mirror sub-community Q, a second set of one or more users (different from the first set of one or more users) may be selected for spotlighting and/or a second subset of prioritized users (different from the first subset of prioritized users) may be identified and made prominent within the display during display of the workout video. Within smart mirror sub-community R, a third set of one or more users (different from the first and second sets of one or more users) may be selected for spotlighting and/or a third subset of prioritized users (different from the first and second subsets of prioritized users) may be identified and made prominent within the display during display of the workout video. Within smart mirror sub-community S, a fourth set of one or more users (different from the first, second, and third sets of one or more users) may be selected for spotlighting and/or a fourth subset of prioritized users (different from the first, second, and third subsets of prioritized users) may be identified and made prominent within the display during display of the workout video.

In some embodiments, an instructor may select (via a GUI of a display of the instructor's smart mirror) a user from a subset of prioritized users, or from a smart mirror community, or from a smart mirror sub-community, to virtually "demonstrate" an exercise. In response to the instructor selection, in some embodiments, a camera (e.g., within a smart mirror or a mobile device) of the selected user may be automatically activated (i.e., turned on, to capture live video). In other embodiments, in response to the instructor selection, a prompt may be generated and presented to the selected user via a GUI of a display of the smart mirror or mobile device of the selected user, optionally requesting the selected user to "accept" an invitation to demonstrate the exercise. In response to the selected user interacting with the prompt to accept the invitation, the camera of the selected user may be turned on, to capture live video. In still other embodiments, in response to the instructor selection, the camera of the selected user may be turned on, to capture live video, without an intervening prompt being displayed via the GUI of the display of the smart mirror or mobile device of the selected user. In some embodiments, the camera of the selected user is deactivated (i.e., turned off) in response to one of: the instructor terminating the demonstration, the user manually turning the camera off, or a predetermined time duration elapsing.

In some embodiments, a representation of the one or more users from the subset of prioritized users may be displayed to a trainer (e.g., via a mirror or smart device display of the trainer) during the display of the workout video. Alternatively or in addition, a live video of the one or more users from the subset of prioritized users may be displayed to the trainer (e.g., via a mirror or smart device display of the trainer) during the display of the workout video. Alternatively or in addition, a trainer may be prompted (e.g., via a mirror or smart device display of the trainer) to provide real-time audio, video and/or text feedback to one or more users from the subset of prioritized users during the display of the workout video.

In some embodiments, the display of the representation of the subset of prioritized users is performed during a predefined time period that is less than a time duration of the workout video. In other embodiments, the display of the representation of the subset of prioritized users is performed throughout the display of the workout video.

In some embodiments, the representation of the subset of prioritized users includes one of: a graphical image, a video, or an animation.

In some embodiments, the at least one criterion includes the historical participation level, and the identifying the subset of prioritized users from a plurality of users includes comparing the historical participation level with a predefined threshold participation level.

In some embodiments, the at least one criterion includes the historical participation level, the method further comprising causing display, to at least one prioritized user from the subset of prioritized users and via the associated at least one smart mirror, of a message including an indication that the workout video is a preferred workout video of the at least one prioritized user from the subset of prioritized users.

In some embodiments, the at least one criterion includes the historical participation level and the display of the workout video is performed during a time period, the method further comprising causing display, to at least one prioritized user from the subset of prioritized users and via the associated at least one smart mirror, of a message including an indication that the time period is a preferred time period of the at least one prioritized user from the subset of prioritized users.

In some embodiments, the at least one criterion includes the historical participation level and the display of the workout video is performed during a time slot, the method further comprising causing display, to at least one prioritized user from the subset of prioritized users and via the associated at least one smart mirror, of a message including an indication that the time slot is a preferred time slot.

In some embodiments, the prioritized users are designated as "front row" users, and a representation of a front row status may be stored in memory for each prioritized user (e.g., in a record that associates a given prioritized user with the front row status).

In some embodiments, the prioritized users are designated as "regulars," and a representation of a "regular" status may be stored in memory for each prioritized user (e.g., in a record that associates a given prioritized user with the regular status).

CONCLUSION

All parameters, dimensions, materials, and configurations described herein are meant to be exemplary and the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Other substitutions, modifications, changes, and omissions may be made in the design, operating conditions and arrangement of respective elements of the exemplary implementations without departing from the scope of the present disclosure. The use of a numerical range does not preclude equivalents that fall outside the range that fulfill the same function, in the same way, to produce the same result.

The above-described embodiments can be implemented in multiple ways. For example, embodiments may be implemented using hardware, software or a combination thereof. When implemented in software, the software code can be executed on a suitable processor or collection of processors, whether provided in a single computer or distributed among multiple computers.

Further, a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in a suitable form, including a local area network or a wide area network, such as an enterprise network, an intelligent network (IN) or the Internet. Such networks may be based on a suitable technology, may operate according to a suitable protocol, and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Some implementations may specifically employ one or more of a particular operating system or platform and a particular programming language and/or scripting tool to facilitate execution.

Also, various inventive concepts may be embodied as one or more methods, of which at least one example has been provided. The acts performed as part of the method may in some instances be ordered in different ways. Accordingly, in some inventive implementations, respective acts of a given method may be performed in an order different than specifically illustrated, which may include performing some acts simultaneously (even if such acts are shown as sequential acts in illustrative embodiments).

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
   identifying, via a processor and based on at least one criterion, a subset of prioritized users from a plurality of users, the at least one criterion including at least one of: a milestone, an achievement, or a historical participation level, each user from the plurality of users associated with a smart mirror from a plurality of smart mirrors forming a smart mirror network; and
   causing display of a live or pre-recorded video of the subset of prioritized users during display of a workout video on at least a subset of smart mirrors from the plurality of smart mirrors, the workout video depicting an instructor and the live or pre-recorded video of the subset of prioritized users appearing behind the instructor, each smart mirror from the plurality of smart mirrors configured such that both the workout video and a reflected image of a user associated with that smart mirror are viewable via that smart mirror by the user associated with that smart mirror when that user associated with that smart mirror is positioned in front of the smart mirror during display of the workout video.

2. The method of claim 1, wherein the display of the live or pre-recorded video of the subset of prioritized users is performed during a predefined time period that is less than a time duration of the workout video.

3. The method of claim 1, wherein the display of the live or pre-recorded video of the subset of prioritized users is performed throughout the display of the workout video.

4. The method of claim 1, wherein the at least one criterion includes the historical participation level, and the identifying the subset of prioritized users from a plurality of users includes comparing the historical participation level with a predefined threshold participation level.

5. The method of claim 4, further comprising:
   designating each user from the subset of prioritized users as a regular participant in response to the historical participation levels exceeding the predefined threshold participation level.

6. The method of claim 4, further comprising causing display of a reminder, to each user from the subset of prioritized users and an associated smart mirror from the plurality of smart mirrors, of an upcoming workout.

7. The method of claim 1, further comprising modifying a news feed of the smart mirror network such that a prominence of data associated with the subset of prioritized users is increased relative to the remainder of users from the plurality of users.

8. The method of claim 1, wherein the at least one criterion includes the historical participation level, the method further comprising causing display, to at least one prioritized user from the subset of prioritized users and via the associated at least one smart mirror, of a message including an indication that the workout video is a preferred workout video of the at least one prioritized user from the subset of prioritized users.

9. The method of claim 1, wherein the at least one criterion includes the historical participation level and the display of the workout video is performed during a time period, the method further comprising causing display, to at least one prioritized user from the subset of prioritized users and via the associated at least one smart mirror, of a message including an indication that the time period is a preferred time period of the at least one prioritized user from the subset of prioritized users.

10. The method of claim 1, wherein the at least one criterion includes the milestone, and the milestone includes one of a birthday, an anniversary, a new membership, or an updated member status.

11. The method of claim 1, wherein the at least one criterion further includes a social media related statistic.

12. An apparatus, comprising:
a processor; and
a memory storing instructions that, when executed by the processor, cause the processor to:
identify, based on at least one criterion, a subset of prioritized users from a plurality of users, the at least one criterion including at least one of: a milestone, an achievement, or a historical participation level, each user from the plurality of users associated with a smart mirror from a plurality of smart mirrors forming a smart mirror network; and
cause display of a video of the subset of prioritized users during display of a workout video on at least a subset of smart mirrors from the plurality of smart mirrors, the workout video depicting an instructor and the video of the subset of prioritized users appearing behind the instructor, each smart mirror from the plurality of smart mirrors configured such that both the workout video and a reflected image of a user associated with that smart mirror are viewable via that smart mirror by the user associated with that smart mirror when that user associated with that smart mirror is positioned in front of the smart mirror during display of the workout video.

13. The apparatus of claim 12, wherein the video of the subset of prioritized users includes at least one of: live video imagery of each user from the subset of prioritized users, or pre-recorded video imagery of each user from the subset of prioritized users.

14. The apparatus of claim 12, wherein the subset of prioritized users is a first subset of prioritized users and the at least a subset of smart mirrors is a first subset of smart mirrors, the memory further storing instructions that, when executed by the processor, cause the processor to:
identify a second subset of prioritized users from the plurality of users; and
cause display of a video of the second subset of prioritized users during display of a workout video on a second subset of smart mirrors from the plurality of smart mirrors, the second subset of smart mirrors being different from the first subset of smart mirrors.

15. The apparatus of claim 12, wherein the at least a subset of smart mirrors from the plurality of smart mirrors includes a first sub-community of smart mirrors and a second sub-community of smart mirrors different from the first sub-community of smart mirrors, the instructions to cause the processor to cause display of the video of the subset of prioritized users including instructions to:
identify a first prioritized user from the subset of prioritized users as being associated with the first sub-community of smart mirrors;
cause display of the video of the first prioritized user to smart mirrors of the first sub-community of smart mirrors and not to smart mirrors of the second sub-community of smart mirrors, in response to identifying the first prioritized user as being associated with the first sub-community of smart mirrors;
identify a second prioritized user from the subset of prioritized users as being associated with the second sub-community of smart mirrors; and
cause display of the video of the second prioritized user to smart mirrors of the second sub-community of smart mirrors and not to smart mirrors of the first sub-community of smart mirrors, in response to identifying the second prioritized user as being associated with the second sub-community of smart mirrors.

16. The apparatus of claim 15, wherein the instructions to cause the processor to identify the first prioritized user from the subset of prioritized users as being associated with the first sub-community of smart mirrors include instructions to determine that the first prioritized user is at least one of: connected via a social media platform with at least one user associated with the first sub-community of smart mirrors, located within a predefined geographic region associated with the first sub-community of smart mirrors, associated with a predefined range of performance metrics associated with the first sub-community of smart mirrors, or associated with a milestone associated with the first sub-community of smart mirrors.

17. A non-transitory, processor-readable medium storing instructions that, when executed by the processor, cause the processor to:
identify, based on at least one criterion, a subset of prioritized users from a plurality of users, the at least one criterion including at least one of: a milestone, an achievement, or a historical participation level, each user from the plurality of users associated with a smart mirror from a plurality of smart mirrors forming a smart mirror network; and
cause display of a video of the subset of prioritized users during display of a workout video on at least a subset of smart mirrors from the plurality of smart mirrors, the workout video depicting an instructor and the video of the subset of prioritized users appearing behind the instructor, each smart mirror from the plurality of smart mirrors configured such that both the workout video and a reflected image of a user associated with that smart mirror are viewable via that smart mirror by the user associated with that smart mirror when that user associated with that smart mirror is positioned in front of the smart mirror during display of the workout video.

18. The non-transitory, processor-readable medium of claim 17, wherein each smart mirror from the at least a subset of smart mirrors is associated with a community user from a plurality of community users, the community users from the plurality of community users having in common with one another at least one of: a social network, a geographic region, a performance metric range, or a milestone type.

19. The non-transitory, processor-readable medium of claim 17, wherein the video of the subset of prioritized users includes at least one of: live video imagery of each user from the subset of prioritized users, or pre-recorded video imagery of each user from the subset of prioritized users.

20. The non-transitory, processor-readable medium of claim 17, wherein the video of the subset of prioritized users includes at least one of a halo effect, an illumination overlay, or a strobe effect.

* * * * *